(12) United States Patent
Heier et al.

(10) Patent No.: US 12,281,304 B2
(45) Date of Patent: Apr. 22, 2025

(54) COMPOSITIONS AND METHODS FOR TREATING AND PREVENTING MUSCULAR DISORDERS AND DYSTROPHIES, STEROID SIDE EFFECTS, AND INFLAMMATION

(71) Applicant: Children's National Medical Center, Washington, DC (US)

(72) Inventors: Christopher Heier, Washington, DC (US); Alyson Fiorillo, Washington, DC (US)

(73) Assignee: Children's National Medical Center, Washington, DC (US)

( * ) Notice: Subject to any disclaimer, the term of this patent is extended or adjusted under 35 U.S.C. 154(b) by 186 days.

(21) Appl. No.: 17/059,700

(22) PCT Filed: Jun. 3, 2019

(86) PCT No.: PCT/US2019/035264
§ 371 (c)(1),
(2) Date: Nov. 30, 2020

(87) PCT Pub. No.: WO2019/232548
PCT Pub. Date: Dec. 5, 2019

(65) Prior Publication Data
US 2021/0198669 A1 Jul. 1, 2021

Related U.S. Application Data

(60) Provisional application No. 62/679,529, filed on Jun. 1, 2018.

(51) Int. Cl.
*C12N 15/113* (2010.01)
*A61K 31/573* (2006.01)
*A61K 31/7088* (2006.01)
*A61P 21/00* (2006.01)
*C12Q 1/68* (2018.01)

(52) U.S. Cl.
CPC .......... *C12N 15/113* (2013.01); *A61K 31/573* (2013.01); *A61K 31/7088* (2013.01); *A61P 21/00* (2018.01); *C12N 2310/11* (2013.01); *C12N 2320/31* (2013.01); *C12N 2320/35* (2013.01)

(58) Field of Classification Search
None
See application file for complete search history.

(56) References Cited

U.S. PATENT DOCUMENTS

| | | | |
|---|---|---|---|
| 11,186,838 B2* | 11/2021 | Thum | A61P 9/00 |
| 2009/0023670 A1 | 1/2009 | Sebestyen | |
| 2013/0177624 A1* | 7/2013 | Corry | A61K 45/06 |
| | | | 435/6.12 |
| 2014/0256792 A1* | 9/2014 | Ferdinandy | A61K 31/713 |
| | | | 435/6.12 |
| 2016/0362689 A1* | 12/2016 | Shi | C12Q 1/6886 |
| 2018/0016578 A1* | 1/2018 | Hoffman | A61P 21/00 |
| 2019/0136236 A1* | 5/2019 | Thum | A61P 9/04 |
| 2020/0157627 A1* | 5/2020 | Sharma | C12N 15/113 |
| 2021/0363525 A1* | 11/2021 | Sætrom | A61P 11/00 |

FOREIGN PATENT DOCUMENTS

WO    WO 2005/013901 A2    2/2005

OTHER PUBLICATIONS

Written Opinion issued on Nov. 27, 2019 in PCT/US2019/035264 filed on Jun. 3, 2019, 6 pages.
Mandolesi et al., "miR-142-3p Is a Key Regulator of IL-1β-Dependent Synaptopathy in Neuroinflammation", The Journal of Neuroscience, 2017, vol. 37, No. 3, pp. 546-561.
Wang et al., "Elevated expression of miR-142-3p is related to the pro-inflammatory function of monocyte-derived dendritic cells in SLE", Arthritis Research and Therapy, 2016, vol. 18, No. 263, pp. 1-11.
United Kingdom Office Action issued Mar. 24, 2022 in United Kingdom Patent Application No. 2018908.0, 2 pages.

* cited by examiner

*Primary Examiner* — Sean McGarry
(74) *Attorney, Agent, or Firm* — Oblon, McClelland, Maier & Neustadt, L.L.P.

(57) ABSTRACT

The present disclosure relates to compositions comprising an antisense RNA sequence comprising a region of complementarity that is substantially complementary to an miRNA. Pharmaceutical compositions comprising the antisense RNA molecule, optionally further comprising an anti-inflammatory corticosteroid are also disclosed. Methods of treating or preventing inflammation, a steroid side effect, or a muscle disease using the one or the pharmaceutical compositions are also disclosed.

24 Claims, 19 Drawing Sheets
Specification includes a Sequence Listing.

| NF-кB motif | a | G | G | G | g | a | T | T | T | C | C | a | . | . | SEQ ID NO: 75 |
|---|---|---|---|---|---|---|---|---|---|---|---|---|---|---|---|
| miR-142 site 1 | T | G | G | G | G | C | T | T | T | C | C | A | A | G | G | SEQ ID NO: 76 |
| miR-142 site 2 | A | G | G | G | G | C | T | T | T | C | C | A | A | A | T | SEQ ID NO: 77 |
| miR-142 site 3 | A | G | G | G | T | A | T | T | T | C | C | G | G | G | A | SEQ ID NO: 78 |
| miR-142 site 5 | G | G | G | G | A | C | T | T | C | C | T | A | G | A | G | SEQ ID NO: 79 |
| miR-142 site 12 | A | G | G | G | G | A | T | T | C | T | C | A | C | G | T | SEQ ID NO: 80 |

| miRNA | Promoter Regulation | Pathophysiological Roles | Sources |
|---|---|---|---|
| 142-5p | NF-κB | φ-induced inflammation and fibrosis; Neuroinflammation | (66,74) |
| 142-3p | NF-κB | Inflammatory program of MoDCs; Neuroinflammation | (74,76) |
| 146a | NF-κB | Serum biomarker of inflammation; senescence | (24,49,51,68) |
| 301a | NF-κB | Pro-inflammatory, targets NKRF in NF-κB positive feedback loop | (35,74) |
| 324-3p | IL4, STAT6 | Pro-inflammatory; Induces NF-κB; pro-fibrotic φ pathway | (6,10,13) |
| 455-5p | NF-κB | Muscle atrophy, adipocyte formation | (72,74) |
| 455-3p | NF-κB, TWEAK | Inflammatory muscle wasting; resides in intron of COL27A1 | (48,51,67,74) |
| 497 | NF-κB, GR | Pulmonary fibrogenesis | (5,74) |
| 652 | NF-κB | Acute coronary syndrome marker | (54,74) |

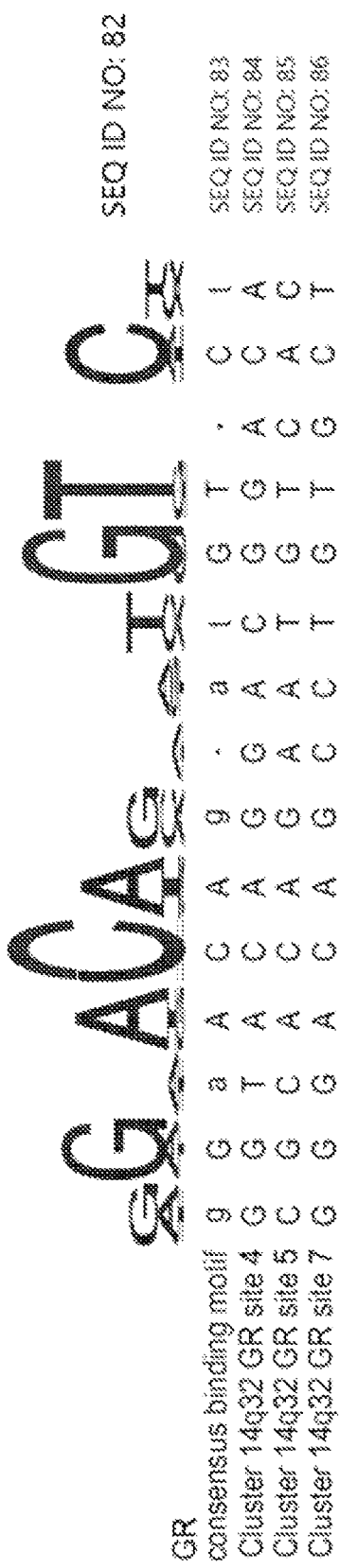

| GR consensus binding motif | g | a | C | a | g | . | a | — | g | T | C |   |
|---|---|---|---|---|---|---|---|---|---|---|---|---|
| Cluster 14q32 GR site 4 | G | T | A | C | A | G | · | — | G | T | C | SEQ ID NO: 83 |
| Cluster 14q32 GR site 5 | C | C | A | C | A | C | A | — | G | T | A | SEQ ID NO: 84 |
| Cluster 14q32 GR site 6 | G | G | A | C | A | A | T | — | T | G | A | SEQ ID NO: 85 |
| Cluster 14q32 GR site 7 | G | G | G | C | A | G | C | — | T | C | T | SEQ ID NO: 86 |

SEQ ID NO: 82

| miRNA | Regulated by | Sources | Upregulation of miRNA is associated with: |
|---|---|---|---|
| miR-134 | GR↑ | (22,43,73,74) | Insulin resistance, stress, heart failure, fibrosis |
| miR-370 | GR↑ | (74,81) | Type II Diabetes and insuline resistance |
| miR-409-3p | GR↑ | (45,74) | Fibrosis |
| miR-433 | GR↑ | (69,74) | Heart fibrosis |
| miR-493 | GR↑ | (74,84) | Stress, depression and mood disturbances |
| miR-543 | GR↑ | (11,74) | Insulin resistance, hypertension, osteosarcoma |

FIG. 4C

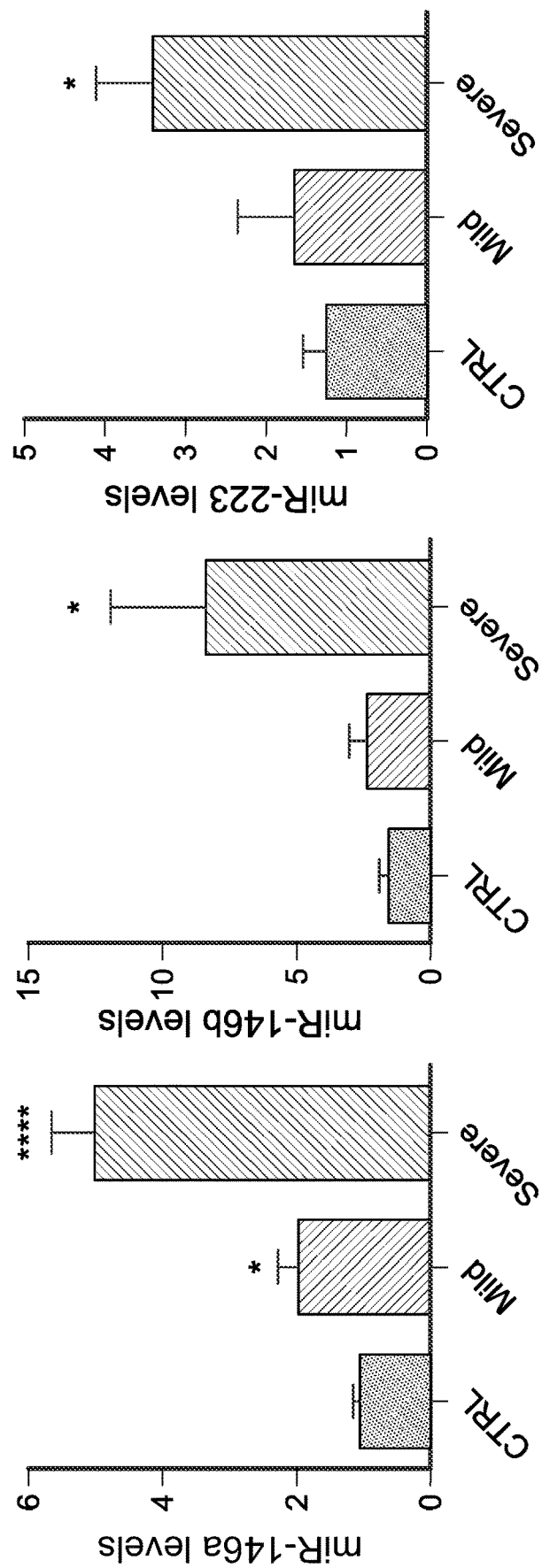

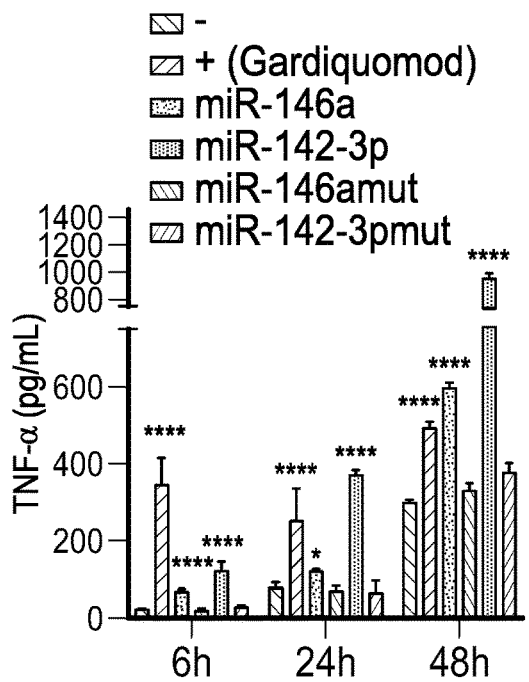
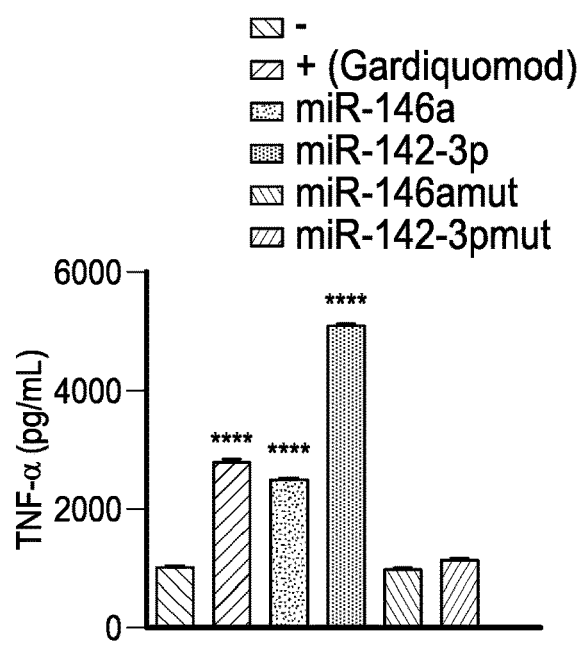
FIG. 11A  FIG. 11B
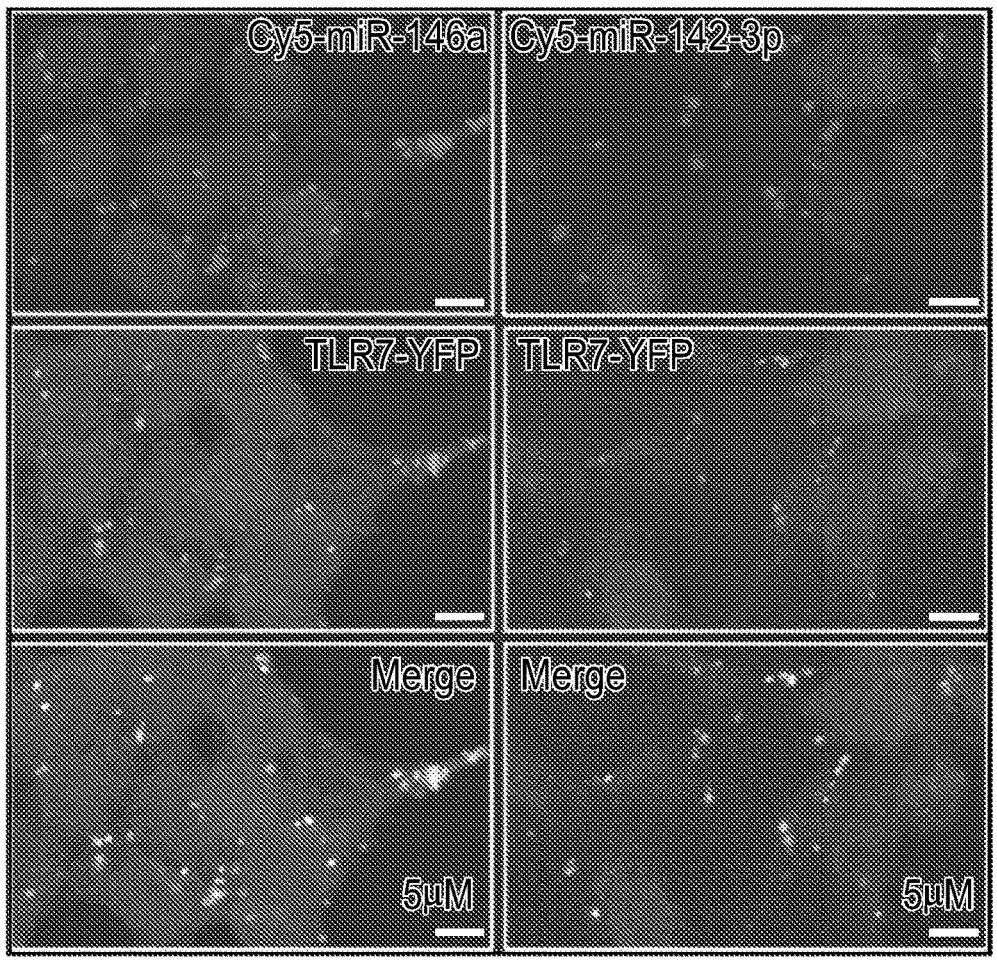
FIG. 11C

SEQUENCE LISTING

<160> NUMBER OF SEQ ID NOS: 86

<210> SEQ ID NO 1
<211> LENGTH: 23
<212> TYPE: RNA
<213> ORGANISM: Homo sapiens

<400> SEQUENCE: 1
uguaguguuu ccuacuuuau gga                                              23

<210> SEQ ID NO 2
<211> LENGTH: 21
<212> TYPE: RNA
<213> ORGANISM: Homo sapiens

<400> SEQUENCE: 2
cauaaaguag aaagcacuac u                                                21

<210> SEQ ID NO 3
<211> LENGTH: 22
<212> TYPE: RNA
<213> ORGANISM: Homo sapiens

<400> SEQUENCE: 3
ugagaacuga auuccauggg uu                                               22

<210> SEQ ID NO 4
<211> LENGTH: 23
<212> TYPE: RNA
<213> ORGANISM: Homo sapiens

<400> SEQUENCE: 4
cagugcaaua guauugucaa agc                                              23

<210> SEQ ID NO 5
<211> LENGTH: 20
<212> TYPE: RNA
<213> ORGANISM: Homo sapiens

<400> SEQUENCE: 5
acugccccag gugcugcugg                                                  20

<210> SEQ ID NO 6
<211> LENGTH: 21
<212> TYPE: RNA
<213> ORGANISM: Homo sapiens

<400> SEQUENCE: 6
gcaguccaug ggcauauaca c                                                21

<210> SEQ ID NO 7
<211> LENGTH: 21
<212> TYPE: RNA
<213> ORGANISM: Homo sapiens

<400> SEQUENCE: 7
gcaguccaug ggcauauaca c                                                21

<210> SEQ ID NO 8
<211> LENGTH: 21
<212> TYPE: RNA
<213> ORGANISM: Homo sapiens

<400> SEQUENCE: 8

-continued aauggcgcca cuaggguugu g                                         21

<210> SEQ ID NO 9
<211> LENGTH: 22
<212> TYPE: RNA
<213> ORGANISM: Homo sapiens

<400> SEQUENCE: 9
ugucaguuug ucaaauaccc ca                                        22

<210> SEQ ID NO 10
<211> LENGTH: 22
<212> TYPE: RNA
<213> ORGANISM: Homo sapiens

<400> SEQUENCE: 10
ugagaacuga auuccauagg cu                                        22

<210> SEQ ID NO 11
<211> LENGTH: 22
<212> TYPE: RNA
<213> ORGANISM: Homo sapiens

<400> SEQUENCE: 11
aaaagcuggg uugagagggc ga                                        22

<210> SEQ ID NO 12
<211> LENGTH: 23
<212> TYPE: RNA
<213> ORGANISM: Mus musculus

<400> SEQUENCE: 12
uguaguguuu ccuacuuuau gga                                       23

<210> SEQ ID NO 13
<211> LENGTH: 21
<212> TYPE: RNA
<213> ORGANISM: Mus musculus

<400> SEQUENCE: 13
cauaaaguag aaagcacuac u                                         21

<210> SEQ ID NO 14
<211> LENGTH: 22
<212> TYPE: RNA
<213> ORGANISM: Mus musculus

<400> SEQUENCE: 14
ugagaacuga auuccauggg uu                                        22

<210> SEQ ID NO 15
<211> LENGTH: 23
<212> TYPE: RNA
<213> ORGANISM: Mus musculus

<400> SEQUENCE: 15
cagugcaaua guauugucaa agc                                       23

<210> SEQ ID NO 16
<211> LENGTH: 20
<212> TYPE: RNA
<213> ORGANISM: Mus musculus

```
<400> SEQUENCE: 16
ccacugcccc aggugcugcu                                              20

<210> SEQ ID NO 17
<211> LENGTH: 21
<212> TYPE: RNA
<213> ORGANISM: Mus musculus

<400> SEQUENCE: 17
gcaguccacg ggcauauaca c                                            21

<210> SEQ ID NO 18
<211> LENGTH: 22
<212> TYPE: RNA
<213> ORGANISM: Mus musculus

<400> SEQUENCE: 18
cagcagcaca cugugguuug ua                                           22

<210> SEQ ID NO 19
<211> LENGTH: 21
<212> TYPE: RNA
<213> ORGANISM: Mus musculus

<400> SEQUENCE: 19
aauggcgcca cuaggguugu g                                            21

<210> SEQ ID NO 20
<211> LENGTH: 22
<212> TYPE: RNA
<213> ORGANISM: Mus musculus

<400> SEQUENCE: 20
ugucaguuug ucaaauaccc ca                                           22

<210> SEQ ID NO 21
<211> LENGTH: 22
<212> TYPE: RNA
<213> ORGANISM: Mus musculus

<400> SEQUENCE: 21
ugagaacuga auuccauagg cu                                           22

<210> SEQ ID NO 22
<211> LENGTH: 22
<212> TYPE: RNA
<213> ORGANISM: Mus musculus

<400> SEQUENCE: 22
aaaagcuggg uugagagggc ga                                           22

<210> SEQ ID NO 23
<211> LENGTH: 23
<212> TYPE: RNA
<213> ORGANISM: Artificial Sequence
<220> FEATURE:
<223> OTHER INFORMATION: RNA 1

<400> SEQUENCE: 23
uccauaaagu aggaaacacu aca                                          23

<210> SEQ ID NO 24
<211> LENGTH: 21
```

```
<212> TYPE: RNA
<213> ORGANISM: Artificial Sequence
<220> FEATURE:
<223> OTHER INFORMATION: RNA 2

<400> SEQUENCE: 24
aguagugcuu ucuacuuuau g                                          21

<210> SEQ ID NO 25
<211> LENGTH: 22
<212> TYPE: RNA
<213> ORGANISM: Artificial Sequence
<220> FEATURE:
<223> OTHER INFORMATION: RNA 3

<400> SEQUENCE: 25
aacccaugga auucaguucu ca                                         22

<210> SEQ ID NO 26
<211> LENGTH: 23
<212> TYPE: RNA
<213> ORGANISM: Artificial Sequence
<220> FEATURE:
<223> OTHER INFORMATION: RNA 4

<400> SEQUENCE: 26
gcuuugacaa uacuauugca cug                                        23

<210> SEQ ID NO 27
<211> LENGTH: 20
<212> TYPE: RNA
<213> ORGANISM: Artificial Sequence
<220> FEATURE:
<223> OTHER INFORMATION: RNA 5

<400> SEQUENCE: 27
agcagcaccu ggggcagugg                                            20

<210> SEQ ID NO 28
<211> LENGTH: 22
<212> TYPE: RNA
<213> ORGANISM: Artificial Sequence
<220> FEATURE:
<223> OTHER INFORMATION: RNA 6

<400> SEQUENCE: 28
ccagcagcac cugggcagug gg                                         22

<210> SEQ ID NO 29
<211> LENGTH: 21
<212> TYPE: RNA
<213> ORGANISM: Artificial Sequence
<220> FEATURE:
<223> OTHER INFORMATION: RNA 7

<400> SEQUENCE: 29
guguauaugc ccguggacug c                                          21

<210> SEQ ID NO 30
<211> LENGTH: 21
<212> TYPE: RNA
<213> ORGANISM: Artificial Sequence
<220> FEATURE:
<223> OTHER INFORMATION: RNA 8

<400> SEQUENCE: 30
```

```
gugauaaugc ccauggacug c                                              21

<210> SEQ ID NO 31
<211> LENGTH: 21
<212> TYPE: RNA
<213> ORGANISM: Artificial Sequence
<220> FEATURE:
<223> OTHER INFORMATION: RNA 8

<400> SEQUENCE: 31
acaaaccaca gugugcugcu g                                              21

<210> SEQ ID NO 32
<211> LENGTH: 21
<212> TYPE: RNA
<213> ORGANISM: Artificial Sequence
<220> FEATURE:
<223> OTHER INFORMATION: RNA 9

<400> SEQUENCE: 32
cacaacccua guggcgccau u                                              21

<210> SEQ ID NO 33
<211> LENGTH: 22
<212> TYPE: RNA
<213> ORGANISM: Artificial Sequence
<220> FEATURE:
<223> OTHER INFORMATION: RNA 9

<400> SEQUENCE: 33 uggguauuu gacaaacuga ca                                              22

<210> SEQ ID NO 34
<211> LENGTH: 21
<212> TYPE: RNA
<213> ORGANISM: Artificial Sequence
<220> FEATURE:
<223> OTHER INFORMATION: RNA 10

<400> SEQUENCE: 34
agcuauggaa uucaguucuc a                                              21

<210> SEQ ID NO 35
<211> LENGTH: 22
<212> TYPE: RNA
<213> ORGANISM: Homo sapiens

<400> SEQUENCE: 35
ucgcccucuc aacccagcuu uu                                             22

<210> SEQ ID NO 36
<211> LENGTH: 22
<212> TYPE: RNA
<213> ORGANISM: Homo sapiens

<400> SEQUENCE: 36
ugugacuggu ugaccagagg gg                                             22

<210> SEQ ID NO 37
<211> LENGTH: 22
<212> TYPE: RNA
<213> ORGANISM: Homo sapiens

<400> SEQUENCE: 37
gccugcuggg guggaaccug gu                                             22
```

```
<210> SEQ ID NO 38
<211> LENGTH: 22
<212> TYPE: RNA
<213> ORGANISM: Homo sapiens

<400> SEQUENCE: 38
gaauguugcu cggugaaccc cu                                              22

<210> SEQ ID NO 39
<211> LENGTH: 22
<212> TYPE: RNA
<213> ORGANISM: Homo sapiens

<400> SEQUENCE: 39
aucaugaugg gcuccucggu gu                                              22

<210> SEQ ID NO 40
<211> LENGTH: 22
<212> TYPE: RNA
<213> ORGANISM: Homo sapiens

<400> SEQUENCE: 40
ugaaggucua cugugugcca gg                                              22

<210> SEQ ID NO 41
<211> LENGTH: 22
<212> TYPE: RNA
<213> ORGANISM: Homo sapiens

<400> SEQUENCE: 41
aaacauucgc ggugcacuuc uu                                              22

<210> SEQ ID NO 42
<211> LENGTH: 22
<212> TYPE: RNA
<213> ORGANISM: Mus musculus

<400> SEQUENCE: 42
ugugacuggu ugaccagagg gg                                              22

<210> SEQ ID NO 43
<211> LENGTH: 22
<212> TYPE: RNA
<213> ORGANISM: Mus musculus

<400> SEQUENCE: 43
gccugcuggg guggaaccug gu                                              22

<210> SEQ ID NO 44
<211> LENGTH: 22
<212> TYPE: RNA
<213> ORGANISM: Mus musculus

<400> SEQUENCE: 44
gaauguugcu cggugaaccc cu                                              22

<210> SEQ ID NO 45
<211> LENGTH: 22
<212> TYPE: RNA
<213> ORGANISM: Mus musculus

<400> SEQUENCE: 45
```
aucaugaugg gcuccucggu gu                                                22

<210> SEQ ID NO 46
<211> LENGTH: 23
<212> TYPE: RNA
<213> ORGANISM: Mus musculus

<400> SEQUENCE: 46
ugaagguccu acugugugcc agg                                               23

<210> SEQ ID NO 47
<211> LENGTH: 22
<212> TYPE: RNA
<213> ORGANISM: Mus musculus

<400> SEQUENCE: 47
aaacauucgc ggugcacuuc uu                                                22

<210> SEQ ID NO 48
<211> LENGTH: 34916
<212> TYPE: RNA
<213> ORGANISM: Artificial Sequence
<220> FEATURE:
<223> OTHER INFORMATION: meg3 sequence

<400> SEQUENCE: 48
agccccuagc gcagacggcg gagagcagag agggagcgcg ccuuggcucg cuggccuugg        60
cggcggcucc ucaggagagc uggggcgccc acgagaggau cccucacccg gugagugguu       120
ggccauccuu gccgcaaagg augugcaaaa ggaagacggc auccgcuucu gggaugggcu       180
cuguccuccu ggacaugccg agagccugcc ugauccuggg uccugcugcu ggaggcggcc       240
acuucgccug guccccgagc guccgcaaca aaauuuguca gaaagaaaau cuugaggcac       300
auuucccugg ggggaaguca gggcuccucu cuggaggguc caguccuuaa ggguggggcug      360 gguggguaggg acuucaguuc agaggagcgg gaggaaucag auggaacucc ucuuggauuc      420
ggguauacgg cagucacugg ggggcgaacc ccggauuucc uguauuagaa gccgccucua       480
gaaucgcguu aauagugggga gauauggcgg cgaugccuuc ugcgugcccc augaauuagg      540
gggggaagca cccgaauaga agggucuccc gggcauauuu gccucgccag cuguuggcca       600
gguuuugggu ggaucguggg cgggaggagu ggagguuccu cuucgcgagg uuuccgaau        660 ccaaauacac agguuuagug cagugugggac cccaggcaaa auguggagua aaauuucuac      720
ccgauaucau cugguucugc ccugaucagc cacuuucaca guggagagag auggcgccca      780
agugcaaacc ugccaguagc ccccuaggau cagguccuugc cgaagggggg ucugggauu       840 gggggcacug ggagaauaga gcagggggu gguugggga ggagaaagg ccguguccuu         900 gggucuggga agagggagga gagaaaugca gaaaagggg uguuugcug gggucuggac        960 gcugggagcu ggggauggg ugccgcgggg gucuucagag cguugcgugg uggcgcucg       1020 aaaauccuga caguugcag ucuuggacuu uuggucaaau cgccuuuugc cauuccuuu      1080 gucagaguca agcccccca ggccgcccc ucccaccucg ggccggcggg ccugguggg        1140 gcgcaggcgg guggcuacgu ggcagguuuc ugaagguuu ccggcuggc cgcgagaggg       1200 cgcuggcggc acugcggaau uuggggggc gggugggga gggaggugg ccuugucu          1260 ccugauggag ggguucgggc gcgggaucua cuggaggauc cuggauucgu uuacccaaga      1320
gggaacaguu uugagacccc ccggauucac ugccgagugg ccgcagaggc cggggucggc      1380
cuuugcgccg uggcuucggg uguuguggag gcgcacagag gcacguuagu ugauuuccag     1440

```
ugguuuuugg uuucgggggu cuuaggaagg uguggcucau uugagcagga uggagagaga   1500
ggcugugaca aggucaguga ggggccaucg ugcgggggcu agaaauuguu guuguggcga   1560
aggagggagg cacgacuuug gaggcgugau guugaugccu gggggcgaag gcggggagcg   1620
gcgugguggc ccccuuugcg uuacuuucca gcgaugucac agguucuguc ucucguuccg   1680
agaccaccca caugcgugac agcggugccu ggaggacugg gucuuucuga cuuuagugaa   1740
cguguguuua auuggauuga cgaagguggg agucgggauu ucugcuuuuc ccuguagcag   1800
gcggagcggc gcuccagagg ggccuggcgc agguccgcug gguggcccac cuuccucugg   1860
ggcuggggcc cgguggcugg gggcgcagga ggcgccuggu gcgggcggga ggcgcugcgc   1920
cgcagccaca ggugggcucu ggcuggviggu ggcuggagag gcguccaggg ggcguagcga   1980
ccuggcgcgg uggccugggg ugggcugugg agcccuuccu agccugagac cuguggggca   2040
cccccugucc auccaggccc gccgggcgcg ggccggggcg ccgcaggugg cugcugcacu   2100
ccugggsuuac gggugcgggc cgcgcgcccc cuagcggugu gugccagccc cgcuaccuug   2160
gguuuugagu ugcgcacacg cacacagcua acacuuguga ccgucagsuc aaaucauccu   2220
uaccccsuacc cacuccucuc cuccacsauccc cauuucuccu cucccuccsac ccuuucusau   2280
uccucgucc cuccucccccc uccuauuuuu cuucucccuc cuccculsucuuu ccucuuccsu   2340
ccucccucsuu ccccccucsau uuccucsauc ucucuuuuccc ccuccccuuc ucuccucsccc   2400
ucuccclsugcc cccculccuuc cucccuccsau accccsuccccu cuucccuccc agccccsuccc   2460
uacugcsuuc cucagccculc cccuuusgccsa cuccucccusg ccuuucccuc ugccugccc   2520
cusuuusgccucsu cugcsuguuscc ggusgccugsgcc guuagagsguc acgaagsaugsg uuuscuasaccusu   2580
gccccccucc caugccsaulsag ggucsucuccsu cagggsauglsuac aucauccsguc caccucssculug   2640
ucusuccsasags ccaccuccsuc uccsaulgssugsla gcscugsuccgssg cca aggssgggscssugsc uguccccaulcusa   2700
caccucacssg uacuucaacc cuccugcusau cauusucauaa ccaacsguggsc gggsscaggsaussussc   2760
ucccssaaccsccc accaccauscc uusgccssaccsacc cssccagaccsscssasa csuagcasauussa aaaugacaasassu   2820
ssuuaaaauuussua acusaaaucasgc ssuuuasaussugsua auusaauugaasc usuaasacusguaa ausuuauugaaucsuu   2880
aggcsuugggssc uuussuasagcsasg guucuscussaac cuusugsaucsaaa uugcsagasggg cacusagssgasgc   2940
ascgguuccsu ggauccscsacc aascausacaasa gcssagcsacusc asccugssaccscscccs aggssaccsassgga   3000
uggssccaaaassgssga ugssaasgaggssassc cggaassacussgasc cagssccassgsscussg uccsccucusuassc cuaassagssasacusu   3060
aaaccasaaaussgsssc ccsuasgsuusgasggs gggscassuusgssssggss csassuuaasgsccsssc ussgsaacsccsuusussgsc uasussusgsccscusaassss ussa   3120
cusuusugasscucussusc as

| | |
|---|---|
| cauuuccagg ugaggaugca uuugguagug uugauuuuug uaauuaaaag aagcugaaag | 3840 |
| ggagagagga cccgugagga cugaacucuc ugucccaugg gguagggcuu acauuuacau | 3900 |
| uaaagaaaca gaaacuugcu gggaggugua aguauuuggu cacauugcug gcaacagaag | 3960 |
| ggguuggagu uggacccagg gugccacgcu agcugcccuc accccuucuu ccccucuggc | 4020 |
| ccagaguuau acuaagaguc cuuuuauuuc aaaccaaaug uuugacaaug ggacagucug | 4080 |
| uuugaaaucc cagcugccug ggugggucuc ggggucugg guggcccag ugcugguacc | 4140 |
| augugcuggc uucaccuuuu aauaacagug ugaccuuaaa caagucgcuu aacuacucua | 4200 |
| aguuucaguu ucuuucaugg ucuaaaugga gauuaaaaca cacacacaca cacacacaca | 4260 |
| cacacacaca cacacacccc cucguguauc uaccccacag ggcgcuuuug aagaccaaau | 4320 |
| gcuguaacua cuaugaaagu gcuuuguaaa uugcugugga aagugugagc uacucaagca | 4380 |
| cccgaggcug ucccuccuug ucacaugu cagcccaauu ucccuuagu gagaacagca | 4440 |
| cucaguaggu gcugugugug uuuguguuca auuaagaaau uccagaauaa auaaaaauga | 4500 |
| auuaauucaa caaacauuuu cugggcacc gacaaucugc ccagugcacc aggcuaggua | 4560 |
| ucugauacaa agauaaugaa aacagucucu uggaaccuaa uuggggu ccu cauuugacca | 4620 |
| ggaauuucuu ucgucccguu uuaagccaac caguuuuguc cggacaagac aaaaacaacu | 4680 |
| ugggcugcuu uagagaagcc cagcucagug uagacaauag cugcccagcc ucugaaaggg | 4740 |
| gcugauugga uuaugggca aauggaggug caaggaugac uggacggug acaaaugaag | 4800 |
| ugggcggaga ccugcuuuga guuaauccag gcauuagga ggggaccuuu ugucuuccag | 4860 |
| agacuggcag gagcuuuuac caguggu uuu uacauccuua auguucagga cgaauaauuu | 4920 |
| auggucagug aaaauccagg ccccagugag auucgagugg gcuguaaaau cgagaguccu | 4980 |
| gcucccagug aguaauggua gugaaugu uu cugucacuuu uugcaaccgu ccauucauuu | 5040 |
| gauccucaca acucccuguc cugagccagg accggccacu gccacuccca gggaaacaga | 5100 |
| ggcugucaag aggcuccaca gauugggccc cacuggauca uugaaccccu guucccugag | 5160 |
| uucuagagga agaauuguac cugucucagu cccggccacc uccagaaggc cucccucugc | 5220 |
| auuucgacu uugcugugcc ggcagccugg agcucccag gucccugcug ucaucuuuuc | 5280 |
| uagccacuac agucucuguc uuuccuuuca cagccaagcu ucuugaaagg ccugucuaca | 5340 |
| cuugcugucu uccuuccuca ccuccaauuu cccuuucaac ccacugcuuc cugacucgcu | 5400 |
| cuacuccgug gaagcacgcu cacaaaggua aagacuuuuc uguggcuuaa ccuugucau | 5460 |
| guuucggcu cauggacaca aggacacauu ucaugccuu cucucacagg gcucugcguc | 5520 |
| uccgguucac uucguguucu uuacacuccc uucacagaga cacuugcucc cccuucucuc | 5580 |
| guucuuagca uccccuagga acuugcacac ccaggucucu cgacuucugg accgcuucu | 5640 |
| uaccaugccg ucuuaagcag ucaggagucg cugccugggu ucgaguccua guuaaauuac | 5700 |
| uuagugcuga gaccuggggg uagguaaacu uuuccaagcc agguuuaucu caguuucaaa | 5760 |
| auagggguuaa ucgucuuuau cuggcaggu caggugggaug ucucacaggu aagcaccaga | 5820 |
| ugccauuuga aaggcuugaa gcaaagucaa uaaagcauuc augggaaaau acaacuggag | 5880 |
| gcaccacuag auuuucguau acauuagguu cccacgggga ggaccgaaga gagaagaaag | 5940 |
| aaguggaaag ggaggagcgu gcaggagaga caggagaaga gaauaacuaa acaaagacau | 6000 |
| uaaagacaaa aaaaaaguag gaaagggaga cuuagaaaau auuaaagcc accaaaaaca | 6060 |
| cauccaaaga cgguuucccc uuacguuagu ugggcuaaaa gaaagcaaau gggagagagg | 6120 |
| uuuuaaauug auuauccag ugacaaaucc caggaagcuu ucacaucaaa ucacccuauu | 6180 |

```
cugggiuuuu aacuccuucc aucgaguuua accucuuuac cucccacauc cugguaaacc    6240 cugccccuc ccuaccgccc ccuuugcugg ugauuaaauc cugaagguac acgaaguauu    6300
ucagugaaug aauggcuaac agaaaagggc uccccuccc ccuuacccug gcggguguuu    6360 ucaguuuau uccacuuucc gcccuuuucc cuuaaugaac acagggcuaa ucucgggccu    6420
ugucgaagga agaggcugca gacguuaaug agguuagcug cuggauucca guauucgucg    6480
cauaaggauc cuucuuuguc ugcgaaggaa aaacacacug auuaucauaa ugaggugaac    6540
uggccaccgc cgggccgggg cgaugggcu ucuuaagcca cacucuaauu uugggugaug    6600
gagccgacau uucuuuggcu ucucauuuaa gucuuugccu cugucccagu gcgaagucca    6660
uucagcgggg uugaaaguug caggcagcuu ugggaagggg ggcgucggac aggguugcau    6720
uguagaaagu ggcuuuguuc gauccucgc acagaugcaa auggccagag cauucauucc    6780 cuucuucaa gagcugagga cuggggggc cacggugau caguuccaa ucuagcucu    6840 ccucugacuc aucucaggac ccauugagga cauccaaaac ucaccaaga ucaccaagug    6900 guaggaaagu acuaacuccu gggcauagcc cuagggagu gacuacaaug ugaauacuca    6960
uggaaugccu agccaggug agaagugaau gcauguuggc aucccagagg gacccccuu    7020 aagagggcau aguuggggu ucagauuuga uccagcaua uguugaaau ugggcacagg    7080 gggcuaguga uuagucagga ucaaucagug gagaggagu uaaaacucac aucggagu    7140 ccggaaucag aacuguagu ucuuuuuuu gaaauggagu cucgcucugu cgcccaggcu    7200
ggagugcagu ggcugaucu cggcucacug caaccucugc cuccgggguu caagcaauuc    7260
ucccaccuca gccuccugag uagcugggau uacaggcgcc caccaccaca gccggcuacu    7320
uuuuguauuu uuaggagaga cggggguuuca ccauguuggu caggcugguc uugaacuccu    7380
gaccucauga uccaccugcc uuagccuccc aaagugcugg gauuacaggc gugagccacc    7440
augcccagcc cuauaguagu ucuucuuug ccccuuaaua ucuucaccca caugcccugu    7500
acccugccug aacccuccuc cucuuuuugu ucugaucuu gagcucccua gagcccauaa    7560
uucuuuagag cagguaugu ccgagucuga aacaugcccu uauuugccc agcucugga    7620 cauucucac cccaaggcgg aucaaucaug auuaaaucac uccaauuaaa cuuuaggcuc    7680
cagucagacc uucagccaaa uggaaaaaaa aacuagggga uaaggaggu aguuggagca    7740 agaaaauguu auuaguugaa accuuacggg accuccuccc cuuagugagu cuguuggcua    7800
aagguuccuc ggcucgguga auuagaaucg gauacuguuu ccaaguuagc aaaaccaacu    7860
cuaccccagc accccacgag gaagaaugug gaaggaucuc ccauuggccg guuggggcaa    7920
aagccugagg caaucuuuca uccccuuuug ccaaggcgag acuuucccag ugacggugau    7980
guaguuggcc acucugacua ugggguggacu cggguguaga ccucgaagc ugagaucaca    8040 cgaaaaccug gccucccgc cauguagcug uuggagagua gaaaaauaga gcacgccuga    8100
uguuucuaaa ugagaagacu uucaauagua augaagaauc cauggcacuc uccccacccu    8160
caaacacaug gcagucauuc acauacaggc cccaaagcca cuguuagugc ugcaguagcu    8220
ccuguggaca uuggaaagcc cggagagggc guggaagaaa ucagcuggcc cccggcaggu    8280
ucucuggggu uuugugccca aggcccuggg agcccuaaaa acuuucaaaa guuaacuccc    8340
cacgucccca uccugcuugg guuucuggac uuuucugagg caccggcaga ggggucucgu    8400
ugcucccuug aguguagggg cagcccuuua accggcucc uugagucccu gcuuuucug    8460 cuucuguugc cuucuuccuc gucuuccucu cucucaauau cuccccucucu uugucccucc    8520
```

```
ccaguuccug accuggccau cccggggugc ccuugaccag ccccgugucu ccucagggug    8580
ucccagcacc agccggcac agagugggggc ucaguuagag uaugugggau guugguuucg    8640
ccaggugagu gaaugaaagg acucgaccac cacagcugag ccacuagcug ggccaugcga    8700
agaguucuag gugcaaaggc uggaggguggg aauucauuuu ugagaggugu gugagcagcu    8760
uccgaccccu gccccauuug aacgggggcc uugcuggucg cgucccugca uucacccgcg    8820
cggccauccc gucauccaac aguugauccu aacugagcac gcccacggcc cuggucuggc    8880
cugggcaccg gccaccguag cccaucccuu gauggccucu gucccccag gagggcgggc    8940
cggggggguug cccaggggcu ggagcagugg acuguggcuc cauagaggua ggccggaggg    9000
ugugagggca gauucaagcu aucccccaggg cucugcucug gucggagcca gccccuucuc    9060
ccucucugcc uucccgccc cauuccugau gcugaacugu ucuggacccc uggcccugag    9120
ucucucagga ccaaaguggg cacgggaaca gcuguagugu gucccccccc gggcuuugcc    9180
cacagucuc ccucucgagg ugugguugu acgcgacccc ucccuugcc gugaugccuu    9240
ccuccccgg ggcuugguccc agcuccuuca cucucuagca gcugcggggg cccacccccc    9300
augccgagga ccagcagggg aaaccuccag ggagcaucug caggcucugc uucugcccgg    9360
cugcuggcuu gcucucccug guggcucucc agcggcagc uucccaccc acccggcacu    9420
ccgcuuugcu cugucuccug agguggggcu gaccaaccuc cccuucucug ccucaguccc    9480
ugggcuccag ggcucagcuc cacagcccuc ugccuagcag gcugguucuc ccugccaagc    9540
ccauaccugu ggucaccugg cccuccugug gucugaguac cacuccccug cccaggagc    9600
cacucccacu ccagcugccu guuuccagca gguuccagu gccccgaca agccccugcu    9660
ggugucucca ucuccugcca agcauccucc agugccuccu ccugugggcc uggccucagg    9720
gcuauggaca gacuccuguc ccaucccaga gacccccgu gaucgugccc uggugggugu    9780
ugccccgcc ugccuuugcc uccgccgugg cccgagagu ccugggcucu gccccgcccg    9840
gucccuugcu ccccacucag uucggauuu gggcugccc cuaacccagc ccguugcugc    9900
uuugcaccuu uccugucau ugggcauccc ccaguaguca cccacuccaa ccgaaaagua    9960
aacugcaggu gaggccgugc cccgagucuu cuuucgugu guuugcuuuu uccggggcgc    10020
uugccuugcc augauucuaa cucucugccc uuccccaagg cacgugggcc guggcccggc    10080
ugggucggcu gaagaacugc ggauggaagc ugcggaagag gcccugaugg ggcccaccau    10140
cccggacccca agcuucuuc cuggcgggcc ucucgucucc uuccugguuu ggggugaguu    10200
ucuugcuuuc uugagaccca ggauuuuauu agggucagcu caugcucucc cucucugauc    10260
aacaagagug ucaacauuua auugggggag gaggcacccu gccaaggugua auucucuuca    10320
caucagcccc agggggucugg ggccggaga gcugccugga guggagaccc uugcuauacc    10380
cagcaagcau gugugggggu ccacccuggc ugauggcaug cugugggccg gcgacgguag    10440
gugggggagug uccaccucca cucuagaccc ccgagagcgg ucgggccag gcacucagga    10500
gcccucagua cggcuuugcu gaacacauug caaaagggau ccaggggca cuugcccgc    10560
ccacacccgg cccagggacc ccuucggaga ggaggaaaug ggaaugcuug ccugcuccuc    10620
agcuaggaag acauuucuuu ccaccagcca uguagcguc accccugug agaaccgugg    10680
uuucucacac augaggcuuu gauaaugcc uuuaaucaaa uagugguuuu ugagcaaguu    10740
cuucucuuuc cuccuuuccu cacccccgaa auugcaauga gacgggaaug uuuuguuug    10800
uuuaauaaa acagcaaugg uagagaagaa gaaagcggga uggagccac acaauucacu    10860
cgaggaccca ucauuuguuu auuuguguuu uacuaauuca agaugcagcc gggagccguc    10920
```

```
cagggcucgg gccuggggüu guucgggggc gccuaaggcu gggcuuugca cuaaggacca    10980
gagggucuac uugggugccg uggagcaccc augcagcaag guggcuugca cagcagccag    11040
gcgaggüguc gücgagggcg ggggcucagg guggcaugcu ggacggccau gccaggcuga    11100
aguuugggcu ggcaggaaga gaggaggcuc agcugaggcc acuuccuuu cuggggguçc     11160
cagggacuga gücuguggcu cacucagggc gauggggugu uuuagagcc acugcccugg     11220
gaggcagugu caggauccug gcaccccuca uauaugacgc cccggggug gccauugugg     11280
ugaaugagug caguuagacu ucccagagaa gcugggggg cgcugagaaa ggücugaacc     11340
guggggugag gcuggcucca uuccccaga cauuuaugga ggcuugaggg ggcccuagca     11400
cuguccuugg cccagaugcc aauacucccc ucuggacgcc cacgauggg gucucugaga    11460
aggaagugga ugaacacagc ugcacgcugg gugggccca gccucuaguc ucagccaug     11520
ugcacgcauc agcccuugug caggccuccg cccuccgcca cccccaccc ccggagüguc    11580
ucugguuucc gacgcagccu cguaaugcuc uuuaaucaaa cagaggauuu ggagacagcu   11640
cuccugcagc ccugcacuuc uccccugaaa uugaaauggg augggguauau uuuuaaa     11700
caaaaucügg cagcguaggc agaggggca gaggcgcucu aaccgggggc uguugccuu     11760
gucugcuugu uucugcucuc uggagagccc cagagccugg agagacgggg aggggaguug   11820
gugcccaggg cuaaacccag ggaggggcc caggaaggcu cugccccgug acauuuacuc    11880
caaggcuagc auuugcugag ccaccugcaa acacaguggau gugagaaga ggccccgggag  11940
gggaggüugu cacaggggca ggcugcuggg guccuggggg gauccugucc caagcuuacu   12000
agaaugcauu cgaguaacug gucugagcca gaugcccuca gcucuggac ugguuucuca    12060
cggacaucuc aggacuuucc caaggguggac uaagcccagg gacaaagüca aagugaaggc   12120
caggggcaca caggagaggc ccagauagga ccaagcuuug gcagcccügu gcucucaggg   12180
guugaaaugg aacccucuuu gcacugaguu guauuucagg uacucaugag uguucggüc    12240
ucaggcaaac acauauuugg gguuuugugu ucauuaggu auaaauagg uaaaauaugc     12300
cacguucuca augaaagaag uugaaacgug acüüacuacg ucagccuuge ugguugaucuu  12360
cucgggaacu gccgaaaggc cacuaguaag ugcugaaaga caugaucauu uucaggaaaa    12420
uucuauuuug auggauuggc caaugccuga gccauagcgg guggagauga gacccugacu    12480
gacuaggcag ugagccacag aggacccugu cacaucagcg gagggcggug aggggucucu   12540
ggccauuugu caucgügcug auuccuaggg ggcugccucu aguggggacuc uucugggügg   12600
gugcaaguügu caggguaaag acggcggücu ggucuggaaa cuggcucucc ucucgcaccu   12660
gcccgcccug gguugguuggg aaaggaaacc aagagggüag cucaggccug agcucgugga   12720
aaggaagaac augaccccuc auucgcucac ucgccccac auucucucac cugcgaguug    12780
cucauugcug cuuucagggc cccugaccuc augccuccug aguugauu caaaccccaa     12840
augaauuucc aaguacauüu uccaaauaa ugucaaaacc uggcaagacu uaagggcaac    12900
aggaugcaug uguuucuuau ucauucauuu acauaaaaua acuuaagügu guuuuuaug    12960
agcaaucuga cuuccaaaaa gaaugaaaag gaaaaucuac ccaucuuuaa ugaacuugcu   13020
aaugaauuuu uccuugcaaa gaggaaggga gcuuccuaca gaagggggug uggagggaga   13080
cagauucagg uccaagggg uuaaagggca guggacaaug cggaagccag cauugugagc    13140
ugcaguggaa aagcccuggg ucgcuggag uggcuucuuu uuaggagacu ggaauuaaug    13200
aguugugaag ugucccaagg acugguuccc ccucccugcu guuucucuga gcccugüccc   13260
```

```
cucuuccaaa ggaggaauaa ggaggucuag cuucgucucc cauccccgau uugagcagau    13320
ggaagagucu agaaaagagg uguaccuuuu gaaacgaggc cucagaugug gguuccugg     13380
ucuggaaagg ggaaggauga aucuggggua ggagagggcu ucguauggag ccccauucag    13440
acagggcagu cccacaccug ggcugcccac agguucuugg gggagcuaaa ggaaagggga    13500
gccacagaac aggcuugccu ccuuggcaug gauuggguca guguuucaga gccaggaaag    13560
guggagugu ggggggccu cggggcugau gagggcgugc agaccucccc cucccaccuc      13620
cugucccagg agcccugcag acacugcagc aggagggcac ucugccagaa gaggggguucc  13680
agcuccagcc gggauccagca gacauggaga gaccccuuau cuuugccaag acgagcucug  13740
cggugccuga gaggcccgua ggucuggaau ucuagggccu ucuggguuug agucagucc    13800
ugaggccagg gccugggccc ugauccucac cauggaaaac uggucacuuu acucaggaua   13860
aacugugaug aggacuuggg acauaucucu gucuguccuc ucagcucgcg ucacccuga    13920
gcccuuggcg aucgugggcg gcccguguac agagcaggug cugggucacu ggggccgccg   13980
ugggccuccc aacaugaggg acugugugug agagaggagu ucauuaaggg agaggauggu   14040
ggugaagggu guagccauga cuuucuuaac ugcucuccaa uuucuuugag cuuaaaaaua   14100
aauccagaug gagaguucuu aagucccccua uccuggagga aaggaaggcu gcccaccacc  14160
uucggcuugc cucgacucug agcagugaau agggucuuug gcaggggcuu aaggaggaga   14220
cucuuagccu gggagcuccc agggcuguuu cagauggaaa caaaggcuca ggccgagagg   14280
aaugugggg agcccccgu ggggaacagc caccugggga uaauugggag ggcugagcgc     14340
agaugaguuu uccagguuc ugugaaugcg cccuuucaau ggaagugcc uuuuuucca      14400
gaugaaaga agaaaacguc aauuaccuuc cccugaaacg gagugugugu guguucccuc    14460
ccaggggguug uguggggccc cuugcccuug ugugugugguc gggagcucca aggcugcaca  14520
augacgcacu uaaccagcca cugggguucgc gcgacccugg gaugcucacg cucuuagauu   14580
cuagggcuug auuuugaaag uuucuuagca aaggggaauc agagugauug agccuguaaa    14640
caaaauuug aucaaccugg gccugaugcc ugaaauauag ccaaagagac agaaugggc     14700
ugcggggaga gaggggccagg auggaaaguu ggggaaggag gacagucggg ggccaaaggc   14760
ugaccgcaug ucugcgccgg ccuccgcgcu cacagcuggg cugcuccuuc ugccaccca    14820
gcccuuucuc ugggccuucc uggcaguggga cauagaguga uucccuacuc aggaaguugg   14880
cgguaggggg cucagaaauc cacagggcug uuguuucaca guuagccagg agaggagggg   14940
gucauggugu cccgcaggga uggugggcag cugcgagaga ggggacgcuu cagguuagag   15000
cgaagcuguu ugcaccacca cugccccaga cugccguaag gguagggcca cuccagaggc   15060
accagggaca aagucccugc cgugacagga ggggggcaca ggucagaguc uuggcugguc   15120
acugacuuug cugcugcugg cuucugagcc ucagagaggu cagcagucuu ccagagaccu   15180
gguuagagcc ugugcucagc ccugacuaug ggugugaccu uggccccugu uccagcccc    15240
uuaggccuca guuuucccgu cuacgaaaug ggcgagugca ggcccauggu cguccgagug   15300
gcucggggu ucuucaggcc uccuggagg ucaucugucg uuuguuugcu gggucuuugg     15360
aguuguggg acuuuggggg ucacggucc gcugcccccu cugcuuuaga gguggggaaa    15420
ccagcgaucc cagaggcccg gagccuugcc cgagguugca cggugagccg gcagcaggcc   15480
cuggagguga agcccccugcc aguuuccagc uccugugucga ccuugugguugu cgggggggu 15540
cacagucacc ggucauuagu gugggucaga gcucuugccc aaagaagguu ccaaggggcu   15600
gccccaugag cugggaugca gggaucgugu uuuauggggc auuauuccaa acaggcaggc   15660
```

```
ugcuggucug gucuggaaca ccuuuuuggu cuguagagug acucuuguuu aaugagacug   15720
gacuuguggc uucagaacca ggagauguuc guucccccaa cccccguggc ucaccuugug   15780
ccuuuugggu ccugagaccc ucgccagcgc ucucuguggc acggggcccc agucggcuga   15840
gaacuuccug aaaaagccaa caggaugaca acuucuggaa aagugaucau cacccgccug   15900
cacuggcugc ccaucuuaga cucagcuuug ccaacauucc cagcuaucuc ugugugcugc   15960
aguguguagu aaugaacagc ucacaaaacc uccggcuggg ccugaccug guuauuaccg    16020 ugguggcug cagcuuuugu uuugugaccu ugguugcuac aauaccugcg agcugaaaug    16080
aggaaucgaa aaauugccag cuucaauuag acgggcagac ugcuucccca aggcugccuc   16140
cgccacucca uccauuaacg guaaacaggc accaaauagg cccuaauucu cucuaauugc   16200
ccacuccuga agcaaagagg ugaaauucca ggaagaggcg uauguaaaca uccucuguaa   16260
ccugaccaag uaaaauuaga gggcugaugg gggccugcga gagagagggg acaugauuuc   16320
aaaagauguc ccaauuaccu cuccuauuuu cauaaauggg ucuguaaugu ccagggcccc   16380
ggccucacaa agguacagga aauuagcucu gcaaagagcu ugcauuuguc aggggaaguu   16440 guaaggggu gguguuuacu caacagguag gaaguacgag aucgaggca agacugauua     16500 uuuguguaac gacgggcucu auuucuugag aucaacauuu aauaaaagu cauccuuuua    16560 gguccuuuug uguuugaaac agccauaagu uguuuauacc aaagacaugc cagaucaguu   16620
aggugcuguu ugccuccaga aaagaggaac uuuuaaaauc cuaagaugca gagcuagagu   16680
uuucuaaucc cauuaagcug uggaagaugu uuuggagug uucaccaaug cuuucugcgu    16740
gggucaugag cucacugcac gcacuuauga ggucuuccau caaaugcuug ugacaauuac   16800
uccucuggac ucuauaagga ggccucgugu uuuucuuugg uuccagacag ugacucaucu   16860
cugcagcuuu ucugacauuu guuaagauuc uagcccagca cugcguuauu aacacaucac   16920
agcaagccca gagcuggcac acgcagcuuu uaaaccaagg cacgaauuug cuggggcuuc   16980
ucuguagcag agcagccugc ggucugcaca caagaguuaa uuaaggacgg ucagggacuc   17040
ugagguuuca ugggguccu ggagcagaag caggaaaaaa cccagaugcu ccuuccugcu    17100
ucugauuucu ccgucccuau uaaaaacaca aaaagaaca aaacaaaaac agccaaacaa    17160
agcacccgcc ucugauuccu gcgggaaaug gcagugccuu uggucgcgcu uguguuucuu   17220
ggccugaguc ucguugccac cuuaggacgu ggcgauggug agaggccacc ccagccacgc   17280
acagucucgg agggagggug ggaaacgguc ucgaguggug gucaguagau aaugggugg    17340 cuggcagccu uuagguaacc gaagucggcc cccagucac ccaugcacug aucauugcuu    17400
cacuaacacu uauuuaaga cuuguuguuu cugguuauc aaauuaacca guuauggcag     17460
aacaggguuu augaagggca aggcaggga aggagauuuu aggaagauuu ggaggcaaga    17520 agucccca gugcccuggc cgggucuugg acauccuggc uggagacaug acuaggaaua     17580
gagaggcaga ggcagcaggg guggcccaga uggcaggggu gggguuggaga gaucccugag   17640 aggccugagg acaggcggca gucuugggag ccccugaaga ccugcagugg ggcaggcagc   17700
uggagucagg ugucucccgg gaccuguuuu uuuuuuuuuu uuuuuuuuuu gagacagagu   17760
cuuguucugu uguccaggcu ggagggguagu ggcgcaaucu uggcucacug uaaucucugc   17820 ucccacguu caagcgauuc uccugucuca gccucccgag uagcugagac cauaggcaca    17880
uaccaccacg cugagcuagu uuuuaguaga acgggguuu caucauguug gucagguugg    17940
ucucgaacuc cugaccucag gcgauccacc ugccucagcc cccaaagcg cugggaugac    18000
```

```
aggcaugagc caccccccug gggcugguac cugggucug uggcuucugc cugcccuggu   18060
gcccccacau cucucucaug gccuuucugu uccugggug gcuugugggg ggugucccau   18120
ggucuccccc uggcuuccug ucuccaccug ugccuaaucc aggaaacggu ccccagagau   18180
gguguuuuca aacagaccuu ggcccugucc uccuggccca gccccuggcu gcccuaucac   18240
cuagcuugcu gcguuggugg gaccucagcu gucacaggcu accuuucuau gacgccuccu   18300
caccuuaagu agacucugaa cagauuuuaa aagccauuca uucaacacau uuuuuaaaug   18360
aauaaacuuu uuuucugugu aguuucagu uuacagaaac auuggugga aaguacagag   18420 aauucccaga ucccgucccc accaucccc cugucauuca cacguugccu ccguguggug   18480
uggucuguuu guuccgaucg auggaacgac ucgauacau gauuaacuag aggccuuggu   18540
ucacaucauu agggcucacu cuuuguggcg cacauccugu gggucuugac aaauguguca   18600
ugauacgugu cugacauugc ugaagucacc uuuucuaaaa gcuuaacauu uugggaguau   18660 ucgaacuau guugggccca gccugcugcc cgauuuuuau aaaaagaaa aaacaaaaca   18720 aaacaaaaaa acaaguuaaa acguaaggca gaucuugaca cugaagacuc gaugugccug   18780
gccauggugc uucccggggc cuacugcacu gugaacaaaaa uugccacagu ggaguugucu   18840
guccaggcac acaacgugug ugccauggu uugggaaacg cugcccauua auagcccugc   18900
agcccucugu gggcugcccu ccccggccaca ccccgcuucc cuggucuccu ccagggccag   18960
ccauccugcu cgccgaccug ggcaccuugc uucugccaga gcacagguuc augcccuguc   19020
uucagggccu gggccacccc cguuucucau cuaugcaggg uccuaagccu uggguccca   19080 cagagcacga cuucgucccg ugaacagcac caacccaagu cuguuccaug ucuccacacc   19140
ugccccuucc gcuccauagg cagcuggugg gugagguggag ucaggagaga aaugcguggc   19200
uucuccaauu ccacacuugc uggagguugg ggagucucug cuccaggcca ccccugcccg   19260 cccccccagag cuguuguccu caauccgcccu ccuccuccuc gccggccuga gugagguucu   19320
acucugugac cuagugccuu cuuguuacag cggaagccau caccuggaug ccuacgugg   19380 aagggaccuc gaaugugggga ccccagcccc ucuccagcuc gaaaucguaa guggcuggag   19440
uguaaagaac acacaugugg ccuugcugcu gagggugggg ccagcugccc ggagcacacc   19500
gccaggcgga ccucguggag gggcuggcgg gcacuggccg ggggucugug caccgggagg   19560
ugggugccca ucgagucaag ccaagugcag accgggggc uccuguuuc uaagacagga   19620 gccccugcc uccuugguguu gucucugugg caaaagaauu cuauaggcgg gcuucaaaug   19680 ucggaccccca aaagaauuuuc uucuuuuuca cucuucuaaa ugaauggcuc uuucauuauu   19740
gagucucccu uuggcucuug ugccgcaggg cagacuagga uggaagugcc cugugagcug   19800 ggggggcccuu caaagggcca aggagaaaac gcaggccgag ggaccagccu uccaaauggg   19860
cuucaagcuc caaugaccuc cgcucgcccc cucgaaaugu cuggaaaaca uaaugggcag   19920
auuuucuguc uucaaaguuu ccggcuaaac cucuucaagu ucuuuaugu uugggacuga   19980 gacacucagc cauguuaaug gguaguuucu uuuguauuug ccugaaagg ccaaaauauu   20040 uuuauauugc cacagacaaa gccaccuauu uaaaaaugaa cuccaugucc gucguuuccc   20100
accaggagac uauguaccau guguguucu cuauguauuc ugggggucuug aaacaggauu   20160 cucaugggga uggcauuca ccacggucca gaggggcaga acaggcggcg cuugccuugc   20220 ccaggggggcc uggggaacgu gggcccucau cucagaucug ccccccaguau guuuaggacg   20280 cgagccccag aaggaucugg gaguaaacuu aacauucacu gugucucugc ucugcauccg   20340
ccauuugugu guguuucugg acugugggcu gugugaccu ugguugguga cucagugaga   20400
```

```
agaagcagga augccaaaga uacugugaau guucugaguu uuguugcugu uguuguugag   20460
agguuguuuc acugguaucu auugcauugu auaauaaaug accagaugaa ugaaugagug   20520
aagcaagaga gaaugaauaa acaaguaaau agguaaagaa guaagcaagc caggaugaga   20580
gugugaguac acaagaccau gguucauccg cuuugauggc uaggcaauca auauauaaau   20640
agaaaaaaac cagugaauca cuaaguaaua gggcaacaca caaagcgaua ucaggugauu   20700
auggacuaag ggguaugugu aacucaaaua uaugccucug acauuugaca augaaaaaga   20760
accuaaauga aagaaagaau ggauguauga guagugaagu gcagaaugag acauagauuu   20820
ugaggcccgu caaaugaaa agaugcaagu uagggaacaa gugaucaaaa gggagaaggg    20880
aaagguuuuu uuuaaaaaac caaacaaca aagaaagguu aaaaaaaaaa acagacuaga    20940
ggaugaguaa ugaguaacuc uguaaggagg accaugucag acuauuguaa gcuaagcauu   21000
aggacugaua caaauaauau augccucugg cauagaaaaa uaaaccacag agaacgaguu   21060
caaagaauag caaagaaaga aagaggaccc aguggcgaa agaugagagu guacuuuuac     21120
caaaaguuau cuaagccuga gcacuugaag ucugcacaua aauaaauaaa ugacaaaaga   21180
aagaaaaaaa ggccaaaaag ucuacauugc gugugggau ggaugaauga gcagugggag    21240
ugcagcgcca ggugacaaga uguugugagg gguuugagu caaccagucc uggccacuga    21300
ggucuguuag augaaaggau augagaaagg uaauauuggu aaauaaagaa auaggaaaca   21360
auguaacaaa uguuaaguac agaaauacau uaaugggugg uaaauaaaga uguaaaagaa   21420
ggcaaugcga ucgauggugg caaaagauca ucacagauua agggcuaugg cugguccacu   21480
ucuagaaaac cacaggcugu ccauuaaaua augaacaucu aagugaacaa gucagugagu   21540
accuaaauag acaaggauga ggugaaugag aagacauggc cccauggguc cuccugauga   21600
ggguguuggg gucccccug ggcaccccag cugcaugaaa augaaggaca ggagguaugg     21660
aaagcuauga cagaagagag aaaggaacgg uaaaaagaaa uaacaaccaa auggauaaau   21720
ggguagaucc acgagaagag uuaggcuagg acuugucaua agggcaccug acuccacuaa   21780
uagaggaaua aaugccuaau aaaaagagag caagcaggaa ggaaggaugc uaugaaugca   21840
ggaaggaagu aaugagugag acguggaacc gcacggccaa ggauggacgu uugcgggugg   21900
cuuuuugaug cguacagcca agccacucca uggcaaugag ucccgaagac aaagugcaag   21960
agagaaugag ugagagagug agagagagag aaacaauaaa aaaugggaag aaauguaaaa   22020
aggaagaaag gaagagaggu aauauauuaa ggaauaaaua caugcaugca gauuuaagac   22080
agagccaugc uagaacagga augaaaggcu gugugaacca agcagaccgc uuaauuggca   22140
ccagugcugc ugguaugguc aaucaccuac ucaacuaagg aacggcucaa agcauacaca   22200
ugggagggag gaguggggcc acagagagag ggcccauuag uugcagauua cgauguaucc   22260
aguuaggugc accugccuuc gagaagugua aaauaaguaa uuuacauaga aagaaagacu   22320
gaauggaugc acggugaaug caugaaugau ugaacgacag aaaagauuug cauugaccga   22380
ugaggagggc auuguagaca gggaugaggg ucauugaucc uggugcaga ucuccaaaag     22440 aaugacagaa agaaagaggg aguggaggaa agaaacaaua ggaugggaaa aaaugaaaau   22500
agaaaaaagg aagugaaaga gauaauaaau aauuagauca aauaaguuga ugaagggga     22560 cugguuuagc acaagccauc cacauuaauu caaaccugug gcucugaagu uuguuuuua     22620 aaugaccaca aguguaagac ugaaugaaag aauaaaugcg ugcauccauu aggaugcaag   22680
aaaggagugu aggaauggga aaauuggaag aacgagagag ggagagaugu aagaaaagaa   22740
```

```
aggaaaagug aaguaggcau augaaagaaa aggcacuucu uggacaagca cugaaauaua   22800
augagacagu uuuacccauu aaauauaaua aacaguaaac guugagguuc aucaauaaaa   22860
gcacagauac cugaauagag gagugaccug aauagaauuc guucagccga acgaaugaga   22920
auggaugauu uucacuaucc ugugcacuca aggcccaaaa gagaaagcaa gagaggagag   22980
aauauggaaa cguaugacag gauguauaua agcaauacaa acauauugaa ugaauaaaua   23040
aagacauaaa uauggggag aguggaccac gcaaggacaa aaagaggaga aaggcagca     23100 agaauuauga cuaauucaaa acugguucc ugagauaguu aaauaaaucc ugcaccaaau    23160
ccccaggggg agaaauuaac aaacaaaaga cagccccaca cggaccagug ugcagaaggc   23220
uccaggaacc gcagauuaug guuaauccaa uucugugcac cugaggucca uaaauaaaag   23280
aauaaguauu gaaaugaaag aaugacagaa agaaugaaug gacacaugaa cgacugaauu   23340
agaaauggaa augccuggca cagccaggaa ggagcugccc augggauugu cauucaucuc   23400
acucugggca ccugaggucc auaagcguga aagaggcag gaagagaagu gucagggagu    23460
caaagauaga gcuaaggaaa ggcaaaaaug aaacuaaaug aaagcgaaag ggaaaauaaa   23520
gaaaaaccaa uaaaaagag aacgaauacg uggguguauc uguaagagua ggaucuguua    23580
ggauuaguca uaagacuguc aguaauccug aaguggaug agauaauccc ggcccaaggu   23640
cccaggggga gggaaaaugg agaaaauaua aaagaugug aaaaggaaa aaggaaaggu   23700 aauaaacaaa caaccaaagu gauaaaugga uaguuaaggg aggugucug aacagggau    23760 auaauuaguu uacauacaua cuccuuaaac agauaaauac auuacaccuu ucaaagaaua   23820
aaugaaaaau agagagacau accuggcucc aaaacaaggc uguaucuucu gccacuguaa   23880
uaaaauagau gcaauugagg uucauaaaua aaagaauaaa acuuaaacg ugaaaggua    23940 cuaaaugcgg ggaagaaaga uugcaaauaa auacaugggc caaagauguu ugguuugccc   24000
auggaguuuu aauuaaaaaa auuaauaagg aaaacaaaua cccaaaauaa ggaagacuga   24060
caaaugagug aguggaugag agagugaaug gugcuugacg uaggagcagu agugcuuuag   24120
ggaccagcau gaaggugug accgggagcc cugauucaug ggauucuguc caccugacuu   24180
uauaagaacc aagaauggcu gggaauggug gcucacgccu guaauccag cacuuuggga   24240 ggccgaggug ggcggaucau gaggucagga guuugagacc agccaguuug agaucagccu   24300
ggccaacaug gugaaauucc aucucuacua aaaaauaca aaauuaugg gcgguggc      24360 accugucugu aauccuagcu acucgggagg cugagagagg agaauugcuu gaacccggga   24420 ggugggguu guagugagcc aagauugcac cacugcacuc cagccuggggc uacagagcaa   24480 gacacuaucu uagaucaaaa aagaaaaaa aaaaagaag gagaaagaac cagagaaaca    24540
uaaggaagag ugagggaag aaagaaagau gcaauuggg aagaaaugaa aaagaauga     24600 auaagaauaa aaauaaugua acggucaaua aauaggacuu ugaauggag gccuuuaggc   24660 caaaggcuau gauuaauuuc aagcuauguu acugaagucc auaaacaaag gacucagauc   24720
uaaauggaug aacgaaugac uggaagaaag ggugguagga agguaggaag aaaggaagga   24780
gggaaaaagg gaagagagga aggaaccuuc uuuccagucc uguguucuag acagugggau   24840
gaaguggucc ccaggagggg uggcuguagg caugucaugu gcuugucaca ugcacuugcc   24900
cuggcaggga ggagcuggcu caggaagacc cugguccuugg ggucuguug cccuaucuug   24960 gcugugggg ccauuucacu gcaucugucu cuuccucagu ucccccaucu guaaaccugg   25020
aguggcacca gcugccuacu agaguugauc uuaugugucu cuguugaugg uaccccaucu   25080
auggccugga uaggcaggaa gggcuuggac ccugagcccc gcagaagguu gcaugaacga   25140
```

```
gugugugaa gccuguuggg uagcuuggcc acucccgcgg cauggguca c cugcacagga  25200 ggUUUUgccc accaggggge agcagagggu cagggageaa uaggcccugg guggagcaug  25260
ggccccgccu gcugugugcc acccugggug uggcaccuac ucacauccag gguuggugc  25320 agggaaaggc cagaaggugg ccaggcgcac cugagaaggg ggaccagaa gccccgggac  25380 ccaggagccc ugggcaagcc accagaaacc uguucuugc aacucucugc agugugccca  25440
ggccacccuc uggccugguc uuccauggg caggegeece accuucuca acucagguuu  25500 cccuggcag caggugcacc ucagcacccc uggguugca gaagugucc gggacccug   25560 gcuuccuuga caugccaucc ccagagccug guucaaggcc ucucugucuu ucggcuguu  25620 ucacgacgug uuuguaacu uggcgggauu gcguuucgcu gucgaggu ugucucuucu   25680 cugacucgcc cuccggggga cugccggggu aaaucuggag aguugcucgu gcugacaguc  25740 cuccccagg gccucccgg uucuguugag ucccuuucu cuguaguga ggaaaugugu    25800 guaguuugu guugugugcc uguuuuguc uguaaaagca aggaccaaag ucccuugu    25860 ugaccucuca auccauuu gggacauaua aaaacacug auucuuaaca agcgccgga    25920 gcaguaggag cacagcuugg auggacucag gacuuguggc agggagcacg ugggaggcag  25980 gggaguggg uggggccagg ccaucuggag ugggaggcgu caugcucaga gugacucugu    26040
agacgcuggg ugggaugggg agugcgggcg caggcaugga uggggcuguu agcuagugug    26100
augcuugagg ucgagcuga uggcagcaaa ugggggugcu caggaaucaa agcuauggg    26160 uuauagacag gauaugaagg agggagggag gcaagaagaa ggggugguu cccacgcuuc  26220 uagcuccggc cgagugau gcaacagcau uggaaggcg gaggacaugg aauucaugug   26280
ucaggagcca ccuuccgagc cuccaguacc acgucagg gccacaugag cugggccucg  26340
ugggccugau guggugcugg ggcucaggg gucugcucuu cuucucuuuc agaaucggg   26400 gcuccaggcu augccuugge uggacugagg ucgggggug cacuuauau cccuggggac   26460 accugcugaa gcuucucccu gacaagcugu gucacguug gaugaggau gggcgggagg   26520 gguucagggc agaagaagac cgggagggu uucaaaaga acucauguac ggcuguuaaa  26580
aaaagucagc agaggcucag gaagacuuaa agugugcaga aggcggggaa gggagggcc   26640 auugcaugca ccaagaggaa auuggaagga acaagcgacg uuggcugcua ggagagccug  26700
cucccaacau cuagggcug uccgacggg ucacagucgg ucgaacugag ccaaugagag    26760
cagcucuggg gagacccacu gguccugg aggcugggug gguuggguu ggaugaauuc   26820 uguguuccu uuuggaaaug uggaggccau gagggggau cagggcucuu agguuuga   26880 cccuuaagag uuuguaucu guaauucaaa gguucuuuag uucuggaug cugagauucg  26940 ggauaggguu ccuaauggca caaaagccag agauaaaaca uccuucacgu gcucccuacc   27000
cgguucuuuc uguaccagac ccacaagguc cgaguuggga uccuagugcu ccugucuggu  27060
cagggccuau cuuuauguguu ucguaaacu uuuaacaug agaauuaauu cugcucuuug    27120
acauugucau uugcaugcuc cccacacaca aauccuuuce ugugacacc aggagcuaca   27180 acucuccuug gccuccucuu gugacuccca acucccuccu ugggaagcuu gccucagga   27240 ccucugggau agacaggcca cgaauccgc ugugucccgu uguguccua auauaaaugg   27300 uguggauggc acuugaccua gagcaguggg aaaugcaugc accacucaac auucugacau  27360
gucacccauu uuacauucu acaggcauac uuuuuuuaaa aaaagagugu cuauucuuua  27420
augagcaucc cuucuuuaaa aaaaccuaau ugccauuauu caccacauac acuuuuuuuu  27480
```

| | | | | | |
|---|---|---|---|---|---|
| uuuuguaucc | ugccucuucu | auuuaauuuu | cugucaucaa | cauuucccu | uguccauga | 27540 |
| aucuucauaa | ccucacuugc | ugcguugugc | cuuguugagu | ggcuauggca | ucauucacag | 27600 |
| aaccauucug | uuauucuuau | guauaaccac | cuuuuaaaaa | uauuaugaau | aaugccacaa | 27660 |
| cuaacugcuu | aaaacacccu | uuuuucauu | cuuaagaauu | auguucuucc | acccagaaau | 27720 |
| uaucauugcu | ucacuacaga | ucaguuuccc | cugcuagacu | gugagcccca | uaagggcaag | 27780 |
| gagcuuauug | aauuggccuu | uguaucucug | augcccaaca | uguuguagac | uauaaauaaa | 27840 |
| ugaugaauga | guggauggaa | gaauggagga | aggagcgagu | gagugagugu | uuggcugaug | 27900 |
| gauaagaggg | uggaaggaua | ggcggaagga | uggauggug | aaugaaugaa | ugaauuuccu | 27960 |
| uugguuaagu | cucuugaaag | aaaggcuaug | gaucuuugua | uggauguuga | auaauuucag | 28020 |
| uaagcuuaca | gcauuuuaca | auguucagca | auguaugacc | acuuaauuaa | gauauggcua | 28080 |
| guuugucucu | guuauaaagu | acuuuugcau | uacuuuaacu | ugcauugcuu | uaauuacuaa | 28140 |
| ugaugggguga | acacuuugac | cuaguuugu | uaacaaauug | uauuuaucu | ucugugaacu | 28200 |
| guuuguccaa | guccuuuggg | ucauggcuuu | cugaagagac | uggcccaga | uguccuuggg | 28260 |
| auguagggag | cccauagcuc | acuggaggca | uucaaggaac | cagccaggca | gcccucagag | 28320 |
| aaaguagugu | uuaggagauu | cucauggugu | gggguuggcc | uagguggccu | ucaggucug | 28380 |
| uuugauguua | ggauugcuu | cucccuggga | agugggugau | gggggaaaaag | acaccuucca | 28440 |
| uuggcaggug | uagacacugc | aggcuggacc | uccggugu | gcuuggcac | uccgaucuug | 28500 |
| cccuugauaa | aaccccugug | ggacaggaau | agcucuuuga | accuccaagg | uccagacagc | 28560 |
| cacauccuag | cacccuguac | aaucaguuag | uggccuuccc | accagcgcag | ucacucauuc | 28620 |
| cuauuagauc | ccgaugaagc | caggcccugg | gguuuccauu | uccacccuc | uuaggggaau | 28680 |
| ugguuucccc | gcguccugug | auaugucagc | aaaugccuc | agcccuggcc | ugcacaugug | 28740 |
| gcccagugg | uggucuuugg | gguuaacug | acgaauggaa | cauuuuggau | caggacugau | 28800 |
| gggagaaucu | ccuuucauuu | uucuucaccu | ggggcaauua | cauucaagg | agcggaauaa | 28860 |
| agggcauguu | cugcccaaag | caucagggcu | cacaggucag | ucacagccau | uuaggagggg | 28920 |
| caugucaccc | aaggagggcu | cgcccuucu | uccagcagcau | ccccgcucu | cagcagagcu | 28980 |
| gcuucugccc | acccauccccu | cuacuauagc | acugagcacu | guuugcccgu | gucagaaucc | 29040 |
| cucacccaca | uguuuagcuu | gguauccgag | uuugggaggc | cggcaaugac | uuucaacaug | 29100 |
| aauugcucca | ucuacccauc | caugcauuug | gccuacuuau | cuugaccccg | ugcuuuugc | 29160 |
| cuuuucuucu | ccugaaagca | aacccuuuca | uuuugggtugg | gcuguguagc | gccaugggcu | 29220 |
| gugguuauga | agcaaacacc | cuucuugua | gcugccuccu | ccggggttuac | ugcccugagc | 29280 |
| acgucccagc | uggaucucgu | cugccacugu | cacccauagc | uucuucccca | uggcuuc | 29340 |
| caugugucac | acaccacgac | ugugacccag | ggucgggguc | aagaguagcc | uggggccaag | 29400 |
| cccuccaccc | caugagcgga | gaaguccucc | ccaggccuca | ccuugccugg | cgcaugguccc | 29460 |
| cucccaugag | cuuugcuuuc | agccuuucag | cuuccuccac | agggugguag | ugguuguaac | 29520 |
| ucauccauuc | auccccuucau | cccuucauuc | auucacucac | agccaacaga | cguuuuaaa | 29580 |
| aaauuagcca | gugcuauacu | agagcuggcu | cccaaggacc | cgcugccgca | uugccuuuug | 29640 |
| aaacaaaaca | augaacacgu | ugguaagggg | gccgugcuug | uguucggug | acaaggcgag | 29700 |
| auccccugagu | caggucaggc | uuguagauuc | gaguucuguu | gcgaguuuga | uugcccucu | 29760 |
| gacuuugucc | ccuguacaac | uagguugauu | aggaaucagc | caacuguguu | cccgggugc | 29820 |
| ucagaaauca | cagcccauau | ccucgagagg | ccaaaaugag | agccagggg | uuccaagaug | 29880 |

-continued

| | |
|---|---|
| aguggcugcu ucuggccggg agcagguuuu caagucauua gaacacucug gccuuuccug | 29940 |
| gaggugaucu uggagccauu ccugccccuu ucaagaggag uuaaugccca gcucuguuua | 30000 |
| gagaaaauug ggggagauga uugcucaugu gggugauaag aaucaccucc cgugcagggg | 30060 |
| ucugcauaga acacccaua ggcaaaccug ggugccaag gcacguggca uuuugcaaac | 30120 |
| ucugggugca gcuccgagcu guccugcagg ucccagacca ggugagaacu cccugaguuc | 30180 |
| cugcugccug ggucggggu gaggcauagg ucuuggggu caaccugga auucugaaug | 30240 |
| ucauucauug cauuggagag gaaggagagu aggcaaagcc aagacccugg aacuggacaa | 30300 |
| acucgugug uuuaaaguca cugugagagc uggaguugag cugccuacg ggggaggacu | 30360 |
| gcggcaccua ccucgcaggg cuguugugag gagcaaugua accgugauuu gaacuguga | 30420 |
| uucuggaagg gcggugugcg uguccccggg ggugugccag gggagugagg agaaaaggcc | 30480 |
| agggagacag ccucacucag gcagcugagu gggagagcau uuaucucuaa accuggaggg | 30540 |
| guauaugug ggacaggagg aauuugggca ggaacuuuca ugcuaggggu uuggggacu | 30600 |
| cgcuggacaa ugccccugga ccccccgggg guacgcguuc acgcucaccu cugagaggcu | 30660 |
| ggaaacgccu ggcugugcuu ucugaaugcu gugugcuucc ugccucugug ccuggccugu | 30720 |
| gugcagcacc uacuugguc cgccuucaaa aggcccuucu gggugcguc cuuuucccca | 30780 |
| aaauauuagg caccagccau caaagauacu gcauuguugc uccccccacc ccuccccca | 30840 |
| acugacaaca uuugggcuca aaugcagcag gcugggugcc caacacagug ccuggcgagu | 30900 |
| gguagcgcuu acguucuuu ucuguugaau ggauggauag cuaaugaaau uguaaccaau | 30960 |
| gacaagccuu gauguuuaua accuuuacua agagauuauu auuugcucu ucauggaccu | 31020 |
| guuacaacc accauaugu aucuacgga cguuuguaug ccacguuuga agagcaggag | 31080 |
| ccuguuucg gcgucauguu gauggaacuu gagcugucug augcgaaucu guguuuuaug | 31140 |
| uuagaaagcg cguagccuua ggaucuggca gacccagggg ccacuuaauu aacccuuugc | 31200 |
| cucuuugacc cucaaucucc uuuucucuaa gccauaggu accugaaagc cuaccucaca | 31260 |
| gggcuguugu gagggccgag ggugggugug uuucaacagu gugcagaugc uggcuuuccc | 31320 |
| ugggaauggg cauauguugg gauuugucuu gaaagcauga gugauggcuu acuagcccu | 31380 |
| aagugaauaa aaagucagcc cugaccuuac gcugggauug cauuccccac agucaguggc | 31440 |
| augugcagac cacuggcaga gcagccugca ggugcuuagc gaugugggcc cagaguaaau | 31500 |
| auuuguuuga uugaugagug auggcuuuuu ccuuccucag aguuugcccu gcccccauu | 31560 |
| ccaacguggg cugcugcuuc uccccagcgg guuguagcug gcaggccgu ugugcuuugg | 31620 |
| gguuugcugu accgucgcu gccgugaggg gacgaucugu cugcccggag ggguuucugc | 31680 |
| aaacauucau guaugccccu gcuucguuu guuaggaga aggaggggg ugaccuagag | 31740 |
| agaggaugag gaaggguuc uggugggcau ccuuggggua ccaacccugc uuccauccug | 31800 |
| cgcucugaau uuccucacag cccuuuucug ucucuggag aaggucaga agguaggcuu | 31860 |
| ugccaccuuc ccugggccug gcaccaagcu cggggggucuu guacacacuu ucccuucucu | 31920 |
| aacuggggug uggggcccauu uccuagauga gcuugcugag aaucaggaca gcugguauca | 31980 |
| gagccaggac uucccagucu ugcacaaaca accugugcau uuuugaguccc accaaauaag | 32040 |
| gccuccugcc uggucggcu caccccugcc agccccagc aaaugcagcc uggugcguuc | 32100 |
| ccaccccugc caagagccca ggagugcucu ggcagagaag ugcagggaug aggaaggagg | 32160 |
| cugugcccuc caggggacuc agcugcguua gaggaggugc ugcugcagug gcaggggucu | 32220 |

```
ccagacaucc cacgcagggg uccuuucaga ucaggcaucu cuuccaccaga ccaccguauu    32280 ccuuuucag cccucgucuc uugcacgugg gggugcagug uuuggcucuc acaucoccac      32340 auuccagcug gugggguuu gagcugggug uuccuucugc uccccacucc ccacucacgg      32400
cccccacccc acgcaagccu cccuugcccc cacucuuugu uccagcuuu cacagccuug      32460 gcgggcaggc ugcugcgccu guugcugccc cggcucucuu ccacccgccu cuucuuucuc     32520
agccugagcu uuaccgugag gucugggcgc cacaccuugg ccccugccau gccugccccc     32580
agaagcaccc acgugggucc ccugauucuc uccucccug ggcuuugcua aggagcccuu      32640 ucauugugc cuuuggugu ugccucaugc ccaucccug uucuugagaa cuuggaagca        32700
gagggggccc cuccuauugc ucccaagagg cuccacagua gggagccccu cccaggagau    32760
ucugagucug uguuaggug ucgauuccgg gguggccuu gggucccu caggccaggc        32820 cugugugug ccuaaggcug gggggcucug ucaggcaccu aguguccuu ggaggugggc      32880 ggggcugggu ccuggucucc ugaggacggg uggggagaca ggcucaggga gauuccacg     32940 aagcugcccu ugaaccccuc cucucgaggcc cacacugccc uggcccuuua cacccugccu   33000
ccugcacuag uaggcacaua auagaugcuc gccaccugug gagggcaggg uuuaaauggc    33060
uggaaagagc ugagugggcu guuugcuag cguacgcgca uuuguuuaaa aggaaagggu     33120
guguuucuug gcaaagacuc uucggaggaa acgcugaacu ggggauggcu cuucuaccugu  33180 ucuggggccu cacugcccu ccugccggg acaggcaguc acuggugggu uuccccccag      33240
uggaaacaca auauuugga aauauuugua ucuaggauaa aacuucaucu ggaccaacau    33300
gucuuuguug uguuguggc ccaggugauu uugagaaugu agaauacauu uggcaauuuc     33360
caaacggagu gaugaccugc uccuccgccc cccaugcccu cccugaggcu ggaggcuuca   33420 gaagcccug ccuugggagg aggcuguucu accagagaag ucuuugugccc caccguuggu   33480 gacaaucagc auugaccugu gaggcaccug ccagguucgg gacgcagcuu uagacaucca   33540
gaaaaccggg ggugaggg ugggugggg gcuuaagacc ccagagcuug auuccuuuua      33600
acugucucau ccccaaagaa ugguacaugg guaccaggua gguacuugga aucacccuga   33660
gccucgauuu uccaccccgu uagaaacagg guaauucaug acaguccg cuugggagac     33720 ggcugugacc ccugagaauu ucgcugcau gccgugggcu ggcucgugag acucaagguc    33780 ugguucgag gcccccgcaa cccuucuga cugugugcc ugggcgaguu uguugutug       33840 aaccuggaaa gcgucacacc ugccuggcac gguuauugug ggcuucaaug agauuguug    33900 ugugaaauaa acgcuuugug acuggcacac aggcgcucuc aucccggcuc uccuggug     33960 cccgaccgc ugggugcugg cugcggaggc ccugugcucc cuggaacugu cugcgcuggu    34020
cccagggacu cuuugggcaga guggagggca aggggggaaag caccagccug cucugggag   34080 acaguggcag agggaagugu uugcuuuuaa auacacucag cagguucaga caggagagga   34140 uccgaggga aauguuuaga gccucagga ggaggaagag accgaguuuu aggaaaaaca    34200
ucaaagcugg auaggugggg cagaagagcu ggggauagca uuagagagg cugagaguocc   34260 ugggugcugg guuuaucaag ugagagaaac cagagguugc cauguguagg ugggcgucag   34320
gacuagagug augcuuccag aaguuucgc aaguggccg agucuaaggu agggcagggu    34380
acgcagaaag uugagggggca cuagguagac aggccgagcu gguggcuggg ugcuccccuc   34440 accuccaug cugcuaggag cccgugagca gggacuugcu cuccuucccc ucocuccugg   34500 ggccugccug ucugucugug aacuucuguc ggccagcgag gccgggagca gguggccuuc   34560
aucugcaacu gugucucucu cagccuccac agccacgggg acacccugca ccuauuccca   34620
```
cgggacaggc uggacccaga gacucuggac ccggggccuc cccuugagua gagacccgcc    34680
cucugacuga uggacgccgc ugaccugggg ucagacccgu gggcuggacc ccugcccacc    34740
ccgcaggaac ccugaggccu aggggagcug uugagccuuc agugucugca uggggaagu    34800 gggcuccuuc accuaccuca cagggcuguu gugaggggcg cugugaugcg guuccaaagc    34860
acagggcuug gcgcacccca cugugcucuc aauaaaugug uuccugucu uaacaa        34916

<210> SEQ ID NO 49
<211> LENGTH: 12199
<212> TYPE: RNA
<213> ORGANISM: Artificial Sequence
<220> FEATURE:
<223> OTHER INFORMATION: meg8 sequence
<400> SEQUENCE: 49
ggucugaaaa augauauuca uuguccuaau guguaaauuu cgacaauuug caaauuugua      60
gauucuuuag aauagaacua acucaagccc uucauucgc agcugaggcu cacugccccc     120 aguggcagu gguccaggg gguuucgag acagggcau gacccagccc ugcugcccc         180 aagauggcac cuggcuugga ggggugaggg gcccuguuag ucugacuuug aagaagacca    240
gccuuccaga cucgcuuggu gcccugacag guaugugugc ucuucucucu cccaccuaac    300
agccccuuuu gggagacagg gucugagagg agucagggue guauaaccuu aacacagugu    360
guuauccaaa aacccacuaa cccuguuacu cuugucuguc ugcuaugga aaccaagggc    420 ggguguuaaag uuuaucacca ugauauacag augugcgugg ggacaucugg gauggggcuc   480
aggggucuac cuggagguca gagagggcag gaucugcuua ggggagaugg augacugugg    540
gggucagaca gggcagggu ugcuuagggg agauggauga cuggacau uggcuguaa        600 aucauccucc ccgucuuaca uaggauggg augcaacuuu caagaguugc cuugauuggu    660
accuuaaagg aaauaaaaca uaaaaugcuu ggcacauagu agaugcucaa cacauagaa    720 aaaggcacuu auuuuaggug gaucugccgc cgaauggccc uuuugcaagc ucuucucauu    780 uuuggaauc caaagggaag gugugggag cagggucggg guggaggga aggacgacgu     840 gagguugcag agggcauuuu cuugaggcaa uggcauaucu uucauggua cuggcugggu    900 uuaugcggac uuugagagga guggagugue uccaaguggg gcuaccccag ccugcagguu    960
ggaugcaggu aacccague uggcacugc auuuuuauuu accauaaaaa uauuucauau   1020
uugcugggug ugguggcuca cgcuuauaau cccagcacuu ucggaggccg aggccggugg    1080
aucaccugag gccaggaguu ugagaccagc cuggccaaca uggugaaacc ccgucucuac    1140
aaaaauacac aaaauuagcu gggcguggug gugcaugccu guaguccag cuacucagga    1200 gacugaggca ugaaauugc ucgaaccugg aaggcagaag uugcaguag ccgagauugc     1260 accauugcac uccagccugg gugacagcaa gacuccgucu caaaaaaaaa aaaagaaag    1320 aaaaauugca aaacuauagc aaucaccuca agguuuucac aggaaucaaa ucaguccaa    1380 acuaaaaugc uguguaauaa auagugggc uucacgucaa ggaaaggcga uuaagagcga    1440
ggcaugcagg ccgagggcug cuuaaccugu cucagauuuc uuccgcacaa agucauggu    1500 gaaauaggu cucugccugg cagggguaa agaaguucuc gaaggccucu gucugcauua    1560
gcuuggugag agggaagaca uuuaaccaau uaccaauua gugaucugug cggauggaga    1620
cugagcagga cgagggugcc acccgacugg guguaaagug ggcuuaguuu ugucuucuug    1680
gugucuggga gccucagugc cuuucuacgu agaugggagu augcuugca cauccuuguc    1740

```
acacaaguaa cccgugccu guuugaggau ccaagagcc ugugacggcu gcagggggcc      1800
cugaagcuua gugugcaagc aggagcuggg gacagagggg cuucugacgg gagucggggu   1860
gccuccucug gaugugggggg ugggcuaggg uggggcaaagg uugcuucccg uucuccugca   1920
gcugacaguu agaaaugcca gugccguuua gccacagucc cucugggguua gagucgggaa   1980
gaaacauggc aguguguguu uuugcacagg aaucaagcug ucagggggca cagugaggcc   2040
ccagcuccuu accagcaagc cgucuaggcu gcgaacgcga gccgccgggc cgcagcucuc   2100
uagaggcccc uguccccacc gccuggcccc aucucaugu c acauuccccc aaggucucau   2160
uccacucggc uaaucuccaa gaacaccggc cagggcauug gcuuucgggu ccuuuuaaag   2220
accaaaaagu aaagcacucc cccgugggug cuggacagcu ugggagggau uuggggcugu   2280
gggugguguggaa aucacagccc ugggcacaca ccugccagcc cgaugucacu gacaggcugc   2340
ucggaggcuu ggggcuccag ugagagcaua uagauauuuu uuaaaaaaca uauucgcgau   2400
aaaauaaauc cccugugucu gcagaacuug cucugggcau guacccacuc ccaauccauc   2460
aggaaacaug cccuuugcuu uguauuugua aaaacagaaa caaaaacaaa aacaacccac   2520
aggcgaacaa gcaaauuaaa ucccccccac acaaaauguu uauucuaauu augcaagaaa   2580
uggauugaua auuaauacac gcauuaguaa aaaucaaaca cugcagauaa agccaucuuu   2640
aaugcuuccc ucgaucccuc cccaucaccc cccagcaaau uaacugcucu ucucaguuuc   2700
aggcgucugg uuccagauau uuuuuucugu gcauuugcau auguagauaa auauaccucu   2760
aaaaucuaug acuuuguuua uuuuuuacau aaacuauauc auaguguaca uuccucucg   2820
cagcagcuug uguucuucc uucaagaguc ugcuuagaga uaauaaagau caacacuauu   2880
ccuuauaaca acaccucagu auccugcgag cuguacacac cagaguuuau uuaaccaccu   2940
ugcugcuggc augaaagccu cagguccuuu acccugguug gcgggggggg ggguggggg   3000
gugggggggcg ggggggggca gugaauggu ggcggcaggu guaaguaauu gcugagauuu   3060
ggguuuggg aguggggcuca cgaguguuua ugacauuauu auaaaugaau auaugagugc   3120
auaaauuagc aaaauaaaag ggggcuuuuc uggaccaaug augagacagu guuuaugaac   3180
aaaagaucau gauuaaucca guucugcaca aaacacugag guccauuaga agacaauagg   3240
ucuuggcugu uucauuccuu uuaagagcug uuuaauauuc cacgguaugu augcaccauu   3300
guugauuaca cucuucuacu guugaaaauc ccagcugaaa gugcucuggg ggaggagaag   3360
cuuuggucac aguccuagcc gucaggguggg gucacagauu cauagguguu cauuaaauua   3420
uuuuuuaaaa aagaauacau aaaaauggug cuuaaugcag aucagugagg aagcguguca   3480
caaaucgagg uuuuaauuaa uacgauucug cucaacuaau gcccgauaaa aaagaucuaa   3540
gcuguuucca uuuuuuguug cuguuaccaa cgacacugca gugagcauuc uugcagcuaa   3600
aucuguaaac acauccucga cuguuccuuu accccagcuu cuuagagaug gguggugggg   3660
uuaaauuguu ugcaaaaguu uauuuucauu gagugaucuu ucuaaaaugg cauuuugacc   3720
uuguuacugu cuugcuuuaa agccuccauc ugacuuccug gagcuuccgg gacggggucc   3780
aaaaaauaag gccuuauccu ggcauggaag acccuuuagg gucugucuug gaacuugcca   3840
gccucagccc cuccccacug guguuuaccu gcuaggcgca ccucaccccc acggggcuac   3900
cuguuucucu cagcgggcuc ccuacuucuu aggcuuugcg cggccgugcc uuucagcca   3960
guuucucccc ggccuuaaag agcaggcuug aaauauccu guggggagc ccaaaguuag    4020
augggccca cgaaacacug uguucagaag cccaccgaag cccugacccu ggaagugga    4080
ugccucauug acauuuuuuu cccaauuaaa gggaauguuu ugcauuuuuc uagaauugau   4140
```

```
gaaacugguc aacuguuacu cacccuccuu ccuuugcccc uuucuaggag cccugggcuc    4200 ccccagu guu gccuggg ucu gacuuugccu cagugaaaac ugccucgaau ucuuucuugc   4260 accgauggge agaugggcag gucggagga ucgu gucauc ugucccgugg cgcugg guaa    4320 gucugcagug uuguaaagcu gcaaacaccc uucggguggg ggcucaggcu ggcaccccccc   4380 cacugccccca gccugcgcua uaccacguuc cccugaugcu ugccuugugc cgggcccccag  4440 aacccagagu caugggg ucc acagcgcggg aguagcgucu cagu uguguga aguucugggg 4500 augagg uucg ggguaugauu acagcuugga aauggcugau ugccauuaug gcuccucccuu  4560 gccagag gua aacggg ucug gucccagaac aggaggagga caugaug augcug gaguaac 4620 gaugagg ggc ucuggggaag gacagggcug agagcaagug cugggaccuu ugggaccgag  4680
ucauauucua aaaagagcac aggcuuuggg ggagaggagc ugugaggcca aggcagcauc   4740 cccc ugggga gcuug ucagg aguaacagga gccacuggca g uguuug ggc uuuug uccc 4800 uuuuuuucuc ucccaggggga aggg agaagg aggcauugca ggaagccagc cacccugagc  4860
acagacccag cuacagaaca gacuuugagcu gcguguccuu ggcaaauccc caag uguuuc 4920 ugugccuugg uuuccugauu uuaaaaaaaa aaaaaaggac ucauaaucuc ucucacacag    4980
ggcuauugag aucucaauga ggaaauaacg caaauaaauc auccagcaca guagccaaca  5040
cgcaguaccc agcaaaaacuc gguagcucuc cccaucuuac cccgucauga aaugcuuaac  5100
ccccucccug agacgggcag cugcucccuu ucagggcagg gagacccaac agaggacaac   5160
acaaaugcca gagagagugu gagggg caau aaaagcu gau gcucgccucc cucccagaca  5220
ucuucccagg gaaaagugug cuuucuugaa caccuggggg ccggggaagg ggcugcccua   5280
ccacuuugaa ucggguuucc cgaaaag uuu ggugagagu u uauuuuuaug uaaauaacau  5340
auaaaaaguc agacuucucc acaggcagau uuuugaggc ucauauuuua cagacuuugg    5400
caagggucac ucggaaggaa caguggguac agucccagag ggu uca uaau uccuggaaaa  5460 acuucuggcc aaaccugacu ucuccuaaau uucacagaaa auucucccug ggcugggcuc    5520
aggcuaaaug agcuuuuugu uguuuagcuac agccuuaccu aguggaagca ugacuuugcac 5580 guugcccuuu acacaaaagg gaaccuccuc ggccgcugug aacaaaggcu ccgcucuccg   5640
aaauguuuga uuuguuuacu cgggagcgug agccugguca ggcacaug uc ugauacuggg  5700 gcuauuucuc ugcggccaua uguagagcug uccaggucuc ugcaauuuaa cccgcgcuu    5760 caugccagaa ucccauuucc uaacuuccuc aagcaacggg gcaagggaac cacagcaaaa   5820
aggaguguag ggggagug uu cccuccgugu ccggcagggg cuaaaggggcu ugcugcccug  5880 ug gcgucugc cucuaaauag ggauuggggu cggugacuuu ucacaucuac accaaagccc   5940
uucagaaccc uuucugcacc accagcuauc cugaaccaga aaucccuguu cacagaauuu   6000 cccaugugg g ugccucu ugu ucugcacccu gcaucgcgcc cccucccccg uuuauguaaa   6060 ugacacaug u aaaugucacu cucccaaaca uuucacacc ugcagcuuca aaucaaaccuu  6120 uuaauagg uu aaaacaacag caccaacaaa aaccaacaaa aacagaggcu cccgagaaac    6180
aaacaguuuu ucccgaaggg cuugcaguge cuaacugagc ugccagggcc gucugucugu   6240 cuguuag cca ggaaggcaaa ccagccgcg cacuccaccu gcaacacgau gcugcccccc    6300
cacggcgggu cggagcagcu gugcgacccc cagggcugac agauugggu u gucaggagca  6360 ggacaaugag gcugcaguga ggaugggcuc cauccuugaa ugacucugcc cuccuugaaa   6420
uuuuucugcu ccauggaggu gcaucucugc ccccgaggac cuugggcauu ucacagacaa    6480
```

```
ggagcccugg cuggccucgc agccaucccc cauaugcaca cacgcacacg cacagacaug   6540
cgcgcacaca cacaugcuga gugccugcac ugggagcaua aggcagaaaa cuccuuugga   6600
aacugcagaa cagagccuug ucuagcagag gucccccugau aaagguccca caguccugg   6660 gaacugaacc ccugugaaug ggccaggaga ggcagucccc gacucccgug ugggcugcau   6720
ucaucagcag gccggcaccc cagcccuguc acugugugag gagcuuucau gaguccacug   6780
aacauguaag ucacagucug gcagcuggcu gcaucugugg uugcugcuca gccuccagaa   6840 aagggcccu caaccugcca gaccuccucg cuccuuccac ucacucugcc agccuguugc   6900
cccagagagg acacaggcca gccucugugg gcucaggagc cagggcaggu gcuuggccac   6960 ucuaggguguu cuggcccuca agaggggagu uggcagcagg acaguccccca ccucccccca   7020 ccagcccugg gcacucaacc ccauucucug cuccucuccc ucauugccuu auugggacag   7080 aggcacccg ccaaccaucu cugugcccuuu gccauuuagc ccagggcaag cuacucggga   7140
gaggccaaau ggccucauac ugaccccugc cugguccccu cuggccaccu cgcucacuug   7200
cccgcuugcc ugcucaggag uuggugcugu gggagcuucu caaaggccua aacauguggg   7260
cugccagccu gggcaggaaa ccgugcugca gccuucucag ccaagcacug gccugccucu   7320
cuccccucgg augccuccug uaacaggag cucccuccu cccaggcag ccugcucagg   7380 gcucgcacgc agagcugcuu ugcugagccc uccccugccu uuugcaucug ccuccucggc   7440
ugugcagcag cccccuugcc cccucugccc uccgaucucu gcaggcugug ggcucccucu   7500 cuuucaguc cucuccuuuc ugugcugaau ggcauaccc ccaccaaugg ugggaacagg   7560 auggcgcc ucuacaccug uccuaacacc ucugucucug uucuuuuaga ccugggacag   7620
agcccuuugc ccugcuguuc ugcuaaaagc ccaggggagg gcguggugcu cccuccuugg   7680
ggccagcugc uccaugucua ucguugagc ggcuucucag cccucuuggg uuucuaugg   7740 ccccuuuucc aguugcuagg gagaacgcuc uguaugcagc cccccugccuu uucugcagga   7800 gcugcuggcc uccggccag cccuggucag cccugcagua gcagcagcag cagcagcagc   7860
agcaguaggc agccacagca gggcugggg ucccgagcc aggcagaccg gcuugacucc   7920
cugcucucua gcugcaagac aauucccuuu acuuuucaga cucggcuuuu ccccugugaa   7980
auggagauga gaguuucucc gucacuggcg ugaagugagg acuaaaugag auaaguguag   8040
gcuugcacac aucagacacu ucauaaaugc uuguggagua gacggugggga cccagggagg   8100 gagagagagg uauguaacaa gugucgcaag agagaaaaca gccuggccuu ucaagacccu   8160
gcucccaaua caaacgggaa ccucuccugg cagaguccccc ucugcugcu uaaucgcaca   8220 aaucaaguca gccggaggca gcccccggcc uguggaacuc acaguagaug cagcaggcag   8280
cauaaaugac augcagagcc cacaucugca uuuaauagac cgagaauuug cauuguauau   8340
aacagcacga gggguaaagc augaaggcau aaaggaacag uuuuucccgg cggcuuccuu   8400
gaagggccag cuuagacagg ggucgggga ggagaaacuc agcggggucc ggcaucccca   8460
uagacuaugg gacagacauc cauccaugca cucauucucc aagccaccac aguguaccua   8520
ccuuccccgg gccaguccc aagcgugagg cuggggauga agugaugccg guggcuuagu   8580
gaugccggug gcuuccuguc cucgaagcuc agcggucug ugggggaaa caaacaggga   8640 auaagacacu ggaauugag gugaucaaga gggggugcag gcauggagau uuauggagcc   8700
ccgucuugga gccaaguccc gaacggggcu gucugcaaag aacucacccg ggcaauaacc   8760
cugcacacug gucucaugag ccccauuaga uugaugagga aacugaggca cagaaaggca   8820
aaguccuaua cucaccgucu cucagcuggu gugaggcugg gccaggaugg aaccccagac   8880
```

```
ucuccgaggc uccccaccac acccugcugc ugaaggcugc ucagcgaggc ugugccgagu   8940 gcugggggg ugugggugg cagggggacgg auugauuagu uauaagcacc ucccagcggu   9000
gcuugagauc ccagcuccuc uguggcccaa uccguuugaa gggcagauuc aaaauuaggu   9060
gguagcaccu augggcagag gcuuaugaaa augggcauuau uaaccugaug uggagagggc   9120
ccugccuguc ugcaaguaga uugcagauag agacggaggg ggcugggcuu guuugugugg   9180
acagugaguu agagaggaca gagaacaucc agggccccuc cagggcuucc ggacggggag   9240
aaccagaucu ggagggggcug gacaagugg agggggaaga ggggguacguc uuaagggugc   9300 cccggcaccu cagggaaaug ccccaggcug gacuuggagg aggaucucca gccuugacuc   9360
ugacacagac agggacuaug gcccuccccg caccucgguu ucccaucugu gagauaagag   9420
auggaaacca aacgucauuu cgagaaaagc ccccauuccc accacccucc uggccccccc   9480
cuucccccac caccccaauc acguuugcca gacaccuguc ugcuugucag agcaauauuc   9540
aacaggagag uuccuucgcu uccucccugg agggagaagg gagaggugug gacggggaga   9600
ggggagggga gaggugcccc ccacucagag aggccgcuga gcagaguucu gcaucgggua   9660
ggaguugggc caccgaagau uugugccaac ucacggugcg guggaaucag acagucugaa   9720
uucuucagac accagccaag agucuguggc gcccccacgu gccacaaggg ggcugccugg   9780
gccacauuuc ugagcccgaa aagugaggag ggggacaguc aagagggacc ggcgcuuuug   9840
cucuggcagc ggcgcuuuua acugcgacag augcgugcgg ugcggcgggg gagccggccg   9900
ugccggggcu gggggcugcu gggcgggggu ggucggggcg gggggcgggg gcugcagguu   9960
gcgccccucc cucacagacg gcugcgcugc aaugcagcag gcugcgggag cuguccccggg   10020 agcuguccug uccgguggcc ggcuuuccaa agugggggaac gagagaugag ggagggagca   10080
cuuccaggcg cugcguggug gccaggcgcc caggaagccg aggggcccga gacucugcag   10140
cggggccaga aagagaagag uggggaggga ggccggagu ggugcaugga ccaggggguua   10200 gagggaggug ggguguggacc uggggucggg cgccagucag cuugcagccu augaaggacg   10260
gaaaggaggg cuacagagau aggggaagag uggggcugag gauagccaga gcggcuuggc   10320
acacaguuuu aggguaaaag caucaacucu uaucuuucca aaagaaauaa aaaagccaaa   10380
aaaaaaaaaa aaggcauuug aaagcuagac agcugaaucc uucccagcau gacucuagccg   10440 gucacuccag ggucuuccuu caaagcgugu cuaauggga acagcguugu cccaguaacc   10500
aaauugggac cagagucccca gggaagggcu caucaggugg ccgcucugcc uugaagagug   10560
guacccucag gcccuuuucc agccagggu caggagaga gcuggagggc ucggggaggc   10620
agggacuggg agggagagug gggagaggag cgcuggggcc ugcaggaggg ucucugggca   10680
gcuggcgggu gucucguucc gcaacacucu gcaccugguu acaucguccu ccguccacuc   10740 aacgguggaau gauucucuuc ccucuggauc cagccccucu aguucccuuu ucacuuugag   10800
gcauuugccc ccugugaauc aguucccugc uacuccagaa aaauuucucuc auaccccagg   10860 ccccucuguu cuuuuaaaug gcacccuuca cccccagccc uucaucuucu gcacuguauu   10920
uucacuuguu gauuuaaaaaa ucccuuuauu augggaaauu gcaaacaaca caaaaguaga   10980
gaaaauagua cguauuuuua cuguuuacuc aauuucauc uugccauuac ccggacacgu   11040
uugccgucaa acccuggccc cucuuguuuc aucuaaaccc uaaacugucc cucuacuccc   11100
acugcccaac cccuaccccu ggacuauuuc gaagcaaauu ucagacacca uccuguuuucc   11160 ucugagcauu uuuuaguuug uaucucuaaa uaagaagcuu uuguuucuua aaauaaaac   11220
```

| | | |
|---|---|---|
| cacaacacca uuaucacaag uuaaaaaauu aauagccuuu ccuuaauauc auccaccauc | 11280 | |
| uauguagcau uccaauauuc uugauugacu cauaaauuuc uuuuacaguu ggcuugguca | 11340 | |
| agucagυguu caaacuaucu ccugcucuuu caaggggauc uggggcucua gaagguaagu | 11400 | |
| auggcuacac auuuaggggu ugaauaucug ccuggaccuu aaaugagaaa ucaaccuca | 11460 | |
| gcaaaccuca guguucucac ugaaaauggg gcaaguucug ggucucuccu uggggucauug | 11520 | |
| agagggguuag agcauuaacc ccugaagccc cagccgcaug ucuaauaugu cagagacacu | 11580 | |
| cagcaaacag uagcugcgag aaugauucuu uucccagaa acguuaaag gggauuuggg | 11640 | |
| caggggcagg caaaacauag cuggcuauug uccauaaaac aaaaggcucc uggcagucca | 11700 | |
| gguccccuga gugguuaaaa cagcacaugc acuacauccc aaaaagggca gccuacaguc | 11760 | |
| uggggggcugg guucgccugg accuccuggc uugccguuua gcugccugac ucagcuguu | 11820 | |
| gugaccuggg accaacaggg gaccccggca ggugccuauc cacuagaugg cacucucuac | 11880 | |
| ugugagucca gggggaccca ccaccccaaa cugcuuuggc cacugcccag cccgggguc | 11940 | |
| caccggaaga ugcacaccac uaaaacaucg cagauaauuu cuaaaaagca cuucucaaca | 12000 | |
| ugucaugcaa aagaugcggu gguuuauuuc cuugcauaaa ucccaaccag auugcagaag | 12060 | |
| cagagggaau gaacauuuaa ugacuuugcu gaggccagac acugguaugu cuacgcucuc | 12120 | |
| uuuaaauccu caucccagcg acaucugauu cccuucauu uuacagauua gaggacuugg | 12180 | |
| agagguuagu gacuugcuc | 12199 | |

<210> SEQ ID NO 50
<211> LENGTH: 3026
<212> TYPE: RNA
<213> ORGANISM: Artificial Sequence
<220> FEATURE:
<223> OTHER INFORMATION: meg9

<400> SEQUENCE: 50

| | | |
|---|---|---|
| ccacucugca cagacacguu ggcuggugca guccuggaga cccacggagc ucacggucgu | 60 | |
| caggggguccu caaggauuca gagaaccccc aaaugucagg gcugcuccu ucuugcccug | 120 | |
| ccucucugcu cacacccuug gacagguaag aaaaacugagg uccacagagg cagggugca | 180 | |
| uugcugugc uuuuguucug agcacugucu ccccagcuuu ggggguugaga cucuggaguc | 240 | |
| aagacccacc ucugaugaac gagcggcuuc cuucuuuugua aaaauugagg cgacccagac | 300 | |
| caagaagggc ugcaaaauca ccaagccagg accucaauac ccaaggggcu ggggguucgg | 360 | |
| ccacccugug gcagagcuuu uagaagccag ggcccuuggc ucggcagugc uggcucauag | 420 | |
| uaggugcuua guucaugccu gucuccuugg augaaaucug accauagaca ccagugcaaa | 480 | |
| gcaggguguuc aacacaggag ggguguacuga acccgaucuc ucuauaccca ggaggaagca | 540 | |
| cacgggaggc acucagagaa cguuugugga augaauaaau aaaagcauau uugagggaa | 600 | |
| uaaagaagca gaaaaacaaa gaagaaucug gggaagaugg gcauaaaucu ccaccaagug | 660 | |
| cugccaaggc uucccaggcg aggcugcuga aaagacccug uggagguaga gggacaauuu | 720 | |
| gucauggaug ggaaugggcu ugagggccgg gaagcagggc augaugggc cucauucauc | 780 | |
| auuuucccgu uacccagca gcgugcaggg gagcagguac agcaccugcc ugugcagcug | 840 | |
| cacugccugc ccgaaggccc uaggcccugg gccaaguagag ugaccagagg gggacuggga | 900 | |
| auggaaagga ccucaaggaa ggacaagcug agcucuggga ggccaccucc uccaggaagc | 960 | |
| cuucсccugau ucauccuuca cагggcagucu caauuugcag ucagauaucc acugcucuga | 1020 | |
| uucuuagauc agcaaguauc ucccuaccca gacugcaggc ucugcugggg ccgcggcugu | 1080 | |

```
uucugacuug ugcacaaugg caucccugua ccuagcacag gacugagucc agagaaagug     1140
cucagugaug cuuguuggcc uugucucucc ucguggggca gcacagggca cccggcgggu     1200
ccugagggug uggacauccc acggcagagc cugcgguuga ucccgaccau gaaccaaggc     1260
cuggggcggg ggugggccaca ucaggccacu cugccagga gagaugugggc ugugagcugg    1320 gggucuggcc uguccccgga ggcauuccuu ggguuugcau ccaucagaag auccacuggu     1380
ugccucuauu ugggccugga gcagggaugg gauuuuucca agguacaugg ggucuagggg    1440
agacccaggc ccauuauuag ggucggucuu gagaaggcag agaucaggcc accacuuuau     1500
uugguguagc uccucgcucc auggugugu gcugagugaa ugaaugcauc agggacuccu     1560
gcuuccugcc cagagccccc uccgcacccc acacagccuu gcuccaagga aaggggguca    1620
gagccaacug gacagugcua cagcaugggg agccucgacc aggcucggcc ucgacgaug     1680 ggauaggcag acagcccccu gugcaaggca gcuagcuugc agggucccga gaggccaaag    1740
gcccuggucu uuccuggggc aagaggcugc ugagaaggug cacagagccu ggugcagga     1800 aaccauccag aaugcugcuu cccgccaucu gugagaucuu cguuucucu aacacucaaa     1860 aauagauguu ucuguauagc ucucucguug gcaggggagc ggcaggaccu gccaaggccu    1920 ggggggagccc gccagccugc ugaguucuac uguacaaaca guuggggagg gggcgcuguc    1980
ucuguuaacu ugaaauuccc cgaucaguaa acaugccaau uuaaagugua auuaacucag    2040
gccggaaaaa auucagauuu ggacugcuuu ucacaguuga gguuguuuuu cuuuuauuua    2100
uuuaucucuu ccggggugug gugguaucug uggcugguuu uagccaggaa aaauagaagg    2160
gggaccgggu ggggaggggg cugguuggga gaggaaaggc uggaaggaaa ggaagagaaa   2220
cgggcgggug gccugacacc cagcagccag gugucuauag guuuucuguc cugggagggg    2280
gcugucaggg ugaugcccgc cugcagagag ggggucauuc ugcgagguug ggcugcagac    2340
cccugugcca gcgggccugg ugauucgaa augaugggggc acuggggaga accccagga    2400 aaacacccag ugcugcuuuu gacauucucu cuccaucucc ccuuucagcg gcugcucugc    2460
cugggauaaa cacauuucaa gagucucagu ccccgcuuug ccaccaucuc cuccucugau    2520
cuccuuuccu gcuucaaaag acuccagaau cuuucuccgguu cucagagaag gcugaaucca    2580
ccuaugaccu aguggagca cccgugccg aaacguuuua ccuucugguc cccggagcca    2640 uggggucacga ccugggccuc auguaggccc gcuccccage agaccccaau cugcggcuuc     2700
ucccaccuca cuggggaaga aggagagccc uggggaugug gagaagccac cccccaccccc   2760 gccacauccc ccacaaucuua cagaaaucucg auuugaaucc cgggggcaca ucccucagca    2820
ggacagcaac agucuuugcc gcagccuggg gagggcugug cuggggauga gcgccgagug    2880 gccgggugaacu aagugaagga aaugaccaug cuucucccc agcuggaugg cgaggccggg    2940
caggaaccgc ggaauuccug cucuucguuu ucaaacacuu ugcugucaag cuauuugaau    3000
aauaaauaca cauuauaaaa auguaa                                          3026
```

<210> SEQ ID NO 51
<211> LENGTH: 22
<212> TYPE: RNA
<213> ORGANISM: Homo sapiens

<400> SEQUENCE: 51
ugugacuggu ugaccagagg gg                                              22

<210> SEQ ID NO 52

```
<211> LENGTH: 22
<212> TYPE: RNA
<213> ORGANISM: Homo sapiens

<400> SEQUENCE: 52
gccugcuggg guggaaccug gu                                              22

<210> SEQ ID NO 53
<211> LENGTH: 22
<212> TYPE: RNA
<213> ORGANISM: Homo sapiens

<400> SEQUENCE: 53
gaauguugcu cggugaaccc cu                                              22

<210> SEQ ID NO 54
<211> LENGTH: 22
<212> TYPE: RNA
<213> ORGANISM: Homo sapiens

<400> SEQUENCE: 54
aucaugaugg gcuccucggu gu                                              22

<210> SEQ ID NO 55
<211> LENGTH: 22
<212> TYPE: RNA
<213> ORGANISM: Homo sapiens

<400> SEQUENCE: 55
ugaaggucua cugugugcca gg                                              22

<210> SEQ ID NO 56
<211> LENGTH: 22
<212> TYPE: RNA
<213> ORGANISM: Homo sapiens

<400> SEQUENCE: 56
aaacauucgc ggugcacuuc uu                                              22

<210> SEQ ID NO 57
<211> LENGTH: 22
<212> TYPE: RNA
<213> ORGANISM: Mus musculus

<400> SEQUENCE: 57
ugugacuggu ugaccagagg gg                                              22

<210> SEQ ID NO 58
<211> LENGTH: 22
<212> TYPE: RNA
<213> ORGANISM: Mus musculus

<400> SEQUENCE: 58
gccugcuggg guggaaccug gu                                              22

<210> SEQ ID NO 59
<211> LENGTH: 22
<212> TYPE: RNA
<213> ORGANISM: Mus musculus

<400> SEQUENCE: 59
gaauguugcu cggugaaccc cu                                              22
```

```
<210> SEQ ID NO 60
<211> LENGTH: 22
<212> TYPE: RNA
<213> ORGANISM: Mus musculus

<400> SEQUENCE: 60
aucaugaugg gcuccucggu gu                                             22

<210> SEQ ID NO 61
<211> LENGTH: 23
<212> TYPE: RNA
<213> ORGANISM: Mus musculus

<400> SEQUENCE: 61
ugaagguccu acugugugcc agg                                            23

<210> SEQ ID NO 62
<211> LENGTH: 22
<212> TYPE: RNA
<213> ORGANISM: Mus musculus

<400> SEQUENCE: 62
aaacauucgc ggugcacuuc uu                                             22

<210> SEQ ID NO 63
<211> LENGTH: 22
<212> TYPE: RNA
<213> ORGANISM: Homo sapiens

<400> SEQUENCE: 63 cccccucuggu caaccaguca ca                                            22

<210> SEQ ID NO 64
<211> LENGTH: 22
<212> TYPE: RNA
<213> ORGANISM: Homo sapiens

<400> SEQUENCE: 64
accagguucc accccagcag gc                                             22

<210> SEQ ID NO 65
<211> LENGTH: 22
<212> TYPE: RNA
<213> ORGANISM: Homo sapiens

<400> SEQUENCE: 65
aggggUUcac cgagcaacau uc                                             22

<210> SEQ ID NO 66
<211> LENGTH: 22
<212> TYPE: RNA
<213> ORGANISM: Homo sapiens

<400> SEQUENCE: 66
acaccgagga gcccaucaug au                                             22

<210> SEQ ID NO 67
<211> LENGTH: 23
<212> TYPE: RNA
<213> ORGANISM: Homo sapiens

<400> SEQUENCE: 67
ccuggcacac aguaggaccu uca                                            23
```

-continued

```
<210> SEQ ID NO 68
<211> LENGTH: 22
<212> TYPE: RNA
<213> ORGANISM: Homo sapiens

<400> SEQUENCE: 68
ccuggcacac aguagaccuu ca                                             22

<210> SEQ ID NO 69
<211> LENGTH: 22
<212> TYPE: RNA
<213> ORGANISM: Homo sapiens

<400> SEQUENCE: 69
aagaagugca ccgcgaaugu uu                                             22

<210> SEQ ID NO 70
<211> LENGTH: 22
<212> TYPE: RNA
<213> ORGANISM: Homo sapiens

<400> SEQUENCE: 70
ugagaacuga auuccauggg uu                                             22

<210> SEQ ID NO 71
<211> LENGTH: 23
<212> TYPE: RNA
<213> ORGANISM: Homo sapiens

<400> SEQUENCE: 71
uguaguguuu ccuacuuuau gga                                            23

<210> SEQ ID NO 72
<211> LENGTH: 22
<212> TYPE: DNA
<213> ORGANISM: Homo sapiens

<400> SEQUENCE: 72
agagaacaga aaaccacggg aa                                             22

<210> SEQ ID NO 73
<211> LENGTH: 23
<212> TYPE: RNA
<213> ORGANISM: Homo sapiens

<400> SEQUENCE: 73
agaagagaaa ccaacaaaau gga                                            23

<210> SEQ ID NO 74
<211> LENGTH: 22
<212> TYPE: RNA
<213> ORGANISM: Homo sapiens

<400> SEQUENCE: 74
uacaaaccac agugugcugc ug                                             22

<210> SEQ ID NO 75
<211> LENGTH: 13
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is  a, t or g
```

```
<220> FEATURE:
<221> NAME/KEY: misc_feature
<222> LOCATION: (4)..(4)
<223> OTHER INFORMATION: n is g or t
<220> FEATURE:
<221> NAME/KEY: misc_feature
<222> LOCATION: (5)..(5)
<223> OTHER INFORMATION: n is  g or a
<220> FEATURE:
<221> NAME/KEY: misc_feature
<222> LOCATION: (6)..(6)
<223> OTHER INFORMATION: n is  a, c or t
<220> FEATURE:
<221> NAME/KEY: misc_feature
<222> LOCATION: (7)..(7)
<223> OTHER INFORMATION: n is  t or a
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (10)..(11)
<223> OTHER INFORMATION: n is t or c
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (13)..(13)
<223> OTHER INFORMATION: n is  a, g, or c
<220> FEATURE:
<221> NAME/KEY: misc_feature
<222> LOCATION: (13)..(13)
<223> OTHER INFORMATION: n is a, g, or c

<400> SEQUENCE: 75
nggnnnntnn nnn                                                          13

<210> SEQ ID NO 76
<211> LENGTH: 15
<212> TYPE: DNA
<213> ORGANISM: Homo sapiens
<220> FEATURE:
<221> NAME/KEY: misc_feature
<222> LOCATION: (13)..(15)
<223> OTHER INFORMATION: n is a, c, g, or t

<400> SEQUENCE: 76
aggggatttc cannn                                                        15

<210> SEQ ID NO 77
<211> LENGTH: 15
<212> TYPE: DNA
<213> ORGANISM: Homo sapiens

<400> SEQUENCE: 77
tggggctttc caagg                                                        15

<210> SEQ ID NO 78
<211> LENGTH: 15
<212> TYPE: DNA
<213> ORGANISM: Homo sapiens

<400> SEQUENCE: 78
aggggctttc aaaat                                                        15

<210> SEQ ID NO 79
<211> LENGTH: 15
<212> TYPE: DNA
```

<213> ORGANISM: Homo sapiens

<400> SEQUENCE: 79
aggtattttc cggga                                                    15

<210> SEQ ID NO 80
<211> LENGTH: 15
<212> TYPE: DNA
<213> ORGANISM: Homo sapiens

<400> SEQUENCE: 80
ggggacttcc tagag                                                    15

<210> SEQ ID NO 81
<211> LENGTH: 15
<212> TYPE: DNA
<213> ORGANISM: Homo sapiens

<400> SEQUENCE: 81
aggggattct cacgt                                                    15

<210> SEQ ID NO 82
<211> LENGTH: 15
<212> TYPE: DNA
<213> ORGANISM: homo sapiens
<220> FEATURE:
<221> NAME/KEY: misc_feature
<222> LOCATION: (1)..(1)
<223> OTHER INFORMATION: n is g, a or c
<220> FEATURE:
<221> NAME/KEY: misc_feature
<222> LOCATION: (2)..(2)
<223> OTHER INFORMATION: n is g, a or t
<220> FEATURE:
<221> NAME/KEY: misc_feature
<222> LOCATION: (3)..(3)
<223> OTHER INFORMATION: n is a, c, g or t
<220> FEATURE:
<221> NAME/KEY: misc_feature
<222> LOCATION: (4)..(4)
<223> OTHER INFORMATION: n is a, t or g
<220> FEATURE:
<221> NAME/KEY: misc_feature
<222> LOCATION: (6)..(6)
<223> OTHER INFORMATION: n is a or t
<220> FEATURE:
<221> NAME/KEY: misc_feature
<222> LOCATION: (7)..(7)
<223> OTHER INFORMATION: n is g, c or a
<220> FEATURE:
<221> NAME/KEY: misc_feature
<222> LOCATION: (8)..(8)
<223> OTHER INFORMATION: n is a, g or c
<220> FEATURE:
<221> NAME/KEY: misc_feature
<222> LOCATION: (9)..(9)
<223> OTHER INFORMATION: n is a or c
<220> FEATURE:
<221> NAME/KEY: misc_feature
<222> LOCATION: (10)..(10)
<223> OTHER INFORMATION: n is t, c, or a
<220> FEATURE:
<221> NAME/KEY: misc_feature
<222> LOCATION: (12)..(12)
<223> OTHER INFORMATION: n is t or g
<220> FEATURE:
<221> NAME/KEY: misc_feature
<222> LOCATION: (13)..(13)
<223> OTHER INFORMATION: n is a, c or g
<220> FEATURE:
<221> NAME/KEY: misc_feature
<222> LOCATION: (14)..(14)
<223> OTHER INFORMATION: n is c or a

```
<220> FEATURE:
<221> NAME/KEY: misc_feature
<222> LOCATION: (15)..(15)
<223> OTHER INFORMATION: n is t, c or a

<400> SEQUENCE: 82
nnnncnnnnn gnnnn                                                    15

<210> SEQ ID NO 83
<211> LENGTH: 15
<212> TYPE: DNA
<213> ORGANISM: homo sapiens
<220> FEATURE:
<221> NAME/KEY: misc_feature
<222> LOCATION: (8)..(8)
<223> OTHER INFORMATION: n is a, c, g or t
<220> FEATURE:
<221> NAME/KEY: misc_feature
<222> LOCATION: (13)..(13)
<223> OTHER INFORMATION: n is a, c, g or t

<400> SEQUENCE: 83
ggaacagnat gtnct                                                    15

<210> SEQ ID NO 84
<211> LENGTH: 15
<212> TYPE: DNA
<213> ORGANISM: homo sapiens

<400> SEQUENCE: 84
ggtacaggac ggaca                                                    15

<210> SEQ ID NO 85
<211> LENGTH: 15
<212> TYPE: DNA
<213> ORGANISM: homo sapiens

<400> SEQUENCE: 85
cgcacagaat gtcac                                                    15

<210> SEQ ID NO 86
<211> LENGTH: 15
<212> TYPE: DNA
<213> ORGANISM: homo sapiens

<400> SEQUENCE: 86
gggacagcct gtgct                                                    15
```

COMPOSITIONS AND METHODS FOR TREATING AND PREVENTING MUSCULAR DISORDERS AND DYSTROPHIES, STEROID SIDE EFFECTS, AND INFLAMMATION

GOVERNMENT SUPPORT

This invention was made with government support under grant W81XWH-17-1-0475 from the Department of Defense and grants L40AR070539, R00HL130035, U54HD090254, and L40AR068727 from the NIH The government has certain rights in the invention.

BACKGROUND

Duchenne muscular dystrophy (DMD) is a lethal genetic disease with pediatric onset, and is characterized by progressive muscle degeneration with chronic inflammation. The current DMD standard-of-care is chronic treatment with high dose corticosteroids (prednisone, deflazacort). Prednisone and deflazacort both increase DMD patient strength, prolong ambulation, and reduce scoliosis, however their long term use is associated with many side effects that negatively impact patient quality of life (1). Side effects noted as particular concerns to DMD children and their families include stunted growth, bone fragility, mood disturbances and weight gain.

Examples of the side effects of glucocorticoid treatments include: aggravation or induction of infections, concealment of symptoms, or impaired immunity; adrenocortical insufficiency; impaired glucose tolerance such as induction or aggravation of diabetes and elevation of blood glucose level; gastrointestinal tract ulcer, gastrointestinal hemorrhage, gastrointestinal perforation, and hemorrhagic pancreatitis; cramp and intracranial hypertension; mental disorders and state of depression; decreased bone metabolism such as osteoporosis (particularly, compression fracture of the spine); aseptic necrosis of bone head (femoral and humerus bone fractures); myopathy (loss of muscle strength accompanied by muscular atrophy, particularly, decreased muscle weight and loss of muscle strength of proximal muscle, and decreased muscle function) or a decrease of muscle mass, and body weight loss; glaucoma, high eye pressure, posterior capsular cataract, and thrombus (hypercoagulability); cardiac rupture due to myocardial infarction; aggravation of asthma attack; anaphylaxis due to injection; moon-shaped face and buffalo hump; elevation of blood pressure due to mineral effect; sodium-water retention (e.g., edema), body weight increase and hypokalemic alkalosis; development disorders in childhood; menstrual disorder; decrease in sperm motility and number; acne, hypertrichosis, hair loss, and deposit of pigment; dermal thinning, weakening, subcutaneous congestion, linear purpura, facial erythema, panniculitis, and cellulitis; hindrance of wound healing; hypersensitiveness (e.g., rash), itching, and hiccup; euphoria, insomnia, headache, and dizziness; dyshidrosis, excessive urination, and leukocytosis; fatty liver and nitrogen imbalance; GOT, GPT, and ALP increase; hyperlipidemia, hypercholesterolemia, and steroidnephropathy; nausea, vomiting, stomachache, heartburn, sense of abdominal fullness, dry mouth, diarrhea, and excessive appetite; retinal disorder or eyophthalmos due to central serous chorioretinopathy; muscular pain, arthritic pain, fever, and feeling of fatigue; atrophy in topical tissue due to muscle, intradermal or subcutaneous injection, depression, and body weight loss; thrombus, phlebitis, pain, swelling, and tenderness aggravation during intravenous injection; withdrawal syndrome; systemic symptom: fever, headache, inverse fatigue, generalized tiredness, feeling of weakness, and shock as systemic symptoms; anorexia, loss of appetite, nausea and vomiting, and diarrhea; nerve system-associated symptoms such as headache, anxiety, excitement/cramp, disturbance of consciousness, muscular pain, arthritic pain, and the like.

Accordingly, the development of effective drugs that are safer than corticosteroids is an important goal for DMD and other chronic disorders currently treated with steroids.

To develop an improved drug, it is important to dissect how prednisone works at the molecular level. The drug target of prednisone is the glucocorticoid receptor (GR). Once activated by prednisone the GR exerts its effects by: 1) binding to other proteins to affect their functions, and 2) moving into the nucleus where it directly binds to DNA promoters to affect gene expression through glucocorticoid response elements (GREs). Many anti-inflammatory effects of prednisone are believed to be caused by GR protein interactions, where the GR inhibits the inflammatory transcription factor NF-κB (58). However, some have hypothesized that prednisone efficacy in DMD is mediated through other functions, either by the direct actions of the GR in binding to DNA to activate GREs in gene promoters (57), or by gross physiological effects such as growth stunting (20). Moving forward, it is important to determine which of these GR properties can be selectively activated, as well as which GR properties are expendable versus which properties are essential for efficacy in treating DMD and other chronic disorders.

Vamorolone (VBP15) is a first-in-class dissociative steroid that binds the GR with high affinity (23). Data to date on individual gene targets suggests that vamorolone/GR complexes retain many protein binding activities of prednisone/GR complexes (e.g. NF-κB inhibition), but vamorolone/GR complexes do not activate gene targets as do prednisone/GR complexes (e.g. GRE transactivation). Thus, vamorolone loses transactivation (gene transcription) activities associated with side effect profiles of corticosteroids, while maintaining anti-inflammatory activities associated with efficacy.

miRNAs are small, non-coding RNAs that are involved in regulating gene expression through different mechanisms, including translational repression. miRNAs are initially transcribed from DNA as lengthy primary miRNA transcripts ("pri-miRNAs"), ranging in size from hundreds to thousands of nucleotides. Pri-miRNA is processed in the nucleus by the enzyme complex Drosha-DGCR8 to form stem-loop precursor miRNA ("pre-miRNAs"). Pre-miRNA is transported to the cytoplasm by the protein exportin 5, where it is cleaved by the enzyme Dicer to generate mature (functional) miRNA. The human genome encodes over 1300 miRNAs, which have been cataloged at "miRBase: The microRNA Database" (http://www.mirbase.org/). miRNA expression has been reported in a wide array of cell and tissue types, and extracellularly, e.g., in biological fluids.

miRNAs have been found to be detectable in a variety of human body fluids, including blood, saliva, and urine. miRNAs that are present in the circulation, including those in plasma and serum, are protected from endogenous ribonuclease activity, allowing them to remain remarkably stable. Because of this, circulating miRNAs hold great promise to serve as potentially useful biomarkers to monitor pathophysiological changes and the prognosis disease. Moreover, because the deregulation of miRNAs also contributes to the development of various human diseases, these molecules are becoming attractive targets for miRNA-based therapeutic interventions.

Recently, miRNAs have emerged as a promising new class of biomarkers and therapeutic targets. Specific pro-inflammatory microRNAs are becoming increasingly implicated in chronic inflammatory states, as reviewed in (64). miRNAs are relatively stable, are highly conserved across species, and since miRNAs are not translated into a protein product, their expression can be directly correlated to function. Typically, miRNAs exert their functions by binding to the 3' untranslated region (UTR) of mRNA and either inhibiting their translation or promoting mRNA decay, thereby downregulating corresponding protein expression (80). Their stability and conservation across species contribute to their appeal as biomarkers (33, 46). miRNAs are also becoming increasingly attractive therapeutic targets (31).

SUMMARY OF EMBODIMENTS

The present invention is based, at least in part, on the discovery of an association between certain miRNAs and their presence and function in dysfunctional cells that contribute to a muscle disease or an inflammatory disorder. The disclosure relates to new therapeutics to treat muscle disorders, dystrophies, inflammation, and the side effects of steroid treatments base dupon inactivating the function of miRNAs and/or long non-coding RNAs. In one embodiment, the therapy is an antisense oligonucleotide, such oligonucleotide complementary to any one or more seed sequences or miRNA sequences disclosed herein.

An aspect of the present disclosure includes a composition comprising one or a combination of antisense oligonucleotides complementary to a seed sequence disclosed herein or complementary to a sequence that comprises at least 70% sequence homology to any seed sequence or microRNA disclosed herein or long non-coding RNAs disclosed herein. In some embodiments, the one or combination of oligonucleotides includes a nucleic acid sequence including a first nucleotide sequence domain including from about 10 to about 30 nucleotides that are complementary to any seed sequence or microRNA sequence disclosed herein or complementary to a nucleotide sequence that comprises at least about 70% sequence homology to any seed sequence or microRNA disclosed herein. In some embodiments, the first nucleotide sequence domain is sufficiently complementary to a seed sequence disclosed herein or sufficiently complementary to a miRNA sequence disclosed herein, such that the miRNA sequence or seed sequence loses from about 0.1% of its biological activity to about 100% of its biological activity. In some embodiments, the oligonucleotide is at least 70% complementary to one or a combination of miR-146b, miR-223, miR-142-3p, miR-142-5p, miR-652, miR-455-3p, and miR-455-5p or at least 70% complementary to a seed sequence from miR-146b, miR-223, miR-142-3p, miR-142-5p, miR-652, miR-455-3p, and miR-455-5p. In some embodiments, the one or combination of oligonucleotides includes from about 1% to about 99% of non-natural nucleotides. In some embodiments, the first domain includes a ribonucleic acid sequence at least about 70% complementary to one or a combination of miRNA sequences disclosed herein or one or a combination of seed regions disclosed herein and is capable of inhibiting the regulatory activity of the miRNA sequence and/or the seed regions of the miRNA sequence. In some embodiments, the composition includes more than one antisense oligonucleotide, each oligonucleotide on a separate oligonucleotide molecule and each oligonucleotide including at least one domain including from about 10 to about 30 nucleotides sufficiently complementary to a seed sequence disclosed herein or sufficiently complementary to a sequence that comprises at least 70% sequence homology to any seed sequence or microRNA disclosed herein. In some embodiments, the composition includes more than one antisense oligonucleotide, each oligonucleotide including at least one domain including from about 10 to about 30 nucleotides sufficiently complementary to a sequence that comprises at least 70% sequence homology to any seed sequence or microRNA disclosed herein and at least one domain including a nucleotide sequence encoding an anti-inflammatory agent. In some embodiments, an anti-inflammatory agent is included. In some embodiments, the one or combination of antisense oligonucleotides is encapsulated inside of a liposome. In some embodiments, the one or combination of antisense oligonucleotides is encapsulated inside or a viral vector.

Another aspect of the present disclosure includes a pharmaceutical composition. In some embodiments, the pharmaceutical composition includes a pharmaceutically effective amount of the composition disclosed herein or a salt thereof and a pharmaceutically acceptable carrier. In some embodiments, the pharmaceutical composition includes a therapeutically effective amount of an anti-inflammatory agent or a gene therapy vector. In some embodiments, the pharmaceutical composition includes a nanoparticle that encapsulates the pharmaceutically effective amount of the one or combination of antisense oligonucleotides. In some embodiments, the pharmaceutically effective amount of at least one oligonucleotide is from about 0.001 micrograms/mL to about 10 micrograms/mL in weight of composition over volume of pharmaceutically acceptable carrier. In some embodiments, the pharmaceutically effective amount of at least one oligonucleotide is from about 0.1 micrograms/mL to about 1 micrograms/mL in weight of composition over volume of pharmaceutically acceptable carrier.

Another aspect of the present disclosure includes a cell including any one or more of either or combination of: the antisense oligonucleotides described herein or the pharmaceutical compositions described herein.

Another aspect of the present disclosure includes a method of treating and/or preventing a dystrophin disorder in a subject in need thereof. In some embodiments, the method includes administering a pharmaceutically effective amount of any one of combination of antisense oligonucleotides described herein or pharmaceutical composition described herein.

Another aspect of the present disclosure includes a method of treating and/or preventing inflammation of a tissue or an inflammatory disorder in a subject in need thereof. In some embodiments, the method includes administering a pharmaceutically effective amount of any one or combination of antisense oligonucleotides described herein or pharmaceutical compositions described herein.

Another aspect of the present disclosure includes a method of reducing the toxicity of steroid therapy in a subject in need thereof. In some embodiments, the method includes administering a therapeutically effective amount of any one or combination of antisense oligonucleotides described herein or pharmaceutical compositions described herein.

Another aspect of the present disclosure includes a method of reducing or eliminating the biological activity of microRNA in a cell. In some embodiments, the method includes contacting a cell with a therapeutically effective amount of any one or combination of the nucleic acid sequence described herein or any one or combination of pharmaceutical compositions described herein. Another aspect of the present invention is a method of treating and/or preventing a dystrophin disorder or an inflammatory disorder in a subject in need thereof comprising administering to the subject a therapeutically effective amount of an inhibitor of a miRNA sequence disclosed herein.

BRIEF DESCRIPTION OF THE DRAWINGS

FIG. 1A depicts a Venn diagram illustrates the proportion of miRNAs that are significantly different than untreated mdx muscle in the WT, prednisolone, and vamorolone groups. The 9 miRNAs which were significantly different in all three groups versus untreated mdx, highlighted here, were chosen as a focus set of efficacy-associated miRNAs. FIG. 1B depicts a heat map visualization of the expression of the 9 efficacy associated miRNA markers within each individual mouse. FIG. 1C depicts a bar graph showing the number of miRNAs that significantly increased or decreased in response to either of the drug treatments. FIG. 1D depicts a heat map of the eight unique miRNAs that were increased by prednisolone. (Heat map: red=increased, green=decreased; Pred=prednisolone, Vam=vamorolone)

FIG. 3A-3C depict promoter analysis of miRNAs that indicates NF-κB signaling is a shared target of effective drugs. Transcription factor (NF-κB, GR) binding sites and histone (H3) modifications that mark regulatory regions were examined using ChIP-seq data from ENCODE. DNA binding motifs for each transcription factor were identified through the Factorbook repository. FIG. 3A depicts a schematic of the gene locus for miR-142, illustrating the binding site of 13 neighboring DNA loci that are bound directly by NF-κB. Corresponding epigenetic modification maps are provided showing the location of histone modifications associated with active promoters (H3K4me3) and poised/active enhancers (H3K4me1 and H3K27Ac) in the immediate vicinity of miR-142. FIG. 3B depicts a sequence logo pictogram of base frequency at NF-κB binding sites, with the consensus NF-κB motif provided immediately below. Also provided are five representative NF-κK binding site sequences near miR-142, listed in order from the 5' to 3' direction. FIG. 3C depicts a summary of promoter analysis and literature data indicating each miRNA and known factors or conditions associated with its transcriptional regulation. (Abbreviations: COL27A1, Collagen type 27 alpha 1 chain; IL4, Interleukin 4; MoDCs, Monocyte-induced Dendritic Cells; φ, Macrophage; STATE, Signal transducer and activator of transcription 6).

FIG. 4A-4C depict prednisolone increases miRNAs associated with GR regulation and the 14q32 mega cluster. For the conserved miRNAs that were specifically elevated in prednisolone-treated mouse muscle, the genomic loci, transcription factor binding sites (GR and NF-κB), and histone (H3) modifications were analyzed using ChIP-seq data from ENCODE. DNA motifs bound by the GR were identified through Factorbook. FIG. 4A depicts all six of the miRNAs are transcribed from a well-conserved non-coding RNA cluster (mouse 12F1) which is extensively characterized in humans at the 14q32 locus; that human cluster is depicted here along with corresponding GR binding sites, as well as histone modifications that correspond to active gene promoters (H3K4me3) and poised or active gene enhancer elements (H3K4me1, H3K27Ac). No NF-κB binding sites are found at this locus. FIG. 4B depicts sequence logo pictogram of base frequency at GR binding sites, with the consensus GR motif sequence provided immediately below. Also provided are three representative GR binding site sequences from this locus numbered from the 5' to 3' direction. FIG. 4C depicts a summary of bioinformatic analyses for each miRNA, with a list of conditions that are associated with increased levels of each miRNA. (†=encoded by the 14q32 cluster of miRNAs with GR-bound enhancers; Abbreviations: lncRNA, long non-coding RNA; snoRNA, Small nucleolar RNA)

Levels of miRNAs were assayed by TLDA array cards. Expression levels of miR-142-5p, miR-301a, and miR-455-5p did not reach detection thresholds in any healthy control patient. In contrast, these three inflammatory miRNAs were expressed at levels that were able to be detected and quantified in serum from patients in the DMD group. This is consistent with our findings in mdx muscle and with the chronic inflammation disease state present in DMD.

Figure 8:
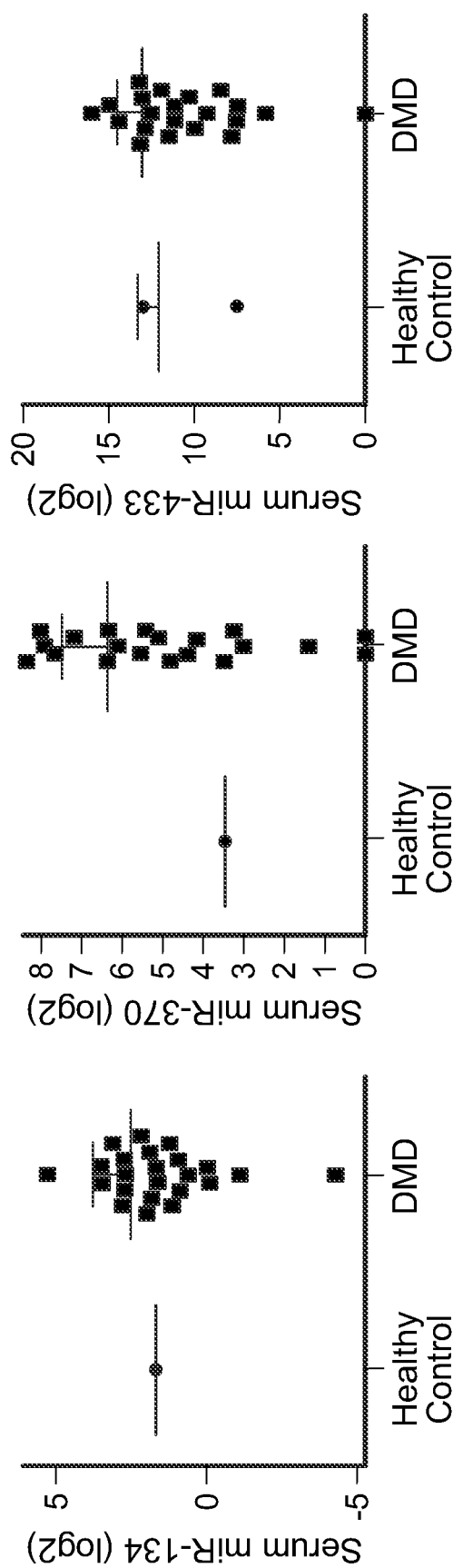

FIG. 8 is a panel of graphs that depict glucocorticoid-regulated miRNAs from the 14q32 non-coding RNA megacluster are increased in serum from DMD patients. Serum was collected from 36 individuals, which included 26 DMD patients and 10 healthy controls. Levels of miRNAs were assayed by TLDA array cards. In healthy controls, miR-134, miR-370, and miR-433 were only shown to be present at levels above detection thresholds in 1 (miR-134 and miR-370) or 2 (miR-433) patients each. In contrast, each of these miRNAs was found to be present and expressed at levels above detection threshold levels in a majority of DMD patient serum samples.

Figure 9B:
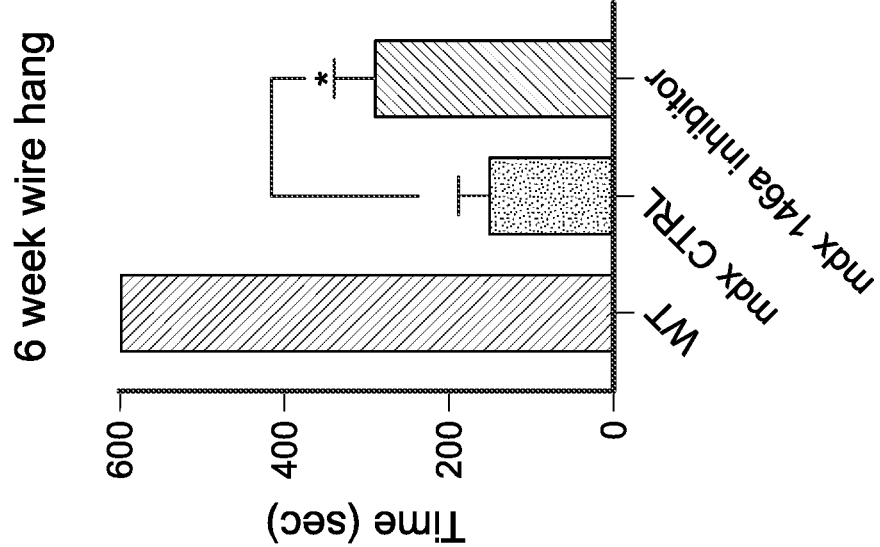

FIG. 9 is a graph that depicts 1-week old mdx mice were given bi-weekly injections of an antisense oligonucleotide complementary to miR-146a (miR-146a inhibitor, n=4), or a non-specific control sequence (CTRL, n=6) (12.5 mg/kg/injection, intra-peritoneal administration, vivo-morpholino chemistry, Gene Tools LLC). Age-matched Wild-type mice (WT) receiving an equal volume of saline were used as a control. At 3 and 6 weeks of the muscle function of mice was measured using a two-limbed wire hang test as previously described [2]. Results show that administration of the miR-146a inhibitor significantly increases muscle function in mdx mice. (**$p<0.01$; *$p<0.05$ one-tailed unpaired Student's t-test.)

Figure 10A:
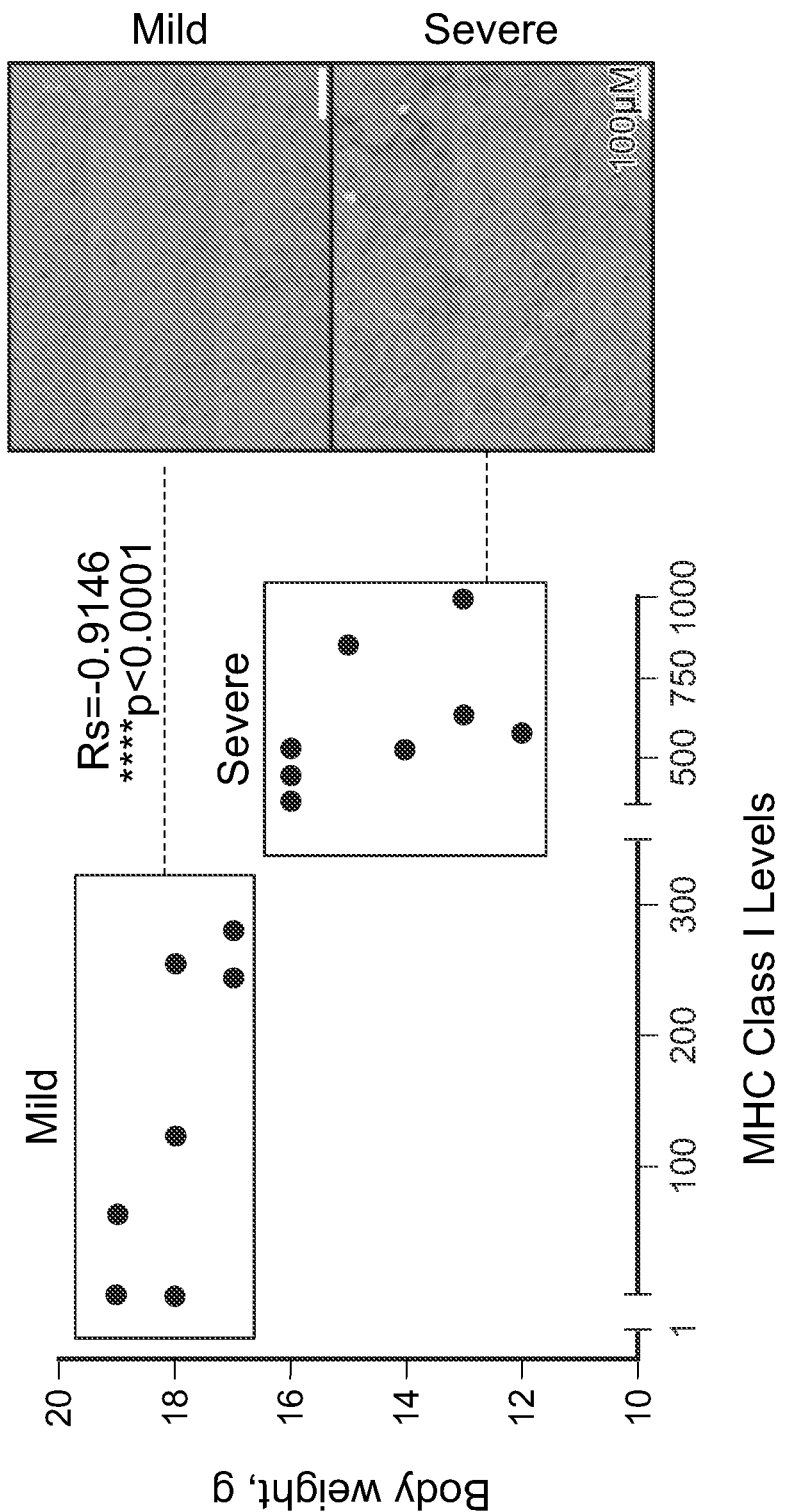
Figure 10B:
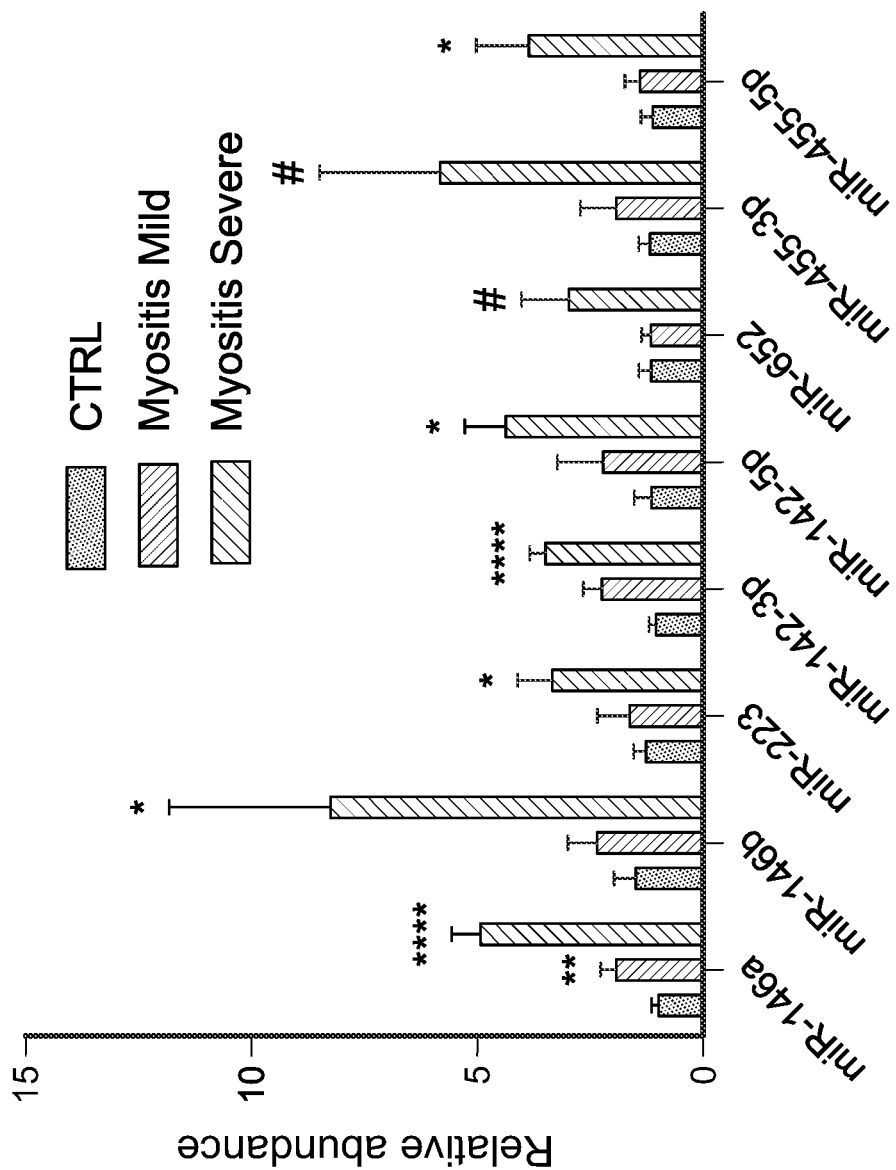
Figures 10F, 10G, 10H:
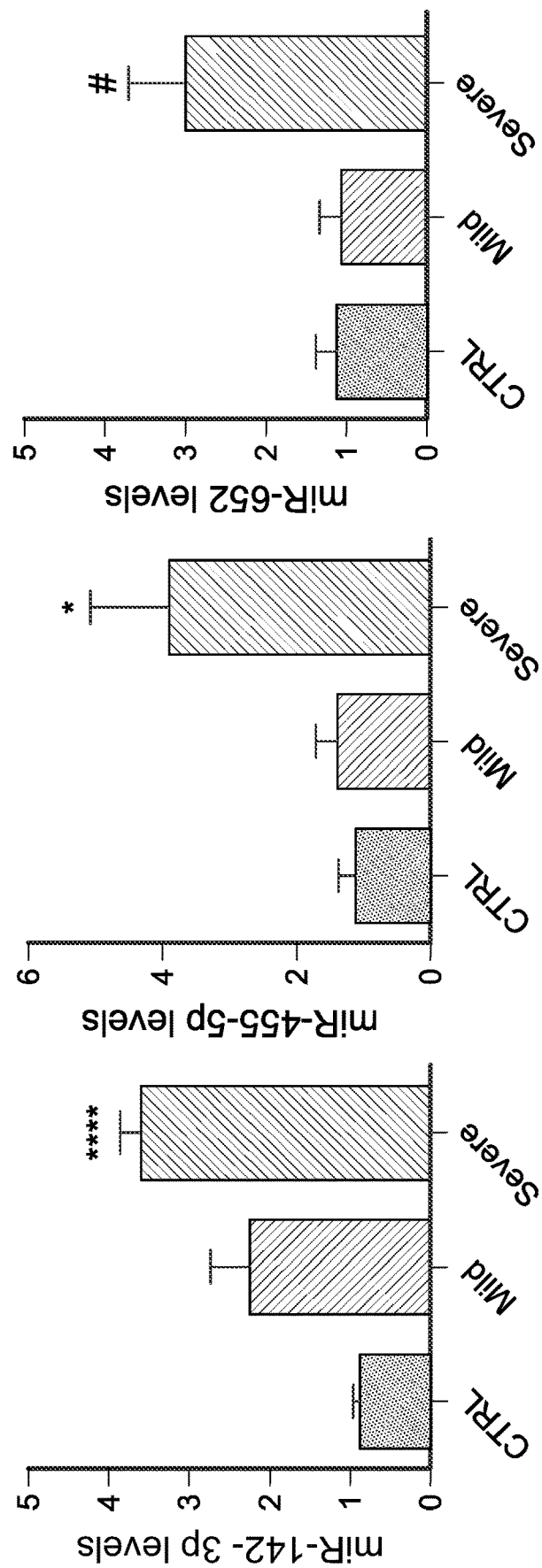

FIG. 10 A-H is a panel of graphs that depict inflammatory microRNAs are elevated in myositis muscle and correspond with disease severity. Inflammatory microRNAs were assessed in a mouse model of myositis, an autoimmune inflammatory muscle disorder. The generation and characterization of the mouse model, referred to at the HT myositis mouse, has been previously described (Nagaraju K et al. Conditional up-regulation of MHC class I in skeletal muscle leads to self-sustaining autoimmune myositis and myositis-specific autoantibodies. Proceedings of the National Academy of Sciences of the United States of America 97: 9209-9214, 2000). HT myositis mice have transgenic expression of a Major Histocompatibility Complex Class I (MHC Class I) transgene which drives disease and has been shown to be highly variable. FIG. 10A Disease severity of these mice was classified by their weight at sacrifice (we had observed severe mice weigh <16 g at time of sacrifice) and by extent of transgene expression via qRT-PCR. Severe myositis mice were classified as mice weighing 16 g or less and having transgene expression of >350-fold. FIG. 10B qRT-PCR was performed to quantify the indicated miRNAs using RNA extracted from the quadriceps of HT myositis mice with mild or severe disease. (FIG. 10C-FIG. 10H) Same qRT-PCR data from FIG. 10A showing the most significantly elevated miRNAs in severe HT mice. Age-matched Wild-type mice were used as controls. One-way ANOVA; #$p<0.10$; *$p<0.05$; $p<0.01$; *$p<0.001$; ****$p<0.000$.

FIG. 11A-11C depict how miR-146a and miR-142-3p bind to and activate the inflammatory Toll-like receptor 7. 11A) RAW 264.7 murine macrophage cells were treated with indicated treatments for 6, 24 and 48 h: 1) negative CTRL (−)=no treatment; 2) Gardiquimod (3 ug/mL)=+control for TLR7 activation; 3) miR-146a (5 ug) sequence: ugagaacugaauuccauggguu (SEQ ID NO:70), 4) miR-142-3p (5 ug) uguaguguuccuacuuuaugga (SEQ ID NO:71); 5) miR-146amut (5 ug, sequence: agagaacagaaaaccacgggaa (SEQ ID NO:72)); 6) miR-142-3pmut (5 ug, sequence: agaagagaaaccaacaaaaugga (SEQ ID NO:73)). After the indicated timepoints, media was collected and an ALPHA-LISA was performed to measure the amount of secreted TNF-α. Results demonstrate miR-146a and miR-142-3p activate secretion of TNF-α while mutation of the uridines prevents activation and suggest both microRNAs activate TLR7. B) RAW 264.7 murine macrophage cells were treated with gardiquimod or the indicated microRNAs for 48 h, where peak activation was observed. Secreted TNF-α was assessed as in A) using an ALPHA-LISA. C) HEK 293 cells were transfected with a plasmid encoding TLR7-YFP (green) and either a Cy5-miR-146a or Cy5-miR-142-3p (red). 48 h post-transfection cells were fixed and confocal microscopy was performed using an Olympus FV-1000 at 100× magnification. Results show co-localization of TLR7 and the Cy5-labeled miRNAs suggesting these microRNAs are binding to TLR7. Data collectively show that both miR-146a and miR-142-3p act as ligands of TLR7, promoting downstream activation of inflammatory gene expression.

Figure 12A:
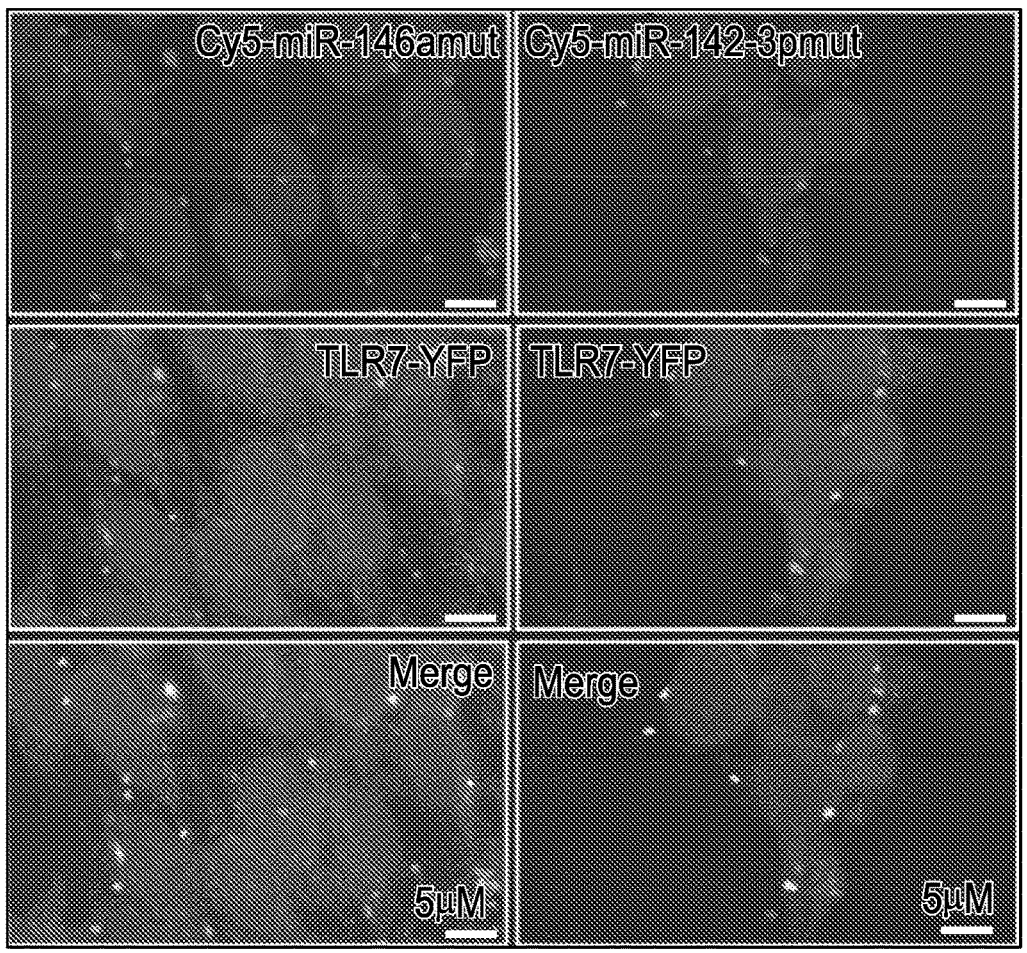
Figure 12B:
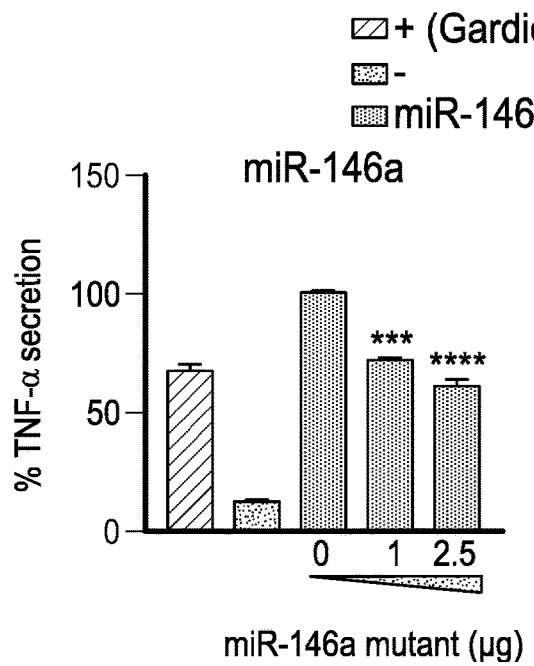
Figure 12C:
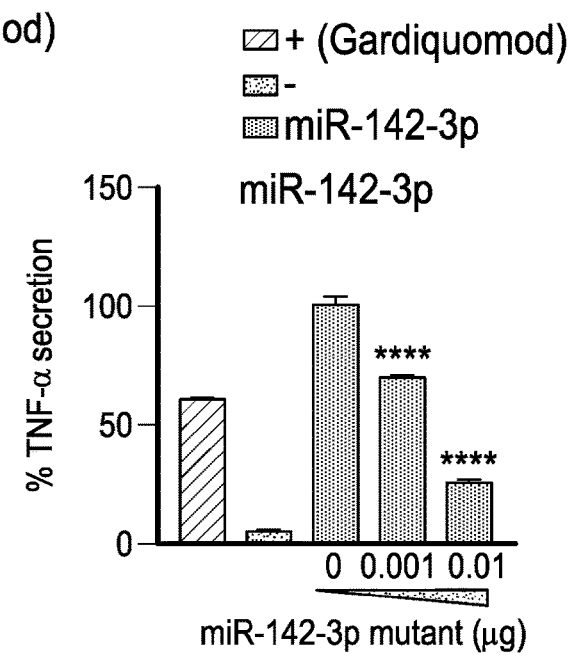
Figure 13A:
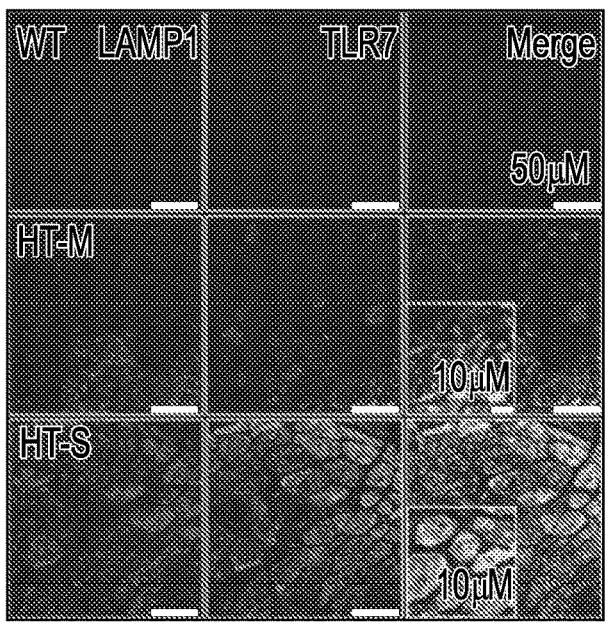
Figure 13B:
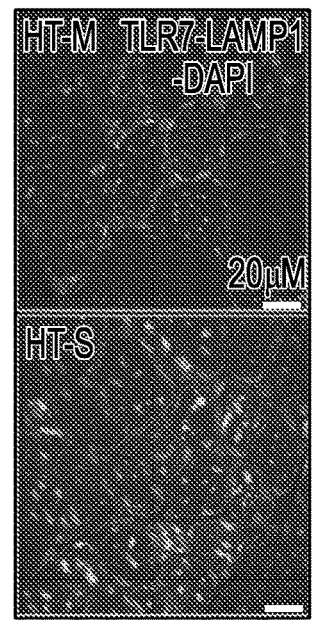
Figure 13C:
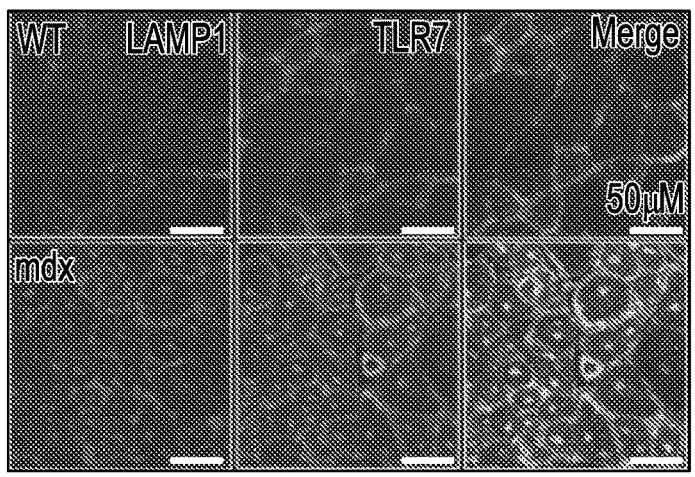
Figure 13D:
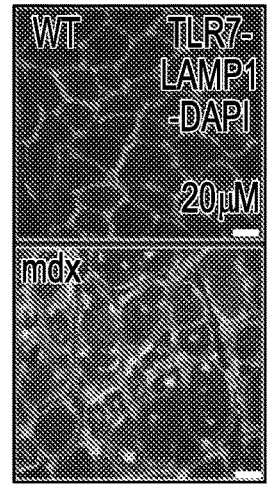
Figure 13E:
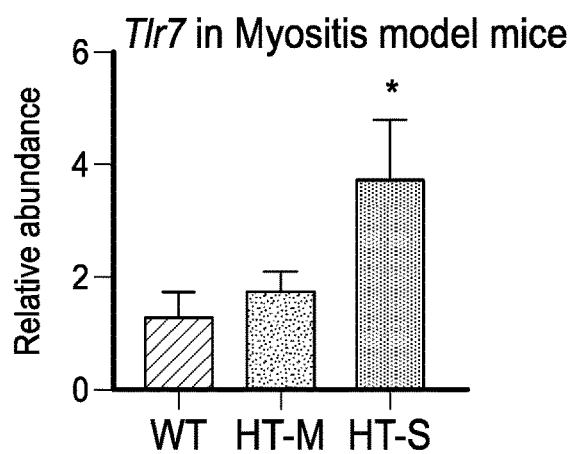
Figure 13F:
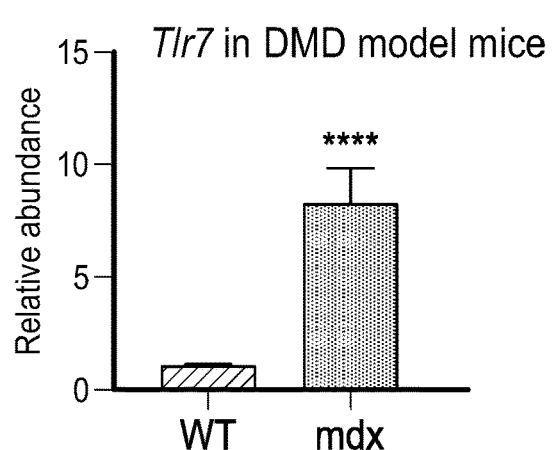

FIG. 12A-12C depict how miR-146a and miR-142-3p mutant microRNAs bind to TLR7 and can compete away TLR7 activation by miR-146a and miR-142-3p. A) HEK 293 cells were transfected with a plasmid encoding TLR7-YFP (green) and either a Cy5-miR-146a mutant microRNA or Cy5-miR-142-3p mutant microRNA (red) 0.48 h post-transfection cells were fixed and confocal microscopy was performed using an Olympus FV-1000 at 100× magnification. Results show co-localization of TLR7 with the mutant Cy5-labeled miRNAs suggesting these uridine-deficient microRNAs can bind to TLR7 in a similar manner to the uridine-containing miR-146a and miR-142-3p sequences. B) RAW 264.7 murine macrophage cells were treated with a constant dose of miR-146a with increasing doses of a uridine-deficient miR-146a mutant. 48 hours later TLR7 activation was assessed via secreted TNF-α. Results demonstrate that miR-146amut can compete away the activation of TLR7 by miR-146a. C) RAW 264.7 murine macrophage cells were treated with a constant dose of miR-12-3p with increasing doses of a uridine-deficient miR-142-3pmutant. 48 hours later TLR7 activation was assessed via secreted TNF-α.

FIG. 13A-13F. Increased TLR7 staining and macrophage infiltration in severe myositis and mdx muscles. (13A-13B) Representative images of WT, Mild (HT-M), and Severe (HT-S) myositis quadriceps immunolabeled with an antibody against TLR7 (middle panels) and LAMP1 (left hand-side panels—dark grey). DAPI counterstain was to visualize nuclei and is shown in blue. (13A) Images were taken using a VS-120 scanning microscope at 20× magnification, Bar=50 uM. (13B) Images from a second set of stained sections (stained as in A) were taken using confocal microscopy Bar=20 μM. (13C-13D) Representative images of WT and mdx quadriceps muscles immunolabeled with an antibody against TLR7 (grey) and LAMP1 (dark grey). DAPI counterstain was to visualize nuclei and is shown in blue. In (13C) images were taken using a VS-120 scanning microscope as in (13A) and in (13D) images were taking using confocal microscopy as in (13B). (13E-13F) Quantitative RT-PCR was performed to assess expression of: (13A) Tlr7, mRNA using RNA extracted from the quadriceps of (13E) Myositis mild (HT-M), Myositis severe (HT-S), or WT mice (n=5, 6 and 8 for WT, mild and HT-S, respectively, ANOVA)

or (13F) WT and mdx mice (n=6, ANOVA). Data were normalized to 18s rRNA and are presented as ±SEM. *P<0.05; ****p<0.0001).

DETAILED DESCRIPTION OF EMBODIMENTS

Definitions

The term "about" as used herein when referring to a measurable value such as an amount, a temporal duration, and the like, is meant to encompass variations of ±20%, ±10%, ±5%, ±1%, ±0.9%, ±0.8%, ±0.7%, ±0.6%, ±0.5%, ±0.4%, ±0.3%, ±0.2% or ±0.1% from the specified value, as such variations are appropriate to perform the disclosed methods.

"AAV virion" refers to a complete virus particle, such as for example a wild type AAV virion particle, which comprises single stranded genome DNA packaged into AAV capsid proteins. The single stranded nucleic acid molecule is either sense strand or antisense strand, as both strands are equally infectious. A "rAAV virion" refers to a recombinant AAV virus particle, i.e. a particle which is infectious but replication defective. It is composed of an AAV protein shell and comprises a rAAV vector. In the context of the present invention the protein shell may be of a different serotype than the rAAV vector. An AAV virion of the invention may thus be composed a protein shell, i.e. the icosahedral capsid, which comprises capsid proteins (VP1, VP2, and/or VP3) of one AAV serotype, e.g. AAV serotype 6, whereas the rAAV vector contained in that AAV6 virion may be any of the rAAVX vectors described above, including a rAAV6 vector. An "rAAV6 virion" comprises capsid proteins of AAV serotype 6, while e.g. a rAAV2 virion comprises capsid proteins of AAV serotype 2, whereby either may comprise any of rAAVX vectors of the invention. "AAV helper functions" generally refers to the corresponding AAV functions required for rAAV replication and packaging supplied to the rAAV virion or rAAV vector in trans. AAV helper functions complement the AAV functions which are missing in the rAAV vector, but they lack AAV ITRs (which are provided by the rAAV vector). AAV helper functions include the two major ORFs of AAV, namely the rep coding region and the cap coding region or functional substantially identical sequences thereof. Rep and Cap regions are well known in the art, see e.g. Chiorini et al. (1999, J. of Virology, Vol 73(2): 1309-1319) or U.S. Pat. No. 5,139,941, incorporated herein by reference in its entirety. The AAV helper functions can be supplied on a AAV helper construct. Introduction of the helper construct by into the host cell can occur e.g. by transformation or transduction prior to or concurrently with the introduction of the rAAV vector. The AAV helper constructs of the invention may thus be chosen such that they produce the desired combination of serotypes for the rAAV virion's capsid proteins on the one hand and for the rAAV vector replication and packaging on the other hand.

"AAV helper virus" provides additional functions required for AAV replication and packaging. Suitable AAV helper viruses include adenoviruses, herpes simplex viruses (such as HSV types 1 and 2) and vaccinia viruses. The additional functions provided by the helper virus can also be introduced into the host cell via vectors, as described in U.S. Pat. No. 6,531,456 incorporated herein by reference in its entirety.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, the term "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, "either," "one of," "only one of," or "exactly one of." "Consisting essentially of," when used in the claims, shall have its ordinary meaning as used in the field of patent law.

As used herein, the phrase "integer from X to Y" means any integer that includes the endpoints. That is, where a range is disclosed, each integer in the range including the endpoints is disclosed. For example, the phrase "integer from X to Y" discloses about 1, 2, 3, 4, or 5 as well as the range from about 1 to about 5.

As used herein, "activity" in the context of interfering RNA activity refers to the ability of a nucleic acid to bind to a target miRNA sequence and inhibit or reduce the activity of the target miRNA. Such activity can be measured in a variety of ways as known in the art. For example, mRNA expression, activity, or level of an miRNA sequence can be measured. For example, a cell can be transfected with, transformed with, or contacted with an interfering RNA molecule disclosed herein. The activity can be measured by monitoring the amount of miRNA-target mRNA expressed or polypeptide translated and comparing mRNA expression amount or polypeptide translation to a amounts in a cell not transfected, transformed, or contacted with an interfering RNA molecule disclosed herein.

The term "analog" as used herein refers to compounds that are similar but not identical in chemical formula and share the same or substantially similar function of the compound with the similar chemical formula. In some embodiments, the analog is a mutant, variant or modified sequence as compared to the non-modified or wild-type sequence upon which it is based. In some embodiments, compositions of the disclosure include modifications or analogs that are complementary to a nucleotide sequence that is at least about 70%, about 75%, about 80%, about 85%, about 90% about 91%, about 92%, about 93%, about 94%, about 95%, about 96%, about 97%, about 98% or about 99% homology to any of the disclosed nucleic acids herein. In some embodiments the analog is a functional fragment of any of the disclosed nucleic acid sequences. In some embodiments, the analog is a salt of any of the disclosed nucleic acid sequences. In some embodiments, the analog may retain about 99%, 98%, 97%, 96%, 95%, 94%, 93%, 92%, 91%, 90%, 85%, 80%, 75%, 70% or less biological activity as compared to the natural or wild-type sequences upon which it is based. In some embodiments, the analog is capable of inhibiting the biological activity of any of the disclosed miRNA sequences or seed sequences disclosed herein by about 99%, 98%, 97%, 96%, 95%, 94%, 93%, 92%, 91%, 90%, 85%, 80%, 75%, 70% or less (e.g. to less than about 1.0%).

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The term "functional fragment" means any portion of a polypeptide or nucleic acid sequence from which the respective full-length polypeptide or nucleic acid relates that is of a sufficient length and has a sufficient structure to confer a biological affect that is at least similar or substantially similar to the full-length polypeptide or nucleic acid upon which the fragment is based. In some embodiments, a functional fragment is a portion of a full-length or wild-type nucleic acid sequence that encodes any one of the nucleic acid sequences disclosed herein, and said portion encodes a polypeptide of a certain length and/or structure that is less than full-length but encodes a domain that still biologically functional as compared to the full-length or wild-type protein. In some embodiments, the functional fragment may have a reduced biological activity, about equivalent biological activity, or an enhanced biological activity as compared to the wild-type or full-length polypeptide sequence upon which the fragment is based. In some embodiments, the functional fragment is derived from the sequence of an organism, such as a human. In such embodiments, the functional fragment may retain 99%, 98%, 97%, 96%, 95%, 94%, 93%, 92%, 91%, or 90% sequence identity to the sequence upon which the sequence is derived. In some embodiments, the functional fragment may retain 85%, 80%, 75%, 70%, 65%, or 60% sequence homology to the wild-type sequence upon which the sequence is derived. In such embodiments, the functional fragment may retain about 99%, 98%, 97%, 96%, 95%, 94%, 93%, 92%, 91%, 90%, 85%, 80%, 75%, 70% or less biological activity as compared to the natural or wild-type sequences upon which it is based. In some embodiments, the composition provided comprises one, two, three or more a nucleic acid sequences or salts thereof that are complementary to functional fragments retaining 99%, 98%, 97%, 96%, 95%, 94%, 93%, 92%, 91%, 90%, 85%, 80%, 75%, or 70% sequence identity to any sequence identified in Tables 1, 2, 3 or 4. In some embodiments, the composition provided comprises a therapeutically effective amount of a nucleic acid molecule or multiple nucleic acid molecules or salts thereof that comprise one, two, three or more a nucleic acid sequences or salts thereof that are individually or collectively complementary to variants having 99%, 98%, 97%, 96%, 95%, 94%, 93%, 92%, 91%, 90%, 85%, 80%, 75%, or 70% sequence identity to any sequences identified in Tables 1, 2, 3 or 4. In the case of bispecific antisense oligonucleotides, such embodiments comprise a composition comprising a therapeutically effective amount of a nucleic acid molecule or multiple nucleic acid molecules or salts thereof, wherein each nucleic acid molecule or salt thereof comprises a first and a second nucleic acid sequences that comprise at least one domain that is complementary to a variant having 99%, 98%, 97%, 96%, 95%, 94%, 93%, 92%, 91%, 90%, 85%, 80%, 75%, or 70% sequence identity to any sequence identified in Tables 1-4.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence. In some embodiments, association or binding of a disclosed nucleic acid sequence is hybridizing with a nucleic acid sequence or molecule within a target cell.

As used herein, "sequence identity" also termed "sequence homology" is determined by using the standalone executable BLAST engine program for blasting two sequences (bl2seq), which can be retrieved from the National Center for Biotechnology Information (NCBI) ftp site, using the default parameters (Tatusova and Madden, FEMS Microbiol Lett., 1999, 174, 247-250; which is incorporated herein by reference in its entirety). The "percent identity" or "percent homology" of two polynucleotide or two polypeptide sequences is determined by comparing the sequences using the GAP computer program (a part of the GCG Wisconsin Package, version 10.3 (Accelrys, San Diego, Calif.)) using its default parameters. "Identical" or "identity" as used herein in the context of two or more nucleic acids or amino acid sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may he performed manually or by using a computer sequence algorithm such as BLAST or BLAST 2.0. Briefly, the BLAST algorithm, which stands for Basic Local Alignment Search Tool is suitable for determining sequence similarity. Software for performing BLAST analyses is publicly available through the National Center for Biotechnology Information (http://www.ncbi.nlm.nih.gov). This algorithm involves first identifying high scoring sequence pair (HSPs) by identifying short words of length Win the query sequence that either match or satisfy some positive-valued threshold score T when aligned with a word of the same length in a database sequence. T is referred to as the neighborhood word score threshold (Altschul et al., supra). These initial neighborhood word hits act as seeds for initiating searches to find HSPs containing them. The word hits are extended in both directions along each sequence for as far as the cumulative alignment score can be increased. Extension for the word hits in each direction are halted when: 1) the cumulative alignment score falls off by the quantity X from its maximum achieved value; 2) the cumulative score goes to zero or below, due to the accumulation of one or more negative-scoring residue alignments; or 3) the end of either sequence is reached. The Blast algorithm parameters W, T and X determine the sensitivity and speed of the alignment. The Blast program uses as defaults a word length (W) of 11, the BLOSUM62 scoring matrix (see Henikoff et al., Proc. Natl. Acad. Sci. USA, 1992, 89, 10915-10919, which is incorporated herein by reference in its entirety) alignments (B) of 50, expectation (E) of 10, M=5, N=4, and a comparison of both strands. The BLAST algorithm (Karlin et al., Proc. Natl. Acad. Sci. USA, 1993, 90, 5873-5787, which is incorporated herein by reference in its entirety) and Gapped BLAST perform a statistical analysis of the similarity between two sequences. One measure of similarity provided by the BLAST algorithm is the smallest sum probability (P(N)), which provides an indication of the probability by which a match between two nucleotide sequences would occur by chance. For example, a nucleic acid is considered similar to another if the smallest sum probability in comparison of the test nucleic acid to the other nucleic acid is less than about 1, less than about 0.1, less than about 0.01, and less than about 0.001. Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

The present disclosure also relates to isotopically-enriched compounds, which are structurally similar to the nucleic acid sequences disclosed herein, but for the fact that one or more atoms of the nucleic acid sequence are replaced by an atom having an atomic mass or mass number different from the atomic mass or mass number usually found in nature. Examples of isotopes that can be incorporated into compounds of the disclosure include isotopes of hydrogen, carbon, nitrogen, oxygen, phosphorous, fluorine and chlorine, such as $^2H$, $^3H$, $^{13}C$, $^{14}C$, $^{15}N$, $^{16}O$, $^{17}O$, $^{31}F$, $^{32}F$, $^{35}S$, $^{18}F$, and $^{36}Cl$. Nucleic acids of the present disclosures that contain the aforementioned isotopes and/or other isotopes of other atoms are within the scope of this disclosure. Certain isotopically-labelled compounds of the present disclosure, for example those into which radioactive isotopes such as 3H and 14C are incorporated, are useful in drug and/or substrate tissue distribution assays. Tritiated, i.e., 3H, and carbon-14, i.e., 14C, isotopes are particularly preferred for their ease of preparation and detection. Further, substitution with heavier isotopes such as deuterium, i.e., 2H, can afford certain therapeutic advantages resulting from greater metabolic stability, for example increased in vivo half-life or reduced dosage requirements and, hence, may be preferred in some circumstances. Isotopically enriched compounds of this disclosure can generally be prepared by substituting a readily available isotopically labeled reagent for a non-isotopically enriched reagent. In some embodiments, the compositions of the disclosure comprise one or more nucleic acid sequences disclosed herein comprising an miRNA domain with one or more atoms replaced with a radioisotope. In some embodiments, such radioactive nucleic acid sequences may be a component in a pharmaceutical composition that delivers a radioisotope to a cancer cell after administration to a subject in need of the treatment. In some embodiments, the radioactive nucleic acid sequence can be used as a targeted imaging agent whereupon, after administration to a subject, one or more imaging techniques may be used to detect where within a subject one or a plurality of cancer cells may exist within the subject. Such imaging techniques include PET scanning or CT scanning.

The disclosure relates to nucleic acids disclosed herein unsolvated forms as well as solvated forms, including hydrated forms. The compounds of the disclosure also are capable of forming both pharmaceutically acceptable salts, including but not limited to acid addition and/or base addition salts. Furthermore, compounds of the present disclosure may exist in various solid states including an amorphous form (noncrystalline form), and in the form of clathrates, prodrugs, polymorphs, bio-hydrolyzable esters, racemic mixtures, non-racemic mixtures, or as purified stereoisomers including, but not limited to, optically pure enantiomers and diastereomers. In general, all of these forms can be used as an alternative form to the free base or free acid forms of the compounds, as described above and are intended to be encompassed within the scope of the present disclosure.

"Nucleoside" means a nucleobase linked to a sugar moiety.

"Nucleotide" means a nucleoside having a phosphate group covalently linked to the sugar portion of a nucleoside. In some embodiments, the nucleotide is characterized as being modified if the 3' phosphate group is covalently linked to a contiguous nucleotide by any linkage other than a phosphodiester bond.

The disclosure relates to any nucleic acid sequence disclosed herein also comprising one or a plurality of modified nucleotides. In some embodiments, the compositions of the disclosure comprise a nucleic acid sequence disclosed herein comprising one or a plurality of modified oligonucleotides. In some embodiments, the composition comprises any one, two, three or more nucleic acid sequences disclosed herein comprising a modified oligonucleotide consisting of a number of linked nucleosides. Thus, the compound or compounds may include additional substituents or conjugates. Unless otherwise indicated, the compound does not include any additional nucleosides beyond those of the modified oligonucleotide.

"Modified oligonucleotide" means an oligonucleotide having one or more modifications relative to a naturally occurring terminus, sugar, nucleobase, and/or internucleoside linkage. A modified oligonucleotide may comprise unmodified nucleosides at one or a plurality of any of the positions of the disclosed nucleic acids.

"Single-stranded modified oligonucleotide" means a modified oligonucleotide which is not hybridized to a complementary strand. In some embodiments, the compositions of the disclosure relate to a nucleic acid molecule that is a single-stranded modified oligonucleotide comprising any one or more domains disclosed herein.

The nucleic acid sequences of the disclosure can comprise one or more modified nucleosides. The terms "modified nucleoside" mean a nucleoside having any change from a naturally occurring nucleoside. A modified nucleoside may have a modified sugar, and an unmodified nucleobase. A modified nucleoside may have a modified sugar and a modified nucleobase. A modified nucleoside may have a natural sugar and a modified nucleobase. In certain embodiments, a modified nucleoside is a bicyclic nucleoside. In certain embodiments, a modified nucleoside is a non-bicyclic nucleoside.

A "polymorph" refers to solid crystalline forms of the one or more nucleic acid sequences disclosed herein. In some embodiments, one or more nucleic acids disclosed herein are in a polymorph form. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Different physical properties of polymorphs can affect their processing.

The nucleic acid sequences, proteins or other agents of the present disclosure can be administered, inter alia, as pharmaceutically acceptable salts, esters, or amides. The term "salts" refers to inorganic and organic salts of compounds of the present disclosure. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," J Pharm Sci, 66: 1-19 (1977), which discloses salt forms of nucleic acids and which is incorporated by reference in its entirety in its entirety.

The terms "polynucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after synthesis or polymerization, such as by conjugation with a labeling component.

The oligonucleotides of the disclosure also include those nucleic acid sequences disclosed herein that comprise nucleosides connected by charged linkages, and/or whose sequences are divided into at least two subsequences. In some embodiments, a first, second, and third subsequence or domains include an aptamer domain and a miRNA domain. In some embodiments the nucleic acid sequence comprises a sgRNA guide sequence with a nucleotide binding domain (or DNA-binding domain), a Cas-binding domain, and a transcription terminator domain. In some embodiments, a first, second, third, fourth, and/or fifth subsequence or domains include a nucleotide binding domain, a Cas-binding domain, and a transcription terminator sequence, but, if any two domains are present they must be oriented such that the aptamer domain precedes the miRNA domain. If the embodiment includes a sgRNA sequence or sequence elements, such sequences, in some embodiments, the nucleic acid sequence comprises a nucleotide binding domain which precede a Cas-binding domain which, in turn precedes the transcription terminator domain in a 5' to 3' orientation. Any of the nucleosides within any of the domains may be 2'-substituted-nucleosides linked by a first type of linkage. The second subsequence includes nucleosides linked by a second type of linkage.

In the context of this disclosure, the term "oligonucleotide" also refers to a plurality of nucleotides joined together in a specific sequence from naturally and non-naturally occurring nucleobases. Nucleobases of the disclosure are joined through a sugar moiety via phosphorus linkages, and may include any one or combination of adenine, guanine, cytosine, uracil, thymine, xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thiolalkyl guanines, 8-hydroxyl guanine and other 8-substituted guanines, other aza and deaza uracils, other aza and deaza thymidines, other aza and deaza cytosines, other aza and deaza adenines, other aza and deaza guanines, 5-trifluoromethyl uracil and 5-trifluoro cytosine. The sugar moiety may be deoxyribose or ribose. The sugar moiety may be a modified deoxyribose or ribose with one or more modifications on the $C_1$, $C_2$, $C_3$, $C_4$, and/or $C_5$ carbons. The oligonucleotides of the disclosure may also comprise modified nucleobases or nucleobases having other modifications consistent with the spirit of this disclosure, and in particular modifications that increase their nuclease resistance in order to facilitate their use as therapeutic, diagnostic or research reagents.

The terms "polypeptide", "peptide" and "protein" are used interchangeably herein to refer to polymers of amino acids of any length. The polymer may be linear or branched, it may comprise modified amino acids, and it may be interrupted by non-natural amino acids or chemical groups that are not amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

As used herein, "more than one" or "two or more" 2, 3, 4, 5, 6, 7, 8, 9, or 10 or more where "more" may be an positive integer above 10 that corresponding to the length of nucleotides in the nucleotide sequences. In some embodiments, "more than one" means 2, 3, 4, or 5 of the amino acids or nucleic acids or mutations described herein. In some embodiments, "more than one" means 2, 3, or 4 of the amino acids or nucleic acids or mutations described herein. In some embodiments, "more than one" means 2 or 3 of the amino acids or nucleic acids or mutations described herein. In some embodiments, "more than one" means 2 of the amino acids or nucleic acids or mutations described herein.

"Sugar moiety" means a naturally occurring furanosyl or a modified sugar moiety.

"Modified sugar moiety" means a substituted sugar moiety or a sugar surrogate.

"Substituted sugar moiety" means a furanosyl that is not a naturally occurring furanosyl. Substituted sugar moieties include, but are not limited to sugar moieties comprising modifications at the 2'-position, the 5'-position and/or the 4'-position of a naturally occurring furanosyl. Certain substituted sugar moieties are bicyclic sugar moieties.

"Sugar surrogate" means a structure that does not comprise a furanosyl and that is capable of replacing the naturally occurring furanosyl of a nucleoside, such that the resulting nucleoside is capable of (1) incorporation into an oligonucleotide and (2) hybridization to a complementary nucleoside. Such structures include relatively simple changes to the furanosyl, such as rings comprising a different number of atoms (e.g., 4, 6, or 7-membered rings); replacement of the oxygen of the furanosyl with a non-oxygen atom (e.g., carbon, sulfur, or nitrogen); or both a change in the number of atoms and a replacement of the oxygen. Such structures may also comprise substitutions corresponding with those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholinos, cyclohexenyls and cyclohexitols. In some embodiments, the nucleic acid of the disclosure comprises one or a plurality of sugar surrogates at one or a plurality of nucleotide positions.

The term "therapeutically effective amount" mean a quantity sufficient to achieve a desired therapeutic and/or prophylactic effect, for example, an amount which results in the prevention or amelioration of or a decrease in the symptoms associated with a disease that is being treated. The amount of composition administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The regimen of administration can affect what constitutes an effective amount. The compound of the disclosure can be administered to the subject either prior to or after the onset of disease or disorder. Further, several divided dosages, as well as staggered dosages, can be administered daily or sequentially, or the dose can be continuously infused, or can be a bolus injection. Further, the dosages of the compound(s) of the disclosure can be proportionally increased or decreased as indicated by the exigencies of the therapeutic or prophylactic situation. Typically, an effective amount of the compounds of the present disclosure, sufficient for achieving a therapeutic or prophylactic effect, range from about 0.000001 mg per kilogram body weight per day to about 10,000 mg per kilogram body weight per day. Preferably, the dosage ranges are from about 0.0001 mg per kilogram body weight per day to about 100 mg per kilogram body weight per day. A therapeutically effective amount of a pharmaceutical composition comprising any one or a plurality of any of the nucleic acid sequences disclosed herein can also be administered in combination with two, three, four or more nucleic acid sequences disclosed herein, or with one or more additional therapeutic compounds. Those skilled in the art will recognize and determine a therapeutically effective amount of any of the nucleic acid sequences disclosed herein whether calculated when administered alone or part of a therapeutic regimen that includes one or more inflammatory corticosteroids and/or one or more one or more other therapeutic agents and/or one or more other therapeutic treatments or interventions. Generally, therapeutically effective amount refers to an amount of a nucleic acid sequence that alone or in combination with one or a plurality of other therapeutic compounds causes a transfection of the nucleic acid sequence into a target cell and/or hybridization of the one or more miRNA sufficient reduce or inhibit activity of the miRNA within the cell, thereby ameliorating symptoms, or reversing, preventing or reducing the rate of progress of disease, or extend life span of a subject when administered alone or in combination with other therapeutic agents or treatments as compared to the symptoms, rate of progress of disease, or life span of an individual not receiving a therapeutically effective amount the one or plurality of nucleic cells disclosed herein.

As used herein, the terms "treat," "treated," or "treating" can refer to therapeutic treatment wherein the object is to slow down (lessen) an undesired physiological condition, disorder or disease, or obtain beneficial or desired clinical results. For purposes of the embodiments described herein, beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of condition, disorder or disease. Treatment can also include eliciting a clinically significant response without excessive levels of side effects. Treatment also includes prolonging survival as compared to expected survival if not receiving treatment. Thus, "treatment of inflammation" means an activity that prevents, alleviates or ameliorates any of the primary phenomena or secondary symptoms associated with inflammation; "treatment of a steroid side effect" means an activity that prevents, alleviates or ameliorates any of the primary phenomena or secondary symptoms associated with a steroid treatment; and "treatment of a muscle disease" means an activity that prevents, alleviates or ameliorates any of the primary phenomena or secondary symptoms associated with a muscle disease. Any of the variants or antisense sequences disclosed herein may treat inflammation or a muscle disorder.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another. In some embodiments, the composition of the disclosure comprises one or a plurality of tautomers of given forms. It will be apparent to one skilled in the art that, in some embodiments, the compositions of this disclosure comprise nucleic acid sequences or molecules with nucleic acids that may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by 13C- or 14C-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium (3H), iodine-125 (125I), or carbon-14 (14C) including the radioisotopes of Table 2. All isotopic variations of the compounds of the present disclosure, whether radioactive or not, are encompassed within the scope of the present disclosure.

A "base," as used herein, means a group selected from the following: adenine, guanine, cytosine, uracil, thymine, uridine, pyrimidine, purine, pseudouridine, inosine, hypoxanthine, rhodamine, fluroscein, 2-aminopurine, cytidine, 2'-deoxycytidine, 1,3-Diaza-2-oxophenothiazine, dihydrouridine, queuosine, wyosine, cyanophage S-2L diaminopurine, isoguanine, isocytosine, diaminopyrimidine, 2,4-difluorotoluene, 4-methylbenzimidazole, isoquinoline, pyrrolo[2,3-b]pyridine, 2-amino-6-(2-thienyl)purine, pyrrole-2-carbaldehyde, 2,6-bis(ethylthiomethyl)pyridine, pyridine-2,6-dicarboxamide, 2'-deoxyinosine, 2-amino-8-(2-thienyl)purine, pyridine-2-one, 7-(2-thienyl)imidazo [4,5-b] pyridine, pyrrole-2-carbaldehyde, 4-[3-(6-aminohexanamido)-1-propynyl]-2-nitropyrrole, or modified derivative thereof.

The terms "subject," "individual," and "patient" are used interchangeably herein to refer to a vertebrate, preferably a mammal, more preferably a human. Mammals include, but are not limited to, murines, simians, humans, farm animals, cows, pigs, goats, sheep, horses, dogs, sport animals, and pets. Tissues, cells and their progeny obtained in vivo or cultured in vitro are also encompassed by the definition of the term "subject." The term "subject" is also used throughout the specification in some embodiments to describe an animal from which a cell sample is taken or an animal to which a disclosed cell or nucleic acid sequences have been administered. In some embodiment, the animal is a human. For treatment of those conditions which are specific for a specific subject, such as a human being, the term "patient" may be interchangeably used. In some instances in the description of the present disclosure, the term "patient" will refer to human patients suffering from a particular disease or disorder. In some embodiments, the subject may be a non-human animal from which an endothelial cell sample is isolated or provided. The term "mammal" encompasses both humans and non-humans and includes but is not limited to humans, non-human primates, canines, felines, murines, bovines, equines, caprines, and porcines.

As used herein, the phrase "in need thereof" means that the animal or mammal has been identified or suspected as having a need for the particular method or treatment. In some embodiments, the identification can be by any means of diagnosis or observation. In any of the methods and treatments described herein, the animal or mammal can be in need thereof. In some embodiments, the animal or mammal is in an environment or will be traveling to an environment in which a particular disorder or condition is prevalent or more likely to occur.

"Administering" when used in conjunction with a therapeutic means to administer a therapeutic directly into or onto a target tissue or to administer a therapeutic to a patient whereby the therapeutic positively impacts the tissue to which it is targeted. Thus, as used herein, the term "administering", when used in conjunction with an interfering RNA molecule, can include, but is not limited to, providing the interfering RNA molecule into or onto the target tissue; providing interfering RNA molecule systemically to a patient by, e.g., intravenous injection whereby the therapeutic reaches the target; providing interfering RNA molecule in the form of the encoding sequence thereof to the target (e.g., by so-called gene-therapy techniques). "Administering" a composition may be accomplished intradermally, intramucosally, subcutaneously, sublingually, orally, intravaginally, intramuscularly, intracavernously, intraocularly, intranasally, into a sinus, intrarectally, gastrointestinally, intraductally, intrathecally, subdurally, extradurally, intraventricular, intrapulmonary, into an abscess, intra articularly, into a bursa, subpericardially, into an axilla, intrauterinely, into the pleural space, intraperitoneally, or transmucosally.

"Inflammatory response" or "inflammation" is a general term for the local accumulation of fluid, plasma proteins, and white blood cells initiated by physical injury, infection, or a local immune response. Inflammation is an aspect of many diseases and disorders, including but not limited to diseases related to immune disorders, viral infection, arthritis, autoimmune diseases, collagen diseases, allergy, asthma, pollinosis, and atopy. Inflammation is characterized by rubor (redness), dolor (pain), calor (heat) and tumor (swelling), reflecting changes in local blood vessels leading to increased local blood flow which causes heat and redness, migration of leukocytes into surrounding tissues (extravasation), and the exit of fluid and proteins from the blood and their local accumulation in the inflamed tissue, which results in swelling and pain, as well as the accumulation of plasma proteins that aid in host defense. These changes are initiated by cytokines produced by activated macrophages. Inflammation is often accompanied by loss of function due to replacement of parenchymal tissue with damaged tissue (e.g., in damaged myocardium), reflexive disuse due to pain, and mechanical constraints on function, e.g., when a joint swells during acute inflammation, or when scar tissue bridging an inflamed joint contracts as it matures into a chronic inflammatory lesion. Inflammation can result from, e.g., inflammatory bowel disease, Crohn's Disease, ulcerative colitis, eosinophilic esophagitis, asthma, chronic obstructive pulmonary disease, chronic inflammatory demyelinating polyneuropathy, a rheumatic disorder, arthritis, psoriatic arthritis, rheumatoid arthritis, ankylosing spondylitis, acute bursitis, subacute bursitis, acute nonspecific tenosynovitis, acute gouty arthritis, post-traumatic osteoarthritis, synovitis of osteoarthritis, epicondylitis, an allergy, epilepsy, Addison's Disease, adrenal insufficiency, hypercalcemia, thyroiditis, laryngitis, tuberculosis, hives, lipid pneumonitis, pericarditis, multiple sclerosis, nephrotic syndrome, lupus, myasthenia gravis, Duchenne muscular dystrophy, poison oak, poison ivy, organ transplantation, dermatitis, migraine, acute lymphoblastic leukemia, Hodgkin's lymphoma, multiple myeloma, syphilis, uveitis, congenital adrenal hyperplasia, sarcoidosis, heart failure, preterm labor, temporal arteritis, hepatitis, autoimmune hepatitis, brain tumor, brain injury, cancer, bronchopulmonary dysplasia, granuloma annulare, eczema, intertrigo, lichen planus, llichen sclerosus, necrobiosis lipoidica diabeticorum, plantar fibromatosis, plaque psoriasis, proctitis, pruritus, psoriasis, seborrheic dermatitis, urticaria, stomatitis, necrotizing enterocolitis, limb girdle muscular dystrophy, sickle cell disease, miyoshi myopathy, distal myopathy, or a combination thereof.

"Anti-inflammatory" refers to the ability of a compound to prevent or reduce the inflammatory response, or to soothe inflammation by reducing the symptoms of inflammation such as redness, pain, heat, or swelling. Inflammatory responses can be triggered by injury, for example injury to skin, muscle, tendons, or nerves. Inflammatory responses can also be triggered as part of an immune response. Inflammatory responses can also be triggered by infection, where pathogen recognition and tissue damage can initiate an inflammatory response at the site of infection. Generally, infectious agents induce inflammatory responses by activating innate immunity. Inflammation combats infection by delivering additional effector molecules and cells to augment the killing of invading microorganisms by the frontline macrophages, by providing a physical barrier preventing the spread of infection, and by promoting repair of injured tissue. "Inflammatory disorder" is sometimes used to refer to chronic inflammation due to any cause.

An "anti-inflammatory corticosteroid" refers to a natural or synthetic steroid hormone having anti-inflammatory activity. An anti-inflammatory corticosteroid can be a glucocorticoid or a mineralcorticoid. Exemplary anti-inflammatory corticosteroids include cortisone, dexamethasone, hydrocortisone, prednisolone, prednisone, methylprednisolone, aldosterone, fludrocortisone, vamorolone, betamethasone, budesonide, flunisolide, mometasone, ciclesonide, fluticasone, beclomethasone, triamcinolone, desonide, halcinonide, diflorasone, fluocinolone, clobetasol, desoximetasone, prednicarbate, clocorolone, alclometasone, flurandrenolide, amcinonide, and halobetasol.

A "steroid side effect" is any type of reaction of a subject to a natural or synthetic steroid, whether through administration of the steroid to the subject or production of the steroid by the subject. Exemplary steroid side effects include skin atrophy, striae rubrae distensae, skin delayed wound healing, acne, perioral dermatitis, erythema, teleangiectasia, petechia, hypertrichosis, hirsutism, muscle atrophy, muscle myopathy, osteoporosis, bone necrosis, stomach ulcer, muscle pain, avascular necrosis, sensitive teeth, glaucoma, cataract, brain damage, mood shift, behavioral shift, memory loss, cognition loss, insomnia, hyperactivity, anxiety, irritability, depression, fatigue, steroid psychosis, steroid dependence, cerebral atrophy, Cushing's syndrome, weight gain, facial swelling, increased appetite, diabetes mellitus, adrenal atrophy, adrenal suppression, adrenal insufficiency, growth retardation, hypogonadism, delayed puberty, increased Na+ retention, increased K+ excretion, increased thirst, increased urination, increased diarrhea, hypertension, dyslipidemia, thrombosis, hypofibrinolysis, vasculitis, increased risk of infection, reactivation of latent virus, peptic ulcer, gastrointestinal bleeding, pancreatitis, fatty liver, or a combination thereof.

A "muscle disease" is a weakening or breakdown of muscle fibers or an impairment of nervous system regulation of muscle function, including, but not limited to, any myopathy, dystrophy, myotonia, myositis, myalgia, atrophy, myasthenia, cramp, sclerosis, paresthesia, or neuromuscular disorder. A muscle disease can be a genetic disorder or a non-genetic disorder. Exemplary muscle diseases include Becker muscular dystrophy, congenital muscular dystrophy, Bethlem congenital muscular dystrophy, Fukuyama congenital muscular dystrophy, a muscle-eye-brain disease, a rigid spine syndrome, Ullrich congenital muscular dystrophy, a Walker-Warburg syndrome, Duchenne muscular dystrophy, Emery-Dreifuss muscular dystrophy, faciocapulohumeral muscular dystrophy, a limb-girdle muscular dystrophy, myotonic dystrophy, oculopharyngeal muscular dystrophy, a congenital myopathy, a cap myopathy, a centronuclear myopathy, a congenital myopathy with fiber-type disproportion, a core myopathy, central core disease, a multiminicore myopathy, a myosin storage myopathy, myotubular myopathy, a nemaline myopathy, a distal myopathy, GNE myopathy, Nonaka myopathy, hereditary inclusion-body myopathy, Laing distal myopathy, Markesberg-Griggs late-onset distal myopathy, Miyoshi myopathy, Udd myopathy, tibial muscular dystrophy, vocal cord distal myopathy, pharyngeal distal myopathy, Welander distal myopathy, an endocrine myopathy, hyperthyroid myopathy, hypothyroid myopathy, an inflammatory myopathy, dermatomyositis, inclusion-body myositis, polymyositis, a metabolic myopathy, acid maltase deficiency, Pompe disease, carnitine deficiency, carnitine palmityl transferase deficiency, debrancher enzyme deficiency, Cori disease, Forbes disease, lactate dehydrogenase deficiency, myoadenylate deaminase deficiency, phosphofructokinase deficiency, Tarui disease, phosphoglycerate kinase deficiency, phosphoglycerate mutase deficiency, phosphorylase deficiency, McArdle disease, a myofibrillar myopathy, scapuloperoneal myopathy, myasthenia gravis, a congenital myasthenic syndrome, Lambert-Eaton myasthenic syndrome, or a combination thereof.

"Variants" are intended to mean substantially similar sequences. For nucleic acid molecules, a variant comprises a nucleic acid molecule having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide. As used herein, a "native" nucleic acid molecule or polypeptide comprises a naturally occurring nucleotide sequence or amino acid sequence, respectively. For nucleic acid molecules, conservative variants include those sequences that, because of the degeneracy of the genetic code, encode the amino acid sequence of one of the polypeptides of the disclosure. Variant nucleic acid molecules also include synthetically derived nucleic acid molecules, such as those generated, for example, by using site-directed mutagenesis but which still encode a protein of the disclosure. Generally, variants of a particular nucleic acid molecule of the disclosure will have at least about 70%, 75%, 80%, 85%, 90%, 91%, 92%, 93%, 94%, 95%, 96%, 97%, 98%, 99% or more sequence identity to that particular polynucleotide as determined by sequence alignment programs and parameters as described elsewhere herein.

Variants of a particular nucleic acid molecule of the disclosure (i.e., the reference DNA sequence) can also be evaluated by comparison of the percent sequence identity between the polypeptide encoded by a variant nucleic acid molecule and the polypeptide encoded by the reference nucleic acid molecule. Percent sequence identity between any two polypeptides can be calculated using sequence alignment programs and parameters described elsewhere herein. Where any given pair of nucleic acid molecule of the disclosure is evaluated by comparison of the percent sequence identity shared by the two polypeptides that they encode, the percent sequence identity between the two encoded polypeptides is at least about 70%, 75%, 80%, 85%, 90%, 91%, 92%, 93%, 94%, 95%, 96%, 97%, 98%, 99% or more sequence identity. In some embodiments, the term "variant" protein is intended to mean a protein derived from the native protein by deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. Variant proteins or polynucleotides encompassed by the present disclosure are biologically active, that is they continue to possess the desired biological activity of the native or claimed protein or polynucleotide as described herein. Such variants may result from, for example, genetic polymorphism or from human manipulation. Biologically active variants of a protein of the disclosure will have at least about 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the disclosure may differ from that protein by as few as 1-15 amino acid residues, as few as 1-10, such as 6-10, as few as 5, as few as 4, 3, 2, or even 1 amino acid residue. The polynucleotides of the disclosure may be altered in various ways including substitutions, deletions, truncations, and insertions. Methods for such manipulations are generally known in the art. For example, amino acid sequence variants and fragments of the proteins can be prepared by mutations in the nucleic acid sequence that encodes the amino acid sequence recombinantly.

"Viral vector" as disclosed herein means, in respect to a vehicle, any virus, virus-like particle, virion, viral particle, or pseudotyped virus that comprises a nucleic acid sequence that directs packaging of a nucleic acid sequence in the virus, virus-like particle, virion, viral particle, or pseudotyped virus. In some embodiments, the virus, virus-like particle, virion, viral particle, or pseudotyped virus is capable of transferring a vector (such as a nucleic acid vector) into and/or between host cells. In some embodiments, the virus, virus-like particle, virion, viral particle, or pseudotyped virus is capable of transferring a vector (such as a nucleic acid vector) into and/or between target cells, such as a muscle cell of a subject.

A "viral particle" as that term is used herein, means a small particle of about ten nanometers to about one micrometer, comprising a structural protein (such as a viral core protein), around which one or a plurality of nucleic acid molecules are contained. Viral particles comprise a group of particles called lipoparticles which include enveloped virus-like particles. In some preferred embodiments, the lipoparticles are enveloped virus-like particles which comprise an enveloped viral core protein, a lipid bilayer, and an additional polypeptide on its surface. The viral particle may be about ten nm to about 500 nm, about 100 to about 500 nm, about 200 to about 400 nm, about 300 to about 399 nm, about 500 nm to about 1000 nm, about 600 to about 900 nm, or about 700 to about 800 nm. In some embodiments, the viral particle does not encompass or comprise (free of) cell membrane vesicles, which are typically produced using empirical methods and which are usually heterogeneous in size. In some embodiments, the lipoparticle also does not encompass liposomes, which typically lack core proteins that induce their formation. In some embodiments, the lipoparticle is dense, spherical, and/or homogeneous in size.

The lipoparticle is based on retrovirus structures and enables structurally intact cellular proteins to be purified away from the cell. Briefly, when a retrovirus is produced from a cell, the protein core of the virus buds through the membrane of the cell. As a consequence, the virus becomes enwrapped by the cellular membrane. Once the membrane 'pinches' off, the virus particle is free to diffuse. Normally, the virus also produces its own membrane protein (Envelope) that is expressed on the cell surface and that becomes incorporated into the virus. However, if the gene for the viral membrane protein is deleted, virus assembly and budding can still occur. Under these conditions, the membrane enwrapping the virus contains a number of cellular proteins.

In some embodiments, any natural or non-natural nucleic acid formula may be repeated across 1, 2, 3, 4, 5, 6, 7, 8, 9, 10 or more nucleic acids in contiguous nucleic acids or in a non-contiguous nucleotides across the length of the nucleic acid. In some embodiments, the disclosed nucleic acid sequences comprise 1, 2, 3, 4, 5, 6, 7, 8, 9, 10, 11, 12, 13, 14, 15, 16, 17, 18, 19, 20 or more contiguous or non-contiguous modified nucleic acids across a length of the nucleic acid.

In some embodiments, the composition or pharmaceutical composition disclosed herein comprises a nucleic acid disclosed herein that comprises ribonucleic acid and about 10%, 11%, 12%, 13%, 14%, 15%, 16%, 17%, 18%, 19%, 20%, 22%, 25%, 27%, 30%, 32%, 35%, 37%, 40%, 42%, 45%, 47%, 50%, 52%, 55%, 57%, 60%, 62%, or 65% modified nucleotides.

In some embodiments, any of the forgoing formulae may comprise one or a plurality of LNA molecules positioned between or bound to one or a plurality of modified or unmodified nucleotides.

In some embodiments, the composition or pharmaceutical composition disclosed herein comprises a nucleic acid sequence comprising a total of about 20, 25, 30, 35, 40, 45, 50, 55, 60, 65, 70, 75, 80, 85, 90, 95, 100, 150, or 200 nucleotides in length (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 60, 61, 62, 63, 63, 64, 65, 66, 67, 68, 69, 70, 71, 72, 73, 74, 75, 76, 77, 78, 79, 80, 81, 82, 83, 84, 85, 86, 87, 88, 89, 90, 91 92, 93, 94, 95, 96, 97, 98, 99, or about 100 nucleotides in length, or longer).

Compositions

The disclosure relates to interfering RNA molecules comprising an antisense strand, wherein the antisense strand comprises a region of complementarity that is substantially complementary to an miRNA. In some embodiments, the target miRNA is an NF-κB-regulated miRNA whose expression becomes activated in response to inflammation. Exemplary NF-κB-regulated miRNAs are provided in Table 1.

TABLE 1

Inflammatory miRNA identities and sequences

| human microRNA | SEQ ID NO./ Mature microRNA Human | miRBase ID Human | Seed sequence |
|---|---|---|---|
| hsa-miR-142-3p | 1 uguaguguuuccuacuuuaugga | MIMAT0000434 | guaguguu |
| hsa-miR-142-5p | 2 cauaaaguagaaagcacuacu | MIMAT0000433 | auaaagua |
| hsa-miR-146a-5p | 3 ugagaacugaauuccauggguu | MIMAT0000449 | gagaacug |
| hsa-miR-301a-3p | 4 cagugcaauaguauugucaaagc | MIMAT0000688 | agugcaau |
| hsa-miR-324-3p | 5 acugccccaggugcugcugg | MIMAT0000762 | cacugccc |
| hsa-miR-455-3p | 6 gcaguccaugggcauauacac | MIMAT0004784 | caguccac |
| hsa-miR-497-5p | 7 cagcagcacacugugguuugu | MIMAT0002820 | agcagcac |
| hsa-miR-652-3p | 8 aauggcgccacuaggguugug | MIMAT0003322 | auggcgcc |
| hsa-miR-223-3p | 9 ugucaguuugucaaauacccca | MIMAT0000280 | gucaguuu |
| hsa-miR-146b-5p | 10 ugagaacugaauuccauaggcu | MIMAT0002809 | gagaacug |
| hsa-miR-320a | 11 aaaagcuggguugagagggcga | MIMAT0000510 | aaagcugg |

| mouse microRNA | SEQ ID NO./ Mature microRNA mouse | miRBase ID Mouse | Seed Sequence |
|---|---|---|---|
| mmu-miR-142-3p | 12/ uguaguguuuccuacuuuaugga | MIMATT0000155 | guaguguu |
| mmu-miR-142-5p | 13/ cauaaaguagaaagcacuacu | MIMAT0000154 | auaaagua |
| mmu-miR-146a | 14/ ugagaacugaauuccaugguu | MIMAT0000158 | gagaacug |
| mmu-miR-301a | 15/ cagugcaauaguauugucaaagc | MIMAT0000379 | agugcaau |
| mmu-miR-324-3p | 16/ ccacugccccaggugcugcu | MIMAT0000556 | ccacugcc |
| mmu-miR-455 | 17/ gcaguccacgggcauauacac | MIMAT0003742 | caguccau |
| mmu-miR-497 | 18/ cagcagcacacugugguuugua | MIMAT0003453 | agcagcac |
| mmu-miR-652 | 19/ aauggcgccacuaggguugug | MIMAT0003711 | auggcgcc |
| mmu-miR-miR-223-3p | 20/ ugucaguuugucaaauacccca | MIMAT0000665 | gucaguuu |
| mmu-miR-146b-5p | 21/ ugagaacugaauuccauaggcu | MIMAT0003475 | gagaacug |
| mmu-miR-320-3p | 22/ aaaagcugggungagagggcga | MIMAT0017057 | aaagcugg |

In some embodiments, the interfering RNA molecule or RNA/DNA hybrid molecule comprises a nucleotide sequence that is substantially complementary to the NF-κB-regulated miRNA. In some embodiments, the interfering RNA molecule is fully complementary to the NF-κB-regulated miRNA.

The interfering RNA molecule can, in some embodiments, have substantial complementarity to only the "seed sequence" of the target miRNA. The "seed sequence" of an miRNA is nucleotides 2-7 or 2-8 of an miRNA that is essential for miRNA binding to its target mRNA. In some embodiments, the interfering RNA molecule has perfect complementarity to its target miRNA's seed sequence.

In some embodiments, the interfering RNA molecule comprises the nucleotide sequence AACACUAC, UACUUUAU, CAGUUCUC, AUUGCACU, GGGCAGUG, GGCAGUGG, GUGGACUG, AUGGACUG, GUGCUGCU, GGCGCCAU, AAACUGAC, CAGUUCUC, or CCAGCUUU, which have perfect complementarity to the miRNA seed sequences found in Table 1. In some embodiments, the interfering RNA molecule comprises the nucleotide sequence UCCAUAAAGUAGGAAACACUACA (SEQ ID NO:23), AGUAGUGCUUUCUACUUUAUG (SEQ ID NO:24), AACCCAUGGAAUUCAGUUCUCA (SEQ ID NO:25), GCUUUGACAAUACUAUUGCACUG (SEQ ID NO: 26), AGCAGCACCUGGGGCAGUGG (SEQ ID NO:27), CCAGCAGCACCUGGGCAGUGGG (SEQ ID NO:28), GUGUAUAUGCCCGUGGACUGC (SEQ ID NO:29), GUGAUAAUGCCCAUGGACUGC (SEQ ID NO:30), UACAAACCACAGUGUGCUGCUG (SEQ ID NO:30), ACAAACCACAGUGUGCUGCUG (SEQ ID NO:31), CACAACCCUAGUGGCGCCAUU (SEQ ID NO:32), UGGGGUAUUUGACAAACUGACA (SEQ ID NO:33), AGCUAUGGAAUUCAGUUCUCA (SEQ ID NO:34), or UCGCCCUCUCAACCCAGCUUUU (SEQ ID NO:35), which have perfect complementarity to the miRNA sequences in Table 1. In some embodiments, the disclosure relates to a composition comprising an interfering RNA sequence comprising AACACUAC, UACUUUAU, CAGUUCUC, AUUGCACU, GGGCAGUG, GGCAGUGG, GUGGACUG, AUGGACUG, GUGCUGCU, GGCGCCAU, AAACUGAC, CAGUUCUC, or CCAGCUUU; or, in some embodiments, the disclosure relates to a composition comprising an interfering RNA sequence comprising at least about 70%, 75%, 80%, 85%, 90%, 91%, 92%, 93%, 94%, 95%, 96%, 97%, 98%, 99% or 100% sequence identity to SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35. In some embodiments, the disclosure relates to a composition comprising an interfering RNA sequence comprising at least about 70%, 75%, 80%, 85%, 90%, 91%, 92%, 93%, 94%, 95%, 96%, 97%, 98%, 99% or 100% sequence identity to AACACUAC, UACUUUAU, CAGUUCUC, AUUGCACU, GGGCAGUG, GGCAGUGG, GUGGACUG, AUGGACUG, GUGCUGCU, GGCGCCAU, AAACUGAC, CAGUUCUC, or CCAGCUUU. In some embodiments, the disclosure relates to a composition comprising an RNA sequence from about 5 to about 35 nucleic acids in length, the RNA comprising a region of at least about 75% sequence identity to any one or combination of nucleic acid sequences chosen from: AACACUAC, UACUUUAU, CAGUUCUC, AUUGCACU, GGGCAGUG, GGCAGUGG, GUGGACUG, AUGGACUG, GUGCUGCU, GGCGCCAU, AAACUGAC, CAGUUCUC, and CCAGCUUU. In some embodiments, the disclosure relates to a composition comprising an RNA sequence from about 5 to about 35 nucleic acids in length, the RNA comprising a region of at least about 75% sequence identity to any one or combination of nucleic acid sequences chosen from: SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35. In some embodiments, the interfering RNA is complementary to about 5, 6, 7, 8, 9, 10, 11, 12, 13, 14, 15, 16, 17, 18, 19, 20, 21, 22, 23, 24, 25 or more nucleotides of those sequence in Tables, 1, 2, 3, or 4. In some embodiments, the interfering RNA is about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or about 35 nucleotides in length and is at least about 75% complementary to any one of the seed regions disclosed in Table 1, 2, 3, or 4.

In some embodiments, the target miRNA is a corticosteroid-activated miRNAs that activate in response to corticosteroid treatment or upregulation. Exemplary corticosteroid-activated miRNAs are provided in Table 2.

In some embodiments, the disclosure relates to a composition comprising an RNA sequence from about 10 to about 25 nucleic acids in length, the RNA sequence comprising a region of at least about 75% sequence identity to any one or combination of nucleic acid sequences chosen from: SEQ ID NO:72 or SEQ ID NO:73. In some embodiments, the disclosure relates to a composition comprising an RNA sequence from about 5 to about 35 nucleic acids in length, the RNA sequence comprising a region of at least about 75% sequence identity to any one or combination of nucleic acid sequences chosen from: SEQ ID NO:72 or SEQ ID NO:73. In some embodiments, the disclosure relates to a composition comprising an RNA sequence from about 15 to about 25 nucleic acids in length, the RNA sequence comprising or consists of a region of at least about 75% sequence identity to any one or combination of nucleic acid sequences chosen from: SEQ ID NO:72 or SEQ ID NO:73. In some embodiments, the disclosure relates to a composition comprising an RNA sequence from about 18 to about 25 nucleic acids in length, the RNA sequence comprising a region of at least about 75% sequence identity to any one or combination of nucleic acid sequences chosen from: SEQ ID NO:72 or SEQ ID NO:73. In some embodiments, the composition comprises or consists of an interfering RNA sequence that is at least 70%, 75%, 80%, 85%, 90%, 91%, 92%, 93%, 94%, 95%, 96%, 97%, 98%, 99% or 100% sequence identity complementary to SEQ ID NO: 70 or 71. In some embodiments, the composition comprises or consists of an interfering RNA sequence that is at least 70%, 75%, 80%, 85%, 90%, 91%, 92%, 93%, 94%, 95%, 96%, 97%, 98%, 99% or 100% sequence identity complementary to SEQ ID NO: 70 or 71 and has at least from about 1% to about 100% modified uridines. In some embodiments, the composition comprises or consists of an interfering RNA sequence that is at least 70%, 75%, 80%, 85%, 90%, 91%, 92%, 93%, 94%, 95%, 96%, 97%, 98%, 99% or 100% sequence identity complementary to SEQ ID NO: 70 or 71 and has at least from about 10% to about 100% modified uridines. In some embodiments, the composition comprises or consists of an interfering RNA sequence that is at least 70%, 75%, 80%, 85%, 90%, 91%, 92%, 93%, 94%, 95%, 96%, 97%, 98%, 99% or 100% sequence identity complementary to SEQ ID NO: 70 or 71 and has from about 20% to about 100% modified uridines. In some embodiments, the composition comprises or consists of an interfering RNA sequence that is at least 70%, 75%, 80%, 85%, 90%, 91%, 92%, 93%, 94%, 95%, 96%, 97%, 98%, 99% or 100% sequence identity complementary to SEQ ID NO: 70 or 71 and has from about 30% to about 100% modified uridines. In some embodiments, the composition comprises or consists of an interfering RNA sequence that is at least 70%, 75%, 80%, 85%, 90%, 91%, 92%, 93%, 94%, 95%, 96%, 97%, 98%, 99% or 100% sequence identity complementary to SEQ ID NO: 70 or 71 and has from about 40% to about 100% modified uridines. In some embodiments, the composition comprises or consists of an interfering RNA sequence that is at least 70%, 75%, 80%, 85%, 90%, 91%, 92%, 93%, 94%, 95%, 96%, 97%, 98%, 99% or 100% sequence identity complementary to SEQ ID NO: 70 or 71 and has from about 50% to about 100% modified uridines. In some embodiments, the composition comprises or consists of an interfering RNA sequence that is at least 70%, 75%, 80%, 85%, 90%, 91%, 92%, 93%, 94%, 95%, 96%, 97%, 98%, 99% or 100% sequence identity complementary to SEQ ID NO: 70 or 71 and has from about 60% to about 100% modified uridines. In some embodiments, the composition comprises or consists of an interfering RNA sequence that is at least 70%, 75%, 80%, 85%, 90%, 91%, 92%, 93%, 94%, 95%, 96%, 97%, 98%, 99% or 100% sequence identity complementary to SEQ ID NO: 70 or 71 and has from about 70% to about 100% modified uridines. In some embodiments, the composition comprises or consists of an interfering RNA sequence that is at least 70%, 75%, 80%, 85%, 90%, 91%, 92%, 93%, 94%, 95%, 96%, 97%, 98%, 99% or 100% sequence identity complementary to SEQ ID NO: 70 or 71 and has from about 80% to about 100% modified uridines. In some embodiments, the composition comprises or consists of an interfering RNA sequence that is at least 70%, 75%, 80%, 85%, 90%, 91%, 92%, 93%, 94%, 95%, 96%, 97%, 98%, 99% or 100% sequence identity complementary to SEQ ID NO: 70 or 71 and has from about 90% to about 100% modified uridines. In some embodiments, the composition comprises or consists of an interfering RNA sequence that is at least 70%, 75%, 80%, 85%, 90%, 91%, 92%, 93%, 94%, 95%, 96%, 97%, 98%, 99% or 100% sequence identity complementary to SEQ ID NO: 70 or 71 and has from about 25% to 100% modified uridines. In some embodiments, the composition comprises or consists of an interfering RNA sequence that is at least 70%, 75%, 80%, 85%, 90%, 91%, 92%, 93%, 94%, 95%, 96%, 97%, 98%, 99% or 100% sequence identity complementary to SEQ ID NO: 70 or 71 and has at least about 15% to about 100% modified uridines. In some embodiments the modified uridines are replaced with adenine or a modified base.

In some embodiments, the disclosure relates to compositions, including pharmaceutical compositions that comprise a cell that comprises any one or more of the disclosed antisense sequences.

The disclosure also relates to compositions, pharmaceutical compositions and cells comprising modified miRNA sequences disclosed in Table 1. In some embodiments, the disclosure relates to a composition comprising an RNA sequence comprising at least about 70%, 75%, 80%, 85%, 90%, 91%, 92%, 93%, 94%, 95%, 96%, 97%, 98%, 99% or 100% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12. In some embodiments, the disclosure relates to a composition comprising an RNA sequence comprising at least about 70%, 75%, 80%, 85%, 90%, 91%, 92%, 93%, 94%, 95%, 96%, 97%, 98%, 99% or 100% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 but with from about 5% to about 100% of modified uridines. the disclosure relates to a composition comprising an RNA sequence comprising at least about 70%, 75%, 80%, 85%, 90%, 91%, 92%, 93%, 94%, 95%, 96%, 97%, 98%, 99% or 100% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 with from about 5% to about 100% of uridines replaced with adenines or an adenine based nucleoside. In some embodiments, the disclosure relates to a composition comprising an RNA sequence comprising at least about 70%, 75%, 80%, 85%, 90%, 91%, 92%, 93%, 94%, 95%, 96%, 97%, 98%, 99% or 100% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 but is free of a sequence capable of stimulating inflammatory activity. In some embodiments, the disclosure relates to a composition comprising an RNA sequence comprising at least about 70%, 75%, 80%, 85%, 90%, 91%, 92%, 93%, 94%, 95%, 96%, 97%, 98%, 99% or 100% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 but is free of a sequence capable of stimulating inflammatory activity as measured by monitoring TLR7 activity. In some embodiments, the disclosure relates to a composition comprising an RNA sequence comprising at least about 70%, 75%, 80%, 85%, 90%, 91%, 92%, 93%, 94%, 95%, 96%, 97%, 98%, 99% or 100% sequence identity to SEQ ID NO:1 through SEQ ID NO:22 but is free of a sequence capable of stimulating inflammatory activity as measured by monitoring TLR7 activity.

TABLE 2

Corticosteroid-activated miRNAs and non-coding RNAs located at the human 14q32 mega cluster

| human microRNA | SEQ ID NO:/ Mature microRNA Human | miRBase ID Human | Seed Sequence |
|---|---|---|---|
| hsa-miR-134-5p | 36/ UGUGACUGGUUGACCAGAGGGG | MIMAT0000447 | GUGACUGG |
| hsa-miR-370 | 37/ GCCUGCUGGGGUGGAACCUGGU | MIMAT0000722 | CCUGCUGG |
| hsa-miR-409-3p | 38/ GAAUGUUGCUCGGUGAACCCCU | MIMAT0001639 | AAUGUUGC |
| hsa-miR-433-4p | 39/ AUCAUGAUGGGCUCCUCGGUGU | MIMAT0001627 | UCAUGAUG |
| hsa-miR-493-3p | 40/ UGAAGGUCUACUGUGUGCCAGG | MIMAT0003161 | GAAGGUCC |
| hsa-miR-543 | 41/ AAACAUUCGCGGUGCACUUCUU | MIMAT0004954 | AACAUUCG |

| mouse microRNA | SEQ ID NO:/ Mature microRNA mouse | miRBase ID Mouse | Seed Sequence |
|---|---|---|---|
| mmu-miR-134-5p | 42/ UGUGACUGGUUGACCAGAGGGG | MIMAT0000146 | GUGACUGG |
| mmu-miR-370-3p | 43/ GCCUGCUGGGGUGGAACCUGGU | MIMAT0001095 | CCUGCUGG |
| mmu-miR-409-3p | 44/ GAAUGUUGCUCGGUGAACCCCU | MIMAT0001090 | AAUGUUGC |
| mmu-miR-433-3p | 45/ AUCAUGAUGGGCUCCUCGGUGU | MIMAT0001420 | UCAUGAUG |

| mouse microRNA | SEQ ID NO:/ Mature microRNA mouse | miRBase ID Mouse | Seed Sequence |
| --- | --- | --- | --- |
| mmu-miR-493-3p | 46/ UGAAGGUCCUACUGUGUGCCAGG | MIMAT0004888 | GAAGGUCU |
| mmu-miR-543-3p | 47/ AAACAUUCGCGGUGCACUUCUU | MIMAT0003168 | AACAUUCG |

| long non-coding RNA | mouse | human |
| --- | --- | --- |
| MEG3 (maternally expressed 3) | Mm00522599_m1 | Hs00292028_m1 |
| MEG8 (maternally expressed 8) | Mm01325842_g1 | Hs00419701_m1 |
| MEG9 (maternally expressed 9) | Mm01335848_m1 | Hs01593046_s1 |

In some embodiments, the interfering RNA molecule comprises a nucleotide sequence that is substantially complementary to the corticosteroid-activated miRNA. In some embodiments, the interfering RNA molecule is fully complementary to the corticosteroid-activated miRNA.

The interfering RNA molecule can, in some embodiments, have substantial complementarity to only the seed sequence of the target miRNA. In some embodiments, the interfering RNA molecule has perfect complementarity to its target miRNA's seed sequence.

In some embodiments, the interfering RNA molecule comprises the nucleotide sequence CCAGUCAC, CCAGCAGG, GCAACAUU, CAUCAUGA, GGACCUUC, AGACCUUC, or CGAAUGUU, which have perfect complementarity to the miRNA seed sequences found in Table 2. In some embodiments, the interfering RNA molecule comprises the nucleotide sequence:
CCCCUCUGGUCAACCAGUCACA (SEQ ID NO: 63),
ACCAGGUUCCACCCCAGCAGGC (SEQ ID NO: 64),
AGGGGUUCACCGAGCAACAUUC (SEQ ID NO: 65),
ACACCGAGGAGCCCAUCAUGAU (SEQ ID NO: 66),
CCUGGCACACAGUAGGACCUUCA (SEQ ID NO: 67),
CCUGGCACACAGUAGACCUUCA, or (SEQ ID NO: 68),
AAGAAGUGCACCGCGAAUGUUU (SEQ ID NO: 69),
which have perfect complementarity to the miRNA sequences in Table 2. In some embodiments, the disclosure relates to a composition comprising an interfering RNA sequence comprising CCAGUCAC, CCAGCAGG, GCAACAUU, CAUCAUGA, GGACCUUC, AGACCUUC, or CGAAUGUU; or, in some embodiments, the disclosure relates to a composition comprising an interfering RNA sequence comprising at least about 70%, 75%, 80%, 85%, 90%, 91%, 92%, 93%, 94%, 95%, 96%, 97%, 98%, 99% or 100% sequence identity to:
CCCCUCUGGUCAACCAGUCACA (SEQ ID NO:63),
ACCAGGUUCCACCCCAGCAGGC (SEQ ID NO: 64),
AGGGGUUCACCGAGCAACAUUC (SEQ ID NO: 65),
ACACCGAGGAGCCCAUCAUGAU (SEQ ID NO: 66),
CCUGGCACACAGUAGGACCUUCA (SEQ ID NO: 67),
CCUGGCACACAGUAGACCUUCA (SEQ ID NO: 68), or
AAGAAGUGCACCGCGAAUGUUU (SEQ ID NO: 69),
In embodiments, the disclosure relates to a composition comprising an interfering RNA sequence comprising at least about 70%, 75%, 80%, 85%, 90%, 91%, 92%, 93%, 94%, 95%, 96%, 97%, 98%, 99% or 100% sequence identity to AACACUAC, UACUUUAU, CAGUUCUC, AUUGCACU, GGGCAGUG, GGCAGUGG, GUGGACUG, AUGGACUG, GUGCUGCU, GGCGCCAU, AAACUGAC, CAGUUCUC, or CCAGCUUU. In some embodiments, the disclosure relates to a composition comprising an RNA sequence from about 5 to about 35 nucleic acids in length, the RNA comprising a region of at least about 75% sequence identity to any one or combination of nucleic acid sequences chosen from: CCAGUCAC, CCAGCAGG, GCAACAUU, CAUCAUGA, GGACCUUC, AGACCUUC, or CGAAUGUU. In some embodiments, the disclosure relates to a composition comprising an RNA sequence from about 5 to about 35 nucleic acids in length, the RNA comprising a region of at least about 75% sequence identity to any one or combination of nucleic acid sequences chosen from:
CCCCUCUGGUCAACCAGUCACA (SEQ ID NO:63),
ACCAGGUUCCACCCCAGCAGGC (SEQ ID NO: 64),
AGGGGUUCACCGAGCAACAUUC (SEQ ID NO: 65),
ACACCGAGGAGCCCAUCAUGAU (SEQ ID NO: 66),
CCUGGCACACAGUAGGACCUUCA (SEQ ID NO: 67),
CCUGGCACACAGUAGACCUUCA (SEQ ID NO: 68), or
AAGAAGUGCACCGCGAAUGUUU (SEQ ID NO: 69), In some embodiments, the interfering RNA molecule comprises a nucleotide sequence having partial (for instance at least about 70%, 80%, 90%, 95% or more) or full complementarity to MEG3 (Mm00522599 ml), MEG3 (Hs00292028 ml), MEG8 (Mm01325842_gl), MEG8 (Hs00419701 ml), MEG9 (Mm01335848_ml), or MEG9 (Hs01593046_sl). In some embodiments, the interfering RNA molecule comprises a nucleotide sequence having partial (for instance at least about 70%, 80%, 90%, 95% or more) or full complementarity to at least about 10, 11, 12, 13, 14, 15, 16, 17, 18, 19, 20, 21, 22, 23, 24, 25, 26, 27, 28, 29, 30, 31, 32, 33, 34, 35 nucleic acids of any of MEG3 (Mm00522599_ml), MEG3 (Hs00292028_ml), MEG8 (Mm01325842_gl), MEG8 (Hs00419701_ml), MEG9 (Mm01335848_ml), or MEG9 (Hs01593046_sl).

RNA Sequences for the long non-coding RNA MEG3
MEG3 full sequence
(SEQ ID NO: 48)
AGCCCCUAGCGCAGACGGCGGAGAGCAGAGAGGGAGCGCGCCUUGGCUCG

CUGGCCUUGGCGGCGGCUCCUCAGGAGAGCUGGGGCGCCCACGAGAGGAU

CCCUCACCCGGUGAGUGGUUGGCCAUCCUUGCCGCAAAGGAUGUGCAAAA

GGAAGACGGCAUCCGCUUCUGGGAUGGGCUCUGUCCUCCUGGACAUGCCG

AGAGCCUGCCUGAUCCUGGGUCCUGCUGCUGGAGGCGGCCACUUCGCCUG

GUCCCCGAGCGUCCGCAACAAAAUUUGUCAGAAAGAAAAUCUUGAGGCAC

AUUUCCCUGGGGGGAAGUCAGGGCUCCUCUCUGGAGGGUCCAGUCCUUAA

```
GGGUGGGCUGGGUGGUAGGGACUUCAGUUCAGAGGAGCGGGAGGAAUCAG
AUGGAACUCCUCUUGGAUUCGGGUAUACGGCAGUCACUGGGGGGCGAACC
CCGGAUUUCCUGUAUUAGAAGCCGCCUCUAGAAUCGCGUUAAUAGUGGGA
GAUAUGGCGGCGAUGCCUUCUGCGUGCCCCAUGAAUUAGGGGGGGAAGCA
CCCGAAUAGAAGGGUCUCCCGGGCAUAUUUGCCUCGCCAGCUGUUGGCCA
GGUUUUUGGUGGAUCGUGGGCGGGAGGAGUGGAGGUUCCUCUUCGCGAGG
UUUUCCGAAUCCAAAUACACAGGUUUAGUGCAGUGUGGACCCCAGGCAAA
AUGUGGAGUAAAAUUUCUACCCGAUAUCAUCUGGUUCUGCCCUGAUCAGC
CACUUUCACAGUGGAGAGAUGGCGCCCAAGUGCAAACCUGCCAGUAGC
CCCCUAGGAUCAGUCCUUGCCGAAGGGGGUCUGUGGGAUUGGGGCACUG
GGAGAAUAGAUGCAGGGGUGGGUUGGGAGGAGAGAAGGCCGUGUCCUU
GGGUCUGGGAAGAGGGAGGAGAGAAAUGCAGAAAAGGGGGUGUGUUCUG
GGGUCUGGACGCUGGGAGCUGGGGAUGGGGUGCCGCGGGGUCUUCAGAG
CGUUGCGUGGUGGUCGCUCGAAAAUCCUGACAUGUUCAGUCUUGGACUU
UUGGUCAAAUCGCCUUUUGCCAUUUCCUUUGUCAGAGUCAAGCCCCCCA
GGCCGCCCCUCCCACCCUGGGCCGGCGGGCCUGGUGGGGCGCAGGCGG
GUGGCUACGUGGCAGGUUUCUGGAAGGUUUCCUGGCUGGCCGCGAGAGGG
CGCUGGCGGCACUGCGGAAUUUUGGGGGGCGGGGUGGGGAGGGGAGGUGG
CCUUUGUUCUCCUGAUGGAGGGGGUCGGGCGCGGGAUCUACUGGAGGAUC
CUGGAUUCGUUUACCCAAGAGGGAACAGUUUUGAGACCCCCCGGAUUCAC
UGCGGAGUGGCCGCAGAGGCCGGGGUCGGCCUUUGCGCCGUGGCUUCGGG
UGUUGUGGAGGCGCACAGAGGCACGUUAGUUGAUUUCCAGUGGUUUUUGG
UUUCGGGGGUCUUAGGAAGGUGUGGCUCAUUUGAGCAGGAUGGAGAGAGA
GGCUGUGACAAGGUCAGUGAGGGGCCAUCGUGCGGGGGCUAGAAAUUGUU
GUUGUGGCGAAGGAGGGAGGCACGACUUUGGAGGCGUGAUGUUGAUGCCU
GGGGGCGAAGGCGGGGAGCGGCGUGGUGGCCCCCUUUGCGUUACUUUCCA
GCGAUGUCACAGGUUCUGUCUCUCGUUCCGAGACCACCCACAUGCGUGAC
AGCGGUGCCUGGAGGACUGGGUCUUUCUGACUUUAGUGAACGUGUGUUUA
AUUGGAUUGACGAAGGUGGGAGUCGGGAUUUCUGCUUUUCCCUGUAGCAG
GCGGAGCGGCGCUCCAGAGGGGCCUGGCGCAGGUCCGCUGGGUGGCCCAC
CUUCCUCUGGGGCUGGGCCCGGUGGCUGGGGCGCAGGAGGCGCCUGGU
GCGGGCGGGAGGCGCUGCGCCGCAGCCACAGGUGGGCUCUGGCUGGUGGU
GGCUGGAGAGGCGUCCAGGGGCGUAGCGACCUGGCGCGUGGCCUGGG
UGGGCUGUGGAGCCCUUCCUAGCCUGAGACCUGUUGGGCACCCCCUGUCC
AUCCAGGCCCGCCGGGCGCGGGCCGGGCGCCGCAGGUGGCUGCUGCACU
CCUGGGUUACGGGUGCGGGCCGCGCGCCCCCUAGCGGUGUGUGCCAGCCC
CGCUACCUUGGGUUUUGAGUUGCGCACACGCACACAGCUAACACUUGUGA
CCUGUCAGUCAAAUCAUCCUUACCCCCUCCCACUCCUCUCCUCCACCUCC
CAUUUCUCCUCUCCCUCCACCCUUUCUCAUUUCCUCGUCCCUCCUCCCCC
UCCUAUUUUCUUCUCCCUCCUCCCUCUUUCCUCUUCCCUCCUCCCUCUU

CCCCCCUCAUUUUCCUCAUCUCUCUUUUCCCCUCCCCUUCUCUCCUCCCC
UCUCCCUGCCCCCCUCCUUCCUCCCUCCAUACCCCUCCCUCUUUCCCUCCC
AGCCCCUCCCUACUGCCUUCCUCAGUCCUCCCCUUUGCCACUCCUCCCUG
CCUUUCCCUCUGCCUGCCCCCUUUUGCUCUCUGCUGUUCCGGUGCUGGCC
GUUAGAGGUCACGAAGAUGGUUUCUAACCUGCCCCCCUCCCAUGCCAUAG
GGUCUCUCCUCAGGGAUGACAUCAUCCGUCCACCUCCUUGUCUUCAAGGA
CCACCUCCUCUCCAUGCUGAGCUGCUGCCAAGGGGCCUGCUGCCCAUCUA
CACCUCACGGUACUUCAACCCUCCUGCUAUCAUUUCAUAACCAACGUGGC
GGGCAGAAUCUCCCAACCCCACCACCAUCCUUGCACCACCCCCAGACCCA
CUAGCAAUUAAAAGACAAUUUUAAAUUUUAACUAAUCAGCUUUAAUUGUA
AUUAAUGAACUUAAACUGUAAUUAUGAUCUAGGCUUGGGCUUUUAAGCAG
GUUCUCUAACCUUUGAUCAAUUGCAGAGGGCACUAGGAGCACGGUUUCCU
GGAUCCCACCAACAUACAAAGCAGCCACUCACUGACCCCCAGGACCAGGA
UGGCAAAGGAUGAAGAGGACCGGAACUGACCAGCCAGCUGUCCCUCUUAC
CUAAAGACUUAAACCAAUGCCCUAGUGAGGGGCAUGGGCAUUAAGCCC
UGACCUUUGCUAUGCUCAUACUUUGACUCUAUGAGUACUUUCCUAUAAGU
CUUUGCUUGUGUUCACCUGCUAGCAAACUGGAGUGUUUCCCUCCCCAAGG
GGGUGUCAGUCUUUGUCGACUGACUCUGUCAUCACCCUUAUGAUGUCCUG
AAUGGAAGGAUCCCUUUGGGAAAUUCUCAGGAGGGGGACCUGGGCCAAGG
GCUUGGCCAGCAUCCUGCUGGCAACUCCAAGGCCCUGGGUGGGCUUCUGG
AAUGAGCAUGCUACUGAAUCACCAAAGGCACGCCCGACCUCUCUGAAGAU
CUUCCUAUCCUUUUCUGGGGGAAUGGGGUCGAUGAGAGCAACCUCCUAGG
GUUGUUGUGAGAAUUAAAUGAGAUAAAAGAGGCCUCAGGCAGGAUCUGGC
AUAGAGGAGGUGAUCAGCAAAUGUUUGUUGAAAAGGUUUGACAGGUCAGU
CCCUUCCCACCCCUCUUGCUUGUCUUACUUGUCUUAUUUAUUCUCCAACA
GCACUCCAGGCAGCCCUUGUCCACGGGCUCUCCUUGCAUCAGGUAGGGGC
UUUGCAGAGACCAUCGACGGGCUGACUUGAGUAAGAACACGAAUUAUGCA
UGUGGCCAUUUCCAGAGCACUUUCUAUGUGAUAUGAACAUGUGAUUUUUA
UGUAAUAUGUGUAUGUAAACGAGGCAGCCUCAUUUCCAGGUGAGGAUGCA
UUUGGUAGUGUUGAUUUUUGUAAUUUAAAGAAGCUGAAAGGGAGAGAGGA
CCCGUGAGGACUGAACUCUCUGUCCCAUGGGGUAGGGCUUACAUUUACAU
UAAAGAAACAGAAACUUGCUGGGAGGUGUAAGUAUUUGGUCACAUUGCUG
GCAACAGAAGGGGUUGAGUUGGACCCAGGGUGCCACGCUAGCUGCCCUC
ACCCCUUCUUCCCCUCUGGCCCAGAGUUAUACUAAGAGUCCUUUUAUUUC
AAACCAAAUGUUUGACAAUGGGACAGUCUGUUUGAAAUCCCAGCUGCCUG
GGGUGGUCUUGGGGGUCUGGGUGGCCCCAGUGCUGGUACCAUGUGCUGGC
UUCACCUUUUAAUAACAGUGUGACCUUAAACAAGUCGCUUAACUACUCUA
AGUUUCAGUUUCUUUCAUGGUCUAAAUGGAGAUUAAAACACACACACACA
CACACACACACACACACACACACACCCCCUCGUGUAUCUACCCCACAG
GGCGCUUUUGAAGACCAAAUGCUGUAACUACUAUGAAAGUGCUUUGUAAA
UUGCUGUGGAAAGUGUGAGCUACUCAAGCACCCGAGGCUGUCCCUCCUUG
```

-continued

CUCACAUGUCCAGCCCAAUUCUCCCUUAGUGAGAACAGCACUCAGUAGGU
GCUGUGUGUGUUUGUGUUCAAUUAAGAAAUUCCAGAAUAAAUAAAAAUGA
AUUAAUUCAACAAACAUUUUCUGGGGCACCGACAAUCUGCCCAGUGCACC
AGGCUAGGUAUCUGAUACAAAGAUAAUGAAAACAGUCUCUUGGAACCUAA
UUGGGGUCCUCAUUUGACCAGGAAUUUCUUUCGUCCCGUUUUAAGCCAAC
CAGUUUUGUCCGGACAAGACAAAAACAACUUGGGCUGCUUUAGAGAAGCC
CAGCUCAGUGUAGACAAUAGCUGCCCAGCCUCUGAAAGGGGCUGAUUGGA
UUAUGUGGCAAAUGGAGGUGCAAGGAUGACUUGGACGGUGACAAAUGAAG
UGGGCGGAGACCUGCUUUGAGUUAAUCCAGGCUAUUAGGAGGGGACCUUU
UGUCUUCCAGAGACUGGCAGGAGCUUUUACCAGUGGUUUUUACAUCCUUA
AUGUUCAGGACGAAUAAUUUAUGGUCAGUGAAAAUCCAGGCCCCAGUGAG
AUUCGAGUGGGCUGUAAAAUCGAGAGUCCUGCUCCCAGUGAGUAAUGGUA
GUGAAUGUUUCUGUCACUUUUUGCAACCGUCCAUUCAUUUGAUCCUCACA
ACUCCCUGUCCUGAGCCAGGACCGGCCACUGCCACUCCCAGGGAAACAGA
GGCUGUCAAGAGGCUCCACAGAUUGGGCCCCACUGGAUCAUUGAACCCCU
GUUCCCUGAGUUCUAGAGGAAGAAUUGUACCUGUCUCAGUCCCGGCCACC
UCCAGAAGGCCUCCCUCUGCAUUUCUGACUUUGCUGUGCCGGCAGCCUGG
AGCCUCCCAGGUCCUGCUGUCAUCUUUUCUAGCCACUACAGUCUCUGUC
UUUCCUUUCACAGCCAAGCUUCUUGAAAGGCCUGUCUACACUUGCUGUCU
UCCUUCCUCACCUCCAAUUUCCUCUUCAACCCACUGCUUCCUGACUCGCU
CUACUCCGUGGAAGCACGCUCACAAAGGUAAAGACUUUCUGUGGCUUAA
UCCUUGUCAUGUUUCGGCUCAUGGACACAAGGACACAUUUUCAUGCCUU
CUCUCACAGGGCUCUGCGUCUCCGGUUCACUUCUGUGUCUUUACACUCCC
UUCACAGAGACACUUGCUCCCCCUUCUCUCGUUCUUUAGCAUCCCUAGGA
ACUUGCACACCCAGGUCUCUCGACUUCUGGACCUGCUUCUUACCAUGCCG
UCUUAAGCAGUCAGGAGUCGCUGCCUGGGUUCGAGUCCUAGUUAAAUUAC
UUAGUGCUGAGACCUUGGGGUAGGUAAACUUUUCCAAGCCAGGUUUAUCU
CAGUUUCAAAAUAGGGUUAAUCGUCUUUAUCUGGCAGGUCAGGUGGGAUG
UCUCACAGGUAAGCACCAGAUGCCAUUUGAAAGGCUUGAAGCAAAGUCAA
UAAAGCAUUCAUGGGAAAAUACAACUGGAGGCACCACUAGAUUUUCGUAU
ACAUUAGGUUCCCACGGGGAGGACCGAAGAGAGAAGAAAGAAGUGGAAAG
GGAGGAGCGUGCAGGAGAGACAGGAGAAGAGAAUAACUAAACAAAGACAU
UAAAGACAAAAAAAAGUAGGAAAGGGAGACUUAGAAAAUAUUAAAAGCC
ACCAAAAACACAUCCAAAGACGGUUUCCCCUUACGUUAGUUGGGCUAAAA
GAAAGCAAAUGGGAAGAAGGUUUUAAAUUGAUUAUCCCAGUGACAAAUCC
CAGGAAGCUUUCACAUCAAAUCACCCUAUUCUGGGUUUUUAACUCCUUCC
AUCGAGUUUAACCUCUUUACCUCCCACAUCCUGGUAAACCCUGCCCCUC
CCUACCGCCCCCUUUGCUGGUGAUUAAAUCCUGAAGGUACACGAAGUAUU
UCAGUGAAUGAAUGGCUAACAGAAAAGGGCCUCCCCUCCCCCUUACCCUG
GCGGUGUUUUUCAGUUUUUAUUCCACUUUCCGCCCUUUUCCCUUAAUGAAC

-continued

ACAGGGCUAAUCUCGGGCCUUGUCGAAGGAAGAGGCUGCAGACGUUAAUG
AGGUUAGCUGCUGGAUUCCAGUAUUCGUCGCAUAAGGAUCCUUCUUUGUC
UGCGAAGGAAAAACACACUGAUUAUCAUAAUGAGGUGAACUGGCCACCGC
CGGGCCGGGGCGAUGUGGCUUCUUAAGCCACACUUCUAAUUUUGGUGAUG
GAGCCGACAUUUCUUUGGCUUCUCAUUUAAGUCUUUGCCUCUGUCCCAGU
GCGAAGUCCAUUCAGCGGGGUUGAAAGUUGCAGGCAGCUUUGGGAAGGGG
GGCGUCGGACAGGGUUGCAUUGUAGAAAGUGGCUUUGUUCGAUCCUUCGC
ACAGAUGCAAAUGGCCAGAGCAUUCAUUCCCUUUCUUCAAGAGCUGAGGA
CUGGGGGGCCACUGGUGAUCAGUUCCCAACUCUAGCUCUCCUCUGACUC
AUCUCAGGACCCAUUGAGGACAUCCAAAACUCACUCAAGAUCACCAAGUG
GUAGGAAAGUACUAACUCCUGGGCAUAGCCCUAGGGGAGUGACUACAAUG
UGAAUACUCAUGGAAUGCCUAGCCAGGUGAAGAAGUGAAUGCAUGUUGGC
AUCCCAGAGGGACCCCCCUUAAGAGGGCAUAGUUUGGGGUUCAGAUUUGA
CUCCAGCAUACUGUUGAAAUUGGGCACAGGGGGCUAGUGAUUAGUCAGGA
UCAAUCAGUGGAGAGGAGAUUAAAACUCACAUCUGGGGAGUCCGGAAUCAG
AACUUGUAGUUCUUUUUUUGAAAUGGAGUCUCGCUCUGUCGCCCAGGCU
GGAGUGCAGUGGCGUGAUCUCGGCUCACUGCAACCUCUGCCUUCCGGGUU
CAAGCAAUUCUCCCACCUCAGCCUCCUGAGUAGCUGGGAUUACAGGCGCC
CACCACCACAGCCGGCUACUUUUUGUAUUUUUAGGAGAGACGGGGUUUCA
CCAUGUUGGUCAGGCUGGUCUUGAACUCCUGACCUCAUGAUCCACCUGCC
UUAGCCUCCCAAAGUGCUGGGAUUACAGGCGUGAGCCACCAUGCCCAGCC
CUAUAGUAGUUCUUCUUUUGCCCCUUAAUAUCUUCACCCACAUGUCCUGU
ACCCUGCCUGAACCCUCCUCCUCUUUUUGUUCUGAUCUUUGAGCUCCCUA
GAGCCCAUAAUUCUUUAGAGCAGGUAUGUCCCGAGUCUGAAACAUGCCCU
UAUUUGUCCCAAGCUCUGGACAUUUCUCACCCCAAGGCGGAUCAAUCAUG
AUUAAAUCACUCCAAUUAAACUUUAGGCUCCAGUCAGACCUUCAGCCAAA
UGGAAAAAAAACUAGGGGAUAAGGGAGGUAGUUGGAGCAAGAAAAUGUU
AUUAGUUGAAACCUUACGGGACCUUCCUCCCUUAGUGAGUCUGUUGGCUA
AAGGUUCUCUGGCUUCGUGAAUUAGAAUCGGAUACUGUUUCCAAGUUAGC
AAAACCAACUCUACCCCAGCACCCCACGAGGAAGAAUGUGGAAGGAUCUC
CCAUUGGCCGGUUGGGGCAAAAGCCUGAGGCAAUCUUUCAUCCCCUUUUG
CCAAGGCGAGACUUUCCCAGUGACGGUGAUGUAGUUGGCCACUCUGACUA
UGGGUGGACUCGGGUGUAGACCUCUGAAGCUGAGAUCACACGAAAACCUG
GCCUCCCCGCCAUGUAGCUGUUGGAGAGUAGAAAAAUAGAGCACGCCUGA
UGUUUCUAAAUGAAGACUUUCAAUAGUAAUGAAGAAUCCAUGGCACUC
UCCUCACCCUCAAACACAUGGCAGUCAUUCACAUACAGGCCCCAAAGCCA
CUGUUAGUGCUGCAGUAGCUCCUGUGGACAUUGGAAAGCCCGGAGAGGGC
GUGGAAGAAAUCAGCUGGCCCCGGCAGGUUCUCGGGGUUUUGUGCCCA
AGGCUCCUGGAGCCCUAAAAACUUUCAAAAGUUAACUCCCCACGUCCCCA
UCCUGCUUUGGGUUUCUGGACUUUUCUGAGGCACCGGCAGAGGGGUCUCGU
UGCUCCCUUGAGUGUAGGGGCAGCCCUUUAACCUGGCUCCUUGAGUCCCU

-continued

GCUUUUUCUGCUUCUGUUGCCUUCUUCCUCGUCUUCCUCUCUCAAUAU
CUCCCUCUCUUUGUCCCUCCCAGUUCCUGACCUGGCCAUCCCGGGGUGC
CCUUGACCAGCCCCGUGUCUCCUCAGGGUGUCCCAGCACCAGCCUGGCAC
AGAGUGGGGCUCAGUUAGAGUAUGUGGGAUGUUGGUUUCGCCAGGUGAGU
GAAUGAAAGGACUCGACCACCACAGCUGAGCCACUAGCUGGGCCAUGCGA
AGAGUUCUAGGUGCAAAGGCUGGAGGGUGGAAUUCAUUUUUGAGAGGUGU
GUGAGCAGCUUCCGACCCCUGCCCCAUUUGAACGGGGGCCUUGCUGGUCG
CGUCCCUGCAUUCACCCGCGCGGCCAUCCCGUCAUCCAACAGUUGAUCCU
AACUGAGCACGCCCACGGCCCUGGUCUGGCCUGGGCACCGGCCACCGUAG
CCCAUCCCUUGAUGGCCUCUGUGUCCCCAGGAGGGGGCCGGGGGGUUG
CCCAGGGGCUGGAGCAGUGGACUGUGGCUCCAUAGAGGUAGGCCGGAGGG
UGUGAGGGCAGAUUCAAGCUAUCCCCAGGGCUCUGCUCUGGUCGAGCCA
GCCCCUUCUCCCUCUGCCUUCCCGCCCAUUCCUGAUGCUGAACUGU
UCUGGACCCCUGGCCCUGAGUCUCUCAGGACCAAAGUGGGCACGGGAACA
GCUGUAGUGUGUGCCCCCCGGGCUUUGGCCACAGGUCUCCCUCUCGAGG
UGGGUUGUGACUGCGACCCUUCCCUUGCCGUGAUGCCUUCCUCCCCGG
GGCUUGGUCCAGCUCCUUCACUCUCUAGCAGCUGCUGGGGCCCACCUCCC
AUGCCGAGGACCAGCAGGGGAAACCUCCAGGGAGCAUCUGCAGGCUCUGC
UUCUGCCCGGCUGCUGGCUUGCUCUCCCUGGUGGCUCUCCAGCGGCCAGC
UUCCUCACCCACCCGGCACUCCGCUUUGCUCUGUCUCCUGAGGUGGGCCU
GACCAACCUCCCCUUCUCUGCCUCAGUCCCUGGGCUCCAGGGCUCAGCUC
CACAGCCCUCUGCCUAGCAGGCUGGUUCUCCCCUGCCAAGCCCAUACCUGU
GGUCACCUGGCCCUCCUGUGGUCUGAGUACCACUCCCCUGCCCCAGGAGC
CACUCCCACUCCAGCUGCCUGUUUCCAGCAGGUUCCCAGUGCCCCCGACA
AGCCCCUGCUGGUGUCUCCAUCUCCUGCCAAGCAUCCUCCAGUGCCUCCU
CCUGUGGGCCUGGCCUCAGGGCUAUGGACAGACUCCUGUCCCAUCCCAGA
GACCCCUCGUGAUCGUGCCCUGGUGGGUGUUGCCCCGCCUGCCUUUGCC
UCCGCCGUGGCCCUGAGAGUCCUGGGCUCUGCCCCGCCCGGUCCCUUGCU
CCCCACUCAGUUCUGGAUUUGGGGCUGCCCCUAACCCAGCCCGUUGCUGC
UUUGCACCUUUCCUGUCAUUGGGCAUCCCCCAGUAGUCACCCCACUCCA
CCGAAAAGUAAACUGCAGGUGAGGCCGUGCCCCGAGUCUUUCUUCGUGU
GUUUGGCUUUUCCGGGGCGCUUGCCUUGCCAUGAUUCUAACUCUCUGCCC
UUCCCCAAGGCACGUGGGCCGUGGCCCGGCUGGGUCGGCUGAAGAACUGC
GGAUGGAAGCUGCGGAAGAGGCCCUGAUGGGGCCCACCAUCCCGGACCCA
AGUCUUCUUCCUGGCGGGCCUCUCGUCUCCUUCCUGGUUUGGGGUGAGUU
UCUUGCUUUCUUGAGACCCAGGAUUUUAUUAGGGUCAGCUCAUGUCUCUC
CUCUCUGAUCAACAAGAGUGUCAACAUUUAAUUUGGGGAGGAGGCACCCU
GCCAAGGUGAAUUCUUCACAUCAGCCCCAGGGGUCUGGGGCCGGAGA
GCUGCCUGGAGUGGAGACCCUUGCUAUACCCAGCAAGCAUGUGUGGGGU
CCACCCUGGCUGAUGGCAUGCUGUGGGCCGGCGACGGUAGGUGGGGAGUG

UCCACCUCCACUCUAGACCCCCGAGAGCGGCUCGGGCCAGGCACUCAGGA
GCCCUCAGUACGGCUUUGCUGAACACAUUGCAAAAGGGAUCCAGGGGGCA
CUUGCCCUGCCCACACCCGGCCCAGGGACCCCUUCGGAGAGGAGGAAAUG
GGAAUGCUUGCCUGCUCCUCAGCUAGGAAGACAUUUCUUUCCACCAGCCA
UGGUAGCGUCACCCCCUGUGAGAACCGUGGUUUCUCACACAUGAGGCUUU
GAUAAUGUCCUUUAAUCAAAUAGUGGUUUUUGAGCAAGUUCUUCUCUUUC
CUCCUUUCCUCACCCCUGAAAUUGCAAUGAGACGGGAAUGUUUUUGUUUG
UUUAAAUAAAACAGCAAUGGUAGAGAAGAAGAAAGCGGGAUUGGAGCCAC
ACAAUUCACUCGAGGACCCAUCAUUUGUUUAUUUGUGUUUUACUAAUUCA
AGAUGCAGCCGGGAGCCGUCCAGGGCUCGGGCCUGGGGUUGUUCUGGGGC
GCCUAAGGCUGGGCUUUGCACUAAGGACCAGAGGGUCUACUUGGGUGCCG
UGGAGCACCCAUGCAGCAAGGUGGCUUGCACAGCAGCCAGGCGAGGUGUC
GUCGAGGGCGGGGCUCAGGGUGGCAUGCUGGACGGCCAUGCCAGGCUGA
AGUUUGGGCUGGCAGGAAGAGAGGAGGCUCAGCUGAGGCCACUUUCCUUU
CUGGGGGUCCCAGGGACUGAGUCUGUGGCUCACUCAGGGCGAUGGGGUGU
UUUUAGAGCCACUGCCCUGGGAGGCAGUGUCAGGAUCCUGGCACCCCUCA
UAUAUGACGCCCCUGGGGUGGCCAUUGUGGUGAAUGAGUGCAGUUAGACU
UCCCAGAGAAGCUGGGUGGGCGCUGAGAAAGGUCUGAACCGUGGGGUGAG
GCUGGCUCCAUUCCCCAGACAUUUAUGGAGGCUUGAGGGGGCCCUAGCA
CUGUCCUUGGCCCAGAUGCCAAUACUCCCCUCUGGACGCCCACGAAUGGG
GUCUCUGAAGGAAGUGGAUGAACACAGCUGCACGCUGGGUGGGCCCA
GCCUCUAGUCCUCAGCCAUGUGCACGCAUCAGCCCUUGUGCAGGCCUCCG
CCCUCCGCCACCCCCACCCCCGGAGUGUCUCUGGUUUCCGACGCAGCCU
CGUAAUGCUCUUUAAUCAAACAGAGGAUUUGGAGACAGCUCUCCUGCAGC
CCUGCACUUCUCCCCUGAAAUUGAAAUGGGAUGGGGAUAUUAUUUUUAAA
CAAAAUCUGGCAGCGUAGGCAGAGGGGGCAGAGGCGCUCUAACCUGGGGC
UGUUGCCUUUGUCUGCUUGUUUCUGCUCUCUGGAGAGCCCCAGAGCCUGG
AGAGACGGGGAGGGGAGUGUGUGCCCAGGGCUAAACCCAGGGAGGGGGCC
CAGGAAGGCUCUGCCCCGUGACAUUUACUCCAAGGCUAGCAUUUGCUGAG
CCACCUGCAAACACAGUGAUGUGGAGAAGAGGCCCGGGAGGGGAGGUUUG
CACAGGGGCAGGCUGCUGGGGUCCUGGGGGGAUCCUGUCCCAAGCUUACU
AGAAUGCAUUCGAGUAACUGGUCUGAGCCAGAUGCCCUCAGCUCUUGGAC
UGGUUUCUCACGGACAUCUCAGGACUUUCCCAAGGUGGACUAAGCCCAGG
GACAAAGUCAAAGUGAAGGCCAGGGGCACACAGGAGAGGCCCAGAUAGGA
CCAAGCUUUGGCAGCCCCUGGCUCUCAGGGGUUGAAAUGGAACCCUCUUU
GCACUGAGUUGUAUUUCAGGUACUCAUGAGUGUUUCGGCUCAGGCAAAC
ACAUAUUUGGGGUUUUGUGUGUCAUUAGGUAUAAAAUAGGUAAAAUAUGC
CACGUUCUCAAUGAAAGAAGUUGAAACGUGACUUACUACGUCAGCCUUGC
UGGUGAUCUUCUCGGGAACUGCCGAAAGGCCACUAGUAAGUGCUGAAAGA
CAUGAUCAUUUCAGGAAAAUUCUAUUUUGAUGGAUUGGCCAAUGCCUGA
GCCAUAGCGGGUGGAGAUGAGACCCUGACUGACUAGGCAGUGAGCCACAG

-continued

AGGACCCUGUCACAUCAGCGGAGGGCGGUGAGGGGUCUCUGGCCAUUUGU
CAUCGUGCUGAUUCCUAGGGGGCUGCCUCUAGUGGGACUCUUCUGGGUGG
GUGCAAGUGUCAGGGUAAAGACGGCGGUCUGGUCUGGAAACUGGCUCUCC
UCUCGCACCUGCCCGCCCUGGGUGGUUGGGAAAGGAAACCAAGAGGGUAG
CUCAGGCCUGAGCUCGUGGAAAGGAAGAACAUGACCCCUCAUUCGCUCAC
UCGCCCCACAUUCUCUCACCUGCGAGUUGCUCAUUGCUGCUUUCAGGGC
CCCUGACCUCAUGCCUCCUGAGUUGUGAUUCAAACCCCAAAUGAAUUUCC
AAGUACAUUUCUCCAAAUAAUGUCAAAACCUGGCAAGACUUAAGGGCAAC
AGGAUGCAUGUGUUCUUAUUCAUUCAUUUACAUAAAAUAACUUAAGUGU
GUUUUUUAUGAGCAAUCUGACUUCCAAAAAGAAUGAAAAGGAAAAUCUAC
CCAUCUUUAAUGAACUUGCUAAUGAAUUUUUCCUUGCAAAGAGGAAGGGA
GCUUCCUACAGAAGGGGUGUGGAGGGAGACAGAUUCAGGUCCCAAAGGG
UUAAAGGGCAGUGGACAAUGCGGAAGCCAGCAUUGUGAGCUGCAGUGGAA
AAGCCCUGGGUCGCUGGGAGUGGCUUCUUUUUAGGAGACUGGAAUUAAUG
AGUUGUGAAGUGUCCCAAGGACUGGUUCCCCUCCCUGCUGUUUCUCUGA
GCCCUGUCCCCUCUUCCAAAGGAGGAAUAAGGAGGUCUAGCUUCGUCUCC
CAUCCCCGAUUUGAGCAGAUGGAAGAGUCUAGAAAAGAGGUGUACCUUUU
GAAACGAGGCCUCAGAUGUGGGGUUCCUGGUCUGGAAAGGGGAAGGAUGA
AUCUGGGGUAGGAGAGGGUCUCGUAUGGAGCCCCAUUCAGACAGGGCAGU
CCCACACCUGGGCUGCCCACAGGUUCUUGGGGAGUCUAAGGAAAGGGGA
GCCACAGAACAGGCUUGCCUCCUUGGCAUGGAUUGGGUCAGUGUUUCAGA
GCCAGGAAAGGUGGGAGUGUGGGGGCCCUCGGGGCUGAUGAGGGCGUGC
AGACCCUCCCCUCCCACCUCCUGUCCCAGGAGCCCUGCAGACACUGCAGC
AGGAGGGCACUCUGCCAGAAGAGGGGUUCCAGCUCCAGCCGGAUCCAGCA
GACAUGGAGAGACCCCUUAUCUUUGCCAAGACGAGCUCUGCGGUGCCUGA
GAGGCCCGUAGGUCUGGAAUUCUAGGGCCUUCUGGGUUUGAGUCAGGUCC
UGAGGCCAGGGCCUGGGCCCUGAUCCUCACCAUGGAAAACUGGUCACUUU
ACUCAGGAUAAACUGUGAUGAGGACUUGGGACAUAUCUCUGUCUGUCCUC
UCAGCUCGCGUCACCCCUGAGCCCUUGGCGAUCGUGGGCGGCCCGUGUAC
AGAGCAGGUGCUGGGUCACUGGGGCCGCCGUGGGCCUCCCAACAUGAGGG
ACUGUGUGUGAGAGAGGAGUUCAUUAAGGGAGAGGAUGGUGGUGAAGGGU
GUAGCCAUGACUUUCUUAACUGCUCUCCAAUUUCUUUGAGCUUAAAAAUA
AAUCCAGAUGGAGAGUUCUUAAGUCCCUAUCCUGGGAGAAAGGAAGGCU
GCCCACCACCUUCGGCUUGCCUCGACUCUGAGCAGUGAAUAGGGUCUUUG
GCAGGGGCUUAAGGAGGAGACUCUUAGCCUGGGAGCUCCCAGGGCUGUUU
CAGAUGGAAACAAAGGCUCAGGCCGAGAGGAAUGUGGGGAGCCCCCGU
GGGGAACAGCCACCUGGGGAUAAUGGGAGGGCUGAGCGCAGAUGAGUUU
UCCCAGGUUCUGUGAAUGCGCCCUUUCAAUGGAAGGUGCCUUUUUUUCCA
GAUGAAAAGAAGAAAACGUCAAUUACCUUCCCCUGAAACGGAGUGUGUGU
GUGUUCCCUCCCAGGGGUUGUGUGGGGCCCCUUGCCCUUGUGUGUGUGUC

-continued

GGGAGCUCCAAGGCUGCACAAUGACGCACUUAACCAGCCACUGGGUUCGC
GCGACCCUGGGAUGCUCACGCUCUUAGAUUCUAGGGCUUGAUUUUGAAAG
UUUCUUAGCAAAGGGGAAUCAGAGUGAUUGAGCCUGUAAACAAAAAUUUG
AUCAACCUGGGCCUGAUGCCUGAAAUAUAGCCAAAGAGACAGAAUGGGGC
UGCGGGAGAGAGGUCCAGGAUGGAAAGUUGGGGAAGGAGGACAGUCGGG
GGCCAAAGGCUGACCGCAUGUCUGCGCCGGCCUCCGCGCUCACAGCUGGG
CUGCUCCUUCUGCCACCCCAGCCCUUUCUCUGGGCCUUCCUGGCAGUGGA
CAUAGAGUGAUUCCCUACUCAGGAAGUUGGCGGUAGGGGGCUCAGAAAUC
CACAGGGCUGUUGUUUCACAGUUAGCCAGGAGAGGAGGGGGUCAUGGUGG
CCCGCAGGGAUGGUGGGCAGCUGCGAGAGAGGGGACGCUUCAGGUUAGAG
CGAAGCUGUUUGCACCACCACUGCCCCAGACUGCCGUAAGGGUAGGGCCA
CUCCAGAGGCACCAGGGACAAAGUCCCUGCCGUGACAGGAGGGGGGCACA
GGUCUCAGUCUUGGCUGGUCACUGACUUUGCUGCUGCUGGCUUCUGAGCC
UCAGAGAGGUCAGCAGUCUUCCAGAGACCUGGUUAGAGCCUGUGCUCAGC
CCUGACUAUGGGUGUGACCUUGGCCCCUGUCUCCAGCCCCUUAGGCCUCA
GUUUUCCCGUCUACGAAAUGGGCGAGUGCAGGCCCAUGGUCGUCCGAGUG
GCUCGGGGUUUCUUCAGGCCUCCCUGGAGGUCAUCUGUCGUUUGUUUGCU
GGGUCUUUGGAGUUGUUGGGACUUUGGGGGUCACUGGUCCGCUGCCCCCU
CUGCUUUAGAGGUGGGGAAACCAGCGAUCCCAGAGGCCCGGAGCCUUGCC
CGAGGUUGCACGGUGAGCCGGCAGCAGGCCCUGGAGGUGAAGCCCUGCC
AGUUGCCAGCUCCUGUGUGACCUGUGUGGUCGGGGGGGGUCACAGUCACC
GGUCAUUAGUGUGGGUCAGAGCUCUUGCCCAAAGAAGGUUCCAAGGGGCU
GCCCCAUGAGCUGGGAUGCAGGGAUCGUGUUUUAUGGGGCAUUAUUCCAA
ACAGGCAGGCUGCUGGUCUGGUCUGGAACACCUUUUUGGUCUGUAGAGUG
ACUCUUGUUUAAUGAGACUGGACUUGUGGCUUCAGAACCAGGAGAUGUUC
GUUCCCCAACCCCCGUGGCUCACCUUGUGCCUUUUGGGUCCUGAGACCC
UCGCCAGCGCCUCUGUUGGCACGGUGGCCCAGUCGGCUGAGAACUUCCUG
AAAAAGCCAACAGGAUGACAACUUCUGGAAAAGUGAUCAUCACCCGCCUG
CACUGGCUGCCCAUCUUUAGACUCAGCUUUGCCAACAUUCCCAGCUAUCUC
UGUGUGCUGCAGUGUGUAGUAAUGAACAGCUCACAAAACCUCCGGCUGGG
CCUGCACCUGGUUAUUACCGUGGUGGGCUGCAGCUUUUGUUUUGUGACCU
UGGUUGCUACAAUACCUGCGAGCUGAAAUGAGGAAUCGAAAAAUUGCCAG
CUUCAAUUAGACGGGCAGACUGCUUUCCCAAGGCUGCCUCCGCCACUCCA
UCCAUUAACGGUAAACAGGCACCAAAUAGGCCCUAAUUCUCUCUAAUUGC
CCACUCCUGAAGCAAAGAGGUGAAAUUCCAGGAAGAGGCGUAUGUAAACA
UCCUCUGUAACCUGACCAAGUAAAAUUAGAGGGCUGAUGGGGCCUGCGA
GAGAGAGGGGACAUGAUUUCAAAAGAUGUCCCAAUUACCUCUCCUAUUUU
CAUAAAUGGGUCUGUAAUGUCCAGGGCCCCGCCUCACAAAGGUACAGGA
AAUUAGCUCUGCAAAGAGCUUGCAUUUGUCAGGGGAAGUUGUAAGGGGGU
GGUGUUUACUCAACAGGUAGGAAGUACGAGAUCUGAGGCAAGACUGAUUA
UUUGUGUAACGACGGGCUCUAUUUCUUGAGAUCAACAUUUUAAUAAAAGU

-continued

CAUCCUUUUAGGUCCUUUUGUGUUUGAAACAGCCAUAAGUUGUUUAUACC
AAAGACAUGCCAGAUCAGUUAGGUGCUGUUUGCCUCCAGAAAAGAGGAAC
UUUUAAAAUCCUAAGAUGCAGAGCUAGAGUUUUCUAAUCCCAUUAAGCUG
UGGAAGAUGUUUUUGGAGUGUUCACCAAUGCUUUCUGCGUGGGUCAUGAG
CUCACUGCACGCACUUAUGAGGUCUUCCAUCAAAUGCUUGUGACAAUUAC
UCCUCUGGACUCUAUAAGGAGGCCUCGUGUUUUUCUUUGGUUCCAGACAG
UGACUCAUCUCUGCAGCUUUUCUGACAUUUGUUAAGAUUCUAGCCCAGCA
CUGCGUUAUUAACACAUCACAGCAAGCCCAGAGCUGGCACACGCAGCUUUU
UAAACCAAGGCACGAAUUUGCUGGGGCUUCUCUGUAGCAGAGCAGCCUGC
GGUCUGCACACAAGAGUUAAUUAAGGACGGUCAGGGACUCUGAGGUUUCA
UGGGGUCCCUGGAGCAGAAGCAGGAAAAAACCCAGAUGCUCCUUCCUGCU
UCUGAUUUCUCCGCUCCUAUUAAAAACACAAAAAAGAACAAAACAAAAAC
AGCCAAACAAAGCACCCGCCUCUGAUUCCUGCGGGAAAUGGCAGUGCCUU
UGGUCGCGCUGUGUGUUCUUGGCCUGAGUCUCGUUGCCACCUUAGGACGU
GGCGAUGGUGAGAGGCCACCCCAGCCACGCACAGUCUCGGAGGGAGGGUG
GGAAACGGUCUCGAGUGGUGGUCAGUAGAUAAUGGGUGGUCUGGCAGCCU
UUAGGUAACCGAAGUCGGCCCCUCAGUCACCCAUGCACUGAUCAUUGCUU
CACUAACACUUAUUUUAAGACUUGUUGUUUCUUGGUUAUCAAAUUAACCA
GUUAUGGCAGAACAGGGUUUAUGAAGGGCAAGGCCAGGGAAGGAGAUUUU
AGGAAGAUUUGGAGGCAAGAAGUGUCCCCAGUGCCCUGGCCGGGUCUUGG
ACAUCCUGGCUGGAGACAUGACUAGGAAUAGAGAGGCAGAGGCAGCAGGG
GUGGCCCAGAUGGCAGGGGUGGGUUGGAGAGAUCCCUGAGAGGCCUGAGG
ACAGGCGGCAGUCUUGGGAGCCCCUGAAGACCUGCAGUGGGGCAGGCAGC
UGGAGUCAGGUGUCUCCCGGGACCUGUUUUUUUUUUUUUUUUUUUUU
GAGACAGAGUCUUGUUCUGUUGUCCAGGCUGGAGGGUAGUGGCGCAAUCU
UGGCUCACUGUAAUCUCUGCCUCCCACGUUCAAGCGAUUCUCCUGCUCA
GCCUCCCGAGUAGCUGAGACCAUAGGCACAUACCACCACGCUGAGCUAGU
UUUUAGUAGAGACGGGGUUUCAUCAUGUUGGUCAGGCUGGUCUCGAACUC
CUGACCUCAGGCGAUCCACCUGCCUCAGCCUCCCAAAGCGCUGGGAUGAC
AGGCAUGAGCCACCCCCUGGGGCUGGUACCUGUGGUCUGUGGCUUCUGC
CUGCCCUGGUGCCCCACAUCUCUCAUGGCCUUUCUGUUUCCUGGGG
GCUUUGUGGGGUGUCCCAUGGUCUCCCCUGGCUUCCUGUCUCCACCUG
UGCCUAAUCCAGGAAACGGUCCCCAGAGAUGGUGUUUUCAAACAGACCUU
GGCCCUGUCCUCCUGGCCCAGCCCCUGGCUGCCCUAUCACCUAGCUUGCU
GCGUUGGUGGGACCUCAGCUGUCACAGGCUACCUUUCUAUGACGCCUCCU
CACCUUAAGUAGACUCUGAACAGAUUUUAAAAGCCAUUCAUUCAACACAU
UUUUAAAUGAAUAAACUUUUUUCUGUGUAGUUUUCAGUUUACAGAAAC
AUUGGUGGGAAAGUACAGAGAAUUCCCAGAUCCCGUCCCCACCAUCUCCC
CUGUCAUUCACACGUUGCCUCCGUGUGGUGGGUCUGUUUGUUCCGAUCG
AUGGAACGACUCUGAUACAUGAUUAACUAGAGGCCUUGGUUCACAUCAUU

-continued

AGGGCUCACUCUUUGUGGCGCACAUCCUGUGGGUCUUGACAAAUGUGUCA
UGAUACGUGUCUGACAUUGCUGAAGUCACCUUUUCUUAAAGCUUAACAUU
UUGGGAGUAUUCUGAACUAUGUUUGGCCCAGCCUGCUGCCCGAUUUUUAU
AAAAAGAAAAAACAAAACAAAACAAAAAAACAAGUUAAAACGUAAGGCA
GAUCUUGACACUGAAGACUCGAUGUGCCUGGCCAUGGUGCUUCCCGGGGC
CUACUGCACUGUGAACAAAAUUGCCACAGUGGAGUUGUCUGUCCAGGCAC
ACAACGUGUGUGCCAUGGUUUUGGGAAACGCUGCCCAUUAAUAGCCCUGC
AGCCCUCUGUGGGCUGCCCUCCCGGCCACACCCCGCUUCCCUGGUCUCCU
CCAGGGCCAGCCAUCCUGCUCGCCGACCUGGGCACCUUGCUUCUGCCAGA
GCACAGGUUCAUGCCCUGUCUUCAGGGCCUGGGCCACCCCGUUUCUCAU
CUAUGCAGGGUCCUAAGCCUUUGGGUCCCACAGAGCACGACUUCGCUCCG
UGAACAGCACCAACCCAAGUCUGUUCCAUGUCUCCACACCUGCCCCUUCC
GCUCCAUAGGCAGCUGGUGGGUGAGUGGAGUCAGGAGAGAAAUGCGUGGC
UUCUCCAAUUCCACACUUGCUGGAGGUUGGGGGAGUCUCUGCUCCAGGCCA
CCCCUGCCCGCCCCCCAGAGCUGUUGUCCUCAUCCGCCCUCCUCCUCCUC
GCCGGCCUGAGUGAGGUUCUACUCUGUGACCUAGUGCCUUCUUGUUACAG
CGGAAGCCAUCACCUGGAUGCCUACGUGGGAAGGGACCUCGAAUGUGGGA
CCCCAGCCCCUCUCCAGCUCGAAAUCGUAAGUGGCUGGAGUGUAAAGAAC
ACACAUGUGGCCUUGCUGCUGAGGGUGGGGCCAGCUGCCGGAGCACACC
GCCAGGCGGACCUCGUGGAGGGGCUGGCGGGCACUGGCCGGGGGUCUGUG
CACCGGGAGGUGGGUGCCCAUCGAGUCAAGCCAAGUGCAGACCUGGGGGC
UCCUGUUUUCUAAGACAGGAGCCCCCUGCCUCCUUGUGUUGUCUCUGUGG
CAAAAGAAUUCUAUAGGCGGGCUUCAAAUGUCGGACCCCAAAAGAAUUUC
UUCUUUUUCACUCUUCUAAAUGAAUGGCUCUUUCAUUAUUGAGUCUCCCU
UUGGCUCUUGUGCCGCAGGGCAGACUAGGAUGGAAGUGCCCUGUGAGCUG
GGGGGCCCUUCAAAGGGCCAAGGAGAAAACGCAGGCCGAGGGACCAGCCU
UCCAAAUGGGCUUCAAGCUCCAAUGACCUCCGCUCGCCCCCUCGAAAUGU
CUGGAAAACAUAAUGGGCAGAUUUUCUGUCUUCAAAGUUUCCGGCUAAAC
CUCUUCAAGUUCUUUAUUGUUUGGGACUGAGACACUCAGCCAUGUUAAUG
GGUAGUUUCUUUUGUAUUUGCCUUGAAAGGCCAAAAUAUUUUUAUAUUGC
CACAGACAAAGCCACCUAUUUAAAAAUGAACUCCAUGUCCGUCGUUUCCC
ACCAGGAGACUAUGUACCAUGUGUGUGUCUCUAUGUAUUCUGGGGUCUUG
AAACAGGUUUCUCAUGGGGAUGGUCAUUCACCACGGUCCAGAGGGGCAGA
ACAGGCGGCGCUUGCCUUGCCCAGGGGGCCUGGGGAACGUGGGCCCUCAU
CUCAGAUCUGCCCCCAGUAUGUUUAGGACGCGAGCCCCAGAAGGAUCUGG
GAGUAAACUUAACAUUCACUGUGUCUCUGCUCUGCAUCCGCCAUUUGUGU
GUGUUUCUGGACUGUGGGCUGUGUGUACCUUGGUUGUGACUCAGUGAGA
AGAAGCAGGAAUGCCAAAGAUACUGUGAAUGUUCUGAGUUUUGUUGCUGU
UGUUGUUGAGAGGUUGUUUCACUGGUAUCUAUUGCAUUGUAUAAUAAAUG
ACCAGAUGAAUGAGUGAAGCAAGAGAGAAUGAAUAAACAAGUAAAU
AGGUAAAGAAGUAAGCAAGCCAGGAUGAGAGUGUGUGUACACAAGACCAU

-continued

```
GGUUCAUCCGCUUUGAUGGCUAGGCAAUCAAUAUAUAAAUAGAAAAAAAC
CAGUGAAUCACUAAGUAAUAGGGCAACACACAAAGCGAUAUCAGGUGAUU
AUGGACUAAGGGGUAUGUGUAACUCAAAUAUAUGCCUCUGACAUUUGACA
AUGAAAAGAACCUAAAUGAAAGAAAGAAUGGAUGUAUGAGUAGUGAAGU
GCAGAAUGAGACAUAGAUUUUGAGGCCCGUCAAAAUGAAAAGAUGCAAGU
UAGGGAACAAGUGAUCAAAAGGGAGAAGGGAAAGGUUUUUUUUAAAAAAC
CAAAACAACAAAGAAAGGUUAAAAAAAAAAACAGACUAGAGGAUGAGUAA
UGAGUAACUCUGUAAGGAGGACCAUGUCAGACUAUUGUAAGCUAAGCAUU
AGGACUGAUACAAAUAAUAUAUGCUCCUGGCAUAGAAAAAUAAACCACAG
AGAACGAGUUCAAAGAAUAGCAAAGAAAGAAAGAGGACCCAGUGGGCGAA
AGAUGAGAGUGUACUUUUACCAAAAGUUAUCUAAGCCUGAGCACUUGAAG
UCUGCACAUAAAUAAUAAAUGACAAAAGAAAGAAAAAAAGGCCAAAAAG
UCUACAUUGCGUGUGUGGAUGGAUGAAUGAGCAGUGGGAGUGCAGCGCCA
GGUGACAAGAUGUUGUGAGGGGUUUUGAGUCAUCCAGUCCUGGGCACUGA
GGUCUGUUAGAUGAAAGGAUAUGAGAAAGGUAAUAUUGGUAAAUAAAGAA
AUAGGAAACAAUGUAACAAAUGUUAAGUACAGAAAUACAUUAAUGGGUGG
UAAAUAAAGAUGUAAAAGAAGGCAAUGCGAUCGAUGGUGGCAAAAGAUCA
UCACAGAUUAAGGGCUAUGGCUGGUCCACUUCUAGAAAACCACAGGCUGU
CCAUUAAAUAAUGAACAUCUAAGUGAACAAGUCAGUGAGUACCUAAAUAG
ACAAGGAUGAGGUGAAUGAGAAGACAUGGCCCCAUGGGUCCUCCUGAUGA
GGGUGUUGGGGUCCCCCUGGGCACCCCAGCUGCAUGAAAAUGAAGGACA
GGAGGUAUGGAAAGCUAUGACAGAAGAGAGAAAGGAACGUAAAAGAAA
UAACAACCAAAUGGAUAAAUGGGUAGAUCCACGAGAAGAGUUAGGCUAGG
ACUUGUCAUAAGGGCACCUGACUCCACUAAUAGAGGAAUAAAUGCCUAAU
AAAAAGAGAGCAAGCAGGAAGGAAGGAUGCUAUGAAUGCAGGAAGGAAGU
AAUGAGUGAGACGUGGAACCGCACGGCCAAGGAUGGACGUUUGCGGUGG
CUUUUUGAUGCGUACAGCCAAGCCACUCCAUGGCAAUGAGCUCCGAAGAC
AAAGUGCAAGAGAGAAUGAGUGAGAGAGUGAGAGAGAGAGAAACAAUAAA
AAAUGGGAAGAAAUGUAAAAGGAAGAAAGGAAGAGAGGUAAUAUAUUAA
GGAAUAAAUACAUGCAUGCAGAUUUAAGACAGAGCCAUGCUAGAACAGGA
AUGAAAGCUGUGUGAACCAAGCAGACCGCUUAAUUGGCACCAGUGCUGC
UGGUAUGGUCAAUCACCUACUCAACUAAGGAACGGCUCAAAGCAUACACA
UGGGAGGAGGAGUGGGCCACAGAGAGAGGGCCCAUUAGUUGCAGAUUA
CGAUGUAUCCAGUUAGGUGCACCUGCCUUCGAGAAGUGUAAAAAUAAGUA
UUUACAUAGAAAGAAAGACUGAAUGGAUGCACGGUGAAUGCAUGAAUGAU
UGAACGACAGAAAAGAUUUGCAUUGACCGAUGAGGAGGGCAUUGUAGACA
GGGAUGAGGGUCAUUGAUCCUGGGUGCAGAUCUCCAAAAGAAUGACGAA
AGAAAGAGGGAGUGGUGAAAGAAACAAUAGGAUGGGAAAAAUGAAAAU
AGAAAAAAGGAAGUGAAAGAGAUAAUAAAUAAUUAGAUCAAAUAAGUUGA
UGAAAGGGGACUGGUUUAGCACAAGCCAUCCACAUUAAUUCAAACCUGUG
```

```
GCUCUGAAGUUUGUUUUUUAAAUGACCACAAGUGUAAGACUGAAUGAAAG
AAUAAAUGCGUGCAUUCCAUAGGAUGCAAGAAAAGGAGUGAGGAAUGGGA
AAAUUGGAAGAACGAGAGAGGGAGAGAUGUAAGAAAAGAAAGGAAAAGUG
AAGUAGGCAUAUGAAAGAAAAGGCACUUCUUGGACAAGCACUGAAAUAUA
AUGAGACAGUUUUACCCAUUAAAUAUAAUAAACAGUAAACGUUGAGGUUC
AUCAAUAAAAGCACAGAUACCUGAAUAGAGGAGUGACCUGAAUAGAAUUC
GUUCAGCCGAACGAAUGAGAAUGGAUGAUUUUCACUAUCCUGUGCACUCA
AGGCCCAAAAGAGAAAGCAAGAGAGGAGAGAAUAUGGAAACGUAUGACAG
GAUGUAUAAGCAAUACAAACAUAUUGAAUGAAUAAAUAAAGACAUAAA
UAUGUGGGAGAGUGGACCACGCAAGGACAAAAAGAGGAGAGAAGGCAGCA
AGAAUUAUGACUAAUUCAAAACUGGGUUCCUGAGAUAGUUAAAUAAAUCC
UGCACCAAAUCCCCAGGGGGAGAAAUUAACAAACAAAAGACAGCCCCACA
CGGACCAGUGUGCAGAAGGCUCCAGGAACCGCAGAUUAUGGUUAAUCCAA
UUCUGUGCACCUGAGGUCCAUAAAUAAAAGAAUAAGUAUUGAAAUGAAAG
AAUGACAGAAAGAAUGAAUGGACACAUGAACGACUGAAUUAGAAAUGGAA
AUGCCUGGCACAGCCAGGAAGGAGCUGCCCAUGGGAUUGUCAUUCAUCUC
ACUCUGGGCACCUGAGGUCCAUAAGCGUGAAAAGAGGCAGGAAGAGAAGU
GUCAGGGAGUCAAAGAUAGAGCUAAGGAAAGGCAAAAAUGAAACUAAAUG
AAAGCGAAAGGGAAAAUAAAGAAAAACCAAUAAAAAAGAGAACGAAUACG
UGGGUGUAUCUGUAAGAGUAGGAUCUGUUAGGAUUAGUCAUAAGACUGUC
AGUAAUCCUGAAGAUGGAUGAGAUAAUCCAGGCCCAGGUUCCCAGGGGA
GGGAAAAUGGAGAAAAUAUAAAAAGAUGUGAAAAAGGAAAAAGGAAAGGU
AAUAAACAAACAACCAAAGUGAUAAAUGGAUAGUUAAGGGAGGUUGUCUG
AACAGGGAUUAUAAUUAGUUUACAUACAUACUCCUUAAACAGAUAAAUAC
AUUACACCUUUCAAAGAAUAAAUGAAAAAUAGAGAGACAUACCUGGCUCC
AAAACAAGGCUGUAUCUUCUGCCACUGUAAUAAAAUAGAUGCAAUUGAGG
UUCAUAAAUAAAGAAUAAAUACUUAAACGUGAAAGGUGACUAAAUGCGG
GGAAGAAAGAUUGCAAAUAAAUACAUGGGCCAAAGAUGUUUGGUUUGCCC
AUGGAGUUUUAAUUAAAAAAAUUAAUAAGGAAAACAAAUACCCAAAAUAA
GGAAGACUGACAAAUGAGUGAGUGGAUGAGAGAGUGAAUGGUGCUUGACG
UAGGAGCAGUAGUGCUUUAGGGACCAGCAUGAAGGUGGUGACCGGGAGCC
CUGAUUCAUGGGAUUCUGUCCACCUGACUUUAUAAGAACCAAGAAUGGCU
GGGAAUGGUGGCUCACGCCUGUAAUCCCAGCACUUUGGGAGGCCGAGGUG
GGCGGAUCAUGAGGUCAGGAGUUUGAGACCAGCCAGUUUGAGAUCAGCCU
GGCCAACAUGGUGAAAUUCCAUCUCUACUAAAAAAUACAAAAAUUAUGG
GCGUGGUGGCACCUGUCUGUAAUCCUAGCUACUCGGGAGGCUGAGAGAGG
AGAAUUGCUUGAACCCGGGAGGUGGAGGUUGUAGUGAGCCAAGAUUGCAC
CACUGCACUCCAGCCUGGGCUACAGAGCAAGACACUAUCUUAGAUCAAAA
AGAAAAAAAAAAAAAGGAGAAAGAACCAGAGAAACAUAAGGAAGAG
UGAGAGGAAGAAAGAAGAUGCAAUUUGGGAAGAAAUGAAAAGAAAUGA
AUAAAGAAUAAAAUAAUGUAACGGUCAAUAAAUAGGACUUGUGAAUGGAG
```

```
GCCUUUAGGCCAAAGGCUAUGAUUAAUUUCAAGCUAUGUUACUGAAGUCC
AUAAACAAAGGACUCAGAUCUAAAUGGAUGAACGAAUGACUGGAAGAAAG
GGUGGUAGGAAGGUAGGAAGAAAGGAAGGAGGGAAAAAGGGAAGAGAGGA
AGGAACCUUCUUUCCAGUCCUGUGUUCUAGACAGUGGAAUGAAGUGGUCC
CCAGGGAGGGUGGCUGUAGGCAUGUCAUGUGCUUGUCACAUGCACUUGCC
CUGGCAGGGAGGAGCUGGCUCAGGAAGACCCUGGUCUUGGGGUGCUGUUG
CCCUAUCUUGGCUGUGUGGGCCAUUUCACUGCAUCUGUCUCUUCCUCAGU
UUCCCCAUCUGUAAACCUGGAGUGGCACCAGCUGCCUACUAGAGUUGAUC
UUAUGUGUCUCUGUUGAUGGUACCCCAUCUAUGGCCUGGAUAGGCAGGAA
GGGCUUGGACCCUGAGCCCCGCAGAAGGUUGCAUGAACGAGUGGUGUGAA
GCCUGUUGGGUAGCUUGGCCACUCCCGCGGCAUGGGUCACCUGCACAGGA
GGUUUUGCCCACCAGGGGGCAGCAGAGGGUCAGGGAGCAAUAGGCCCUGG
GUGGAGCAUGGGCCCCGCCUGCUGUGUGCCACCCUGGGUGUGGCACCUAC
UCACAUCCAGGGGUUGGUGCAGGGAAAGGCCAGAAGGUGGCCAGGCGCAC
CUGAGAAGGGGGACCCAGAAGCCCCGGGACCCAGGAGCCCUGGGCAAGCC
ACCAGAAACCUUGUUCUUGCAACUCUCUGCAGUGUGCCCAGGCCACCCUC
UGGCCUGGUCUUCCAUGGGGCAGGGCGCCCACCCUUCUCAACUCAGGUUU
CCCUGGGCAGCAGGUGCACCUCAGCACCCCUGGGGUUGCAGAAGUGGUCC
GGGGACCCUGGCUUCCUUGACAUGCCAUCCCCAGAGCCUGGUUCAAGGCC
UCUCUGUCUUCUCGGCUGUUUCACGACGUGUUUUGUAACUUGGCGGAUU
GCGUUUCGCUGUGUCGAGGUUGUCUCUUCUCUGACUCGCCCUCCGGGGA
CUGCCGGGGUAAAUCUGGAGAGUUGCUCGUGCUGACAGUCCUCCCCCAGG
GCCUCCCCGGUUCUGUUGAGUCUCCUUUCUCUGUAGUGGAGGAAAUGUGU
GUAGUUUUGUGUUGUGUGCCUGUGUUUGUCUGUAAAAGCAAGGACCAAAG
UCUCCCUUGUUGACCUCUCAAUUCCUAUUGGGACAUAUAAAAACACUGG
AUUCUUAACAAGCGCCCGGAGCAGUAGGAGCACAGCUUGGAUGGACUCAG
GACUUGUGGCAGGGAGCACGUGGGAGGCAGGGGAGUGGGUGGGGCCAGG
CCAUCUGGAGUGGGAGGCGUCAUGCUCAGAGUGACUCUGUAGACGCUGGG
UGGGAUGGGAGUGCGGGCGCAGGCAUGGAUGGGCUGUUAGCUAGUGUG
AUGCUUGAGGUCUGAGCUGAUGGCAGCAAAGUGGGGUGCUCAGGAAUCAA
AGCUAUGGGUUAUAGACAGGAUAUGAAGGAGGGAGGGAGGCAAGAAGAA
GGGGGUGGUUCCCACGCUUCUAGCUCCGGCCGAGUGGAUGGCAACAGCAU
UUGGAAGCGGAGGACAUGGAAUUCAUGUGUCAGGAGCCACCUUCCGAGC
CUCCAGUACCACGUGUCAGGGCCACAUGAGCUGGGCCUCGUGGGCCUGAU
GUGGUGCUGGGCCUCAGGGGUCUGCUCUUCUUCUCUUUCAGAAUCUGGG
GCUCCAGGCUAUGCCUUGGCUGGACUGAGGUCUGGGGGUGCACUUAUUAU
CCCUGGGGACACCUGCUGAAGCUUCUCCCUGACAAGCUGUGUCACUGUUG
GAUGAGGAUGGGGGGGAGGGGUUCAGGGCAGAAGAAGACCGGGAGGGUC
UUUCAAAAGAACUCAUGUACGGCUGUUAAAAAAGUCAGCAGAGGCUCAG
GAAGACUUAAAGUGUGCAGAAGGCGGGGAAGGGAGGGCCCAUUGCAUGCA
CCAAGAGGAAAUUGGAAGGAACAAGCGACGUUGGCUGCUAGGAGAGCCUG
CUCCCAACAUCUAGGGGCUGUCCUGACGGGUGCACAGUGGGUCGAACUGAG
CCAAUGAGAGCAGCUCUGGGGAGACCCACUGGUGCCCUGGAGGCUGGGUG
GGUUUGGGUUGGAUGAAUUCUGUGUGUCCUUUUGGAAAUGUGGAGGCCAU
GAGGGGGAUCAGGGCUCUUAGGGUUUUGACCCUUAAGAGUUUUGUAUCU
GUAAUUCAAAGGUUCUUUAGUUCUGGGAUGCUGAGAUUCGGGAUAGGGUU
CCUAAUGGCACAAAAGCCAGAGAUAAAACAUCCUUCACGUGCUCCCUACC
CGGUUCUUUCUGUACCAGACCCACAAGGUCCGAGUUGGGAUCCUAGUGCU
CCUGUCUGGUCAGGGCCUAUCUUUAUGUGUUCGUUAAACUUUUAACAAUG
AGAAUUAAUUCUGUCUCUUGACAUUGUCAUUUGCAUGCUCCCCACACACA
AAUCCUUUCCUGGUGACACCAGGAGCUACAACUCUCCUUGGCCUCCUCUU
GUGACUCCCAACUCCCUCCUUGGGAAGCUUGGCCUCAGGACCUCUGGGAU
AGACAGGCCACGAAUCCUGCUGUGUCCCGUUGUGUUCCUAAUAUAAAUGG
UGUGGAUGGCACUUGACCUAGAGCAGUGGGAAAUGCAUGCACCACUCAAC
AUUCUGACAUGUCACCCAUUUUACAUUCUUACAGGCAUACUUUUUUUAAA
AAAAGAGUGUCUAUUCUUUAAUGAGCAUCCCUUCUUUAAAAAAACCUAAU
UGCCAUUAUUCACCACAUACUUUUUUUUUUUGUAUCCUGCCUCUUCU
AUUUAAUUUUCUGUCAUCAACAUUUUCCCUUGUUCCAUGAAUCUUCAUAA
CCUCACUUGCUGCGUUGUGCCUUGUUGAGUGGCUAUGGCAUCAUUCACAG
AACCAUUCUGUUAUUCUUAUGUAUAACCACCUUUUAAAAAUAUUAUGAAU
AAUGCCACAACUAACUGCUUAAAACACCCUUUUUUUCAUUCUUAAGAAUU
AUGUUCUUCCACCCAGAAAAUUAUCAUUGCUUCACUACAGAUCAGUUCCC
CUGCUAGACUGUGAGCCCCAUAAGGGCAAGGAGCUUAUUGAAUUGGCCUU
UGUAUCUCUGAUGCCCAACAUGUUGUAGACUAUAAAUAAAUGAUGAAUGA
GUGGAUGGAAGAAUGGAGGAAGGAGCGAGUGAGUGAUGUUUGGCUGAUG
GAUAAGAGGGUGGAAGGAUAGGCGGAAGGAUGGAUUGGUGAAUGAAUGAA
UGAAUUUCCUUUGGUUAAGUCUCUUGAAAGAAAGGCUAUGGAUCUUUGUA
UGGAUGUUGAAUAAUUUCAGUAAGCUUACAGCAUUUUACAAUGUUCAGCA
AUGUAUGACCACUUAAUUAAGAUAUGGCUAGUUUGUCUCUGUUAUAAAGU
ACUUUUGCAUUACUUUAACUUGCAUUGCUUUAAUUACUAAUGAUGGGUGA
ACACUUUGACCUAUGUUUGUUAACAAAUUGUAUUUUAUCUUCUGUGAACU
GUUUGUCCAAGUCCUUUGGGUCAUGGCUUUCUGAAGAGACUGGUCCCAGA
UGUCCUUGGGAUGUAGGGAGCCCAUAGCUCACUGGAGGCAUUCAAGGAAC
CAGCCAGGCAGCCCUCAGAGAAAGUAGUGUUUAGGAGAUUCUCAUGGUGU
GGGGUUUGGCCUAGGUGGCCUUUCAGGUCUGUUUGAUGUUAGGAUUUGCUU
CUCCCUGGGAAGUGGGUGAUGGGAAAAAGACACCUUCCAUUGGCAGGUG
UAGACACUGCAGGCUGGACCUCCUGGGUGUGCUUGUGGACUCCGAUCUUG
CCCUUGAUAAAACCCCUGUGGGACAGGAAUAGCUCUUUGAACCUCCAAGG
UCCAGACAGCCACAUCCUAGCACCCUGUACAAUCAGUUAGUGGCCUUCCC
ACCAGCGCAGUCACUCAUUCCUAUUGAUCCCGAUGAAGCCAGGCCCUGG
GGUUUCCAUUUCCCACCUCUUAGGGGAAUUGGGUUCCCCGCGUCCUGUG
```

```
AUAUGUCAGCAAAUGUCCUCAGCCCUGGCCUGCACAUGUGGCCUCAGUGG
UGGUCUUUGGGGUUUAACUGACGAAUGGAACAUUUUGGAUCAGGACUGAU
GGGAGAAUCUCCUUUCAUUUUUCUUCACCUGGGGCAAUUACAUUCUAAGG
AGCGGAAUAAAGGGCAUGUUCUGCCCAAAGCAUCAGGGCUCACAGGUCAG
UCACAGCCAUUUAGGGAGGGCAUGUCACCCAAGGAGGGCUCGCCCUUCUU
UCCAGAGCAUCCUCCGCUCUCAGCAGAGCUGCUUCUGCCCACCCAUCCCU
CUACUAUAGCACUGAGCACUGUUUGCCCGUGUCAGAAUCCCUCACCCACA
UGUUUAGCUUGGUAUCCGAGUUUGGGAGGCCGGCAAUGACUUUCAACAUG
AAUUGCUCCAUCUACCCAUCCAUGCAUUUGGCCUACUUAUCUUGACCCCG
UGCUUUGGCCUUUUCUUCUCCUGAAAGCAAACCCUUUCAUUUUGGGUGG
GCUGUGUAGCGCCAUGGGCUGUGGUUAUGAAGCAAACACCCUUUCUUGUA
GCUGCCUCCUCCGGGGUUACUGCCCUGAGCACGUCCCAGCUGGAUCUCGU
CUGCCACUGUCACCCAUAGCUUCUUCCCCAUGGUGCUUUCCAUGUGUCAC
ACACCACGACUGUGACCCAGGGUCGGGGUCAAGAGUAGCCUGGGGCCAAG
CCCUCCCACCCAUGAGCGGAGAAGUCCUCCCCAGGCCUCACCUUGCCUGG
CGCAUGGUCCCUCCCAUGAGCUUUGCUUUCAGCCUUUCAGCUUCCUCCAC
AGGGUGGCAGUGGUUGUAACUCAUCCAUUCAUCCCUUCAUCCCUUCAUUC
AUUCACUCACAGCCAACAGACGUUUUUAAAAAAUUAGCCAGUGCUAUACU
AGAGCUGGCUCCCAAGGACCCGCUGCCGCAUUGCCUUUUGAAACAAAACA
AUGAACACGUUGGUAAAGGGGCCGUGCUUGUGUGUCGGUGACAAGGCGAG
AUCCCUGAGUCAGGUCAGGCUUGUAGAUUCGAGUUCUGUUGCGAGUUUGA
UUGCCCCUCUGACUUUGUCCCCUGUACAACUAGGUUGAUUAGGAAUCAGC
CAACUGUGUUCCCUGGGGUGCUCAGAAAUCACAGCCCAUAUCCUCGAGAGG
CCAAAAUGAGAGCCAGGGGGUUCCAAGAUGAGUGGCUGCUUUCUGGCCGGG
AGCAGGUUUUCAAGUCAUUAGAACACUCUGGCCUUUUCCUGGAGGUGAUCU
UGGAGCCAUUCCUGCCCCUUUCAAGAGGAGUUAAUGCCCAGCUCUGUUUA
GAGAAAAUUGGGGGAGAUGAUUGCUCAUGUGGGUGAUAAGAAUCACCUCC
CGUGCAGGGGUCUGCAUAGAACACUCCAUAGGCAAACCUGGGUGUCCAAG
GCACGUGGCAUUUUGCAAACUCUGGGUGCAGCUCCGAGCUGUCCUGCAGG
UCCCAGACCAGGUGAGAACUCCCUGAGUUCCUGCUGCCUGGGUCGGGGGU
GAGGCAUAGGUCUUGGGGGUUCAACCUGGAAUUCUGAAUGUCAUUCAUUG
CAUUGGAGAGGAAGGAGAGUAGGCAAAGCCAAGACCCUGGAACUGGACAA
ACUCGUGUGGUUUAAAGUCACUGUGAGAGCUGGAGUUGAGUCUGCCUACG
GGGGAGGACUGCGGCACCUACCUCGCAGGGCUGUUGUGAGGAGCAAUGUA
ACCGUGAUUUUGAACUGUGAUUCUGGAAGGCGGUGUGCGUGUCCCGGG
GGUGUGCCAGGGGAGUGAGGAGAAAAGGCCAGGGAGACAGCCUCACUCAG
GCAGCUGAGUGGGAGAGCAUUUAUCUCUAAACCUGGAGGGGUAUAUGGUG
GGACAGGAGGAAUUUGGGCAGGAACUUUCAUGCUAGGGGUUUGGGGGACU
CGCUGGACAAUGCCCCUGGACCCCCGGGGGUACGCGUUCACGCUCACCU
CUGAGAGGCUGGAAACGCCUGGCUGUGCUUUCUGAAUGCUGUGUGCUUCC
UGCCUCUGUGCCUGGCCUGUGUGCAGCACCUACUUGUGUCCGCCUUCAAA
AGGCCCUUCUGGGUGGCGUCCUUUUCCCAAAAUAUUAGGCACCAGCCAU
CAAAGAUACUGCAUUGUUGCCUCCCCCACCCCUCCCCCCAACUGACAACA
UUUGGGCUCAAAUGCAGCAGGCUGGGUGCCCAACACAGUGCCUGGCGAGU
GGUAGCGCUUACGUUUCUUUUCUGUUGAAUGGAUGGAUAGCUAAUGAAAU
UGUAACCAUGACAAGCCUUGAUGUUUAUAACCUUUACUAAGAGAUUAUU
AUUUUGCUCUUCAUGGACCUGUUAACAACCACCAUAUUGUAUCUUACGGA
CGUUUGUAUGCCACGUUUGAAGAGCAGGAGCCUUGUUUCGGCGUCAUGUU
GAUGGAACUUGAGCUGUCUGAUGCGAAUCUGUGUUUUAUGUUAGAAAGCG
CGUAGCCUUAGGAUCUGGCAGACCCAGGGGCCACUUAAUUAACCCUUUGC
CUCUUUGACCCUCAAUCUCCUUUUCUCUAAGCCAUAGGUCACCUGAAAGC
CUACCUCACAGGGCUGUUGUGAGGGCCGAGGGUGGGUGUGUUUCAACAGU
GUGCAGAUGCUGGCUUUCCCUGGGAAUGGGCAUAUGUUGGGAUUUGUCUU
GAAAGCAUGAGUGAUGGCUUUACUAGUCCUAAGUGAAUAAAAAGUCAGCC
CUGACCUUACGCUGGGAUUGCAUUUCCCACAGUCAGUGGCAUGUGCAGAC
CACUGGCAGAGCAGCCUGCAGGUGCUUAGCGAUGUGGGCCCAGAGUAAAU
AUUUGUUUGAUUGAUGAGUGAUGGCUUUUUCCUUCCUCAGAGUUUGCCCU
GCCCCCCAUUCCAACGUGGGCUGCUGCUUCUCCCCAGCGGGUUGUAGCUG
GCAGGGCCGUUGUGCUUUGGGGUUUGCUGUACCUGUCGCUGCCGUGAGGG
GACGAUCUGUCUGCCCGGAGGGGUUUCUGCAAACAUUCAUGUAUGCCCCU
GCUUUCGUUUGUUAGGGAGAAGGAGUGGGGUGACCUAGAGAGAGGAUGAG
GAAGGGGUUCGGGUGGCAUCCUUGGGGUACCAACCCUGCUUCCAUCCUG
CGCUCUGAAUUUCCUCACAGCCCUUUUCUGUCUCUGGUAGAAGGUGCAGA
AGGUAGGCUUUGCCACCUUCCCUGGGCCUGGCACCAAGCUCGGGGGUCUU
GUACACACUUUCCCUUCUCUAACUGGGGUGUGGGCCCAUUUCCUAGAUGA
GCUUGCUGAGAAUCAGGACAGCUGGUAUCAGAGCCAGGACUUCCCAGUCU
UGCACAAACAACCUGUGCAUUUUGAGUCCACCAAAUAAGGCCUCCUGCC
UGGUCCGGCUCACCCCUGCCAGCCCCAGCAAAUGCAGCCUGGUGCGUCC
CCACCCCUGCCAAGAGCCCAGGAGUGCUCUGGCAGAGAAGUGCAGGGAUG
AGGAAGGAGGCUGUGCCCUCCAGGGGACUCAGCUGCGUUAGAGGAGGUGC
UGCUGCAGUGGCAGGGGUCUCCAGACAUCCCACGCAGGGUCCUUUCAGA
UCAGGCAUCUCUUCACCAGACCACCGUAUUCCUUUUUCAGCCCUCGUCUC
UUGCACGUGGGGGUGCAGUGUUUGGCUCUCACAUCCCCACAUUCCAGCUG
GUGGGGUUUGAGCUGGGUGUUCCUUCUGCUCCCCACUCCCCACUCACGG
CCCCCCACCCCACGCAAGCCUCCCUUGCCCCCACUCUUUGUCUCCAGCUUU
CACAGCCUUGGCGGGCAGGCUGCUGCGCCUGUUGCUGCCCCGGCUCUCUU
CCACCCGCCUCUUUCUUUCUCAGCCUGAGCUUUACCGUGAGGUCUGGGCGC
CACACCUUGGCCCCUGCCAUGCCUGCUCCCAGAAGCACCCACGGGGGUCC
CCUGAUUCUCUCCUCCCCUGGGCUUUGCUAAGGAGCCCUUUCAUUGUGGC
CUUUGGUGUCUGCCUCAUGCCCAUCCCCUGUUCUUGAGAACUUGGAAGCA
GAGGGGGCCCCUCCUAUUGCUCCCAAGAGGCUCCACAGUAGGGAGCCCCU
```

```
CCCAGGAGAUUCUGAGUCUGUGUUUAGGUGUCGAUUCCUGGGUGGGCCUU
GGGGUCCCCUCAGGCCAGGCCUGUGUGACCUAAGGCUGGGGGGCUCUG
UCAGGCACCUAGUGUCCCUUGGAGGUGGGGGGGGCUGGGUCCUGGUCUCC
UGAGGACGGGUGGGGAGACAGGCUCAGGGAGAUUCCACGAAGCUGCCCU
UGAACCCCUCCUCUGAGGCCCACACUGCCCUGGCCCUUUACACCCUGCCU
CCUGCACUAGUAGGCACAUAAUAGAUGCUCGCCACCUGUGGAGGGCAGGG
UUUAAAUGGCUGGAAAGAGCUGAGUGGGCUGUUUGGCUAGCGUACGCGCA
UUUGUUUAAAAGGAAAGGGUGUGUUUCUUGGCAAAGACUCUUCGGAGGAA
ACGCUGAACUGGGGAUGGGUCUCUACCUGUUCGGGGCCUCACUGCCCUU
CCUGCCGGGACAGGCAGUCACUGGUGGGUUUCCCCCAGUGGAAACACA
AUAUUUUGGAAAUAUUUGUAUCUAGGAUAAAACUUCAUCUGGACCAACAU
GUCUUUGUUGGUGUUGUGGCCCAGGUGAUUUUGAGAAUGUAGAAUACAUU
UGGCAAUUUCCAAACGGAGUGAUGACCUGCUCCUCCGCCCCCAUGCCCU
CCCUGAGGCUGGAGGCUUCAGAAGCCCUGCCUUUGGGAGGAGGCUGUUCU
ACCUGAGAAGUCUUUGUCCCCACCGUUGGUGACAAUCAGCAUUGACCUGU
GAGGCACCUGCCAGGUUCGGGACGCAGCUUUAGACAUCCAGAAAACCGGG
GGUGGAGGGGUGGGGUGGGGGCUUAAGACCCCAGAGCUUGAUUCCUUUUA
ACUGUCUCAUCCCCAAAGAAUGGUACAUGGGGUACCAGGUAGGUUACUUGA
AUCACCCUGAGCCUCGAUUUUCCCACCCGUUAGAAACAGGGUAAUUCAUG
ACAGUGUCCGCUUGGGAGACGCGCUGUGACCCCUGAGAAUUCUCGCUGCAU
GCCGUGGGCUGGCUCGUGAGACUCAAGGUCUGGGUUCGAGGCCCCCGCAA
CCCCUUCUGACUGUGUGGCCUGGGCGAGUUUGUUGUUUGUAACCUGGAAA
GCGUCACACCUGCCUGGCACGGUUAUUGUGGGCUUCAAUGAGAUUGUUUG
UGUGAAAUAAACGCUUUGUGACUGGCACACAGGCGCUCUCAUCCCGGCUC
UCCUGGUGGGCCCGGACCGCUGGGUGCUGGCUGCGGAGGCCCUGUGCUCC
CUGGAACUGUCUGCGCUGGUCCCAGGGACUCUUGGGCAGAGUGGAGGGCA
AGGGGGAAAGCACCAGCCUGCUCUGGGGAGACAGUGGCAGAGGGAAGUGU
UUGCUUUUAAAUACACUCAGCAGGUUCAGACAGGAGAGGAUCCGAGGGGA
AAUGUUUAGAGCCCUCAGGAGGAGGAAGAGACCGAGUUUUAGGAAAAACA
UCAAAGCUGGAUAGGUUGGGCAGAAGAGCUGGGGAUAGCAUUUAGAGAGG
CUGAGAGUCCUGGGUUCUGGGUUAUCAAGGUGAGAGAAACCAGAGGUUGC
CAGUUGUAGGUGGGCGUCAGGACUAGAGUGAUGCUUCCAGAAGUUUCUGC
AAGUGGCCGAGUCUAAGGUAGGGCAGGGUACGCCAGAAGUUGAGGGGCA
CUAGGUAGACAGGCCGAGCUGGUGGCUGGGUGCUCCCCUCACCCUCCAUG
CUGCUAGGAGCCCGUGAGCAGGGACUUGCUCUCCUCUCCCUCCCUCCUGG
GGCCUGCCUGUCUGUCUGUGAACUCUUGUCGGCCAGCGAGGCCGGGAGCA
GGUGGCCUUCAUCUGCAACUGUGUCUCUCUCAGCCUCCACAGCCACGGGG
ACACCCUGCACCUAUUCCCACGGGACAGGCUGGACCCAGAGACUCUGGAC
CCGGGGCCUCCCCUUGAGUAGAGACCCGCCCUCUGACUGAUGGACGCCGC
UGACCUGGGGUCAGACCCGUGGGCUGGACCCCUGCCCACCCCGCAGGAAC
CCUGAGGCCUAGGGGAGCUGUUGAGCCUUCAGUGUCUGCAUGUGGGAAGU
GGGCUCCUUCACCUACCUCACAGGGCUGUUGUGAGGGGCGCUGUGAUGCG
GUUCCAAAGCACAGGGCUUGGCGCACCCCACUGUGCUCUCAAUAAAUGUG
UUUCCUGUCUUAACAA
```

RNA Sequence for the full length of the long
non-coding RNA MEG8 MEG8 full sequence
(SEQ ID NO: 49)

```
GGUCUGAAAAAUGAUAUUCAUUGUCCUAAUGUGUAAAUUUCGACAAUUUG
CAAAUUUGUAGAUUCUUUAGAAUAGAACUAACUCAAGCCCUUCAUUCUGC
AGCUGAGGCUCACUGCCCCCAGUGGGCAGUGGGUCCAGGGGGUUUCUGAG
GACAGGGCAUGACCCAGCCCUGCUGCCCCCAAGAUGGCACCUGGCUUGGA
GGGGUGAGGGGCCCUGUUAGUCUGACUUUGAAGAAGACCAGCCUUCCAGA
CUCGCUUGGUGCCCUGACAGGUAUGUGUGCUCUCUCUCUCCCACCUAAC
AGCCCCUUUUGGGAGACAGGGUCUGAGAGGAGUCAGGGUCGUAUAACCUU
AACACAGUGUGUUAUCCAAAAACCCACUAACCCUGUUACUCUUGUCUGUC
UGCUAUGUGAAACCAAGGGCGGUGUUAAAGUUUAUCACCAUGAUAUACAG
AUGUGCGUGGGGACAUCUGGGAUGGGCUCAGGGGUCUACCUGGAGGUCA
GAGAGGGCAGGAUCUGCUUAGGGGAGAUGGAUGACUGUGGGGUCAGACA
GGGCAGGGUUUGCUUAGGGGAGAUGGAUGACUGUGGACAUGUGGCUGUAA
AUCAUCCUCCCCGUCUUACAUAGGAUGGGGAUGCAACUUUCAAGAGUUGC
CUUGAUUGGUACCUUAAAGGAAAUAAAACAUAAAAUGCUUGGCACAUAGU
AGAUGCUCAACACAUGUAGAAAAGGCACUUAUUUUAGGUGGAUCUGCCGC
CGAAUGGCCCUUUUGCAAGCUCUUCUCAUUUUUUGGAAUCCAAAGGGAAG
GUGUGGGAGCAGGGUCGGGGUGGAGGGGAAGGACGACGUGAGGUUGCAG
AGGGCAUUUUCUUGAGGCAAUGGCAUAUCUUUCAUUGGUACUGGCUGGGU
UUAUGCGGACUUUGAGAGGAGUGGAGUGUCUCCAAGUGGGGCUACCCCAG
CCUGCAGGUUGGAUGCAGGUAACCUCAGUCUGGGCACUGCAUUUUUAUUU
ACCAUAAAAUAUUUCAUAUUUGCUGGGUGUGGUGGCUCACGCUUUAUAAU
CCCAGCACUUUCGGAGGCCGAGGCCGGUGGAUCACCUGAGGCCAGGAGUU
UGAGACCAGCCUGGCCAACAUGGUGAAACCCCGUCUCUACAAAAAUACAC
AAAAUUAGCUGGGCGUGGUGGUGCAUGCCUGUAGUUCCAGCUACUCAGGA
GACUGAGGCAUGAGAAUUGCUCGAACCUGGAAGGCAGAAGUUGCAGUUAG
CCGAGAUUGCACCAUUGCACUCCAGCCUGGGUGACAGCAAGACUCCGUCU
CAAAAAAAAAAAAAGAAAGAAAAAUUGCAAAACUAUAGCAAUCACCUCA
AGGUUUUCACAGGAAUCAAACUCAGUCCAAACUAAAAUGCUGUGUAAUAA
AUAGUGGGGCUUCACGUGCAGGAAAGGCGAUUAAGAGCGAGGCAUGCAGG
CCGAGGGCUGCUUAACCUGUCUCAGAUUUCUUCCGCACAAAGUCAUGGUU
GAAAAUAGGUCUCUGCCUGGCAGAGGGUAAAGAAGUUCUCGAAGGCCUCU
GUCUGCAUUAGCUUGGUGAGAGGGAAGACAUUUAACCAAUUAACCAAUUA
GUGAUCUGUGCGGAUGGAGACUGAGCAGGACGAGGGUGCCACCCGACUGG
GUGUAAAGUGGGCUUAGUUUUGUCUUCUUGGUGUCUGGGAGCCUCAGUGC
```

-continued

CUUUCUACGUAGAUGGGAGUAUGCUUGUCACAUCCUUGUCACACAAGUAA
CCCUGUGCCUGUUUGAGGAUUCCAAGAGCCUGUGACGGCUGCAGGGGCC
CUGAAGCUUAGUGUGCAAGCAGGAGCUGGGGACAGAGGGGCUUCUGACGG
GAGUCGGGGUGCCUCCUCUGGAUGUGGGGGUGGGCUAGGGUGGGCAAAGG
UUGCUUCCCGUUCUCCUGCAGCUGACAGUUAGAAAUGCCAGUGCCGUUUA
GCCACAGUCCCUCUGGGUUAGAGUCGGGAAGAAACAUGGCAGUUGUGUGU
UUUGCACAGGAAUCAAGCUGUCAGGGGGCACAGUGAGGCCCCAGCUCCUU
ACCAGCAAGCCGUCUAGGCUGCGAACGCGAGCCGCCGGGCCGCAGCUCUC
UAGAGGUCCCUGUCCCCACCGCCUGGCCCCAUCUCAUGUCACAUUCCCCC
AAGGUCUCAUUCCACUCGGCUAAUCUCCAAGAACACCGGCCAGGGCAUUG
GCUUUCGGGUCCUUUUAAAGACCAAAAAGUAAAGCACUCCCCCGUGGGUG
CUGGACAGCUUGGGAGGGAUUGGGGCUGUGGGUGGUGAAAUCACAGCCC
UGGGCACACACCUGCCAGCCCGAUGUCACUGACAGGCUGCUCGGAGGCUU
GGGGCUCCAGUGAGAGCAUAUAGAUAUUUUUUAAAAAACAUAUUCGCGAU
AAAAUAAAUCCCCUGUGUCUGCAGAACUUGCUCUGGGCAUGUACCCACUC
CCAAUCCAUCAGGAAACAUGCCCUUUGUCUUUGUAUUUGUAAAAACAGAAA
CAAAAACAAAAACAACCCACAGGCGAACAAGCAAAUUAAAUCCCCCCCAC
ACAAAAUGUUUAUUCUAAUUAUGCAAGAAAUGGAUUGAUAAUUAAUACAC
GCAUUAGUAAAAAUCAAACACUGCAGAUAAAGCCAUCUUUAAUGCUUCCC
UCGAUCCCUCCCCAUCACCCCCAGCAAAUUAACUGCUCUUCUCAGUUUC
AGGCGUCUGGUUCCAGAUAUUUUUUUCUGUGCAUUUGCAUAUGUAGAUAA
AUAUACCUCUAAAAUCUAUGACUUUGUUUAUUUUUACAUAAACUAUAUC
AUAGUGUACAUUUCCUCUCGCAGCAGCUUGUGUUUCUUCCUUCAAGAGUC
UGCUUAGAGAUAAUAAAGAUCAACACUAUUCCUUAUAACAACACCUCAGU
AUCCUGCGAGCUGUACACACCAGAGUUUAUUUAACCACCUUGCUGCUGGC
AUGAAAGCCUCAGGUCCUUUACCCUGGUUGGCGGGGGGGGGGUGGGGGG
GUGGGGGGCGGGGGGGGCAGUGAAUGGUGGCGGCAGGUGUAAGUAAUU
GCUGAGAUUUGGGUUUGGGAGUGGGCUCACGAGUGUUUAUGACAUUAUU
AUAAAUGAAUAUAUGAGUGCAUAAAUUAGCAAAAUAAAAGGGGCUUUUC
UGGACCAAUGAUGAGACAGUGUUUAUGAACAAAAGAUCAUGAUUAAUCCA
GUUCUGCACAAAACACUGAGGUCCAUUAGAAGACAAUAGGUCUUGGCUGU
UUCAUUCCUUUUAAGAGCUGUUUAAUAUUCCACGGUAUGUAUGCACCAUU
GUUGAUUACACUCUUCUACUGUUGAAAAUCCCAGCUGAAAGUGCUCUGGG
GGAGGAGAAGCUUUGGUCACAGUCCUAGCCGUCAGGGUGGGUCACAGAUU
CAUAGGUGUUCAUUAAAUUAUUUUUAAAAAAGAAUACAUAAAAAUGGUG
CUUAAUGCAGAUCAGUGAGGAAGCGUGUCACAAAUCGAGGUUUUAAUUAA
UACGAUUCUGCUCAACUAAUGCCCGAUAAAAAAGAUCUAAGCUGUUUCCA
UUUUUUGUUGCUGUUACCAACGACACUGCAGUGAGCAUUCUUGCAGCUAA
AUCUGUAAACACAUCCUCGACUGUUCCUUUACCCCAGCUUCUUAGAGAUG
GGGUGGUGGGUUAAAUUGUUUGCAAAAGUUUAUUUUCAUUGAGUGAUCUU

-continued

UCUAAAAUGGCAUUUUGACCUUGUUACUGUCUUGCUUUAAAGCCUCCAUC
UGACUUCCUGGAGCUUCCGGGACGGGGUCCAAAAAAUAAGGCCUUAUCCU
GGCAUGGAAGACCCUUUAGGGUCUGUCUUGGAACUUGCCAGCCUCAGCCC
CUCCCCACUGGUGUUUACCUGCUAGGCGCACCUCACCCCCACGGGGCUAC
CUGUUUCUCUCAGCGGGCUCCCUACUUCUUAGGCUUUGCGCGGCCGUGCC
UUUUCAGCCAGUUUCUCCCCGGCCUUUAAAGAGCAGGCUUGAAAUAUCCCU
GUUGGGGAGCCCAAAGUUAGAUGGGCCCCACGAAACACUGUGUUCAGAAG
CCCACCGAAGCCCUGACCCUGGAAGUGGGAUGCCUCAUUGACAUUUUUUU
CCCAAUUAAAGGGAAUGUUUUGCAUUUUUCUAGAAUUGAUGAAACUGGUC
AACUGUUACUCACCCUCCUUCCUUUGUCCCUUUCUAGGAGCCCUGGGCUC
CCCCAGUGUUGCCUGGGUCUGACUUUGCCUCAGUGAAAACUGCCUCGAAU
UCUUUCUUGCACCGAUGGGCAGAUGGGCAGUGUCGGAGGAUCGUGUCAUC
UGUCCCGUGGCGCUGGGUAAGUCUGCAGUGUUGUAAAGCUGCAAACACCC
UUCUGGGUGGGGCUCAGGCUGGCACCCCCCCACUGCCCCAGCCUGCGCUA
UACCACGUUCCCCUGAUGCUUGCCUUGUGCCGGGCCCCAGAACCCAGAGU
CAUGGGGUCCACAGCGCGGGAGUAGCGUCUCAGUGUUGUGAGUUCUGGGG
AUGAGGUUCGGGGUAUGAUUACAGCUUGGAAAUGGCUGAUUGCCAUUAUG
GCUCCUCCUUGCCAGAGGUAAACGGGUCUGGUCCCAGAACAGGAGGAGGA
CAUGUGAUGACUGGAGUAACGAUGAGGGGCUCUGGGGAAGGACAGGGCUG
AGAGCAAGUGCUGGGACCUUUGGGACCGAGUCAUAUUCUAAAAAGAGCAC
AGGCUUUGGGGAGAGGAGCUGUGAGGCCAAGGCAGCAUCCCCCUGGGGA
GCUUGUCAGGAGUAACAGGAGCCACUGGCAGUGUUUGGGCUUUUGGUCCC
UUUUUUUCUCUCCCAGGGGAAGGGAGAAGGAGGCAUUGCAGGAAGCCAGC
CACCCUGAGCACAGACCCAGCUACAGAACAGACUUGAGCUGCGUGUCCUU
GGCAAAUCCCCAAGUGUUUCUGUGCCUUGGUUUCCUGAUAUUAAAAAAAA
AAAAAAGGACUCAUAAUCUCUCUCACACAGGGCUAUUGAGAUCUCAAUGA
GGAAAUAACGCAAAUAAAUCAUCCAGCACAGUAGCCAACACGCAGUACCC
AGCAAAACUCGGUAGCUCUCCCCAUCUUACCCCGUCAUGAAAUGCUUAAC
CCCCUCCCUGAGACGGGCAGCUGCUCCCUUUCAGGGCAGGGAGACCCAAC
AGAGGACAACACAAAUGCCAGAGAGUGUGAGGGGCAAUAAAAGCUGAU
GCUCGCCUCCCUCCCAGACAUCUUCCCAGGGAAAAGUGUGCUUUCUUGAA
CACCUGGGGCCGGGAAGGGCUGCCCUACCACUUUGAAUCGGGUUUCC
CGAAAAGUUUGGUGAGAGUUUAUUUUUAUGUAAAAUAACAUAUAAAAAGUC
AGACUUCUCCACAGGCAGAUUUUUUGAGGCUCAUAUUUUACAGACUUUGG
CAAGGGUCACUCGAAGGAACAGUGGUUACAGUCUCCAGAGGUUCAUAAU
UCCUGGAAAACUUCUGGCCAAACCUGACUUCUCCUAAAUUUCACAGAAA
AUUCUCCCUGGGCUGGGCUCAGGCUAAAUGAGCUUUUUGUGUGUUAGUAC
AGCCUUACCUAGUGGAAGCAUGACUUGCACGUUGCCCUUUACACAAAAGG
GAACCUCCUCGGCCGCUGUGAACAAAGGCUCCGCUCUCCGAAAUGUUUGA
UUUGUUUACUCGGGAGCGUGAGCCUGGUCAGGCACAUGCUGAUACUGGG
GCUAUUUCUCUGCGGCCAUAUGUAGAGCUGUCCAGGUCUCUGCAAUUUAA

-continued

CCCUGCGCUUCAUGCCAGAAUCCCAUUUCCUAACUUCCUCAAGCAACGGG

GCAAGGGAACCACAGCAAAAAGGAGUGUAGGGGGAGUGUUCCCUCCGUGU

CCGGCAGGGGCUAAAGGGCUUGCUGCCCUGUGGCGUCUGCCUCUAAAUAG

GGAUUUGGGUCGGUGACUUUUCACAUCUACACCAAAGCCCUUCAGAACCC

UUUCUGCACCACCAGCUAUCCUGAACCAGAAAUCCCUGUUCACAGAAUUU

CCCAUGUGGGUGCCUCUUGUUCUGCACCCUGCAUCGCGCCCCUCCCCCG

UUUAUGUAAAUGACACAUGUAAAUGUCACUCUCCCAAACAUUUUCACACC

UGCAGCUUCAAAUCAACCUUUUAAUAGGUUAAAACAACAGCACCAACAAA

AACCAACAAAAACAGAGGCUCCCGAGAAACAAACAGUUUUUCCCGAAGGG

CUUGCAGUGCCUAACUGAGCUGCCAGGGCCGUCUGUCUGUCUGUUAGCCA

GGAAGGCAAACCAGCCUGCGCACUCCACCUGCAACACGAUGCUGCCCCCC

CACGGCGGGUCGGAGCAGCUGUGGCGACCCCAGGGCUGACAGAUUGGGUU

GUCAGGAGCAGGACAAUGAGGCUGCAGUGAGGAUGGGCUCCAUCCUUGAA

UGACUCUGCCCUCCUUGAAAUUUUUCUGCUCCAUGGAGGUGCAUCUCUGC

CCCCGAGGACCUUGGGCAUUUCACAGACAAGGAGCCCUGGCUGGCCUCGC

AGCCAUCCCCCAUAUGCACACACGCACACGCACAGACAUGCGCGCACACA

CACAUGCUGAGUGCCUGCACUGGGAGCAUAAGGCAGAAAACUCCUUUGGA

AACUGCAGAACAGAGCCUUGUCUAGCAGAGGUCCCCUGAUAAAGGUCCCA

CAGUUCCUGGGAACUGAACCCCUGUGAAUGGGCCAGGAGAGGCAGCUCCC

GACUCCCGUGUGGGCUGCAUUCAUCAGCAGGCCGGCACCCCAGCCCUGUC

ACUGUGUGAGGAGCUUUCAUGAGUCCACUGAACAUGUAAGUCACAGUCUG

GCAGCUGGCUGCAUCUGUGGUUGCUGCUCAGCCUCCAGAAAAGGGCCCCU

CAACCUGCCAGACCUCCUCGCUCCUUCCACUCACUCUGCCAGCCUGUUGC

CCCAGAGAGGACACAGGCCAGCCUCUGUGGGCUCAGGAGCCAGGGCAGGU

GCUUGGCCACUCUAGGUGUUCUGGCCCUCAAGAGGGGAGUUGGCAGCAGG

ACAGUCCCCACCUCCCCCCACCAGCCCUGGGCACUCAACCCCAUUCUCUG

CUCCUCUCCCUCAUUGCCUUAUUGGGACAGAGGCACCCCGCCAACCAUCU

CUGUGCCUUUGCCAUUUAGCCCAGGGCAAGCUACUCGGGAGAGGCCAAAU

GGCCUCAUACUGACCCCUGCCUGGUCCCCUCUGGCCACCUCGCUCACUUG

CCCGCUUGCCUGCUCAGGAGUUGGUGCUGUGGGAGCUUCUCAAAGGCCUA

AACAUGUGGGCUGCCAGCCUGGGCAGGAAACCGUGCUGCAGCCUUCUCAG

CCAAGCACUGGCCUGCCUCUCUCCCCUCGGAUGCCUCCUGUAACAGGGAG

CUCCCUCUCUCCCCAGGCAGCCUGCUCAGGGCUCGCACGCAGAGCUGCUU

UGCUGAGCCCUCCCCUGCCUUUUGCAUCUGCCUCCUCGGCUGUGCAGCAG

CCCCCUUGCCCCCUCUGCCCUCCGAUCUCUGCAGGCUGUGGGCUCCCUCU

CUUUUCAGUCCUCUCCUUUCUGUGCUGAAUGGCAAUACCCCCACCAAUGG

UGGGAACAGGAUUGGGCGCCUCUACACCUGUCCUAACACCUCUGUCUCUG

UUCUUUUAGACCUGGGACAGAGCCCUUUGCCCUGCUGUUCUGCUAAAAGC

CCAGGGGAGGGCGUGGUGCUCCCCUCCUGGGGCCAGCUGCUCCAUGUCUA

UCUGUUGAGCGGCUUCUCAGCCCUCCUUGGGUUUUCUAUGGCCCCUUUUCC

-continued

AGUUGCUAGGGAGAACGCUCUGUAUGCAGCCCCCUGCCUUUUCUGCAGGA

GCUGCUGGCCUCCCGGCCAGCCCUGGUCAGCCCUGCAGUAGCAGCAGCAG

CAGCAGCAGCAGCAGUAGGCAGCCACAGCAGGGCUGGGGGCUCCCGAGCC

AGGCAGACCGGCUUGACUCCCUGCUCUCUAGCUGCAAGACAAUUCCCUUU

ACUUUUCAGACUCGGCUUUUCCCCUGUGAAAUGGAGAUGAGAGUUUCUCC

GUCACUGGCGUGAAGUGAGGACUAAAUGAGAUAAGUGUAGGCUUGCACAC

AUCAGACACUUCAUAAAUGCUUGUGGAGUAGACGGUGGGACCCAGGGAGG

GAGAGAGAGGUAUGUAACAAGUGUCGCAAGAGAGAAAACAGCCUGGCCUU

UCAAGACCCUGCUCCCAAUACAAACGGGAACCUCUCCUGGCAGAGUCCCC

UCUGCUGGCUUAAUCGCACAAAUCAAGUCAGCCGGAGGCAGCCCCCGGCC

UGUGGAACUCACAGUAGAUGCAGCAGGCAGCAUAAAUGACAUGCAGAGCC

CACAUCUGCAUUUAAUAGACCGAGAAUUUGCAUUGUAUAUAACAGCACGA

GGGGUAAAGCAUGAAGGCAUAAAGGAACAGUUUUUCCCGGCGGCUUCCUU

GAAGGGCCAGCUUAGACAGGGUCGGGGAGGAGAAACUCAGCGGGGUCC

GGGCAUCCCAUAGACUAUGGGACAGACAUCCAUCCAUGCACUCAUUCUCC

AAGCCACCACAGUGUACCUACCUUCCCCGGGCCCAGUCCCAAGCGUGAGG

CUGGGGAUGAAGUGAUGCCGGUGGCUUAGUGAUGCCGGUGGCUUCCUGUC

CUCGAAGCUCAGUCGGUCGGUGGGGAAACAAACAGGGAAUAAGACACU

GGAAAUUGAGGUGAUCAAGAGGGGUGCAGGCAUGGAGAUUUAUGGAGCC

CCGUCUUGGAGCCAAGUCCCGAACUGGGCUGUCUGCAAAGAACUCACCCG

GGCAAUAACCUGCACACUGGUCUCAUGAGCCCCAUUAGAUUGAUGAGGA

AACUGAGGCACAGAAAGGCAAAGUCCUAUACUCACCGUCUCUCAGCUGGU

GUGAGGCUGGGCCAGGAUGGAACCCCAGACUCUCCGAGGCUCCCCACCAC

ACCCUGCUGCUGAAGGCUGCUCAGCGAGGCUGUGCCGAGUGCUGGGGGGG

UGUGGGUGGGCAGGGGACGGAUUGAUUAGUUAUAAGCACCUCCCAGCGGU

GCUUGAGAUCCCAGCUCCUCUGUGGCCCAAUCCGUUUGAAGGGCAGAUUC

AAAAUUAGGUGGUAGCACCUAUGGGCAGAGGCUUAUGAAAAUGGCAUUAU

UAACCUGAUGUGGAGAGGGCCCUGCCUGUCUGCAAGUAGAUUGCAGAUAG

AGACGGAGGGGCUGGGCUUGUUUGUGUGGACAGUGAGUUAGAGAGGACA

GAGAACAUCCAGGGGCCCUCCAGGGCUUCCGGACGGGAGAACCAGAUCU

GGAGGGGCUGGACAAGUGGGAGGGGAAGAGGGGUACGUCUUAAGGGUGC

CCCGGCACCUCAGGGAAAUGCCCCAGGCUGGACUUGGAGGAGGAUCUCCA

GCCUUGACUCUGACACAGACAGGGACUAUGGCCCUCCCCGCACCUCGGUU

UCCCAUCUGUGAGAUAAGAGAUGGAAACCAAACGUCAUUUCGAGAAAAGC

CCCCAUUCCCACCACCCUCCUGGCCCCCCCUUCCCCCACCACCCCAAUC

ACGUUUGCCAGACACCUGUCUGCUUGUCAGAGCAAUAUUCAACAGGAGAG

UUCCUUCGCUUCCUCCCUGGAGGGAGAAGGGAGAGGUGUGGACGGGGAGA

GGGGAGGGGAGAGGUGCCCCCACUCAGAGAGGCCGCUGAGCAGAGUUCU

GCAUCGGGUAGGAGUUGGGCCACCGAAGAUUUGUGCCAACUCACGGUGCG

GUGGAAUCAGACAGUCUGAAUUCUUCAGACACCAGCCAAGAGUCUGUGGC

GCCCCCACGUGCCACAAGGGGGCUGCCUGGGCCACAUUUCUGAGCCCGAA

-continued

AAGUGAGGAGGGGGACAGUCAAGAGGGACCGGCGCUUUUGCUCUGGCAGC

GGCGCUUUUAACUGCGACAGAUGCGUGCGGUGCGGCGGGGGAGCCGGCCG

UGCCGGGGCUGGGGGCUGCUGGGGGGGGGUGGUCGGGGCGGGGGCGGGG

GCUGCAGGUUGCGCCCUCCCUCACAGACGGCUGCGCUGCAAUGCAGCAG

GCUGCGGGAGCUGUCCCGGGAGCUGUCCUGUCCGGUGGCCGGCUUUCCAA

AGUGGGGAACGAGAGAUGAGGGAGGGAGCACUUCCAGGCGCUGCGUGGUG

GCCAGGCGCCCAGGAAGCCGAGGGGCCCGAGACUCUGCAGCGGGGCCAGA

AAGAGAAGAGUGGGGGAGGAGGCCGGGAGUGGUGCAUGGACCAGGGGUA

GAGGGAGGUGGGUGUGGACCUGGGGUCGGGCGCCAGUCAGCUUGCAGCCU

AUGAAGGACGGAAAGGAGGGCUACAGAGAUAGGGGAAGAGUGGGGCUGAG

GAUAGCCAGAGCGGCUUGGCACACAGUUUUAGGGUAAAAGCAUCAACUCU

UAUCUUUCCAAAAGAAAUAAAAAAGCCAAAAAAAAAAAAAAAGGCAUUUG

AAAGCUAGACAGCUGAAUCCUUCCCAGCAUGACUGAGCCGGUCACUCCAG

GGUCUUCCUUCAAAGCGUGUCUAAUGGGAGACAGCGUUGUCCCAGUAACC

AAAUUGGACCAGAGUCCCAGGGAAGGGCUCAUCAGGUGGCCGCUCUGCC

UUGAAGAGUGGUACCCUCAGGCCCUUUUCCAGCCAGGGGUCAGGGAGAGA

GCUGGAGGGCUCGGGGAGGCAGGGACUGGGAGGGAGAGUGGGGAGAGGAG

CGCUGGGGGCUGCAGGAGGGUCUCUGGGCAGCUGGCGGGUGUCUCGUUCC

GCAACACUCUGCACCCUGGUACAUCGUCCUCCGUCCACUCAACGUGGAAU

GAUUCUCUUCCCUCUGGAUCCAGCCCCUCUAGUUCCCUUUUCACUUUGAG

GCAUUUGCCCCCUGUGAAUCAGUUCCCUGCUACUCCAGAAAAUUUCUCUC

AUACCCCAGGCCCCUCUGUUCUUUUAAAUGGCACCCUUCACCCCCAGCCC

UUCAUCUUCUGCACUGUAUUUUCACUUGUUGAUUUAAAAAUCCCUUUAUU

AUGGGAAAUUGCAAACAACACAAAAGUAGAGAAAAUAGUACGUAUUUUUA

CUGUUUACUCAAUUUUCAUCUUGCCAUUACCCGGACACGUUGCCGUCAA

ACCCUGGCCCCUCUUGUUUCAUCUAAACCCUAAACUGUCCCUCUACUCCC

ACUGCCCAACCCCUACCCCUGGACUAUUUCGAAGCAAAUUUCAGACACCA

UCCUGUUUCCUCUGAGCAUUUUUUAGUUUGUAUCUCUAAAUAAGAAGCUU

UUGUUUCUUAAAAAUAAAACCACAACACCAUUAUCACAAGUUAAAAAUU

AAUAGCCUUUCCUUAAUAUCAUCCACCAUCUAUGUAGCAUUCCAAUAUUC

UUGAUUGACUCAUAAAUUUCUUUUACAGUUGGCUUGGUCAAGUCAGUGUU

CAAACUAUCUCCUGCUCUUUCAAGGGGAUCUGGGGCUCUAGAAGGUAAGU

AUGGCUACACAUUUAGGGGUUGAAUAUCUGCCUGGACCUUAAAUGAGAAA

CUCAACCUCAGCAAACCUCAGUGUUCUCACUGAAAAUGGGGCAAGUUCUG

GGUCUCUCCUUGGGUCAUUGAGAGGGUUAGAGCAUUAACCCCUGAAGCCC

CAGCCGCAUGUCUAAUAUGUCAGAGACACUCAGCAAACAGUAGCUGCGAG

AAUGAUUCUUUUUCCCAGAAACGUUUAAAGGGGAUUUGGGCAGGGGCAGG

CAAAACAUAGCUGGCUAUUGUCCAUAAAACAAAAGGCUCCUGGCAGUCCA

GGUCCCUGAGUGGUUAAAACAGCACAUGCACUACAUCCCAAAAAGGGCA

GCCUACAGUCUGGGGGCUGGGUUCGCCUGGACCUCCUGGCUUGCCGUUUA

-continued

GCUGCCUGACCUCAGCUGUUGUGACCUGGGACCAACAGGGGACCCCGGCA

GGUGCCUAUCCACUAGAUGGCACUCUCUACUGUGAGUCCAGGGGGGACCA

CCACCCCAAACUGCUUUGGCCACUGCCCAGCCCUGGGUGCCACCGGAAGA

UGCACACCACUAAAACAUCGCAGAUAAUUUCUAAAAAGCACUUCUCAACA

UGUCAUGCAAAAGAUGCGGUGGUUUAUUUCCUUGCAUAAAUCCCAACCAG

AUUGCAGAAGCAGAGGGAAUGAACAUUUAAUGACUUUGCUGAGGCCAGAC

ACUGGUAUGUCUACGCUCUCUUUUAAAUCCUCAUCCCAGCGACAUCUGAUU

UCCCUUCAUUUUACAGAUUAGAGGACUUGGAGAGGUUAGUGACUUGCUC

RNA Sequences for the long non-coding RNA MEG9
MEG9 full sequence (SEQ ID NO: 50)

CCACUCUGCACAGACACGUUGGCUGGUGCAGUCCUGGAGACCCACGGAGC

UCACGGUCGUCAGGGGUCCUCAAGGAUUCAGAGAACCCCCAAAUGUCAGG

GCUGCUCCCUUCUUGUCCUGCCUCUCUGCUCACACCCUUGGACAGGUAAG

AAAACUGAGGUCCACAGAGGGCAGGGUGCAUUGCUGUGGCUUUUGUUCUG

AGCACUGUCUCCCCAGCUUUGGGGUUGAGACUCUGGGGUCAAGACCCACC

UCUGAUGAACGAGCGGCUUCCUUCUUUGUAAAAAUUGAGGCGACCCAGAC

CAAGAAGGGCUGCAAAAUCACCAAGCCAGGACCUCAAUACCCAAGGGGCU

GGGGUUUCGGCCACCCUGUGGCAGAGCUUUUAGAAGCCAGGGCCCUUGGC

UCGGCAGUGCUGGCUCAUAGUAGGUGCUUAGUUCAUGCCUGUCUCCUUGG

AUGAAAUCUGACCAUAGACACCAGUGCAAAGCAGGUGUUCAACACAGGAG

GGUGUACUGAACCCGAUCUCUCUAUCACCAGGAGGAAGCACACGGGAGGC

ACUCAGAGAACGUUUGUGGAAUGAAUAAAUAAAAGCAUAUUUUGAGGGAA

UAAAGAAGCAGAAAAACAAAGAAGAAUCUGGGGAAGAUGGGCAUAAAUCU

CCACCAAGUGCUGCCAAGGCUUCCCAGGCGAGGCUGCUGAAAAGACCCUG

UGGAGGUAGAGGGACAAUUUGUCAUGGAUGGGAAUGGGCUUGAGGGCCGG

GAAGCAGGGCAUGAUGGGCCUCAUUCAUCAUUUUCCCGUUAUCCCAGCA

GCGUGCAGGGGAGCAGGUACAGCACCUGCCGUGCAGCUGCACUGCCUGC

CCGAAGGCCCUAGGCCCUGGGCCAAGUGAGUGACCAGAGGGGGACUGGGA

AUGGAAAGGACCUCAAGGAAGGACAAGCUGAGCUCUGGGAGGCCACCUCC

UCCAGGAAGCCUUCCCUGAUUCAUCCUUCACAGGCAGCUCAAUUUGCAG

UCAGAUAUCCACUGCUCUGAUUCUUAGAUCAGCAAGUAUCUCCCUACCCA

GACUGCAGGCUCUGCUGGGGCCGCGGCUGUUUCUGACUUGUGCACAAUGG

CAUCCCUGUACCUAGCACAGGACUGAGUCCAGAGAAAGUGCUCAGUGAUG

CUUGUUGGCCUUGUCUCUCCUCUGUGGGCAGCACAGGGCACCCGGCGGGU

CCUGAGGGUGUGGACAUCCCACGCAGAGCCUGCGGUUGAUCCCGACCAU

GAACCAAGGCCUGGGGCGGGGUGGCCACAUCAGGCCACUUCUGCCAGGA

GAGAUGUGGCUGUGAGCUGGGGGUCUGGCCUGUCCCGGAGGCAUUCCUU

GGGUUUGCAUCCAUCAGAAGAUCCACUGGUUGCCUCUAUUUGGGCCUGGA

GCAGGGAUGGGAUUUUUCCAAGGUACAUGGGGUCUAGGGGAGACCCAGGC

CCAUUAUUAGGGUCGGUCUUGAGAAGGCAGAGAUCAGGCCACCACUUUAU

-continued

UUGGUGUAGCUCCUCGCUCCAUUGGUGUGUGCUGAGUGAAUGAAUGCAUC

AGGGACUCCUGCUUCCUGCCCAGAGCCCCCUCCGCACCCCACACAGCCUU

GCUCCAAGGAGAAGGGGUCAGAGCCAACUGGACAGUGCUACAGCAUGGGG

AGCCUCGACCAGGCUCGGCCCUCGACGAUGGGAUAGGCAGACAGCCCCCU

GUGCAAGGCAGCUAGCUUGCAGGGUCCCGAGAGGCCAAAGGCCCUGGUCU

UUCCUGGGGCAAGAGGCUGCUGAGAAGGUGCACAGAGCCUGGGUGCAGGA

AACCAUCCAGAAUGCUGCUUCCCGCCAUCUGUGAGAUCUUCGUUUUCUCU

AACACUCAAAAAUAGAUGUUUCUGUUAUGCUCUCUCGUUGGCAGGGGAGC

GGCAGGACCUGCCAAGGCCUGGGGGAGCCCGCCAGCCUGCUGAGUUCUAC

UGUACAAACAGUUGGGAGGGGGCGCUGUCUCUGUUAACUUGAAAUUCCC

CGAUCAGUAAACAUGCCAAUUUAAAGUGUAAUUAACUCAGGCCGGAAAAA

AUUCAGAUUUGGACUGCUUUUCACAGUUGAGGUUGUUUUUCUUUUAUUUA

UUUAUCUCUUUCCGGGUGUGGUGGUAUCUGUGGCUGGUUUUAGCCAGGAA

AAAUAGAAGGGGACCGGGUGGGAGGGGGCUGGUUGGGAGAGGAAAGGC

UGGAAGGAAAGGAAGAGAAACGGGCGGGUGGCCUGACACCCAGCAGCCAG

GUGUCUAUAGGUUUUCUGUCCUGGGAGGGGGCUGUCAGGGUGAUGCCCGC

CUGCAGAGAGGGGGUCAUUCUGCGAGGUUGGGCUGCAGACCCCUGUGCCA

GCGGGCCUGGUGAUUCGGAAAUGAUGGGGCACUGUGGAGAGACCCCAGGA

AAACACCCAGUGCUGCUUUUGACAUUCUCUCCAUCUCCCCUUUCAGCG

GCUGCUCUGCCUGGGAUAAACACAUUUCAAGAGUCUCAGUCCCCGCUUUG

CCACCAUCUCCUCCUCUGAUCUCCUUUCCUGCUUCAAAAGACUCCAGAAU

CUUCUCGGUUCUCAGAGAAGGCUGAAUCCACCUAUGACCUAGUGGGAGCA

CCCUGUGCCGAAACUGUUUACCUUCUGGUCCCCGGAGCCAUGGGUCACGA

CCUGGGCCUCAUGUAGGCCCGCUCCUCAGCAGACCCCAAUCUGCGGCUUC

UCCCACCUCACUGGGGAAGAAGGAGAGCCCUGGGGAUGUGGAGAAGCCAC

CCCCACCCCGCCACAUCCCCACAUCUUACAGAAUCUCGAUUGAAUCCC

CGGGGGCACAUCCCUCAGCAGGACAGCAACAGUCUUUGCCGCAGCCUGGG

GAGGGCUGUGCUGGGGAUGAGCGCCGAGUGGCCGUGGACUAAGUGAAGGA

AAUGACCAUGCUCUUCUCCCAGCUGGAUGGCGAGGCCGGGCAGGAACCGC

GGAAUUCCUGCUCUUCGUUUUCAAACACUUUGCUGUCAAGCUAUUUGAAU

AAUAAAUACACAUUAUAAAAAUGUAA

In some embodiments, the target miRNA is a 14q32 mega-cluster miRNA activated in a muscle disease as compared to normal tissue. Exemplary 14q32 mega-cluster miRNAs are provided in Tables 3 and 4.

TABLE 3

Muscle disease-associated non-coding RNAs located at the human 14q32 mega cluster

| Human microRNA | SEQ ID NO:/ Mature microRNA Human | miRBase ID Human |
|---|---|---|
| hsa-miR-134-5p | 51/ UGUGACUGGUUGACCAGAGGGG | MIMAT0000447 |
| hsa-miR-370 | 52/ GCCUGCUGGGGUGGAACCUGGU | MIMAT0000722 |

TABLE 3-continued

Muscle disease-associated non-coding RNAs located at the human 14q32 mega cluster

| Human microRNA | SEQ ID NO:/ Mature microRNA Human | miRBase ID Human |
|---|---|---|
| hsa-miR-409-3p | 53/ GAAUGUUGCUCGGUGAACCCCU | MIMAT0001639 |
| hsa-miR-433-4p | 54/ AUCAUGAUGGGCUCCUCGGUGU | MIMAT0001627 |
| hsa-miR-493-3p | 55/ UGAAGGUCUACUGUGUGCCAGG | MIMAT0003161 |
| hsa-miR-543 | 56/ AAACAUUCGCGGUGCACUUCUU | MIMAT0004954 |

| mouse/microRNA | Mature microRNA mouse | miRBase ID Mouse |
|---|---|---|
| mmu-miR-134-5p | 57/ UGUGACUGGUUGACCAGAGGGG | MIMAT0000146 |
| mmu-miR-370-3p | 58/ GCCUGCUGGGGUGGAACCUGGU | MIMAT0001095 |
| mmu-miR-409-3p | 59/ GAAUGUUGCUCGGUGAACCCCU | MIMAT0001090 |
| mmu-miR-433-3p | 60/ AUCAUGAUGGGCUCCUCGGUGU | MIMAT0001420 |
| mmu-miR-493-3p | 61/ UGAAGGUCCUACUGUGUGCCAGG | MIMAT0004888 |
| mmu-miR-543-3p | 62/ AAACAUUCGCGGUGCACUUCUU | MIMAT0003168 |

TABLE 4

Additional miRNAs from the 14q32 mega cluster upregulated in dystrophic vs. healthy

| human microRNA | mouse/microRNA |
|---|---|
| hsa-miR-154# | hsa-miR-154# |
| hsa-miR-376a# | hsa-miR-376a# |
| hsa-miR-127 | mmu-miR-127 |
| hsa-miR-154 | mmu-miR-154 |
| hsa-miR-337 | mmu-miR-337 |
| hsa-miR-342-3p | mmu-miR-342-3p |
| hsa-miR-345-5p | mmu-miR-345-5p |
| hsa-miR-369-3p | mmu-miR-369-3p |
| hsa-miR-369-5p | mmu-miR-369-5p |
| hsa-miR-376a | mmu-miR-376a |
| hsa-miR-376a# | mmu-miR-376a# |
| hsa-miR-376b | mmu-miR-376b |
| hsa-miR-376b# | mmu-miR-376b# |
| hsa-miR-376c | mmu-miR-376c |
| hsa-miR-379 | mmu-miR-379 |
| hsa-miR-380-5p | mmu-miR-380-5p |
| hsa-miR-382 | mmu-miR-382 |
| hsa-miR-410 | mmu-miR-410 |
| hsa-miR-411 | mmu-miR-411 |
| hsa-miR-431 | mmu-miR-431 |
| hsa-miR-487b | mmu-miR-487b |
| hsa-miR-494 | mmu-miR-494 |
| hsa-miR-495 | mmu-miR-495 |
| hsa-miR-541 | mmu-miR-541 |
| hsa-miR-544 | mmu-miR-544 |
| hsa-miR-665 | mmu-miR-665 |
| hsa-miR-345-3p | rno-miR-345-3p |
| hsa-miR-379# | rno-miR-379# |
| hsa-miR-381 | rno-miR-381 |

In some embodiments, the interfering RNA molecule comprises a nucleotide sequence that is substantially complementary to the 14q32 mega-cluster miRNA. In some embodiments, the interfering RNA molecule is fully complementary to the 14q32 mega-cluster miRNA.

The interfering RNA molecule can, in some embodiments, have substantial complementarity (from about 70% to about 99% complementarity) to only the seed sequence of the target miRNA. In some embodiments, the interfering RNA molecule has perfect complementarity to its target miRNA's seed sequence. In some embodiments, the interfering RNA molecule comprises the nucleotide sequence CCAGUCAC, CCAGCAGG, GCAACAUU, CAUCAUGA, GGACCUUC, AGACCUUC, or CGAAUGUU, which have perfect complementarity to the miRNA seed sequences found in Table 3. In some embodiments, the interfering RNA or RNA/DNA hybrid molecule comprises the nucleotide sequence CCCCUCUGGUCAACCAGUCACA (SEQ ID NO:63),
ACCAGGUUCCACCCCAGCAGGC (SEQ ID NO:64),
AGGGGUUCACCGAGCAACAUUC (SEQ ID NO:65),
ACACCGAGGAGCCCAUCAUGAU (SEQ ID NO:66),
CCUGGCACACAGUAGGACCUUCA (SEQ ID NO:67),
CCUGGCACACAGUAGACCUUCA (SEQ ID NO:68), or
AAGAAGUGCACCGCGAAUGUUU (SEQ ID NO:69), which have perfect complementarity to the miRNA sequences in Table 3. In some embodiments, the disclosure relates to a composition comprising an interfering RNA sequence comprising CCAGUCAC, CCAGCAGG, GCAACAUU, CAUCAUGA, GGACCUUC, AGACCUUC, or CGAAUGUU; or, in some embodiments, the disclosure relates to a composition comprising an interfering RNA sequence comprising at least about 70%, 75%, 80%, 85%, 90%, 91%, 92%, 93%, 94%, 95%, 96%, 97%, 98%, 99% or 100% sequence identity to CCCCUCUGGUCAACCAGUCACA (SEQ ID NO: 63),
ACCAGGUUCCACCCCAGCAGGC (SEQ ID NO: 64),
AGGGGUUCACCGAGCAACAUUC (SEQ ID NO: 65),
ACACCGAGGAGCCCAUCAUGAU (SEQ ID NO: 66),
CCUGGCACACAGUAGGACCUUCA (SEQ ID NO: 67),
CCUGGCACACAGUAGACCUUCA (SEQ ID NO: 68), or
AAGAAGUGCACCGCGAAUGUUU (SEQ ID NO: 69).

In some embodiments, the disclosure relates to a composition comprising an interfering RNA sequence comprising at least about 70%, 75%, 80%, 85%, 90%, 91%, 92%, 93%, 94%, 95%, 96%, 97%, 98%, 99% or 100% sequence identity to CCAGUCAC, CCAGCAGG, GCAACAUU, CAUCAUGA, GGACCUUC, AGACCUUC, or CGAAUGUU. In some embodiments, the disclosure relates to a composition comprising an RNA sequence from about 5 to about 35 nucleic acids in length, the RNA comprising a region of at least about 75% sequence identity to any one or combination of nucleic acid sequences chosen from: CCAGUCAC, CCAGCAGG, GCAACAUU, CAUCAUGA, GGACCUUC, AGACCUUC, or CGAAUGUU. In some embodiments, the disclosure relates to a composition comprising an RNA sequence from about 5 to about 35 nucleic acids in length, the RNA comprising a region of at least about 75% sequence identity to any one or combination of nucleic acid sequences chosen from: SEQ ID NO: 63, 64, 65, 66, 67, 68, or 69. In some embodiments, the interfering RNA or RNA/DNA hybrid molecule comprises a nucleotide sequence having partial (from about 70% to about 99%) or full complementarity to an miRNA listed in Table 4.

The disclosure relates to viral vectors comprising any of the antisense oligonucleotides provided herein. In some embodiments, the viral vector is an AAV viral vector, a lentiviral vector, or a attenuated retroviral vector.

Methods of Making Compositions and Modifications

Oligonucleotides (e.g., certain modified oligonucleotides or portions of oligonucleotides lacking ribonucleotides) can be synthesized using protocols known in the art, for example as described in Caruthers et al., Methods in Enzymology 211:3, 1992; Thompson et al., International PCT Publication No. WO 99/54459; Wincott et al., Nucleic Acids Res. 23:2677, 1995; Wincott et al., Methods Mol. Bio. 74:59, 1997; Brennan et al., Biotechnol. Bioeng. 61:33, 1998; and Brennan, U.S. Pat. No. 6,001,311. All of these references are incorporated herein by reference in its entirety. The synthesis of oligonucleotides makes use of common nucleic acid protecting and coupling groups, such as dimethoxytrityl at the 5'-end, and phosphoramidites at the 3'-end.

The method of synthesis used for antisense RNA can follow the procedure as described in Usman et al., J. Chem. Soc. 109:7845, 1987; Scaringe et al., Nucleic Acids Res. 18:5433, 1990; Wincott et al., Nucleic Acids Res. 23:2677, 1995; and Wincott et al., Methods Mol. Bio. 74:59, 1997; and makes use of common nucleic acid protecting and coupling groups, such as dimethoxytrityl at the 5'-end, and phosphoramidites at the 3'-end.

Alternatively, the nucleic acid molecules can be synthesized separately and joined together post-synthetically, for example, by ligation (Moore et al., Science 256:9923, 1992; Draper et al., International PCT publication No. WO 93/23569; Shabarova et al., Nucleic Acids Res. 19:4247, 1991; Bellon et al., Nucleosides & Nucleotides 16:951, 1997; Bellon et al., Bioconjugate 8:204, 1997), or by hybridization following synthesis and/or deprotection.

An antisense RNA agent can also be assembled from two distinct nucleic acid sequences or fragments wherein one fragment includes the sense region and the second fragment includes the antisense region of the RNA. Antisense RNA can be modified extensively to enhance stability by modification with nuclease resistant groups, for example, 2'-amino, 2'-C-allyl, 2'-fluoro, difluorortoluoyl, 5-allyamino-pyrimidines, 2'-O-methyl, 2'-H (for a review see Usman and Cedergren, Trends in Biochem. Sci. 17:34, 1992). Antisense RNA constructs can be purified by gel electrophoresis using general methods or can be purified by high pressure liquid chromatography (HPLC; see Wincott et al., Nucleic Acids Res. 23:2677, 1995; Wincott et al., Methods Mol. Bio. 74:59, 1997) and re-suspended in water.

In another aspect, antisense RNA can be expressed from transcription units inserted into DNA or RNA vectors. The recombinant vectors can be DNA plasmids or viral vectors. Antisense RNA-expressing viral vectors can be constructed based on, but not limited to, adeno-associated virus, retrovirus, adenovirus, or alphavirus. The recombinant vectors capable of expressing the antisense RNA can be delivered as described herein, and persist in target cells. Alternatively, viral vectors can be used that provide for transient expression of antisense RNA.

In some embodiments, the antisense RNA can comprise a modification, e.g., to a backbone atom, a sugar or a base.

Exemplary modifications include modifications that inhibit endonucleolytic degradation, including the modifications described herein. Modifications include, but are not limited to, 2' modification, e.g., a 2'-O-methylated nucleotide or 2'-deoxy nucleotide (e.g., 2' deoxy-cytodine), or a 2'-fluoro, difluorotoluoyl, 5-Me-2'-pyrimidines, 5-ally-amino-pyrimidines, 2'-.beta.-methoxyethyl, 2'-hydroxy, or 2'-ara-fluoro nucleotide, or a locked nucleic acid (LNA), extended nucleic acid (ENA), hexose nucleic acid (HNA), or cyclohexene nucleic acid (CeNA). In one embodiment, the 2' modification is on the uridine of at least one 5'-uridine-adenine-3' (5'-UA-3') dinucleotide, at least one 5'-uridine-guanine-3' (5'-UG-3') dinucleotide, at least one 5'-uridine-uridine-3' (5'-UU-3') dinucleotide, or at least one 5'-uridine-cytidine-3' (5'-UC-3') dinucleotide, or on the cytidine of at least one 5'-cytidine-adenine-3' (5'-CA-3') dinucleotide, at least one 5'-cytidine-cytidine-3' (5'-CC-3') dinucleotide, or at least one 5'-cytidine-uridine-3' (5'-CU-3') dinucleotide. The 2' modification can also be applied to all the pyrimidines in an antisense RNA. In one embodiment, the 2' modification is a 2'OMe modification on the sense strand of an RNA. In another embodiment the 2' modification is a 2' fluoro modification, and the 2' fluoro is on the sense or antisense strand or on both strands. In some embodiments, at least 1, 2, 3, 4, 5, 6, 7, 8, 9, 10, 11, 12, 13, 14, 15 or more uridines are replaced with at least one adenine.

Modification of the backbone, e.g., with the replacement of an O with an S, in the phosphate backbone, e.g., the provision of a phosphorothioate modification can be used to inhibit endonuclease activity. In some embodiments, an antisense RNA has been modified by replacing one or more ribonucleotides with deoxyribonucleotides. Adjacent deoxyribonucleotides can be joined by phosphorothioate linkages, and the antisense RNA does not include more than four consecutive deoxyribonucleotides on the sense or the antisense strands. Replacement of the U with a C5 amino linker; replacement of an A with a G (sequence changes can be located on the sense strand and not the antisense strand); or modification of the sugar at the 2', 6', 7', or 8' position can also inhibit endonuclease cleavage of the antisense RNA. In some embodiments, one or more of these modifications are present on the sense but not the antisense strand, or embodiments where the antisense strand has fewer of such modifications.

Exemplary modifications also include those that inhibit degradation by exonucleases. Examples of modifications that inhibit exonucleolytic degradation can be found herein. In one embodiment, an antisense RNA includes a phosphorothioate linkage or P-alkyl modification in the linkages between one or more of the terminal nucleotides of an antisense RNA. In another embodiment, one or more terminal nucleotides of an antisense RNA include a sugar modification, e.g., a 2' or 3' sugar modification. Exemplary sugar modifications include, for example, a 2'-.beta.-methylated nucleotide, 2'-deoxy nucleotide (e.g., deoxy-cytodine), 2'-deoxy-2'-fluoro (2'-F) nucleotide, 2'-O-methoxyethyl (2'-O-MOE), 2'-O-aminopropyl (2'-O-AP), 2'-O—N-methylacetamido (2'-O-NMA), 2'-O-dimethylaminoethlyoxyethyl (2'-DMAEOE), 2'-O-dimethylaminoethyl (2'-O-DMAOE), 2'-O-dimethylaminopropyl (2'-O-AP), 2'-hydroxy nucleotide, or a 2'-ara-fluoro nucleotide, or a locked nucleic acid (LNA), extended nucleic acid (ENA), hexose nucleic acid (HNA), or cyclohexene nucleic acid (CeNA). A 2' modification is in some embodiments 2'OMe, and in some embodiments 2' fluoro.

The modifications described to inhibit exonucleolytic cleavage can be combined onto a single antisense RNA. For example, in one embodiment, at least one terminal nucleotide of an antisense RNA has a phosphorothioate linkage and a 2' sugar modification, e.g., a 2'F or 2'OMe modification. In another embodiment, at least one terminal nucleotide of an antisense RNA has a 5' Me-pyrimidine and a 2' sugar modification, e.g., a 2'F or 2'OMe modification. To inhibit exonuclease cleavage, an antisense RNA can include a nucleobase modification, such as a cationic modification, such as a 3'-abasic cationic modification. The cationic modification can be, e.g., an alkylamino-dT (e.g., a C6 amino-dT), an allylamino conjugate, a pyrrolidine conjugate, a pthalamido or a hydroxyprolinol conjugate, on one or more of the terminal nucleotides of the antisense RNA. An alkylamino-dT conjugate can be attached to the 3' end of the sense or antisense strand of an antisense RNA. A pyrrolidine linker can be attached to the 3' or 5' end of the sense strand, or the 3' end of the antisense strand. An allyl amine uridine can be on the 3' or 5' end of the sense strand, and not on the 5' end of the antisense strand.

In another embodiment, the antisense RNA includes a conjugate on one or more of the terminal nucleotides of the antisense RNA. The conjugate can be, for example, a lipophile, a terpene, a protein binding agent, a vitamin, a carbohydrate, a retinoid, or a peptide. For example, the conjugate can be naproxen, nitroindole (or another conjugate that contributes to stacking interactions), folate, ibuprofen, cholesterol, retinoids, PEG, or a C5 pyrimidine linker. In other embodiments, the conjugates are glyceride lipid conjugates (e.g. a dialkyl glyceride derivatives), vitamin E conjugates, or thio-cholesterols. In some embodiments, conjugates are on the 3' end of the antisense strand, or on the 5' or 3' end of the sense strand, and in some embodiments the conjugates are not on the 3' end of the antisense strand and on the 3' end of the sense strand.

In some embodiments, the conjugate is naproxen, and the conjugate can be on the 5' or 3' end of the sense or antisense strands. In some embodiments, the conjugate is cholesterol, and the conjugate can be on the 5' or 3' end of the sense strand and not present on the antisense strand. In some embodiments, the cholesterol is conjugated to the antisense RNA by a pyrrolidine linker, or serinol linker, aminooxy, or hydroxyprolinol linker. In other embodiments, the conjugate is a dU-cholesterol, or cholesterol is conjugated to the antisense RNA by a disulfide linkage. In another embodiment, the conjugate is cholanic acid, and the cholanic acid is attached to the 5' or 3' end of the sense strand, or the 3' end of the antisense strand. In some embodiments, the cholanic acid is attached to the 3' end of the sense strand and the 3' end of the antisense strand. In another embodiment, the conjugate is PEGS, PEG20, naproxen or retinal.

In another embodiment, one or more terminal nucleotides have a 2'-5' linkage. A 2'-5' linkage can be on the sense strand, e.g., the 5' end of the sense strand.

In some embodiments, the antisense RNA includes an L-sugar, e.g., at the 5' or 3' end of the sense strand.

In some embodiment, the antisense RNA includes a methylphosphonate at one or more terminal nucleotides to enhance exonuclease resistance, e.g., at the 3' end of the sense or antisense strands of the antisense RNA.

In some embodiments, an antisense RNA has been modified by replacing one or more ribonucleotides with deoxyribonucleotides. Adjacent deoxyribonucleotides can be joined by phosphorothioate linkages, and the antisense RNA does not include more than four consecutive deoxyribonucleotides on the sense or the antisense strands.

In some embodiments, an antisense RNA having increased stability in cells and biological samples includes a difluorotoluoyl (DFT) modification, e.g., 2,4-difluorotoluoyl uracil, or a guanidine to inosine substitution.

The method of making a viral vector comprising the nucleic acid disclosed herein involves using a cell. Hence in some embodiments the method of making the viral vector involves expression of at least a competent portion of the genome of an virus disclosed herein in a cell. As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

In some embodiments, the host cell is the target of the viral particle, virion, or pseudovirus disclosed herein. In some embodiments, the target of the viral particle, virion, or pseudovirus disclosed herein is any type of fibroblast. In some embodiments, the target of the viral particle, virion, or pseudovirus disclosed herein is any type of myofibroblast, hepatic stellate cell, portal fibroblast, or a cell derived therefrom. In some embodiments, the cell is a myofibroblast.

Host cells may be derived from prokaryotes or eukaryotes, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (www.atcc.org). An appropriate host can be determined-by one of skill in the art based on the vector backbone and the desired result. A plasmid or cosmid, for example, can be introduced into a prokaryote host cell for replication of many vectors. Bacterial cells used as host cells for vector replication and/or expression include DH5.alpha., JM109, and KCB, as well as a number of commercially available bacterial hosts such as SURE®. Competent Cells and SOLOPACK™ Gold Cells (STRATAGENE.®, La Jolla). Alternatively, bacterial cells such as *E. coli* LE392 could be used as host cells for phage viruses.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference in its entirety, and which can be bought, for example, under the name MAXBAC® 2.0 from INVITROGEN® and BAC-PACK™ BACULOVIRUS EXPRESSION SYSTEM FROM CLONTECH®.

Other examples of expression systems include STRATAGENE®'s COMPLETE CONTROL™. Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

Pharmaceutical Compositions and Delivery of Compositions and Pharmaceutical Compositions The interfering RNA molecule may be delivered to the subject as an RNA molecule or partially double stranded RNA sequence, or RNA/DNA hybrid, which was made in vitro by conventional enzymatic synthetic methods using, for example, the bacteriophage T7, T3 or SP6 RNA polymerases according to the conventional methods described by such texts as the Promega Protocols and Applications Guide, (3rd ed. 1996), eds. Doyle, ISBN No. 1-882274-57-1. Alternatively these molecules may be made by chemical synthetic methods in vitro [see, e.g., Q. Xu et al, Nucl. Acids Res., 24(18):3643-4 (September 1996); N. Naryshkin et al, Bioorg. Khim., 22(9):691-8 (September 1996); J. A. Grasby et al, Nucl. Acids Res., 21(19):4444-50 (September 1993); C. Chaix et al, Nucl. Acids Res., 17(18):7381-93 (1989); S. H. Chou et al, Biochem., 28(6):2422-35 (March 1989); O. Odai et al, Nucl. Acids Symp. Ser., 21:105-6 (1989); N. A. Naryshkin et al, Bioorg. Khim, 22(9):691-8 (September 1996); S. Sun et al, RNA, 3(11):1352-1363 (November 1997); X. Zhang et al, Nucl. Acids Res., 25(20):3980-3 (October 1997); S. M. Grvaznov et al, Nucl. Acids Res., 26 (18):4160-7 (September 1998); M. Kadokura et al, Nucl. Acids Symp Ser, 37:77-8 (1997); A. Davison et al, Biomed. Pept. Proteins. Nucl. Acids, 2(1):1-6 (1996); and A. V. Mudrakovskaia et al, Bioorg. Khim., 17(6):819-22 (June 1991)].

Still alternatively, the RNA molecule of this invention can be made in a recombinant microorganism, e.g., bacteria and yeast or in a recombinant host cell, e.g., mammalian cells, and isolated from the cultures thereof by conventional techniques. See, e.g., the techniques described in Sambrook et al, MOLECULAR CLONING, A LABORATORY MANUAL, 2nd Ed.; Cold Spring Harbor Laboratory Press, Cold Spring Harbor, N.Y., 1989, which is exemplary of laboratory manuals that detail these techniques, and the techniques described in U.S. Pat. Nos. 5,824,538 and 5,877, 159, incorporated herein by reference in its entirety.

Such interfering RNA molecules prepared or synthesized in vitro may be directly delivered to the subject as they are made in vitro. The references above provide one of skill in the art with the techniques necessary to produce any of the following specific embodiments, given the teachings provided herein. Therefore, in one embodiment, the "agent" of the composition is a duplex (i.e., it is made up of two strands), either complete or partially double stranded RNA. In another embodiment, the agent is a single stranded RNA sense strand. In another embodiment, the agent of the composition is a single stranded RNA anti-sense strand. The single stranded RNA sense or anti-sense strand can form a hairpin at one or both termini. The single stranded RNA sense or anti-sense strand can form a hairpin at some intermediate portion between the termini. Such a single stranded RNA sense or anti-sense strand may also be designed to fold back upon itself to become partially double stranded in vitro or in vivo. Yet another embodiment of a single stranded RNA sequence comprising both a sense polynucleotide sequence and an anti-sense polynucleotide sequence, optionally separated by a non-base paired polynucleotide sequence. This single stranded RNA sequence has the ability to become double-stranded once it is in the cell, or in vitro during its synthesis. Still another embodiment of this invention is an RNA/DNA hybrid.

Still another embodiment of the interfering RNA molecule is a circular RNA molecule that optionally forms a rod structure [see, e.g., K-S. Wang et al, Nature, 323:508-514 (1986)] or is partially double-stranded, and can be prepared according to the techniques described in S. Wang et al, Nucl. Acids Res., 22(12):2326-33 (June 1994); Y. Matsumoto et al, Proc. Natl. Acad. Sci., USA, 87(19)7628-32 (October 1990); Proc. Natl. Acad. Sci., USA, 91(8):3117-21 (April 1994); M. Tsagris et al, Nucl. Acids Res., 19(7):1605-12 (April 1991); S. Braun et al, Nucl. Acids Res., 24(21): 4152-7 (November 1996); Z. Pasman et al, RNA, 2(6):603-10 (June 1996); P. G. Zaphiropoulos, Proc. Natl. Acad. Sci., USA, 93(13):6536-41 (June 1996); D. Beaudry et al, Nucl. Acids Res., 23(15):3064-6 (August 1995), all incorporated herein by reference in its entirety. Still another agent is a double-stranded molecule comprised of RNA and DNA present on separate strands, or interspersed on the same strand.

Alternatively, the interfering RNA molecule may be formed in vivo and thus delivered by a "delivery agent" which generates such an intefering RNA molecule in vivo after delivery of the agent to the subject. Thus, the agent which forms the composition is, in one embodiment, a double stranded DNA molecule "encoding" one of the above-described RNA molecules. The DNA agent provides the nucleotide sequence which is transcribed within a cell to become a double stranded RNA. In another embodiment, the DNA sequence provides a deoxyribonucleotide sequence which within a cell is transcribed into the above-described single stranded RNA sense or anti-sense strand, which optionally forms a hairpin at one or both termini or folds back upon itself to become partially double stranded. The DNA molecule which is the delivery agent of the composition can provide a single stranded RNA sequence comprising both a sense polynucleotide sequence and an anti-sense polynucleotide sequence, optionally separated by a non-base paired polynucleotide sequence, and wherein the single stranded RNA sequence has the ability to become double-stranded. Alternatively, the DNA molecule which is the delivery agent provides for the transcription of the above-described circular RNA molecule that optionally forms a rod structure or partial double strand in vivo. The DNA molecule may also provide for the in vivo production of an RNA/DNA hybrid as described above, or a duplex containing one RNA strand and one DNA strand. These various DNA molecules may be designed by resort to conventional techniques such as those described in Sambrook, cited above or in the Promega reference, cited above.

Another delivery agent, in a further embodiment, enables the formation in the subject of any of the above-described RNA molecules, can be a DNA single stranded or double stranded plasmid or vector. Expression vectors designed to produce RNAs as described herein in vitro or in vivo may containing sequences under the control of any RNA polymerase, including mitochondria RNA polymerase, RNA polII, and RNA polIII. These vectors can be used to transcribe the desired RNA molecule in a cell. Vectors may be desirably designed to utilize an endogenous mitochondrial RNA polymerase (e.g., human mitochondrial RNA polymerase, in which case such vectors may utilize the corresponding human mitochondrial promoter). Mitochondrial polymerases may be used to generate capped (through expression of a capping enzyme) or uncapped messages in vivo. RNA pol I, RNA pol II, and RNA pol III transcripts may also be generated in vivo. Such RNAs may be capped or not, and if desired, cytoplasmic capping may be accomplished by various means including use of a capping enzyme such as a vaccinia capping enzyme or an alphavirus capping enzyme. The DNA vector is designed to contain one of the promoters or multiple promoters in combination (mitochondrial, RNA polI, II, or polIII, or viral, bacterial or bacteriophage promoters along with the cognate polymerases). Where the promoter is RNA pol II, the sequence encoding the RNA molecule can have an open reading frame greater than about 300 nucleotides to avoid degradation in the nucleus. Such plasmids or vectors can include plasmid sequences from bacteria, viruses, or phages. Such vectors include chromosomal, episomal, and virus-derived vectors, e.g., vectors derived from bacterial plasmids, bacteriophages, yeast episomes, yeast chromosomal elements, and viruses, vectors derived from combinations thereof, such as those derived from plasmid and bacteriophage genetic elements, cosmids, and phagemids. Thus, one exemplary vector is a single or double-stranded phage vector. Another exemplary vector is a single or double-stranded RNA or DNA viral vector. Such vectors may be introduced into cells as polynucleotides, e.g. DNA, by well known techniques for introducing DNA and RNA into cells. The vectors, in the case of phage and viral vectors may also be introduced into cells as packaged or encapsidated virus by well known techniques for infection and transduction. Viral vectors may be replication competent or replication defective. In the latter case, viral propagation generally occurs only in complementing host cells.

In another embodiment, the delivery agent comprises more than a single DNA or RNA plasmid or vector. As one example, a first DNA plasmid can provide a single stranded RNA sense polynucleotide sequence as described above, and a second DNA plasmid can provide a single stranded RNA anti-sense polynucleotide sequence as described above, wherein the sense and anti-sense RNA sequences have the ability to base-pair and become double-stranded. Such plasmid(s) can comprise other conventional plasmid sequences, e.g., bacterial sequences such as the well-known sequences used to construct plasmids and vectors for recombinant expression of a protein. In some embodiments, the sequences which enable protein expression, e.g., Kozak regions, are not included in these plasmid structures.

The vectors designed to produce dsRNAs may be designed to generate two or more, including a number of different dsRNAs homologous and complementary to a target sequence. A single vector may produce many, independently operative dsRNAs rather than a single dsRNA molecule from a single transcription unit and by producing a multiplicity of different dsRNAs, it is possible to self-select for optimum effectiveness. Various means may be employed to achieve this, including autocatalytic sequences as well as sequences for cleavage to create random and/or predetermined splice sites.

Other delivery agents for providing the information necessary for formation of the above-described intefering RNA molecules in the subject include live, attenuated, killed, or inactivated recombinant bacteria, which are designed to contain the sequences necessary for the required RNA molecules. Such recombinant bacterial cells, fungal cells and the like can be prepared by using conventional techniques such as described in U.S. Pat. Nos. 5,824,538 and 5,877,159, incorporated herein by reference in its entirety. Microorganisms useful in preparing these delivery agents include those listed in the above cited reference, including, without limitation, *Escherichia coli, Bacillus subtilis, Salmonella typhimurium*, and various species of *Pseudomonas, Streptomyces*, and *Staphylococcus*.

"Invasive bacteria" include bacteria that are naturally capable of entering the cytoplasm or nucleus of animal cells, as well as bacteria that are genetically engineered to enter the cytoplasm or nucleus of animal cells or cells in animal tissue.

The particular naturally occurring invasive bacteria employed in the present invention is not critical thereto. Examples of such naturally-occurring invasive bacteria include, but are not limited to, *Shigella* spp., *Listeria* spp., *Rickettsia* spp, and enteroinvasive *Escherichia coli*.

Previously, live bacteria have been utilized as vaccines in order to protect against subsequent infection. Attenuated or less virulent *Shigella, Salmonella, Listeria*, and other bacteria have been given orally to immunize against subsequent infection with more virulent forms of these bacteria. Likewise, attenuated bacterial and mycobacterial organisms such as Bacille Calmette-Guerin (BCG) have been administered parenterally to protect against related organisms such as *M. tuberculosis*. Genes from bacteria, viruses, and parasites have been cloned into a variety of bacteria and mycobacteria for the purpose of directing the bacteria to express the foreign antigen or impart on the bacteria certain desired properties for use as a live vaccine. Examples include cloning the invasion genes of *Shigella* into the normally non-invasive *E. coli* rendering the *E. coli* invasive and therefore more suitable for use as a vaccine strain, or cloning of *P. falciparum* malaria genes into *Salmonella typhimurium* which subsequently express these malaria proteins and, following oral administration of the bacteria, induce specific cytotoxic T cell immunity and protection in mice against malaria challenge (Sadoff et al. Science (1988) 240:336-338; Aggrawal et al. J. Exp. Med. (1990) 172:1083-1090). All of these bacterial delivery systems require the bacteria itself to produce the antigen or functional molecule and are dependent on a bacteria which is sufficiently attenuated to be safe for use in a subject, but still able to induce a protective response. A bacterial delivery system is designed to deliver functional nucleic acids which direct eukaryotic cells to produce antigens and other functional molecules. In this case, toxicity to the carrier is eliminated because plasmid-encoded gene expression is dependent upon the machinery of the eukaryotic cell allowing proper folding of the antigen for presentation or direction of cell functions. In addition, if desired, it can be used to deliver prokaryotically produced antigens and functional molecules.

Examples of bacteria which can be genetically engineered to be invasive include, but are not limited to, *Yersinia* spp., *Escherichia* spp., *Klebsiella* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Salmonella* spp., *Vibrio* spp., *Bacillus* spp., and *Erysipelothrix* spp. These organisms can be engineered to mimic the invasion properties of *Shigella* spp., *Listeria* spp., *Rickettsia* spp., or enteroinvasive *E. coli* spp. by inserting genes that enable them to access the cytoplasm of an animal cell.

Examples of such genes include the invasive proteins of *Shigella*, hemolysin or the invasion plasmid of *Escherichia*, or listeriolysin O of *Listeria*, as such techniques are known to result in strains that are capable of entering the cytoplasm of infected animal cells (Formal et al, Infect. Immun., 46:465 (1984); Bielecke et al, Nature, 345:175-176 (1990); Small et al, In: Microbiology-1986, pages 121-124, Levine et al, Eds., American Society for Microbiology, Washington, D.C. (1986); and Zychlinsky et al, Molec. Micro., 11:619-627 (1994)). Any gene or combination of genes, from one or more sources, that mediates entry into the cytoplasm of animal cells will suffice. Thus, such genes are not limited to bacterial genes, and include viral genes, such as influenza virus hemagglutinin HA-2 which promotes endosmolysis (Plank et al, J. Biol. Chem., 269:12918-12924 (1994)).

It is also possible to change the tissue specificity of the invasive bacteria by expression of a gene product singularly or in combination, e.g., the *Plasmodium vivax* reticulocyte binding proteins-1 and -2 bind specifically to erythrocytes in humans and primates (Galinski et al, Cell, 69:1213-1226 (1992)); *Yersinia* Invasin recognizes β1 integrin receptors (Isberg et al, Trends Microbiol., 2:10-14 (1994)); asialoorosomucoid is a ligand for the asilogycoprotein receptor on hepatocytes (Wu et al, J. Biol. Chem., 263:14621-14624 (1988)); presence of insulin-poly-L-lysine has been shown to target plasmid uptake to cells with an insulin receptor (Rosenkranz et al, Expt. Cell Res., 199:323-329 (1992)); p60 of *Listeria monocytogenes* allows for tropism for hepatocytes (Hess et al, Infect. Immun., 63:2047-2053 (1995)) and *Trypanosoma cruzi* expresses a 60 kDa surface protein which causes specific binding to the mammalian extracellular matrix by binding to heparin, heparin sulfate and collagen (Ortega-Barria et al, Cell, 67:411-421 (1991)).

Another delivery agent for providing the information necessary for formation of the desired, above-described intefering RNA molecules in a subject include live, attenuated, killed, or inactivated donor cells which have been transfected or infected in vitro with a synthetic RNA molecule or a DNA delivery molecule or a delivery recombinant virus as described above. These donor cells may then be administered to the subject, as described in detail below, to stimulate the mechanism in the subject which mediates this inhibitory effect. These donor cells can be mammalian cells, such as C127, 3T3, CHO, HeLa, human kidney 293, BHK cell lines, and COS-7 cells, and in some embodiments are of the same species as the subject recipient. Such donor cells can be made using techniques similar to those described in, e.g., Emerich et al, J. Neurosci., 16: 5168-81 (1996). The donor cells may be harvested from the specific mammal to be treated and made into donor cells by ex vivo manipulation, akin to adoptive transfer techniques, such as those described in D. B. Kohn et al, Nature Med., 4(7):775-80 (1998). Donor cells may also be from non-mammalian species, if desired.

Compositions disclosed herein can also include one or more of the selected agents which are described above. The composition can contain a mixture of synthetic RNA molecules described above, synthetic DNA delivery molecules described above, and any of the other delivery agents described above, such as recombinant bacteria, cells, and viruses. The identity of the composition mixture may be readily selected by one of skill in the art.

Compositions for pharmaceutical use can contain an interfering RNA molecule as described above or the agent which provides that interfering RNA molecule to the subject in vivo in a pharmaceutically acceptable carrier, with additional optional components for pharmaceutical delivery. The specific formulation of the pharmaceutical composition depends upon the form of the agent delivering the RNA molecule.

Suitable pharmaceutically acceptable carriers facilitate administration of the polynucleotide compositions but are physiologically inert and/or nonharmful. Carriers may be selected by one of skill in the art. Such carriers include, but are not limited to, sterile saline, phosphate, buffered saline, dextrose, sterilized water, glycerol, ethanol, lactose, sucrose, calcium phosphate, gelatin, dextran, agar, pectin, peanut oil, olive oil, sesame oil, and water and combinations thereof. Additionally, the carrier or diluent may include a time delay material, such as glycerol monostearate or glycerol distearate alone or with a wax. In addition, slow release polymer formulations can be used. The formulation should suit not only the form of the delivery agent, but also the mode of administration. Selection of an appropriate carrier in accordance with the mode of administration is routinely performed by those skilled in the art.

Where the composition contains the intefering RNA molecule or where the agent is another polynucleotide, such as a DNA molecule, plasmid, viral vector, or recombinant virus, or multiple copies of the polynucleotide or different polynucleotides, etc., the composition may be formulated as a "naked" polynucleotide with only a carrier. Alternatively, such compositions can contain optional polynucleotide facilitating agents or "co-agents", such as a local anaesthetic, a peptide, a lipid including cationic lipids, a liposome or lipidic particle, a polycation such as polylysine, a branched, three-dimensional polycation such as a dendrimer, a carbohydrate, a cationic amphiphile, a detergent, a benzylammonium surfactant, or another compound that facilitates polynucleotide transfer to cells. Non-exclusive examples of such facilitating agents or co-agents useful in this invention are described in U.S. Pat. Nos. 5,593,972; 5,703,055; 5,739,118; 5,837,533 and International Patent Application No. WO96/10038, published Apr. 4, 1996; and International Patent Application No WO94/16737, published Aug. 8, 1994, which are each incorporated herein by reference in its entirety.

Where the delivery agent of the composition is other than a polynucleotide composition, e.g., is a transfected donor cell or a bacterium as described elsewhere herein, the composition may also contain other additional agents, such as those discussed in U.S. Pat. Nos. 5,824,538, 5,643,771, and 5,877,159, incorporated herein by reference in its entirety.

Additional components that may be present in any of the compositions are adjuvants, preservatives, chemical stabilizers, or other antigenic proteins. Typically, stabilizers, adjuvants, and preservatives are optimized to determine the best formulation for efficacy in the target human or animal. Suitable exemplary preservatives include chlorobutanol, potassium sorbate, sorbic acid, sulfur dioxide, propyl gallate, the parabens, ethyl vanillin, glycerin, phenol, and parachlorophenol. Suitable stabilizing ingredients which may be used include, for example, casamino acids, sucrose, gelatin, phenol red, N-Z amine, monopotassium diphosphate, lactose, lactalbumin hydrolysate, and dried milk. A conventional adjuvant is used to attract leukocytes or enhance an immune response. Such adjuvants include, among others, Ribi, mineral oil and water, aluminum hydroxide, Amphigen, Avridine, L121/squalene, D-lactide-polylactide/glycoside, pluronic plyois, muramyl dipeptide, killed *Bordetella*, and saponins, such as Quil A.

In addition, other agents which may function as transfecting agents and/or replicating agents and/or inflammatory agents and which may be co-administered with the composition of this invention, include growth factors, cytokines and lymphokines such as alpha-interferon, gamma-interferon, platelet derived growth factor (PDGF), colony stimulating factors, such as G-CSF, GM-CSF, tumor necrosis factor (TNF), epidermal growth factor (EGF), and the interleukins, such as IL-1, IL-2, IL-4, IL-6, IL-8, IL-10 and IL-12. Further, fibroblast growth factor, surface active agents such as immune-stimulating complexes (ISCOMS), Freund's incomplete adjuvant, LPS analog including monophosphoryl Lipid A (MPL), muramyl peptides, quinone analogs and vesicular complexes such as squalene and squalene, and hyaluronic acid may also be used administered in conjunction with the compositions.

The pharmaceutical compositions may also contain other additives suitable for the selected mode of administration of the composition. Thus, these compositions can contain additives suitable for administration via any conventional route of administration, including without limitation, parenteral administration, intraperitoneal administration, intravenous administration, intramuscular administration, subcutaneous administration, intradermal administration, oral administration, topical administration, intranasal administration, intrapulmonary administration, rectal administration, vaginal administration, and the like. All such routes are suitable for administration of these compositions, and may be selected depending on the agent used, patient and condition treated, and similar factors by an attending physician.

The pharmaceutical compositions may also involve lyophilized polynucleotides, which can be used with other pharmaceutically acceptable excipients for developing powder, liquid, or suspension dosage forms, including those for intranasal or pulmonary applications. See, e.g., Remington: The Science and Practice of Pharmacy, Vol. 2, 19.sup.th edition (1995), e.g., Chapter 95 Aerosols; and International Patent Application No. PCT/US99/05547, the teachings of which are hereby incorporated by reference in its entirety. Routes of administration for these compositions may be combined, if desired, or adjusted.

In some embodiments, the pharmaceutical compositions are prepared for administration to subjects in the form of, for example, liquids, powders, aerosols, tablets, capsules, enteric coated tablets or capsules, or suppositories.

The compositions disclosed herein, when used as pharmaceutical compositions, can comprise about 1 ng to about 20 mgs of polynucleotide molecules as the delivery agent of the compositions, e.g., the synthetic RNA molecules or the delivery agents which can be DNA molecules, plasmids, viral vectors, recombinant viruses, and mixtures thereof. In some embodiments, the compositions contain about 10 ng to about 10 mgs of polynucleotide sequences. In other embodiments, the pharmaceutical compositions contain about 0.1 to about 500 µg polynucleotide sequences. In some embodiments, the compositions contain about 1 to about 350 µg polynucleotide sequences. In still other embodiments, the pharmaceutical compositions contain about 25 to about 250 µg of the polynucleotide sequences. In some embodiments, the vaccines and therapeutics contain about 100 µg of the polynucleotide sequences.

The compositions in which the delivery agents are donor cells or bacterium can be delivered in dosages of between about 1 cell to about $10^7$ cells/dose. Similarly, where the delivery agent is a live recombinant virus, a suitable vector-based composition contains between $1 \times 10^2$ pfu to $1 \times 10^{12}$ pfu per dose.

The above dosage ranges are guidelines only. In general, the pharmaceutical compositions are administered in an amount effective to inhibit or reduce the function of the target polynucleotide sequence for treatment or prophylaxis of the diseases, disorders or infections for which such target functions are necessary for further propagation of the disease or causative agent of the disease. The amount of the pharmaceutical composition in a dosage unit employed is determined empirically, based on the response of cells in vitro and response of experimental animals to the compositions of this invention. Optimum dosage is determined by standard methods for each treatment modality and indication. Thus the dose, timing, route of administration, and need for readministration of these compositions may be determined by one of skill in the art, taking into account the condition being treated, its severity, complicating conditions, and such factors as the age, and physical condition of the mammalian subject, the employment of other active compounds, and the like.

Methods

The methods herein can employ the compositions described in detail above, and in some embodiments, anti-inflammatory corticosteroids. These methods reduce or inhibit the function of a target miRNA in a subject. The compositions, pharmaceutical compositions, dosages, and modes of administration described herein are useful, e.g., for the treatment of a variety of disorders, including inflammation, steroid side effects, and muscle diseases. Additionally, the compositions are useful in preventing such disorders.

One embodiment is for treating inflammation in a subject in need thereof comprising administering to the subject a therapeutically effective amount of an interfering RNA molecule that inhibits or reduces the activity of an NF-κB-regulated miRNA. In some embodiments, the NF-κB-regulated miRNA is an miRNA listed in Table 1 above. In some embodiments, the interfering RNA molecule comprises a nucleotide sequence that is substantially complementary to the NF-κB-regulated miRNA. In some embodiments, the interfering RNA molecule is fully complementary to the NF-κB-regulated miRNA.

The disclosure also relates to a method of treating inflammation in a subject in need thereof comprising administering to the subject a therapeutically effective amount of an interfering RNA molecule that binds TLR7 and inhibits binding of miRNAs of any of the disclosed SEQ ID NOs from binding TLR7. The disclosure also relates to a method of treating inflammation in a subject in need thereof comprising administering to the subject a therapeutically effective amount of an interfering RNA molecule that binds TLR7 and inhibits binding of miRNAs of any of the disclosed SEQ ID NO:1 from binding TLR7. The disclosure also relates to a method of treating inflammation in a subject in need thereof comprising administering to the subject a therapeutically effective amount of an interfering RNA molecule that binds TLR7 and inhibits binding of miRNAs of any of the disclosed SEQ ID NO:2 from binding TLR7. The disclosure also relates to a method of treating inflammation in a subject in need thereof comprising administering to the subject a therapeutically effective amount of an interfering RNA molecule that binds TLR7 and inhibits binding of miRNAs of any of the disclosed SEQ ID NO:3 from binding TLR7. The disclosure also relates to a method of treating inflammation in a subject in need thereof comprising administering to the subject a therapeutically effective amount of an interfering RNA molecule that binds TLR7 and inhibits binding of miRNAs of any of the disclosed SEQ ID NO:4 from binding TLR7. The disclosure also relates to a method of treating inflammation in a subject in need thereof comprising administering to the subject a therapeutically effective amount of an interfering RNA molecule that binds TLR7 and inhibits binding of miRNAs of any of the disclosed SEQ ID NO:5 from binding TLR7. The disclosure also relates to a method of treating inflammation in a subject in need thereof comprising administering to the subject a therapeutically effective amount of an interfering RNA molecule that binds TLR7 and inhibits binding of miRNAs of any of the disclosed SEQ ID NO:6 from binding TLR7. The disclosure also relates to a method of treating inflammation in a subject in need thereof comprising administering to the subject a therapeutically effective amount of an interfering RNA molecule that binds TLR7 and inhibits binding of miRNAs of any of the disclosed SEQ ID NO:7 from binding TLR7. The disclosure also relates to a method of treating inflammation in a subject in need thereof comprising administering to the subject a therapeutically effective amount of an interfering RNA molecule that binds TLR7 and inhibits binding of miRNAs of any of the disclosed SEQ ID NO:8 from binding TLR7. The disclosure also relates to a method of treating inflammation in a subject in need thereof comprising administering to the subject a therapeutically effective amount of an interfering RNA molecule that binds TLR7 and inhibits binding of miRNAs of any of the disclosed SEQ ID NO:9 from binding TLR7. The disclosure also relates to a method of treating inflammation in a subject in need thereof comprising administering to the subject a therapeutically effective amount of an interfering RNA molecule that binds TLR7 and inhibits binding of miRNAs of any of the disclosed SEQ ID NO:10 from binding TLR7. The disclosure also relates to a method of treating inflammation in a subject in need thereof comprising administering to the subject a therapeutically effective amount of an interfering RNA molecule that binds TLR7 and inhibits binding of miRNAs of any of the disclosed SEQ ID NO:12 from binding TLR7. The disclosure also relates to a method of treating inflammation in a subject in need thereof comprising administering to the subject a therapeutically effective amount of an interfering RNA molecule that binds TLR7 and inhibits binding of miRNAs of any of the disclosed SEQ ID NO:12 from binding TLR7. The disclosure also relates to a method of treating inflammation in a subject in need thereof comprising administering to the subject a therapeutically effective amount of an interfering RNA molecule that binds TLR7 and inhibits binding of miRNAs of any of the disclosed SEQ ID NO:13 from binding TLR7. The disclosure also relates to a method of treating inflammation in a subject in need thereof comprising administering to the subject a therapeutically effective amount of an interfering RNA molecule that binds TLR7 and inhibits binding of miRNAs of any of the disclosed SEQ ID NO:14 from binding TLR7. The disclosure also relates to a method of treating inflammation in a subject in need thereof comprising administering to the subject a therapeutically effective amount of an interfering RNA molecule that binds TLR7 and inhibits binding of miRNAs of any of the disclosed SEQ ID NO:15 from binding TLR7. The disclosure also relates to a method of treating inflammation in a subject in need thereof comprising administering to the subject a therapeutically effective amount of an interfering RNA molecule that binds TLR7 and inhibits binding of miRNAs of any of the disclosed SEQ ID NO:16 from binding TLR7. The disclosure also relates to a method of treating inflammation in a subject in need thereof comprising administering to the subject a therapeutically effective amount of an interfering RNA molecule that binds TLR7 and inhibits binding of miRNAs of any of the disclosed SEQ ID NO:17 from binding TLR7. The disclosure also relates to a method of treating inflammation in a subject in need thereof comprising administering to the subject a therapeutically effective amount of an interfering RNA molecule that binds TLR7 and inhibits binding of miRNAs of any of the disclosed SEQ ID NO:18 from binding TLR7. The disclosure also relates to a method of treating inflammation in a subject in need thereof comprising administering to the subject a therapeutically effective amount of an interfering RNA molecule that binds TLR7 and inhibits binding of miRNAs of any of the disclosed SEQ ID NO:19from binding TLR7. The disclosure also relates to a method of treating inflammation in a subject in need thereof comprising administering to the subject a therapeutically effective amount of an interfering RNA molecule that binds TLR7 and inhibits binding of miRNAs of any of the disclosed SEQ ID NO:20 from binding TLR7. The disclosure also relates to a method of treating inflammation in a subject in need thereof comprising administering to the subject a therapeutically effective amount of an interfering RNA molecule that binds TLR7 and inhibits binding of miRNAs of any of the disclosed SEQ ID NO:21 from binding TLR7. The disclosure also relates to a method of treating inflammation in a subject in need thereof comprising administering to the subject a therapeutically effective amount of an interfering RNA molecule that binds TLR7 and inhibits binding of miRNAs of any of the disclosed SEQ ID NO:22 from binding TLR7.

In some embodiments, the therapeutically effective amount of an interfering RNA molecule that binds TLR7 is an interfering RNA and is a variant, or functional fragment of any one or combination of: SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12; SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22. In some embodiments, the cell, composition or pharmaceutical composition comprises at least about 70%, 75%, 80%, 85%, 90%, 91%, 92%, 93%, 94%, 95%, 96%, 97%, 98%, 99%, or 100% sequence identity to any one or combination of: SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12; SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22 but at least one of the uridines is replaced or modified. In some embodiments, the cell, composition or pharmaceutical composition comprises at least about 70%, 75%, 80%, 85%, 90%, 91%, 92%, 93%, 94%, 95%, 96%, 97%, 98%, 99%, or 100% sequence identity to any one or combination of: SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12; SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22 but at least one of the uridines is replaced by an adenine. In some embodiments, the cell, composition or pharmaceutical composition comprises at least about 70%, 75%, 80%, 85%, 90%, 91%, 92%, 93%, 94%, 95%, 96%, 97%, 98%, 99%, or 100% sequence identity to any one or combination of: SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12; SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22 or functional fragment thereof, but at least one of the uridines is replaced or modified and the RNA is incapable of activating a Toll-like Receptor. In some embodiments, the cell, composition or pharmaceutical composition comprises a RNA molecule or DNA/RNA hybrid that comprises at least about 70%, 75%, 80%, 85%, 90%, 91%, 92%, 93%, 94%, 95%, 96%, 97%, 98%, 99%, or 100% sequence identity to any one or combination of: SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12; SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22 or functional fragment thereof, but at least one of the uridines is replaced or modified and the RNA is incapable of activating Toll-like Receptor 7.

Another embodiment is a method for treating or preventing a muscle disease and/or inflammation in a subject in need thereof comprising administering to the subject a therapeutically effective amount of an interfering RNA molecule that inhibits any miRNA of Table 1 from binding a TLR7. In some embodiments, the intefering RNA molecule comprises a variant or modified RNA sequence of Table 1. In some embodiments, the RNA molecule comprises an RNA molecule or DNA/RNA hybrid that comprises at least about 70%, 75%, 80%, 85%, 90%, 91%, 92%, 93%, 94%, 95%, 96%, 97%, 98%, 99%, or 100% sequence identity to any one or combination of: SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12; SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22 or functional fragment thereof.

The interfering RNA molecule can, in some embodiments, have substantial complementarity to only the seed sequence of the target miRNA. In some embodiments, the interfering RNA molecule has perfect complementarity to its target miRNA's seed sequence.

In some embodiments, the interfering RNA molecule comprises or consists of the nucleotide sequence AACACUAC, UACUUUAU, CAGUUCUC, AUUGCACU, GGGCAGUG, GGCAGUGG, GUGGACUG, AUGGACUG, GUGCUGCU, GGCGCCAU, AAACUGAC, CAGUUCUC, or CCAGCUUU, which have perfect complementarity to the miRNA seed sequences found in Table 1. In some embodiments, the interfering RNA molecule comprises the nucleotide sequence:

UCCAUAAAGUAGGAAACACUACA (SEQ ID NO: 23),
AGUAGUGCUUUCUACUUUAUG (SEQ ID NO: 24),
AACCCAUGGAAUUCAGUUCUCA (SEQ ID NO: 25),
GCUUUGACAAUACUAUUGCACUG (SEQ ID NO: 26),
AGCAGCACCUGGGGCAGUGG (SEQ ID NO: 27),
CCAGCAGCACCUGGGCAGUGGG (SEQ ID NO: 28),
GUGUAUAUGCCCGUGGACUGC (SEQ ID NO: 29),
GUGAUAAUGCCCAUGGACUGC (SEQ ID NO: 30),
UACAAACCACAGUGUGCUGCUG (SEQ ID NO: 74),
ACAAACCACAGUGUGCUGCUG (SEQ ID NO: 31),
CACAACCCUAGUGGCGCCAUU (SEQ ID NO: 32),
UGGGGUAUUUGACAAACUGACA (SEQ ID NO: 33),
AGCUAUGGAAUUCAGUUCUCA (SEQ ID NO: 34), or
UCGCCCUCUCAACCCAGCUUUU (SEQ ID NO: 35),
which have perfect complementarity to the miRNA sequences in Table 1.

In some embodiments, the method can further comprise administering to the subject a therapeutically effective amount of an anti-inflammatory corticosteroid. In some embodiments, the anti-inflammatory corticosteroid is cortisone, dexamethasone, hydrocortisone, prednisolone, prednisone, methylprednisolone, aldosterone, fludrocortisone, vamorolone, betamethasone, budesonide, flunisolide, mometasone, ciclesonide, fluticasone, beclomethasone, triamcinolone, desonide, halcinonide, diflorasone, fluocinolone, clobetasol, desoximetasone, prednicarbate, clocorolone, alclometasone, flurandrenolide, amcinonide, halobetasol, or a combination thereof. In some embodiments, the anti-inflammatory corticosteroid is prednisone, vamorolone, or a combination thereof.

Another embodiment is for preventing inflammation in a subject in need thereof comprising administering to the subject a therapeutically effective amount of an interfering RNA molecule that inhibits or reduces the activity of an NF-κB-regulated miRNA. In some embodiments, the NF-κB-regulated miRNA is an miRNA listed in Table 1 above. In some embodiments, the interfering RNA molecule comprises a nucleotide sequence that is substantially complementary to the NF-κB-regulated miRNA. In some embodiments, the interfering RNA molecule is fully complementary to the NF-κB-regulated miRNA.

The interfering RNA molecule can, in some embodiments, have substantial complementarity to only the seed sequence of the target miRNA. In some embodiments, the interfering RNA molecule has perfect complementarity to its target miRNA's seed sequence.

In some embodiments, the interfering RNA molecule comprises the nucleotide sequence AACACUAC, UACUUUAU, CAGUUCUC, AUUGCACU, GGGCAGUG, GGCAGUGG, GUGGACUG, AUGGACUG, GUGCUGCU, GGCGCCAU, AAACUGAC, CAGUUCUC, or CCAGCUUU, which have perfect complementarity to the miRNA seed sequences found in Table 1. In some embodiments, the interfering RNA molecule comprises the nucleotide sequence:
UCCAUAAAGUAGGAAACACUACA (SEQ ID NO: 23),
AGUAGUGCUUUCUACUUUAUG (SEQ ID NO: 24),
AACCCAUGGAAUUCAGUUCUCA (SEQ ID NO: 25),
GCUUUGACAAUACUAUUGCACUG (SEQ ID NO: 26),
AGCAGCACCUGGGGCAGUGG (SEQ ID NO: 27),
CCAGCAGCACCUGGGCAGUGGG (SEQ ID NO: 28),
GUGUAUAUGCCCGUGGACUGC (SEQ ID NO: 29),
GUGAUAAUGCCCAUGGACUGC (SEQ ID NO: 30),
UACAAACCACAGUGUGCUGCUG (SEQ ID NO: 74),
ACAAACCACAGUGUGCUGCUG (SEQ ID NO: 31),
CACAACCCUAGUGGCGCCAUU (SEQ ID NO: 32),
UGGGGUAUUUGACAAACUGACA (SEQ ID NO: 33),
AGCUAUGGAAUUCAGUUCUCA (SEQ ID NO: 34), or
UCGCCCUCUCAACCCAGCUUUU (SEQ ID NO: 35),
which have perfect complementarity to the miRNA sequences in Table 1.

In some embodiments, the method can further comprise administering to the subject a therapeutically effective amount of an anti-inflammatory corticosteroid. In some embodiments, the anti-inflammatory corticosteroid is cortisone, dexamethasone, hydrocortisone, prednisolone, prednisone, methylprednisolone, aldosterone, fludrocortisone, vamorolone, betamethasone, budesonide, flunisolide, mometasone, ciclesonide, fluticasone, beclomethasone, triamcinolone, desonide, halcinonide, diflorasone, fluocinolone, clobetasol, desoximetasone, prednicarbate, clocorolone, alclometasone, flurandrenolide, amcinonide, halobetasol, or a combination thereof. In some embodiments, the anti-inflammatory corticosteroid is prednisone, vamorolone, or a combination thereof.

Another embodiment is for treating a steroid side effect in a subject in need thereof comprising administering to the subject a therapeutically effective amount of (a) an anti-inflammatory corticosteroid and (b) an interfering RNA molecule that inhibits or reduces the activity of a corticosteroid-activated miRNA. In some embodiments, the corticosteroid-activated miRNA is an miRNA listed in Table 2 above. In some embodiments, the interfering RNA molecule comprises a nucleotide sequence that is substantially complementary to the corticosteroid-activated miRNA. In some embodiments, the interfering RNA molecule is fully complementary to the corticosteroid-activated miRNA.

The interfering RNA molecule can, in some embodiments, have substantial complementarity to only the seed sequence of the target miRNA. In some embodiments, the interfering RNA molecule has perfect complementarity to its target miRNA's seed sequence.

In some embodiments, the interfering RNA molecule comprises the nucleotide sequence CCAGUCAC, CCAGCAGG, GCAACAUU, CAUCAUGA, GGACCUUC, AGACCUUC, or CGAAUGUU, which have perfect complementarity to the miRNA seed sequences found in Table 2. In some embodiments, the interfering RNA molecule comprises the nucleotide sequence:
CCCCUCUGGUCAACCAGUCACA (SEQ ID NO: 63),
ACCAGGUUCCACCCCAGCAGGC (SEQ ID NO: 64),
AGGGGUUCACCGAGCAACAUUC (SEQ ID NO: 65),
ACACCGAGGAGCCCAUCAUGAU (SEQ ID NO: 66),
CCUGGCACACAGUAGGACCUUCA (SEQ ID NO: 67),
CCUGGCACACAGUAGACCUUCA (SEQ ID NO: 68), or
AAGAAGUGCACCGCGAAUGUUU (SEQ ID NO: 69), which have perfect complementarity to the miRNA sequences in Table 2. In some embodiments, the interfering RNA molecule comprises a nucleotide sequence having partial or full complementarity to MEG3 (Mm00522599_ml), MEG3 (Hs00292028_ml), MEG8 (Mm01325842_gl), MEG8 (Hs00419701_ml), MEG9 (Mm01335848_ml), or MEG9 (Hs01593046_sl).

In some embodiments, the anti-inflammatory corticosteroid is cortisone, dexamethasone, hydrocortisone, prednisolone, prednisone, methylprednisolone, aldosterone, fludrocortisone, vamorolone, betamethasone, budesonide, flunisolide, mometasone, ciclesonide, fluticasone, beclomethasone, triamcinolone, desonide, halcinonide, diflorasone, fluocinolone, clobetasol, desoximetasone, prednicarbate, clocorolone, alclometasone, flurandrenolide, amcinonide, halobetasol, or a combination thereof. In some embodiments, the anti-inflammatory corticosteroid is prednisone, vamorolone, or a combination thereof.

Another embodiment is for preventing a steroid side effect in a subject in need thereof comprising administering to the subject a therapeutically effective amount of (a) an anti-inflammatory corticosteroid and (b) an interfering RNA molecule that inhibits or reduces the activity of a corticosteroid-activated miRNA. In some embodiments, the corticosteroid-activated miRNA is an miRNA listed in Table 2 above. In some embodiments, the interfering RNA molecule comprises a nucleotide sequence that is substantially complementary to the corticosteroid-activated miRNA. In some embodiments, the interfering RNA molecule is fully complementary to the corticosteroid-activated miRNA.

The interfering RNA molecule can, in some embodiments, have substantial complementarity to only the seed sequence of the target miRNA. In some embodiments, the interfering RNA molecule has perfect complementarity to its target miRNA's seed sequence.

In some embodiments, the interfering RNA molecule comprises the nucleotide sequence CCAGUCAC, CCAGCAGG, GCAACAUU, CAUCAUGA, GGACCUUC, AGACCUUC, or CGAAUGUU, which have perfect complementarity to the miRNA seed sequences found in Table 2. In some embodiments, the interfering RNA molecule comprises the nucleotide sequence:
 CCCCUCUGGUCAACCAGUCACA (SEQ ID NO: 63),
 ACCAGGUUCCACCCCAGCAGGC (SEQ ID NO: 64),
 AGGGGUUCACCGAGCAACAUUC (SEQ ID NO: 65),
 ACACCGAGGAGCCCAUCAUGAU (SEQ ID NO: 66),
 CCUGGCACACAGUAGGACCUUCA (SEQ ID NO: 67),
 CCUGGCACACAGUAGACCUUCA (SEQ ID NO: 68), or
 AAGAAGUGCACCGCGAAUGUUU (SEQ ID NO: 69), which have perfect complementarity to the miRNA sequences in Table 2. In some embodiments, the interfering RNA molecule comprises a nucleotide sequence having partial or full complementarity to MEG3 (Mm00522599 ml), MEG3 (Hs00292028 ml), MEG8 (Mm01325842_gl), MEG8 (Hs00419701_ml), MEG9 (Mm01335848_ml), or MEG9 (Hs01593046 sl).

In some embodiments, the anti-inflammatory corticosteroid is cortisone, dexamethasone, hydrocortisone, prednisolone, prednisone, methylprednisolone, aldosterone, fludrocortisone, vamorolone, betamethasone, budesonide, flunisolide, mometasone, ciclesonide, fluticasone, beclomethasone, triamcinolone, desonide, halcinonide, diflorasone, fluocinolone, clobetasol, desoximetasone, prednicarbate, clocorolone, alclometasone, flurandrenolide, amcinonide, halobetasol, or a combination thereof. In some embodiments, the anti-inflammatory corticosteroid is prednisone, vamorolone, or a combination thereof.

Another embodiment is for treating a muscle disease in a subject in need thereof comprising administering to the subject a therapeutically effective amount of an interfering RNA molecule that inhibits or reduces the activity of a 14q32 mega-cluster miRNA. In some embodiments, the 14q32 mega-cluster miRNA is an miRNA listed in Tables 3 and 4 above. In some embodiments, the interfering RNA molecule comprises a nucleotide sequence that is substantially complementary to the 14q32 mega-cluster miRNA. In some embodiments, the interfering RNA molecule is fully complementary to the 14q32 mega-cluster miRNA.

The interfering RNA molecule can, in some embodiments, have substantial complementarity to only the seed sequence of the target miRNA. In some embodiments, the interfering RNA molecule has perfect complementarity to its target miRNA's seed sequence.

In some embodiments, the interfering RNA molecule comprises the nucleotide sequence CCAGUCAC, CCAGCAGG, GCAACAUU, CAUCAUGA, GGACCUUC, AGACCUUC, or CGAAUGUU, which have perfect complementarity to the miRNA seed sequences found in Table 3. In some embodiments, the interfering RNA molecule comprises the nucleotide sequence:
 CCCCUCUGGUCAACCAGUCACA (SEQ ID NO: 63),
 ACCAGGUUCCACCCCAGCAGGC (SEQ ID NO: 64),
 AGGGGUUCACCGAGCAACAUUC (SEQ ID NO: 65),
 ACACCGAGGAGCCCAUCAUGAU (SEQ ID NO: 66),
 CCUGGCACACAGUAGGACCUUCA (SEQ ID NO: 67)
 CCUGGCACACAGUAGACCUUCA (SEQ ID NO: 68), or
 AAGAAGUGCACCGCGAAUGUUU (SEQ ID NO: 69), which have perfect complementarity to the miRNA sequences in Table 3. In some embodiments, the interfering RNA molecule comprises a nucleotide sequence having partial or full complementarity to an miRNA listed in Table 4.

In some embodiments, the method can further comprise administering to the subject a therapeutically effective amount of an anti-inflammatory corticosteroid. In some embodiments, the anti-inflammatory corticosteroid is cortisone, dexamethasone, hydrocortisone, prednisolone, prednisone, methylprednisolone, aldosterone, fludrocortisone, vamorolone, betamethasone, budesonide, flunisolide, mometasone, ciclesonide, fluticasone, beclomethasone, triamcinolone, desonide, halcinonide, diflorasone, fluocinolone, clobetasol, desoximetasone, prednicarbate, clocorolone, alclometasone, flurandrenolide, amcinonide, halobetasol, or a combination thereof. In some embodiments, the anti-inflammatory corticosteroid is prednisone, vamorolone, or a combination thereof.

Another embodiment is for preventing a muscle disease in a subject in need thereof comprising administering to the subject a therapeutically effective amount of an interfering RNA molecule that inhibits or reduces the activity of a 14q32 mega-cluster miRNA. In some embodiments, the 14q32 mega-cluster miRNA is an miRNA listed in Tables 3 and 4 above. In some embodiments, the interfering RNA molecule comprises a nucleotide sequence that is substantially complementary to the 14q32 mega-cluster miRNA. In some embodiments, the interfering RNA molecule is fully complementary to the 14q32 mega-cluster miRNA.

The interfering RNA molecule can, in some embodiments, have substantial complementarity to only the seed sequence of the target miRNA. In some embodiments, the interfering RNA molecule has perfect complementarity to its target miRNA's seed sequence.

In some embodiments, the interfering RNA molecule comprises the nucleotide sequence CCAGUCAC, CCAGCAGG, GCAACAUU, CAUCAUGA, GGACCUUC, AGACCUUC, or CGAAUGUU, which have perfect complementarity to the miRNA seed sequences found in Table 3. In some embodiments, the interfering RNA molecule comprises the nucleotide sequence:

CCCCUCUGGUCAACCAGUCACA (SEQ ID NO: 63),
ACCAGGUUCCACCCCAGCAGGC (SEQ ID NO: 64),
AGGGGUUCACCGAGCAACAUUC (SEQ ID NO: 65),
ACACCGAGGAGCCCAUCAUGAU (SEQ ID NO: 66),
CCUGGCACACAGUAGGACCUUCA (SEQ ID NO: 67),
CCUGGCACACAGUAGACCUUCA (SEQ ID NO: 68), or
AAGAAGUGCACCGCGAAUGUUU (SEO ID NO: 69), which have perfect complementarity to the miRNA sequences in Table 3. In some embodiments, the interfering RNA molecule comprises a nucleotide sequence having partial or full complementarity to an miRNA listed in Table 4.

In some embodiments, the method can further comprise administering to the subject a therapeutically effective amount of an anti-inflammatory corticosteroid. In some embodiments, the anti-inflammatory corticosteroid is cortisone, dexamethasone, hydrocortisone, prednisolone, prednisone, methylprednisolone, aldosterone, fludrocortisone, vamorolone, betamethasone, budesonide, flunisolide, mometasone, ciclesonide, fluticasone, beclomethasone, triamcinolone, desonide, halcinonide, diflorasone, fluocinolone, clobetasol, desoximetasone, prednicarbate, clocorolone, alclometasone, flurandrenolide, amcinonide, halobetasol, or a combination thereof. In some embodiments, the anti-inflammatory corticosteroid is prednisone, vamorolone, or a combination thereof.

Kits

In some embodiments, kits in accordance with the present disclosure may be used to treat or prevent development of a cancer in a subject. In some embodiments, the kits comprise a container comprising one or a plurality of pharmaceutical compositions comprising the nucleic acids, compositions described herein and, optionally, a device used to administer the one or more pharmaceutical compositions. Any nucleic acid, composition, or component thereof disclosed may be arranged in a kit either individually or in combination with any other nucleic acid, composition, or component thereof. The disclosure provides a kit to perform any of the methods described herein. In some embodiments, the kit comprises at least one container comprising a therapeutically effective amount of one or a plurality of oligonucleotides comprising an aptamer domain capable of targeting an apatemer targeting domain on a cell of a subject. In some embodiments, the kit comprises at least one container comprising any of the polypeptides or functional fragments described herein. In some embodiments, the polypeptides are in solution (such as a buffer with adequate pH and/or other necessary additive to minimize degradation of the polypeptides during prolonged storage). In some embodiments, the polypeptides or oligonucleotides are lyophilized for the purposes of resuspension after prolonged storage. In some embodiments, the kit comprises: at least one container comprising one or a plurality of polypeptides comprising or functional fragments disclosed herein and/or oligonucleotides disclosed herein. In some embodiments, the kit optionally comprises instructions to perform any or all steps of any method described herein.

The kit may contain two or more containers, packs, or dispensers together with instructions for preparation of an array. In some embodiments, the kit comprises at least one container comprising the oligonucleotides described herein and a second container comprising a means for maintenance, use, and/or storage of the oligonucleotides such as storage buffer. In some embodiments, the kit comprises a composition comprising any polypeptide disclosed herein in solution or lyophilized or dried and accompanied by a rehydration mixture. In some embodiments, the polypeptides and rehydration mixture may be in one or more additional containers.

The compositions included in the kit may be supplied in containers of any sort such that the shelf-life of the different components are preserved, and are not adsorbed or altered by the materials of the container. For example, suitable containers include simple bottles that may be fabricated from glass, organic polymers, such as polycarbonate, polystyrene, polypropylene, polyethylene, ceramic, metal or any other material typically employed to hold reagents or food; envelopes, that may consist of foil-lined interiors, such as aluminum or an alloy. Other containers include test tubes, vials, flasks, and syringes. The containers may have two compartments that are separated by a readily removable membrane that upon removal permits the components of the compositions to mix. Removable membranes may be glass, plastic, rubber, or other inert material.

Kits may also be supplied with instructional materials. Instructions may be printed on paper or other substrates, and/or may be supplied as an electronic-readable medium, such as a floppy disc, CD-ROM, DVD-ROM, zip disc, videotape, audio tape, or other readable memory storage device. Detailed instructions may not be physically associated with the kit; instead, a user may be directed to an internet web site specified by the manufacturer or distributor of the kit, or supplied as electronic mail.

The disclosure also provides a kit comprising: a nucleic acid sequence disclosed herein; and a vector comprising one or plurality of nucleic acid sequences disclosed herein and a syringe and/or needle. In some embodiments, the kit further comprises at least one of the following: one or a plurality of eukaryotic cells comprising regulatory protein capable of trans-activation of the regulatory element, cell growth media, a volume of fluorescent stain or dye, and a set of instructions, optionally accessible remotely through an electronic medium.

Any and all journal articles, patent applications, issued patents, or other cited references disclosed herein are incorporated by reference in their respective entireties.

EXAMPLES

Example 1. Methods

The Examples described herein were carried out with, but not limited to, the following methods.

Animal Care

All mouse studies were performed in adherence to the NIH Guide for the Care and Use of Laboratory Animals. All experiments were conducted according to protocols that were within the guidelines and approval of the Institutional Animal Care and Use Committee of Children's National Medical Center. All mdx (C57BL/10ScSn-Dmd<mdx>/J) and wild type control (C57BL/10ScSnJ) mice were obtained from The Jackson Laboratory (Bar Harbor, Me.).

Drug Dosing and Mouse Muscle Samples

Archival muscle samples (diaphragm) from two separate preclinical studies were obtained, with each trial showing a significant benefit from both prednisolone and vamorolone drug treatments (23). Prednisolone was used because it is the active form of prednisone, the current DMD standard of care. The first, "discovery set" of diaphragm muscles was from a prophylactic trial design where 2-week old (postnatal day 15) mdx or wild type control mice received oral dosing for 6 weeks with vehicle (cherry syrup), prednisolone (5 mg/kg), or vamorolone (15 mg/kg) as previously reported (23). The second, "validation set" of diaphragm muscles was from an extended trial in older mice where mdx or wild type mice were subjected to treadmill running to unmask mild phenotypes. Mice in this validation set were treated with either vehicle, prednisolone (5 mg/kg) or vamorolone (45 mg/kg) for four months beginning at two months of age (23). At the endpoint of each trial, diaphragm muscles were harvested and frozen in liquid nitrogen-cooled isopentane.

TaqMan miRNA Low-Density Arrays

We extracted total RNA from 5 diaphragm muscles per treatment group in the discovery set of samples from 8-week old mice. RNA was extracted using a modified TRIzol protocol with isopropanol precipitation at −20° C. overnight. This RNA was reverse transcribed to cDNA using a High Capacity cDNA Reverse Transcription Kit with RNase Inhibitor (ThermoFisher; Carlsbad, Calif.), with miRNA-specific Megaplex RT Primers, Rodent Pools Set version 3.0 (ThermoFisher; Carlsbad, Calif.). Levels of each of the miRNAs were profiled in the discovery set using TAQMAN Array Rodent miRNA A+B Cards Set v3.0 (ThermoFisher; Carlsbad, Calif.).

qRT-PCR of Individual miRNAs

Specific miRNAs were quantified in the validation set of samples using individual TaqMan assays specific for each miRNA (ThermoFisher; Carlsbad, Calif.) according to the manufacturer's protocol. Assay IDs used include 000468, 001346, 002455, 001280, 000528, 002352, 000464, 002509, and 002248. Total RNA was converted to cDNA using multiplexed RT primers and High Capacity cDNA Reverse Transcription Kit (ThermoFisher; Carlsbad, Calif.). The cDNA was pre-amplified using TaqMan PreAmp Master Mix (ThermoFisher; Carlsbad, Calif.). The miRNAs were then quantified using individual TaqMan assays on an ABI QuantStudio 7 real time PCR machine (Applied Biosystems; Foster City, Calif.).

Statistical Analysis of miRNA Expression

In the discovery set experiments, levels of each miRNA were quantified in TaqMan low-density arrays using ThermoFisher Cloud software with the Relative Quantification Application (ThermoFisher; Carlsbad, Calif.) tool. Data was analyzed by ANOVA with post-hoc comparison of each group to the mdx vehicle-treated group. To identify focus miRNAs for study relating to drug efficacy, we selected all miRNAs that showed a significant difference for all three groups (WT, prednisolone, and vamorolone) compared to mdx vehicle. A P-value of $P \leq 0.05$ was set as the significance threshold, without adjustment for multiple comparisons. To reduce false-positive discovery in this setting, an evidence-based approach was used to identify efficacy associated miRNAs where 1) results from the multiple groups were cross-referenced, and 2) all candidate miRNAs identified in this discovery set were then assayed in a separate validation set of mice. For the validation set experiments, levels of each individual miRNA were assayed in samples from a second, independent preclinical trial in adult mdx mice. Data from individual TaqMan Assays was quantified using QuantStudio Real-Time PCR version 1.3 software (Applied Biosystems; Foster City, Calif.). The levels of all miRNAs were normalized to the geometric mean of multiple control genes (60, 70). Comparison of groups was made by ANOVA with Holm-Sidak post-hoc test comparing each group to mdx vehicle.

Bioinformatics

We examined the regulation of each miRNA gene promoter to gain insight into the mechanisms of response to treatment. This was done by examining promoter binding by the inflammatory transcription factor nuclear factor-kappa B (NF-κB, or RELA) or by the glucocorticoid receptor (GR, or NR3C1) using chromatin immunoprecipitation sequencing (ChIP-seq) data. For both NF-κB and the GR, ChIP-seq data from the Encyclopedia of DNA Elements (ENCODE) was queried for physical binding to DNA loci encoding the human homologue of each miRNA target of interest (29, 41). In addition, the following histone modifications were examined, which are enriched at regulatory elements such as promoters or enhancers: histone H3K4 trimethylation (found near promoters), H3K4 monomethylation (found near regulatory elements), and H3K27 acetylation (found near active regulatory elements). For each of these analyses, UC Santa Cruz (UCSC) Genome Browser Release 4 (at genome.ucsc.edu/index.html) was used, with alignment to the GRCh37/hg19 genome build. Each ChIP-seq dataset was analyzed using the ENCODE Regulation Super-Track listed under the Regulation menu. Binding by NF-κB or GR was assayed using the Txn Factor ChIP Track. In regions bound by each transcription factor, DNA motifs recognized by that transcription factor were identified through the Factorbook repository within this track. Consensus motif sequence logo pictograms for each transcription factor were also visualized through Factorbook. Histone modifications were examined using the Layered H3K4Me1, Layered H3K4Me3, and Layered H2K27Ac Tracks. Raw data images for visualization of gene loci and ChIP-seq data were obtained using the PDF/PS function in the View menu of the genome browser.

Binding by NF-κB was queried in ChIP-seq datasets produced using TNF-induced lymphocyte cell lines (GM10847, GM12878, GM12891, GM12892, GM15510, GM18505, GM18526, GM18951, GM19099, and GM19193) with ChIP-seq performed using an antibody to an NF-κB subunit (RELA). For the GR, ChIP-seq datasets produced using dexamethasone-treated lung epithelial (A549) and endometrial (ECC-1) cell lines were queried with ChIP-seq performed using an antibody to the GR (NR3C1). Histone modifications were queried in ChIP-seq datasets produced using lymphoblast (GM12878), stem (H1-hESC), myoblast (HSMM), endothelial (HUVEC), lymphoblast (K562), keratinocyte (NHEK), and lung fibroblast (NHLF) cell lines using antibodies specific to each histone modification.

To visualize behavior of miRNAs within individual mice for each group, heat map images were generated. Heat maps were generated using Rq values of TLDA array data exported from the Relative Quantification Application of the ThermoFisher Cloud software (ThermoFisher; Carlsbad, Calif.) tool. Heat maps of miRNA expression were produced using Hierarchical Clustering Explorer Version 3.5 (at www.cs.umd.edu/hcil/multi-cluster/) produced by the Human Computer Interaction Laboratory (University of Maryland; College Park, Md.).

Example 2. Discovery of miRNAome Responses to Muscular Dystrophy Disease and Treatment To examine miRNA expression TaqMan low density qPCR array cards were used to profile approximately 750 miRNAs within diaphragm muscle from a discovery set of mice. Samples for this experiment came from a trial that utilized a prophylactic approach (23). Briefly, mdx mice undergo a stage of peak severity characterized by wide-spread inflammation and necrosis from approximately 3-8 weeks of age, followed by a recovery stage where mice show milder phenotypes (25). For this prophylactic preclinical trial, treatments were initiated in mice at P15 in order to treat before and during the stage of peak severity. The discovery set of samples consisted of diaphragm from 8-week old untreated wild type (vehicle), untreated mdx (vehicle), prednisolone-treated mdx (5 mg/kg), and vamorolone-treated mdx (15 mg/kg) mice. Prednisolone was used here because it is the active form of prednisone, the current DMD standard of care. Diaphragm was examined because respiratory function is important for DMD outcomes, because it is a severely affected muscle in mdx which is more comparable to DMD (65), and because diaphragm muscles are more evenly stressed between mice than purely voluntary muscles of the leg. Previously, in these same mice, it was found that both prednisolone and vamorolone successfully improved grip strength, muscle pathology, and diaphragm inflammation (23). Additionally, it was found in these same mice that prednisolone caused traditional steroid side effects of stunted growth, immunosuppression, and bone loss, while the dissociative steroid vamorolone successfully avoided these side effects. Here, using TLDA qPCR array cards approximately 500 miRNAs expressed in the diaphragm muscle from all groups were detected.

It was found that expression levels of 202 miRNAs showed a significant difference in at least one of the groups compared to the untreated mdx group (Table 5). Comparing untreated mdx to WT mice, expression levels of 136 miRNAs were significantly different in dystrophic muscle. Treatment of mdx mice with the glucocorticoid prednisolone caused a significant change in 76 miRNAs in dystrophic muscle. In contrast, treatment with the dissociative steroid vamorolone only affected about half as many miRNAs, with expression of 41 miRNAs changed in mdx muscle.

TABLE 5

| Group | miRNA Assay Name and ID | Rq | P-Value |
|---|---|---|---|
| WT | hsa-let-7i#-002172 | 1.506 | 0.05 |
| WT | hsa-miR-140-3p-002234 | 1.103 | 0.7 |
| WT | hsa-miR-143-000466 | 2.571 | 0.04 |
| WT | hsa-miR-154#-000478 | 0.288 | 0.03 |
| WT | hsa-miR-190b-002263 | 0.834 | 0.8 |
| WT | hsa-miR-200c-000505 | 2.299 | 0.4 |
| WT | hsa-miR-206-000510 | 0.345 | 0.04 |
| WT | hsa-miR-213-000516 | 1.862 | 0.08 |
| WT | hsa-miR-214#-002293 | 0.377 | 0.001 |
| WT | hsa-miR-214-000517 | 0.466 | 0.02 |
| WT | hsa-miR-22#-002301 | 1.586 | 0.03 |
| WT | hsa-miR-30e-3p-000422 | 2.21 | 0.02 |
| WT | hsa-miR-376a#-001287 | 0.374 | 0.002 |
| WT | hsa-miR-455-001280 | 0.609 | 0.003 |
| WT | hsa-miR-744#-002325 | 1.389 | 0.1 |
| WT | mmu-let-7a-000377 | 0.877 | 0.2 |
| WT | mmu-let-7b-000378 | 0.864 | 0.1 |
| WT | mmu-let-7c-000379 | 0.903 | 0.3 |
| WT | mmu-let-7c-1#-002479 | 1.738 | 0.04 |
| WT | mmu-let-7d#-001178 | 2.466 | 0.03 |
| WT | mmu-let-7d-002283 | 1.157 | 0.1 |
| WT | mmu-let-7e-002406 | 1.042 | 0.7 |
| WT | mmu-let-7i-002221 | 0.858 | 0.02 |
| WT | mmu-miR-100-000437 | 0.959 | 0.7 |
| WT | mmu-miR-1-002222 | 1.597 | 0.04 |
| WT | mmu-miR-103-000439 | 1.06 | 0.6 |
| WT | mmu-miR-122-002245 | 0.589 | 0.7 |
| WT | mmu-miR-125a-3p-002199 | 0.903 | 0.3 |
| WT | mmu-miR-125b#-002508 | 1.114 | 0.7 |
| WT | mmu-miR-125b-3p-002378 | 0.732 | 0.1 |
| WT | mmu-miR-125b-5p-000449 | 0.903 | 0.2 |
| WT | mmu-miR-126-3p-002228 | 1.166 | 0.3 |
| WT | mmu-miR-126-5p-000451 | 1.178 | 0.2 |

TABLE 5-continued

| Group | miRNA Assay Name and ID | Rq | P-Value |
|---|---|---|---|
| WT | mmu-miR-127-000452 | 0.29 | 0 |
| WT | mmu-miR-1274a-121150_mat | 1.693 | 0.04 |
| WT | mmu-miR-128a-002216 | 0.543 | 0 |
| WT | mmu-miR-130a-000454 | 0.781 | 0.01 |
| WT | mmu-miR-130b#-002460 | 0.201 | 0.02 |
| WT | mmu-miR-130b-000456 | 0.618 | 0.02 |
| WT | mmu-miR-133a-002246 | 1.791 | 0.002 |
| WT | mmu-miR-134-001186 | 0.445 | 0.001 |
| WT | mmu-miR-136-002511 | 0.674 | 0.003 |
| WT | mmu-miR-138#-002554 | 0.386 | 0.02 |
| WT | mmu-miR-140-001187 | 0.83 | 0.06 |
| WT | mmu-miR-142-3p-000464 | 0.466 | 0.01 |
| WT | mmu-miR-142-5p-002248 | 0.404 | 0.008 |
| WT | mmu-miR-143-002249 | 1.423 | 0.04 |
| WT | mmu-miR-145-002278 | 1.384 | 0.3 |
| WT | mmu-miR-146a-000468 | 0.563 | 0.001 |
| WT | mmu-miR-146b#-002453 | 0.278 | 0.04 |
| WT | mmu-miR-146b-001097 | 0.844 | 0.3 |
| WT | mmu-miR-148a-000470 | 0.745 | 0.4 |
| WT | mmu-miR-148b-000471 | 0.793 | 0.3 |
| WT | mmu-miR-150#-002570 | 0.821 | 0.8 |
| WT | mmu-miR-150-000473 | 1.514 | 0.05 |
| WT | mmu-miR-151-3p-001190 | 1.232 | 0.01 |
| WT | mmu-miR-152-000475 | 0.89 | 0.2 |
| WT | mmu-miR-154-000477 | 0.03 | 0.002 |
| WT | mmu-miR-155-002571 | 1.021 | 0.7 |
| WT | mmu-miR-15a-000389 | 1.11 | 0.5 |
| WT | mmu-miR-16-000391 | 1.248 | 0.08 |
| WT | mmu-miR-181a-000480 | 0.807 | 0.07 |
| WT | mmu-miR-181c-000482 | 0.908 | 0.5 |
| WT | mmu-miR-185-002271 | 1.544 | 0.009 |
| WT | mmu-miR-186-002285 | 1.359 | 0.08 |
| WT | mmu-miR-18a-002422 | 0.468 | 0.007 |
| WT | mmu-miR-191-002299 | 0.948 | 0.5 |
| WT | mmu-miR-193#-002577 | 0.89 | 0.7 |
| WT | mmu-miR-1941-3p-121130_mat | 1.481 | 0.4 |
| WT | mmu-miR-1943-121174_mat | 2.392 | 0.04 |
| WT | mmu-miR-1944-121189_mat | 0.535 | 0.03 |
| WT | mmu-miR-195-000494 | 0.944 | 0.5 |
| WT | mmu-miR-199a-3p-002304 | 0.498 | 0.001 |
| WT | mmu-miR-199b-001131 | 0.481 | 0.05 |
| WT | mmu-miR-19a-000395 | 0.677 | 0.02 |
| WT | mmu-miR-200c-002300 | 1.886 | 0.4 |
| WT | mmu-miR-203-000507 | 2.584 | 0.3 |
| WT | mmu-miR-204-000508 | 1.592 | 0.02 |
| WT | mmu-miR-20a#-002491 | 0.668 | 0.02 |
| WT | mmu-miR-21#-002493 | 0.5 | 0.05 |
| WT | mmu-miR-210-000512 | 1.233 | 0.4 |
| WT | mmu-miR-21-000397 | 0.242 | 0 |
| WT | mmu-miR-214-002306 | 0.432 | 0.001 |
| WT | mmu-miR-2146-241082_mat | 1.127 | 0.8 |
| WT | mmu-miR-215-001200 | 2.333 | 0.3 |
| WT | mmu-miR-218-000521 | 0.883 | 0.4 |
| WT | mmu-miR-221-000524 | 0.402 | 0.002 |
| WT | mmu-miR-222-002276 | 0.532 | 0.002 |
| WT | mmu-miR-223-002295 | 0.468 | 0 |
| WT | mmu-miR-23b-000400 | 0.893 | 0.5 |
| WT | mmu-miR-25-000403 | 1.033 | 0.8 |
| WT | mmu-miR-26a-000405 | 1.116 | 0.2 |
| WT | mmu-miR-27b-000409 | 0.784 | 0.02 |
| WT | mmu-miR-28-000411 | 1.017 | 0.9 |
| WT | mmu-miR-296-5p-000527 | 0.458 | 0.001 |
| WT | mmu-miR-301a-000528 | 0.799 | 0.05 |
| WT | mmu-miR-301b-002600 | 0.972 | 0.7 |
| WT | mmu-miR-30a-000417 | 1.397 | 0.009 |
| WT | mmu-miR-30b-000602 | 1.541 | 0.004 |
| WT | mmu-miR-30c-000419 | 1.58 | 0.002 |
| WT | mmu-miR-30d-000420 | 1.215 | 0.1 |
| WT | mmu-miR-30e-002223 | 1.365 | 0.009 |
| WT | mmu-miR-31#-002495 | 0.21 | 0.01 |
| WT | mmu-miR-31-000185 | 0.206 | 0.006 |
| WT | mmu-miR-322-001076 | 0.897 | 0.4 |
| WT | mmu-miR-324-3p-002509 | 0.742 | 0.05 |
| WT | mmu-miR-324-5p-000539 | 0.702 | 0.03 |
| WT | mmu-miR-328-000543 | 1.278 | 0.009 |
| WT | mmu-miR-335-3p-002185 | 0.383 | 0 |
| WT | mmu-miR-335-5p-000546 | 0.379 | 0.001 |

TABLE 5-continued

| Group | miRNA Assay Name and ID | Rq | P-Value |
|---|---|---|---|
| WT | mmu-miR-337-3p-002532 | 0.596 | 0 |
| WT | mmu-miR-338-3p-002252 | 1.81 | 0.2 |
| WT | mmu-miR-339-5p-002257 | 0.72 | 0.01 |
| WT | mmu-miR-340-3p-002259 | 1.129 | 0.3 |
| WT | mmu-miR-340-5p-002258 | 0.847 | 0.2 |
| WT | mmu-miR-342-3p-002260 | 0.512 | 0.01 |
| WT | mmu-miR-342-5p-002527 | 0.745 | 0.1 |
| WT | mmu-miR-345-5p-002528 | 1.351 | 0.03 |
| WT | mmu-miR-34a-000426 | 0.617 | 0.007 |
| WT | mmu-miR-34b-3p-002618 | 0.129 | 0 |
| WT | mmu-miR-34c#-002584 | 0.228 | 0.007 |
| WT | mmu-miR-34c-000428 | 0.061 | 0.004 |
| WT | mmu-miR-350-002530 | 0.685 | 0.01 |
| WT | mmu-miR-362-3p-002616 | 0.405 | 0 |
| WT | mmu-miR-362-5p-002614 | 0.272 | 0 |
| WT | mmu-miR-369-3p-000557 | 0.514 | 0.03 |
| WT | mmu-miR-369-5p-001021 | 0.431 | 0.02 |
| WT | mmu-miR-370-002275 | 0.331 | 0.002 |
| WT | mmu-miR-376a#-002482 | 0.599 | 0.04 |
| WT | mmu-miR-376a-001069 | 0.323 | 0 |
| WT | mmu-miR-376b#-002451 | 0.31 | 0.008 |
| WT | mmu-miR-376b-002452 | 0.412 | 0.003 |
| WT | mmu-miR-376c-002450 | 0.564 | 0.007 |
| WT | mmu-miR-379-001138 | 0.407 | 0 |
| WT | mmu-miR-380-5p-002601 | 0.588 | 0.01 |
| WT | mmu-miR-381-000571 | 0.199 | 0.001 |
| WT | mmu-miR-382-000572 | 0.597 | 0.002 |
| WT | mmu-miR-383-001767 | 1.509 | 0.4 |
| WT | mmu-miR-384-5p-002602 | 3.02 | 0.04 |
| WT | mmu-miR-409-3p-002332 | 0.343 | 0.001 |
| WT | mmu-miR-410-001274 | 0.382 | 0.02 |
| WT | mmu-miR-411-001610 | 0.441 | 0 |
| WT | mmu-miR-431-001979 | 0.075 | 0 |
| WT | mmu-miR-433-001028 | 0.198 | 0 |
| WT | mmu-miR-434-5p-002581 | 0.367 | 0 |
| WT | mmu-miR-450a-5p-002303 | 0.743 | 0.05 |
| WT | mmu-miR-455-002455 | 0.621 | 0.03 |
| WT | mmu-miR-467a-002587 | 0.706 | 0.02 |
| WT | mmu-miR-467c-002517 | 0.63 | 0.03 |
| WT | mmu-miR-467F-002886 | 1.473 | 0.3 |
| WT | mmu-miR-483#-002560 | 0.044 | 0.01 |
| WT | mmu-miR-486-001278 | 1.526 | 0.05 |
| WT | mmu-miR-487b-001285 | 0.369 | 0 |
| WT | mmu-miR-489-001302 | 0.683 | 0.04 |
| WT | mmu-miR-491-001630 | 1.332 | 0.03 |
| WT | mmu-miR-493-002519 | 0.141 | 0.006 |
| WT | mmu-miR-494-002365 | 0.644 | 0.02 |
| WT | mmu-miR-495-001663 | 0.399 | 0.001 |
| WT | mmu-miR-497-001346 | 0.724 | 0.02 |
| WT | mmu-miR-500-002606 | 0.295 | 0.001 |
| WT | mmu-miR-501-3p-001651 | 0.066 | 0.004 |
| WT | mmu-miR-503-002456 | 0.339 | 0.002 |
| WT | mmu-miR-511-002549 | 0.391 | 0.07 |
| WT | mmu-miR-532-3p-002355 | 0.425 | 0 |
| WT | mmu-miR-532-5p-001518 | 0.393 | 0 |
| WT | mmu-miR-540-3p-001310 | 0.078 | 0.003 |
| WT | mmu-miR-541-002562 | 0.222 | 0.001 |
| WT | mmu-miR-542-3p-001284 | 0.351 | 0 |
| WT | mmu-miR-542-5p-002563 | 0.541 | 0.03 |
| WT | mmu-miR-543-001298 | 0.18 | 0.003 |
| WT | mmu-miR-543-002376 | 0.281 | 0.001 |
| WT | mmu-miR-544-002550 | 0.528 | 0.001 |
| WT | mmu-miR-574-3p-002349 | 0.79 | 0.2 |
| WT | mmu-miR-652-002352 | 0.654 | 0.05 |
| WT | mmu-miR-665-002607 | 0.08 | 0.006 |
| WT | mmu-miR-669a-001683 | 0.796 | 0.2 |
| WT | mmu-miR-673-001954 | 0.492 | 0.1 |
| WT | mmu-miR-673-3p-002449 | 0.437 | 0.01 |
| WT | mmu-miR-674#-001956 | 0.516 | 0 |
| WT | mmu-miR-674-002021 | 0.537 | 0.008 |
| WT | mmu-miR-675-3p-001941 | 0.512 | 0.002 |
| WT | mmu-miR-682-001666 | 1.16 | 0.7 |
| WT | mmu-miR-690-001677 | 0.949 | 0.7 |
| WT | mmu-miR-706-001641 | 0.98 | 0.9 |
| WT | mmu-miR-708-002341 | 1.461 | 0.2 |
| WT | mmu-miR-720-001629 | 1.801 | 0.009 |
| WT | mmu-miR-802-002029 | 0.683 | 0.8 |
| WT | mmu-miR-805-002045 | 2.341 | 0.03 |
| WT | mmu-miR-99b-000436 | 0.781 | 0.03 |
| WT | rno-miR-1-002064 | 1.703 | 0.03 |
| WT | rno-miR-204#-002076 | 2.201 | 0.009 |
| WT | rno-miR-20b-001326 | 1.231 | 0.4 |
| WT | rno-miR-224-000599 | 0.618 | 0.05 |
| WT | rno-miR-29c#-001818 | 3.365 | 0.008 |
| WT | rno-miR-345-3p-002061 | 1.32 | 0.009 |
| WT | rno-miR-351-002063 | 0.362 | 0 |
| WT | rno-miR-379#-002081 | 0.205 | 0 |
| WT | rno-miR-381-001322 | 0.411 | 0 |
| WT | rno-miR-489-001353 | 1.008 | 1 |
| WT | rno-miR-664-001323 | 1.692 | 0.03 |
| WT | rno-miR-7#-001338 | 1.822 | 0.009 |
| WT | rno-miR-7a#-002062 | 2.232 | 0.02 |

| Group | miRNA Assay Name and ID | Rq | P-Value |
|---|---|---|---|
| mdx | hsa-let-7i#-002172 | 1 | 1 |
| mdx | hsa-miR-140-3p-002234 | 1 | 1 |
| mdx | hsa-miR-143-000466 | 1 | 1 |
| mdx | hsa-miR-154#-000478 | 1 | 1 |
| mdx | hsa-miR-190b-002263 | 1 | 1 |
| mdx | hsa-miR-200c-000505 | 1 | 1 |
| mdx | hsa-miR-206-000510 | 1 | 1 |
| mdx | hsa-miR-213-000516 | 1 | 1 |
| mdx | hsa-miR-214#-002293 | 1 | 1 |
| mdx | hsa-miR-214-000517 | 1 | 1 |
| mdx | hsa-miR-22#-002301 | 1 | 1 |
| mdx | hsa-miR-30e-3p-000422 | 1 | 1 |
| mdx | hsa-miR-376a#-001287 | 1 | 1 |
| mdx | hsa-miR-455-001280 | 1 | 1 |
| mdx | hsa-miR-744#-002325 | 1 | 1 |
| mdx | mmu-let-7a-000377 | 1 | 1 |
| mdx | mmu-let-7b-000378 | 1 | 1 |
| mdx | mmu-let-7c-000379 | 1 | 1 |
| mdx | mmu-let-7c-1#-002479 | 1 | 1 |
| mdx | mmu-let-7d#-001178 | 1 | 1 |
| mdx | mmu-let-7d-002283 | 1 | 1 |
| mdx | mmu-let-7e-002406 | 1 | 1 |
| mdx | mmu-let-7i-002221 | 1 | 1 |
| mdx | mmu-miR-100-000437 | 1 | 1 |
| mdx | mmu-miR-1-002222 | 1 | 1 |
| mdx | mmu-miR-103-000439 | 1 | 1 |
| mdx | mmu-miR-122-002245 | 1 | 1 |
| mdx | mmu-miR-125a-3p-002199 | 1 | 1 |
| mdx | mmu-miR-125b#-002508 | 1 | 1 |
| mdx | mmu-miR-125b-3p-002378 | 1 | 1 |
| mdx | mmu-miR-125b-5p-000449 | 1 | 1 |
| mdx | mmu-miR-126-3p-002228 | 1 | 1 |
| mdx | mmu-miR-126-5p-000451 | 1 | 1 |
| mdx | mmu-miR-127-000452 | 1 | 1 |
| mdx | mmu-miR-1274a-121150_mat | 1 | 1 |
| mdx | mmu-miR-128a-002216 | 1 | 1 |
| mdx | mmu-miR-130a-000454 | 1 | 1 |
| mdx | mmu-miR-130b#-002460 | 1 | 1 |
| mdx | mmu-miR-130b-000456 | 1 | 1 |
| mdx | mmu-miR-133a-002246 | 1 | 1 |
| mdx | mmu-miR-134-001186 | 1 | 1 |
| mdx | mmu-miR-136-002511 | 1 | 1 |
| mdx | mmu-miR-138#-002554 | 1 | 1 |
| mdx | mmu-miR-140-001187 | 1 | 1 |
| mdx | mmu-miR-142-3p-000464 | 1 | 1 |
| mdx | mmu-miR-142-5p-002248 | 1 | 1 |
| mdx | mmu-miR-143-002249 | 1 | 1 |
| mdx | mmu-miR-145-002278 | 1 | 1 |
| mdx | mmu-miR-146a-000468 | 1 | 1 |
| mdx | mmu-miR-146b#-002453 | 1 | 1 |
| mdx | mmu-miR-146b-001097 | 1 | 1 |
| mdx | mmu-miR-148a-000470 | 1 | 1 |
| mdx | mmu-miR-148b-000471 | 1 | 1 |
| mdx | mmu-miR-150#-002570 | 1 | 1 |
| mdx | mmu-miR-150-000473 | 1 | 1 |
| mdx | mmu-miR-151-3p-001190 | 1 | 1 |
| mdx | mmu-miR-152-000475 | 1 | 1 |

| Group | miRNA Assay Name and ID | Rq | P-Value |
|---|---|---|---|
| mdx | mmu-miR-154-000477 | 1 | 1 |
| mdx | mmu-miR-155-002571 | 1 | 1 |
| mdx | mmu-miR-15a-000389 | 1 | 1 |
| mdx | mmu-miR-16-000391 | 1 | 1 |
| mdx | mmu-miR-181a-000480 | 1 | 1 |
| mdx | mmu-miR-181c-000482 | 1 | 1 |
| mdx | mmu-miR-185-002271 | 1 | 1 |
| mdx | mmu-miR-186-002285 | 1 | 1 |
| mdx | mmu-miR-18a-002422 | 1 | 1 |
| mdx | mmu-miR-191-002299 | 1 | 1 |
| mdx | mmu-miR-193#-002577 | 1 | 1 |
| mdx | mmu-miR-1941-3p-121130_mat | 1 | 1 |
| mdx | mmu-miR-1943-121174_mat | 1 | 1 |
| mdx | mmu-miR-1944-121189_mat | 1 | 1 |
| mdx | mmu-miR-195-000494 | 1 | 1 |
| mdx | mmu-miR-199a-3p-002304 | 1 | 1 |
| mdx | mmu-miR-199b-001131 | 1 | 1 |
| mdx | mmu-miR-19a-000395 | 1 | 1 |
| mdx | mmu-miR-200c-002300 | 1 | 1 |
| mdx | mmu-miR-203-000507 | 1 | 1 |
| mdx | mmu-miR-204-000508 | 1 | 1 |
| mdx | mmu-miR-20a#-002491 | 1 | 1 |
| mdx | mmu-miR-21#-002493 | 1 | 1 |
| mdx | mmu-miR-210-000512 | 1 | 1 |
| mdx | mmu-miR-21-000397 | 1 | 1 |
| mdx | mmu-miR-214-002306 | 1 | 1 |
| mdx | mmu-miR-2146-241082_mat | 1 | 1 |
| mdx | mmu-miR-215-001200 | 1 | 1 |
| mdx | mmu-miR-218-000521 | 1 | 1 |
| mdx | mmu-miR-221-000524 | 1 | 1 |
| mdx | mmu-miR-222-002276 | 1 | 1 |
| mdx | mmu-miR-223-002295 | 1 | 1 |
| mdx | mmu-miR-23b-000400 | 1 | 1 |
| mdx | mmu-miR-25-000403 | 1 | 1 |
| mdx | mmu-miR-26a-000405 | 1 | 1 |
| mdx | mmu-miR-27b-000409 | 1 | 1 |
| mdx | mmu-miR-28-000411 | 1 | 1 |
| mdx | mmu-miR-296-5p-000527 | 1 | 1 |
| mdx | mmu-miR-301a-000528 | 1 | 1 |
| mdx | mmu-miR-301b-002600 | 1 | 1 |
| mdx | mmu-miR-30a-000417 | 1 | 1 |
| mdx | mmu-miR-30b-000602 | 1 | 1 |
| mdx | mmu-miR-30c-000419 | 1 | 1 |
| mdx | mmu-miR-30d-000420 | 1 | 1 |
| mdx | mmu-miR-30e-002223 | 1 | 1 |
| mdx | mmu-miR-31#-002495 | 1 | 1 |
| mdx | mmu-miR-31-000185 | 1 | 1 |
| mdx | mmu-miR-322-001076 | 1 | 1 |
| mdx | mmu-miR-324-3p-002509 | 1 | 1 |
| mdx | mmu-miR-324-5p-000539 | 1 | 1 |
| mdx | mmu-miR-328-000543 | 1 | 1 |
| mdx | mmu-miR-335-3p-002185 | 1 | 1 |
| mdx | mmu-miR-335-5p-000546 | 1 | 1 |
| mdx | mmu-miR-337-3p-002532 | 1 | 1 |
| mdx | mmu-miR-338-3p-002252 | 1 | 1 |
| mdx | mmu-miR-339-5p-002257 | 1 | 1 |
| mdx | mmu-miR-340-3p-002259 | 1 | 1 |
| mdx | mmu-miR-340-5p-002258 | 1 | 1 |
| mdx | mmu-miR-342-3p-002260 | 1 | 1 |
| mdx | mmu-miR-342-5p-002527 | 1 | 1 |
| mdx | mmu-miR-345-5p-002528 | 1 | 1 |
| mdx | mmu-miR-34a-000426 | 1 | 1 |
| mdx | mmu-miR-34b-3p-002618 | 1 | 1 |
| mdx | mmu-miR-34c#-002584 | 1 | 1 |
| mdx | mmu-miR-34c-000428 | 1 | 1 |
| mdx | mmu-miR-350-002530 | 1 | 1 |
| mdx | mmu-miR-362-3p-002616 | 1 | 1 |
| mdx | mmu-miR-362-5p-002614 | 1 | 1 |
| mdx | mmu-miR-369-3p-000557 | 1 | 1 |
| mdx | mmu-miR-369-5p-001021 | 1 | 1 |
| mdx | mmu-miR-370-002275 | 1 | 1 |
| mdx | mmu-miR-376a#-002482 | 1 | 1 |
| mdx | mmu-miR-376a-001069 | 1 | 1 |
| mdx | mmu-miR-376b#-002451 | 1 | 1 |
| mdx | mmu-miR-376b-002452 | 1 | 1 |
| mdx | mmu-miR-376c-002450 | 1 | 1 |
| mdx | mmu-miR-379-001138 | 1 | 1 |
| mdx | mmu-miR-380-5p-002601 | 1 | 1 |
| mdx | mmu-miR-381-000571 | 1 | 1 |
| mdx | mmu-miR-382-000572 | 1 | 1 |
| mdx | mmu-miR-383-001767 | 1 | 1 |
| mdx | mmu-miR-384-5p-002602 | 1 | 1 |
| mdx | mmu-miR-409-3p-002332 | 1 | 1 |
| mdx | mmu-miR-410-001274 | 1 | 1 |
| mdx | mmu-miR-411-001610 | 1 | 1 |
| mdx | mmu-miR-431-001979 | 1 | 1 |
| mdx | mmu-miR-433-001028 | 1 | 1 |
| mdx | mmu-miR-434-5p-002581 | 1 | 1 |
| mdx | mmu-miR-450a-5p-002303 | 1 | 1 |
| mdx | mmu-miR-455-002455 | 1 | 1 |
| mdx | mmu-miR-467a-002587 | 1 | 1 |
| mdx | mmu-miR-467c-002517 | 1 | 1 |
| mdx | mmu-miR-467F-002886 | 1 | 1 |
| mdx | mmu-miR-483#-002560 | 1 | 1 |
| mdx | mmu-miR-486-001278 | 1 | 1 |
| mdx | mmu-miR-487b-001285 | 1 | 1 |
| mdx | mmu-miR-489-001302 | 1 | 1 |
| mdx | mmu-miR-491-001630 | 1 | 1 |
| mdx | mmu-miR-493-002519 | 1 | 1 |
| mdx | mmu-miR-494-002365 | 1 | 1 |
| mdx | mmu-miR-495-001663 | 1 | 1 |
| mdx | mmu-miR-497-001346 | 1 | 1 |
| mdx | mmu-miR-500-002606 | 1 | 1 |
| mdx | mmu-miR-501-3p-001651 | 1 | 1 |
| mdx | mmu-miR-503-002456 | 1 | 1 |
| mdx | mmu-miR-511-002549 | 1 | 1 |
| mdx | mmu-miR-532-3p-002355 | 1 | 1 |
| mdx | mmu-miR-532-5p-001518 | 1 | 1 |
| mdx | mmu-miR-540-3p-001310 | 1 | 1 |
| mdx | mmu-miR-541-002562 | 1 | 1 |
| mdx | mmu-miR-542-3p-001284 | 1 | 1 |
| mdx | mmu-miR-542-5p-002563 | 1 | 1 |
| mdx | mmu-miR-543-001298 | 1 | 1 |
| mdx | mmu-miR-543-002376 | 1 | 1 |
| mdx | mmu-miR-544-002550 | 1 | 1 |
| mdx | mmu-miR-574-3p-002349 | 1 | 1 |
| mdx | mmu-miR-652-002352 | 1 | 1 |
| mdx | mmu-miR-665-002607 | 1 | 1 |
| mdx | mmu-miR-669a-001683 | 1 | 1 |
| mdx | mmu-miR-673-001954 | 1 | 1 |
| mdx | mmu-miR-673-3p-002449 | 1 | 1 |
| mdx | mmu-miR-674#-001956 | 1 | 1 |
| mdx | mmu-miR-674-002021 | 1 | 1 |
| mdx | mmu-miR-675-3p-001941 | 1 | 1 |
| mdx | mmu-miR-682-001666 | 1 | 1 |
| mdx | mmu-miR-690-001677 | 1 | 1 |
| mdx | mmu-miR-706-001641 | 1 | 1 |
| mdx | mmu-miR-708-002341 | 1 | 1 |
| mdx | mmu-miR-720-001629 | 1 | 1 |
| mdx | mmu-miR-802-002029 | 1 | 1 |
| mdx | mmu-miR-805-002045 | 1 | 1 |
| mdx | mmu-miR-99b-000436 | 1 | 1 |
| mdx | rno-miR-1-002064 | 1 | 1 |
| mdx | rno-miR-204#-002076 | 1 | 1 |
| mdx | rno-miR-20b-001326 | 1 | 1 |
| mdx | rno-miR-224-000599 | 1 | 1 |
| mdx | rno-miR-29c#-001818 | 1 | 1 |
| mdx | rno-miR-345-3p-002061 | 1 | 1 |
| mdx | rno-miR-351-002063 | 1 | 1 |
| mdx | rno-miR-379#-002081 | 1 | 1 |
| mdx | rno-miR-381-001322 | 1 | 1 |
| mdx | rno-miR-489-001353 | 1 | 1 |
| mdx | rno-miR-664-001323 | 1 | 1 |
| mdx | rno-miR-7#-001338 | 1 | 1 |
| mdx | rno-miR-7a#-002062 | 1 | 1 |

| Group | miRNA Assay Name and ID | Rq | P-Value |
|---|---|---|---|
| Pred | hsa-let-7i#-002172 | 0.714 | 0.5 |
| Pred | hsa-miR-140-3p-002234 | 0.681 | 0.02 |

| Group | miRNA Assay Name and ID | Rq | P-Value |
|---|---|---|---|
| Pred | hsa-miR-143-000466 | 1.096 | 0.8 |
| Pred | hsa-miR-154#-000478 | 1.585 | 0.3 |
| Pred | hsa-miR-190b-002263 | 0.547 | 0.01 |
| Pred | hsa-miR-200c-000505 | 0.486 | 0.08 |
| Pred | hsa-miR-206-000510 | 1.017 | 0.9 |
| Pred | hsa-miR-213-000516 | 0.622 | 0.05 |
| Pred | hsa-miR-214#-002293 | 0.82 | 0.3 |
| Pred | hsa-miR-214-000517 | 0.767 | 0.3 |
| Pred | hsa-miR-22#-002301 | 0.641 | 0.04 |
| Pred | hsa-miR-30e-3p-000422 | 0.739 | 0.2 |
| Pred | hsa-miR-376a#-001287 | 0.978 | 0.9 |
| Pred | hsa-miR-455-001280 | 0.6 | 0.05 |
| Pred | hsa-miR-744#-002325 | 0.537 | 0.003 |
| Pred | mmu-let-7a-000377 | 0.491 | 0.03 |
| Pred | mmu-let-7b-000378 | 0.655 | 0.005 |
| Pred | mmu-let-7c-000379 | 0.651 | 0.005 |
| Pred | mmu-let-7c-1#-002479 | 1.427 | 0.1 |
| Pred | mmu-let-7d#-001178 | 0.556 | 0.3 |
| Pred | mmu-let-7d-002283 | 0.714 | 0.05 |
| Pred | mmu-let-7e-002406 | 0.66 | 0.003 |
| Pred | mmu-let-7i-002221 | 0.775 | 0.08 |
| Pred | mmu-miR-100-000437 | 0.586 | 0.006 |
| Pred | mmu-miR-1-002222 | 0.868 | 0.4 |
| Pred | mmu-miR-103-000439 | 0.679 | 0.007 |
| Pred | mmu-miR-122-002245 | 0.241 | 0.3 |
| Pred | mmu-miR-125a-3p-002199 | 0.666 | 0.03 |
| Pred | mmu-miR-125b#-002508 | 0.453 | 0.01 |
| Pred | mmu-miR-125b-3p-002378 | 0.561 | 0.04 |
| Pred | mmu-miR-125b-5p-000449 | 0.676 | 0.03 |
| Pred | mmu-miR-126-3p-002228 | 0.697 | 0.04 |
| Pred | mmu-miR-126-5p-000451 | 0.682 | 0.04 |
| Pred | mmu-miR-127-000452 | 1.382 | 0.1 |
| Pred | mmu-miR-1274a-121150_mat | 1.138 | 0.4 |
| Pred | mmu-miR-128a-002216 | 0.871 | 0.4 |
| Pred | mmu-miR-130a-000454 | 0.758 | 0.2 |
| Pred | mmu-miR-130b#-002460 | 0.443 | 0.4 |
| Pred | mmu-miR-130b-000456 | 0.757 | 0.1 |
| Pred | mmu-miR-133a-002246 | 0.942 | 0.7 |
| Pred | mmu-miR-134-001186 | 1.922 | 0.008 |
| Pred | mmu-miR-136-002511 | 0.705 | 0.3 |
| Pred | mmu-miR-138#-002554 | 0.214 | 0.03 |
| Pred | mmu-miR-140-001187 | 0.775 | 0.03 |
| Pred | mmu-miR-142-3p-000464 | 0.485 | 0.006 |
| Pred | mmu-miR-142-5p-002248 | 0.438 | 0.001 |
| Pred | mmu-miR-143-002249 | 0.742 | 0.1 |
| Pred | mmu-miR-145-002278 | 0.694 | 0.03 |
| Pred | mmu-miR-146a-000468 | 0.397 | 0 |
| Pred | mmu-miR-146b#-002453 | 0.088 | 0.08 |
| Pred | mmu-miR-146b-001097 | 0.555 | 0 |
| Pred | mmu-miR-148a-000470 | 0.602 | 0.09 |
| Pred | mmu-miR-148b-000471 | 0.512 | 0.04 |
| Pred | mmu-miR-150#-002570 | 0.297 | 0.2 |
| Pred | mmu-miR-150-000473 | 0.516 | 0.008 |
| Pred | mmu-miR-151-3p-001190 | 0.877 | 0.2 |
| Pred | mmu-miR-152-000475 | 0.721 | 0.05 |
| Pred | mmu-miR-154-000477 | 0.606 | 0.3 |
| Pred | mmu-miR-155-002571 | 0.742 | 0.03 |
| Pred | mmu-miR-15a-000389 | 0.635 | 0.02 |
| Pred | mmu-miR-16-000391 | 0.663 | 0.02 |
| Pred | mmu-miR-181a-000480 | 0.728 | 0.006 |
| Pred | mmu-miR-181c-000482 | 0.624 | 0.007 |
| Pred | mmu-miR-185-002271 | 0.818 | 0.2 |
| Pred | mmu-miR-186-002285 | 0.866 | 0.03 |
| Pred | mmu-miR-18a-002422 | 1.284 | 0.2 |
| Pred | mmu-miR-191-002299 | 0.771 | 0.04 |
| Pred | mmu-miR-193#-002577 | 0.799 | 0.3 |
| Pred | mmu-miR-1941-3p-121130_mat | 2.166 | 0.05 |
| Pred | mmu-miR-1943-121174_mat | 0.831 | 0.3 |
| Pred | mmu-miR-1944-121189_mat | 0.877 | 0.1 |
| Pred | mmu-miR-195-000494 | 0.491 | 0.005 |
| Pred | mmu-miR-199a-3p-002304 | 0.844 | 0.3 |
| Pred | mmu-miR-199b-001131 | 0.771 | 0.2 |
| Pred | mmu-miR-19a-000395 | 0.846 | 0.3 |
| Pred | mmu-miR-200c-002300 | 0.508 | 0.03 |
| Pred | mmu-miR-203-000507 | 0.575 | 0.07 |
| Pred | mmu-miR-204-000508 | 0.722 | 0.05 |
| Pred | mmu-miR-20a#-002491 | 0.771 | 0.2 |
| Pred | mmu-miR-21#-002493 | 0.707 | 0.2 |
| Pred | mmu-miR-210-000512 | 0.759 | 0.04 |
| Pred | mmu-miR-21-000397 | 0.659 | 0.06 |
| Pred | mmu-miR-214-002306 | 0.898 | 0.6 |
| Pred | mmu-miR-2146-241082_mat | 1.113 | 0.8 |
| Pred | mmu-miR-215-001200 | 0.792 | 0.6 |
| Pred | mmu-miR-218-000521 | 0.615 | 0.01 |
| Pred | mmu-miR-221-000524 | 0.687 | 0.09 |
| Pred | mmu-miR-222-002276 | 0.666 | 0.007 |
| Pred | mmu-miR-223-002295 | 0.804 | 0.04 |
| Pred | mmu-miR-23b-000400 | 0.621 | 0.04 |
| Pred | mmu-miR-25-000403 | 0.75 | 0.05 |
| Pred | mmu-miR-26a-000405 | 0.7 | 0.08 |
| Pred | mmu-miR-27b-000409 | 0.796 | 0.2 |
| Pred | mmu-miR-28-000411 | 0.759 | 0.05 |
| Pred | mmu-miR-296-5p-000527 | 1.035 | 0.8 |
| Pred | mmu-miR-301a-000528 | 0.687 | 0.04 |
| Pred | mmu-miR-301b-002600 | 0.862 | 0.05 |
| Pred | mmu-miR-30a-000417 | 0.756 | 0.06 |
| Pred | mmu-miR-30b-000602 | 0.785 | 0.3 |
| Pred | mmu-miR-30c-000419 | 0.739 | 0.2 |
| Pred | mmu-miR-30d-000420 | 0.701 | 0.03 |
| Pred | mmu-miR-30e-002223 | 0.785 | 0.2 |
| Pred | mmu-miR-31#-002495 | 0.955 | 0.9 |
| Pred | mmu-miR-31-000185 | 1.028 | 0.9 |
| Pred | mmu-miR-322-001076 | 0.67 | 0.03 |
| Pred | mmu-miR-324-3p-002509 | 0.713 | 0.02 |
| Pred | mmu-miR-324-5p-000539 | 0.859 | 0.4 |
| Pred | mmu-miR-328-000543 | 0.888 | 0.4 |
| Pred | mmu-miR-335-3p-002185 | 1.354 | 0.2 |
| Pred | mmu-miR-335-5p-000546 | 0.756 | 0.3 |
| Pred | mmu-miR-337-3p-002532 | 0.853 | 0.4 |
| Pred | mmu-miR-338-3p-002252 | 0.469 | 0.007 |
| Pred | mmu-miR-339-5p-002257 | 0.652 | 0.1 |
| Pred | mmu-miR-340-3p-002259 | 0.581 | 0.02 |
| Pred | mmu-miR-340-5p-002258 | 0.602 | 0.05 |
| Pred | mmu-miR-342-3p-002260 | 0.407 | 0.005 |
| Pred | mmu-miR-342-5p-002527 | 0.529 | 0.02 |
| Pred | mmu-miR-345-5p-002528 | 0.713 | 0.07 |
| Pred | mmu-miR-34a-000426 | 0.712 | 0.02 |
| Pred | mmu-miR-34b-3p-002618 | 0.607 | 0.1 |
| Pred | mmu-miR-34c#-002584 | 0.623 | 0.08 |
| Pred | mmu-miR-34c-000428 | 0.655 | 0.1 |
| Pred | mmu-miR-350-002530 | 0.796 | 0.1 |
| Pred | mmu-miR-362-3p-002616 | 0.936 | 0.7 |
| Pred | mmu-miR-362-5p-002614 | 1.241 | 0.5 |
| Pred | mmu-miR-369-3p-000557 | 1.192 | 0.3 |
| Pred | mmu-miR-369-5p-001021 | 1.211 | 0.4 |
| Pred | mmu-miR-370-002275 | 1.975 | 0.03 |
| Pred | mmu-miR-376a#-002482 | 1.351 | 0.3 |
| Pred | mmu-miR-376a-001069 | 1.484 | 0.2 |
| Pred | mmu-miR-376b#-002451 | 1.084 | 0.9 |
| Pred | mmu-miR-376b-002452 | 1.602 | 0.1 |
| Pred | mmu-miR-376c-002450 | 0.966 | 0.9 |
| Pred | mmu-miR-379-001138 | 1.085 | 0.7 |
| Pred | mmu-miR-380-5p-002601 | 1.287 | 0.4 |
| Pred | mmu-miR-381-000571 | 1.359 | 0.2 |
| Pred | mmu-miR-382-000572 | 1.017 | 0.9 |
| Pred | mmu-miR-383-001767 | 0.551 | 0.2 |
| Pred | mmu-miR-384-5p-002602 | 0.618 | 0.02 |
| Pred | mmu-miR-409-3p-002332 | 1.906 | 0.03 |
| Pred | mmu-miR-410-001274 | 1.676 | 0.1 |
| Pred | mmu-miR-411-001610 | 1.171 | 0.4 |
| Pred | mmu-miR-431-001979 | 1.819 | 0.1 |
| Pred | mmu-miR-433-001028 | 2.288 | 0.02 |
| Pred | mmu-miR-434-5p-002581 | 1.271 | 0.3 |
| Pred | mmu-miR-450a-5p-002303 | 1.051 | 0.7 |
| Pred | mmu-miR-455-002455 | 0.612 | 0.03 |
| Pred | mmu-miR-467a-002587 | 0.751 | 0.2 |
| Pred | mmu-miR-467c-002517 | 0.992 | 1 |
| Pred | mmu-miR-467F-002886 | 1.346 | 0.5 |
| Pred | mmu-miR-483#-002560 | 1.367 | 0.4 |
| Pred | mmu-miR-486-001278 | 0.917 | 0.5 |
| Pred | mmu-miR-487b-001285 | 1.43 | 0.2 |
| Pred | mmu-miR-489-001302 | 0.792 | 0.4 |
| Pred | mmu-miR-491-001630 | 0.776 | 0.1 |

-continued

| Group | miRNA Assay Name and ID | Rq | P-Value |
|---|---|---|---|
| Pred | mmu-miR-493-002519 | 2.641 | 0.009 |
| Pred | mmu-miR-494-002365 | 1.025 | 0.9 |
| Pred | mmu-miR-495-001663 | 1.448 | 0.2 |
| Pred | mmu-miR-497-001346 | 0.482 | 0.001 |
| Pred | mmu-miR-500-002606 | 0.935 | 0.6 |
| Pred | mmu-miR-501-3p-001651 | 0.97 | 0.9 |
| Pred | mmu-miR-503-002456 | 0.923 | 0.8 |
| Pred | mmu-miR-511-002549 | 0.48 | 0.007 |
| Pred | mmu-miR-532-3p-002355 | 1.067 | 0.7 |
| Pred | mmu-miR-532-5p-001518 | 1.087 | 0.5 |
| Pred | mmu-miR-540-3p-001310 | 0.908 | 0.8 |
| Pred | mmu-miR-541-002562 | 1.165 | 0.5 |
| Pred | mmu-miR-542-3p-001284 | 1.123 | 0.5 |
| Pred | mmu-miR-542-5p-002563 | 0.96 | 0.9 |
| Pred | mmu-miR-543-001298 | 2.644 | 0.05 |
| Pred | mmu-miR-543-002376 | 1.81 | 0.09 |
| Pred | mmu-miR-544-002550 | 1.001 | 1 |
| Pred | mmu-miR-574-3p-002349 | 0.667 | 0.03 |
| Pred | mmu-miR-652-002352 | 0.626 | 0.02 |
| Pred | mmu-miR-665-002607 | 1.683 | 0.2 |
| Pred | mmu-miR-669a-001683 | 0.678 | 0.003 |
| Pred | mmu-miR-673-001954 | 2.031 | 0.05 |
| Pred | mmu-miR-673-3p-002449 | 1.562 | 0.2 |
| Pred | mmu-miR-674#-001956 | 0.857 | 0.5 |
| Pred | mmu-miR-674-002021 | 0.846 | 0.2 |
| Pred | mmu-miR-675-3p-001941 | 1.258 | 0.09 |
| Pred | mmu-miR-682-001666 | 0.702 | 0.2 |
| Pred | mmu-miR-690-001677 | 0.744 | 0.04 |
| Pred | mmu-miR-706-001641 | 0.75 | 0.2 |
| Pred | mmu-miR-708-002341 | 0.636 | 0.04 |
| Pred | mmu-miR-720-001629 | 0.905 | 0.6 |
| Pred | mmu-miR-802-002029 | 0.245 | 0.2 |
| Pred | mmu-miR-805-002045 | 1.066 | 0.8 |
| Pred | mmu-miR-99b-000436 | 0.783 | 0.1 |
| Pred | rno-miR-1-002064 | 0.911 | 0.6 |
| Pred | rno-miR-204#-002076 | 0.729 | 0.3 |
| Pred | rno-miR-20b-001326 | 0.491 | 0.01 |
| Pred | rno-miR-224-000599 | 1.144 | 0.4 |
| Pred | rno-miR-29c#-001818 | 0.826 | 0.5 |
| Pred | rno-miR-345-3p-002061 | 0.859 | 0.2 |
| Pred | rno-miR-351-002063 | 1.366 | 0.2 |
| Pred | rno-miR-379#-002081 | 1.563 | 0.2 |
| Pred | rno-miR-381-001322 | 1.107 | 0.6 |
| Pred | rno-miR-489-001353 | 0.626 | 0.02 |
| Pred | rno-miR-664-001323 | 0.638 | 0.09 |
| Pred | rno-miR-7#-001338 | 0.751 | 0.4 |
| Pred | rno-miR-7a#-002062 | 0.863 | 0.6 |
| Vam | hsa-let-7i#-002172 | 0.939 | 0.8 |
| Vam | hsa-miR-140-3p-002234 | 0.903 | 0.6 |
| Vam | hsa-miR-143-000466 | 1.29 | 0.5 |
| Vam | hsa-miR-154#-000478 | 0.689 | 0.4 |
| Vam | hsa-miR-190b-002263 | 0.822 | 0.2 |
| Vam | hsa-miR-200c-000505 | 0.453 | 0.05 |
| Vam | hsa-miR-206-000510 | 0.983 | 0.9 |
| Vam | hsa-miR-213-000516 | 0.839 | 0.2 |
| Vam | hsa-miR-214#-002293 | 0.889 | 0.5 |
| Vam | hsa-miR-214-000517 | 0.994 | 1 |
| Vam | hsa-miR-22#-002301 | 0.78 | 0.3 |
| Vam | hsa-miR-30e-3p-000422 | 0.849 | 0.4 |
| Vam | hsa-miR-376a#-001287 | 0.845 | 0.5 |
| Vam | hsa-miR-455-001280 | 0.637 | 0.01 |
| Vam | hsa-miR-744#-002325 | 0.816 | 0.08 |
| Vam | mmu-let-7a-000377 | 0.667 | 0.1 |
| Vam | mmu-let-7b-000378 | 0.754 | 0.09 |
| Vam | mmu-let-7c-000379 | 0.691 | 0.02 |
| Vam | mmu-let-7c-1#-002479 | 1.038 | 0.9 |
| Vam | mmu-let-7d#-001178 | 0.61 | 0.5 |
| Vam | mmu-let-7d-002283 | 0.789 | 0.1 |
| Vam | mmu-let-7e-002406 | 0.665 | 0.1 |
| Vam | mmu-let-7i-002221 | 0.777 | 0.07 |
| Vam | mmu-miR-100-000437 | 0.721 | 0.09 |
| Vam | mmu-miR-1-002222 | 0.897 | 0.6 |
| Vam | mmu-miR-103-000439 | 0.628 | 0.01 |
| Vam | mmu-miR-122-002245 | 0.072 | 0.02 |
| Vam | mmu-miR-125a-3p-002199 | 0.828 | 0.4 |
| Vam | mmu-miR-125b#-002508 | 0.803 | 0.3 |
| Vam | mmu-miR-125b-3p-002378 | 0.866 | 0.6 |

-continued

| Group | miRNA Assay Name and ID | Rq | P-Value |
|---|---|---|---|
| Vam | mmu-miR-125b-5p-000449 | 0.682 | 0.07 |
| Vam | mmu-miR-126-3p-002228 | 0.809 | 0.1 |
| Vam | mmu-miR-126-5p-000451 | 0.812 | 0.2 |
| Vam | mmu-miR-127-000452 | 1.107 | 0.5 |
| Vam | mmu-miR-1274a-121150_mat | 1.244 | 0.08 |
| Vam | mmu-miR-128a-002216 | 0.847 | 0.2 |
| Vam | mmu-miR-130a-000454 | 0.717 | 0.03 |
| Vam | mmu-miR-130b#-002460 | 1.164 | 0.8 |
| Vam | mmu-miR-130b-000456 | 0.88 | 0.4 |
| Vam | mmu-miR-133a-002246 | 0.996 | 1 |
| Vam | mmu-miR-134-001186 | 1.353 | 0.1 |
| Vam | mmu-miR-136-002511 | 0.942 | 0.7 |
| Vam | mmu-miR-138#-002554 | 0.384 | 0.08 |
| Vam | mmu-miR-140-001187 | 0.818 | 0.03 |
| Vam | mmu-miR-142-3p-000464 | 0.626 | 0.04 |
| Vam | mmu-miR-142-5p-002248 | 0.576 | 0.05 |
| Vam | mmu-miR-143-002249 | 0.716 | 0.04 |
| Vam | mmu-miR-145-002278 | 0.722 | 0.01 |
| Vam | mmu-miR-146a-000468 | 0.513 | 0.003 |
| Vam | mmu-miR-146b#-002453 | 0.275 | 0.004 |
| Vam | mmu-miR-146b-001097 | 0.645 | 0.1 |
| Vam | mmu-miR-148a-000470 | 0.496 | 0.03 |
| Vam | mmu-miR-148b-000471 | 0.568 | 0.009 |
| Vam | mmu-miR-150#-002570 | 0.293 | 0.05 |
| Vam | mmu-miR-150-000473 | 0.692 | 0.09 |
| Vam | mmu-miR-151-3p-001190 | 0.971 | 0.7 |
| Vam | mmu-miR-152-000475 | 0.785 | 0.08 |
| Vam | mmu-miR-154-000477 | 0.898 | 0.8 |
| Vam | mmu-miR-155-002571 | 0.876 | 0.3 |
| Vam | mmu-miR-15a-000389 | 0.719 | 0.05 |
| Vam | mmu-miR-16-000391 | 0.781 | 0.2 |
| Vam | mmu-miR-181a-000480 | 0.773 | 0.1 |
| Vam | mmu-miR-181c-000482 | 0.71 | 0.03 |
| Vam | mmu-miR-185-002271 | 0.886 | 0.4 |
| Vam | mmu-miR-186-002285 | 0.994 | 0.9 |
| Vam | mmu-miR-18a-002422 | 1.288 | 0.3 |
| Vam | mmu-miR-191-002299 | 0.815 | 0.03 |
| Vam | mmu-miR-193#-002577 | 0.682 | 0.03 |
| Vam | mmu-miR-1941-3p-121130_mat | 1.459 | 0.08 |
| Vam | mmu-miR-1943-121174_mat | 1.268 | 0.2 |
| Vam | mmu-miR-1944-121189_mat | 1.023 | 0.8 |
| Vam | mmu-miR-195-000494 | 0.669 | 0.07 |
| Vam | mmu-miR-199a-3p-002304 | 0.722 | 0.1 |
| Vam | mmu-miR-199b-001131 | 0.667 | 0.05 |
| Vam | mmu-miR-19a-000395 | 0.886 | 0.5 |
| Vam | mmu-miR-200c-002300 | 0.577 | 0.07 |
| Vam | mmu-miR-203-000507 | 0.521 | 0.009 |
| Vam | mmu-miR-204-000508 | 0.627 | 0.1 |
| Vam | mmu-miR-20a#-002491 | 0.825 | 0.4 |
| Vam | mmu-miR-21#-002493 | 0.647 | 0.05 |
| Vam | mmu-miR-210-000512 | 0.746 | 0.05 |
| Vam | mmu-miR-21-000397 | 0.677 | 0.1 |
| Vam | mmu-miR-214-002306 | 0.842 | 0.3 |
| Vam | mmu-miR-2146-241082_mat | 0.413 | 0.03 |
| Vam | mmu-miR-215-001200 | 0.495 | 0.008 |
| Vam | mmu-miR-218-000521 | 0.759 | 0.1 |
| Vam | mmu-miR-221-000524 | 0.674 | 0.2 |
| Vam | mmu-miR-222-002276 | 0.733 | 0.09 |
| Vam | mmu-miR-223-002295 | 0.78 | 0.4 |
| Vam | mmu-miR-23b-000400 | 0.675 | 0.07 |
| Vam | mmu-miR-25-000403 | 0.867 | 0.2 |
| Vam | mmu-miR-26a-000405 | 0.766 | 0.05 |
| Vam | mmu-miR-27b-000409 | 0.82 | 0.2 |
| Vam | mmu-miR-28-000411 | 0.842 | 0.2 |
| Vam | mmu-miR-296-5p-000527 | 0.882 | 0.3 |
| Vam | mmu-miR-301a-000528 | 0.77 | 0.02 |
| Vam | mmu-miR-301b-002600 | 0.917 | 0.2 |
| Vam | mmu-miR-30a-000417 | 0.834 | 0.2 |
| Vam | mmu-miR-30b-000602 | 0.855 | 0.3 |
| Vam | mmu-miR-30c-000419 | 0.818 | 0.2 |
| Vam | mmu-miR-30d-000420 | 0.829 | 0.2 |
| Vam | mmu-miR-30e-002223 | 0.847 | 0.2 |
| Vam | mmu-miR-31#-002495 | 0.821 | 0.3 |
| Vam | mmu-miR-31-000185 | 1.032 | 0.9 |
| Vam | mmu-miR-322-001076 | 0.785 | 0.1 |
| Vam | mmu-miR-324-3p-002509 | 0.748 | 0.04 |

| Group | miRNA Assay Name and ID | Rq | P-Value |
|---|---|---|---|
| Vam | mmu-miR-324-5p-000539 | 0.946 | 0.7 |
| Vam | mmu-miR-328-000543 | 0.858 | 0.2 |
| Vam | mmu-miR-335-3p-002185 | 1.249 | 0.4 |
| Vam | mmu-miR-335-5p-000546 | 0.76 | 0.3 |
| Vam | mmu-miR-337-3p-002532 | 1.078 | 0.6 |
| Vam | mmu-miR-338-3p-002252 | 0.689 | 0.2 |
| Vam | mmu-miR-339-5p-002257 | 0.929 | 0.5 |
| Vam | mmu-miR-340-3p-002259 | 0.75 | 0.06 |
| Vam | mmu-miR-340-5p-002258 | 0.726 | 0.2 |
| Vam | mmu-miR-342-3p-002260 | 0.677 | 0.1 |
| Vam | mmu-miR-342-5p-002527 | 0.644 | 0.2 |
| Vam | mmu-miR-345-5p-002528 | 0.808 | 0.1 |
| Vam | mmu-miR-34a-000426 | 0.789 | 0.07 |
| Vam | mmu-miR-34b-3p-002618 | 0.798 | 0.2 |
| Vam | mmu-miR-34c#-002584 | 0.748 | 0.2 |
| Vam | mmu-miR-34c-000428 | 0.811 | 0.2 |
| Vam | mmu-miR-350-002530 | 0.797 | 0.2 |
| Vam | mmu-miR-362-3p-002616 | 0.902 | 0.6 |
| Vam | mmu-miR-362-5p-002614 | 1.469 | 0.2 |
| Vam | mmu-miR-369-3p-000557 | 0.963 | 0.9 |
| Vam | mmu-miR-369-5p-001021 | 1.023 | 0.9 |
| Vam | mmu-miR-370-002275 | 1.146 | 0.6 |
| Vam | mmu-miR-376a#-002482 | 0.985 | 0.9 |
| Vam | mmu-miR-376a-001069 | 0.991 | 1 |
| Vam | mmu-miR-376b#-002451 | 0.717 | 0.5 |
| Vam | mmu-miR-376b-002452 | 1.153 | 0.5 |
| Vam | mmu-miR-376c-002450 | 0.931 | 0.7 |
| Vam | mmu-miR-379-001138 | 0.987 | 0.9 |
| Vam | mmu-miR-380-5p-002601 | 1.243 | 0.1 |
| Vam | mmu-miR-381-000571 | 1.288 | 0.2 |
| Vam | mmu-miR-382-000572 | 1.081 | 0.5 |
| Vam | mmu-miR-383-001767 | 0.272 | 0.04 |
| Vam | mmu-miR-384-5p-002602 | 0.727 | 0.08 |
| Vam | mmu-miR-409-3p-002332 | 1.266 | 0.3 |
| Vam | mmu-miR-410-001274 | 1.158 | 0.5 |
| Vam | mmu-miR-411-001610 | 1.083 | 0.6 |
| Vam | mmu-miR-431-001979 | 1.358 | 0.3 |
| Vam | mmu-miR-433-001028 | 1.407 | 0.2 |
| Vam | mmu-miR-434-5p-002581 | 1.208 | 0.2 |
| Vam | mmu-miR-450a-5p-002303 | 0.862 | 0.3 |
| Vam | mmu-miR-455-002455 | 0.607 | 0.01 |
| Vam | mmu-miR-467a-002587 | 0.763 | 0.2 |
| Vam | mmu-miR-467c-002517 | 0.844 | 0.7 |
| Vam | mmu-miR-467F-002886 | 0.581 | 0.05 |
| Vam | mmu-miR-483#-002560 | 1.386 | 0.2 |
| Vam | mmu-miR-486-001278 | 0.988 | 0.9 |
| Vam | mmu-miR-487b-001285 | 1.133 | 0.4 |
| Vam | mmu-miR-489-001302 | 0.942 | 0.7 |
| Vam | mmu-miR-491-001630 | 0.842 | 0.1 |
| Vam | mmu-miR-493-002519 | 1.057 | 0.9 |
| Vam | mmu-miR-494-002365 | 0.988 | 0.9 |
| Vam | mmu-miR-495-001663 | 0.897 | 0.6 |
| Vam | mmu-miR-497-001346 | 0.652 | 0.006 |
| Vam | mmu-miR-500-002606 | 0.878 | 0.4 |
| Vam | mmu-miR-501-3p-001651 | 1.158 | 0.5 |
| Vam | mmu-miR-503-002456 | 1.115 | 0.7 |
| Vam | mmu-miR-511-002549 | 0.477 | 0.2 |
| Vam | mmu-miR-532-3p-002355 | 1.069 | 0.6 |
| Vam | mmu-miR-532-5p-001518 | 1.043 | 0.8 |
| Vam | mmu-miR-540-3p-001310 | 0.746 | 0.4 |
| Vam | mmu-miR-541-002562 | 1.043 | 0.8 |
| Vam | mmu-miR-542-3p-001284 | 0.82 | 0.3 |
| Vam | mmu-miR-542-5p-002563 | 1.044 | 0.9 |
| Vam | mmu-miR-543-001298 | 1.176 | 0.6 |
| Vam | mmu-miR-543-002376 | 0.918 | 0.7 |
| Vam | mmu-miR-544-002550 | 0.952 | 0.8 |
| Vam | mmu-miR-574-3p-002349 | 0.692 | 0.04 |
| Vam | mmu-miR-652-002352 | 0.636 | 0.04 |
| Vam | mmu-miR-665-002607 | 1.203 | 0.6 |
| Vam | mmu-miR-669a-001683 | 0.551 | 0.02 |
| Vam | mmu-miR-673-001954 | 1.475 | 0.1 |
| Vam | mmu-miR-673-3p-002449 | 1.148 | 0.5 |
| Vam | mmu-miR-674#-001956 | 0.765 | 0.2 |
| Vam | mmu-miR-674-002021 | 0.892 | 0.3 |
| Vam | mmu-miR-675-3p-001941 | 1.14 | 0.3 |
| Vam | mmu-miR-682-001666 | 0.675 | 0.05 |
| Vam | mmu-miR-690-001677 | 0.861 | 0.4 |
| Vam | mmu-miR-706-001641 | 0.664 | 0.05 |
| Vam | mmu-miR-708-002341 | 0.51 | 0.001 |
| Vam | mmu-miR-720-001629 | 0.957 | 0.9 |
| Vam | mmu-miR-802-002029 | 0.126 | 0.04 |
| Vam | mmu-miR-805-002045 | 1.128 | 0.5 |
| Vam | mmu-miR-99b-000436 | 0.913 | 0.5 |
| Vam | rno-miR-1-002064 | 0.956 | 0.8 |
| Vam | rno-miR-204#-002076 | 0.813 | 0.5 |
| Vam | rno-miR-20b-001326 | 0.711 | 0.04 |
| Vam | rno-miR-224-000599 | 0.837 | 0.5 |
| Vam | rno-miR-29c#-001818 | 0.93 | 0.7 |
| Vam | rno-miR-345-3p-002061 | 0.999 | 1 |
| Vam | rno-miR-351-002063 | 1.376 | 0.2 |
| Vam | rno-miR-379#-002081 | 1.014 | 0.9 |
| Vam | rno-miR-381-001322 | 1.013 | 0.9 |
| Vam | rno-miR-489-001353 | 0.844 | 0.3 |
| Vam | rno-miR-664-001323 | 0.771 | 0.2 |
| Vam | rno-miR-7#-001338 | 0.799 | 0.3 |
| Vam | rno-miR-7a#-002062 | 0.887 | 0.6 |

Figure 1A:
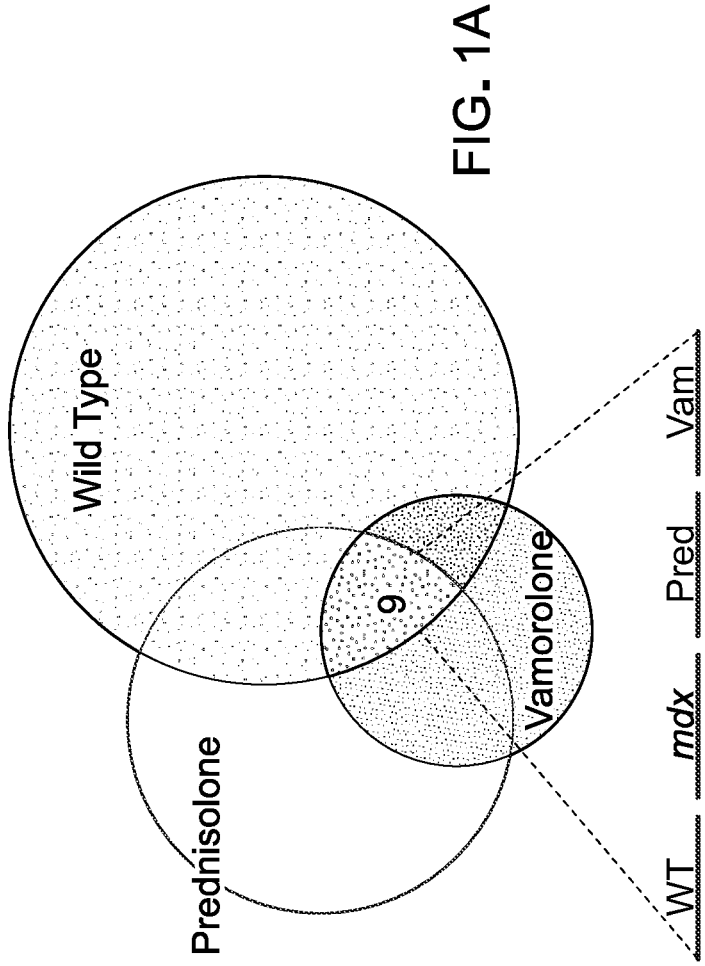
FIG. 1A-1D depict a summary of muscle miRNA changes discovered in response to dystrophy and its treatment. Expression of the miRNAome was quantified in diaphragm muscle of mice from a discovery set of mice (n=5 mice per group). Groups included WT (vehicle), mdx (vehicle), mdx treated with prednisolone (5 mg/kg), and mdx treated with vamorolone (15 mg/kg), with mice treated from 2-8 weeks of age in a prophylactic trial design.
Figure 1B:
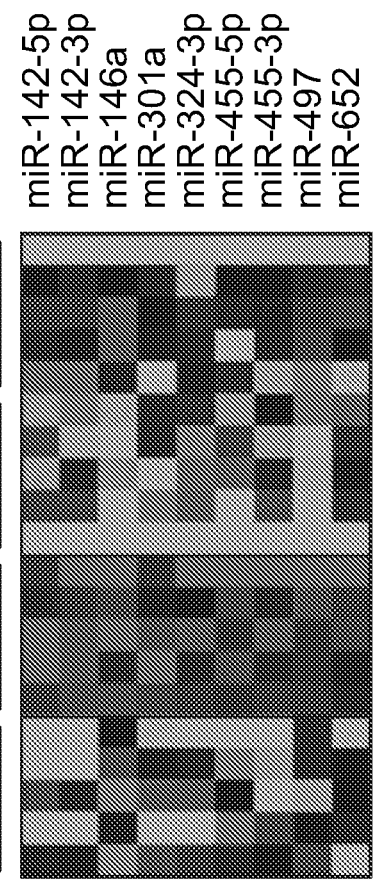

To identify a set of efficacy miRNA markers associated with both the muscular dystrophy disease process and a healthy response to treatment, which miRNAs were different in all three groups (wild type, prednisolone, and vamorolone) was examined, compared to untreated mdx (FIG. 1A-D). Using this approach, a focus set of nine miRNAs were identified (FIG. 1A-B). All nine of these miRNAs were increased in muscular dystrophy and returned towards healthy wild type levels as a result of treatment with both drugs (Table 1). In Table 1, values are expressed as % expression in comparison to mdx vehicle. (*P≤0.05, P≤0.005, *P≤0.0005; ANOVA with post-hoc comparison to mdx vehicle) Abbreviations: Pred, prednislone; Vam, vamorolone; DC, Dendritic Cell; HF, Heart Failure; IBD, inflammatory bowel disease; LGMD2D, Limb Girdle Muscular Dystrophy Type 2D; MG, Myasthenia Gravis; MM, Myoshi Myopathy; MS, Multiple Sclerosis; NF-κB, an inflammatory transcription factor named Nuclear factor kappa-light-chain-enhancer of activated B cells; SLE, Systemic sclerosis

TABLE 1

Nine miRNAs are elevated by dystrophy and respond to both drugs in the discovery set of diaphragm muscle.

| miRNA | WT (%) | mdx (%) | Pred (%) | Vam (%) | miRNA Function/Disease Associations | Sources |
|---|---|---|---|---|---|---|
| 142-5p | 43 ± 20** | 100 ± 23 | 44 ± 11** | 61 ± 23* | Dendritic (DC) Homeostasis; Resolution of acute inflammation/IBD, Alzheimer's, LGMD2D, DMD | (14, 40, 44, 59, 75) |
| 142-3p | 49 ± 19*** | 100 ± 10 | 50 ± 13*** | 65 ± 20** | Innate immunity; DC Homeostasis; Resolution of acute inflammation/SLE, LGMD2B/2D, DMD | (18, 28, 44, 59) |

TABLE 1-continued

Nine miRNAs are elevated by dystrophy and respond to both drugs in the discovery set of diaphragm muscle.

| miRNA | WT (%) | mdx (%) | Pred (%) | Vam (%) | miRNA Function/Disease Associations | Sources |
|---|---|---|---|---|---|---|
| 146a | 56 ± 10*** | 100 ± 20 | 39 ± 6*** | 52 ± 12*** | Stages inflammation/IBD, LGMD2A/2B, Myositis, MM, wasting, HE, MG, Alzheimer's, MS | (9, 15, 34, 36, 39, 49, 51, 68, 71) |
| 301a | 81 ± 15* | 100 ± 11 | 70 ± 18* | 77 ± 12* | NF-κB positive feedback loop/IBD | (21, 35) |
| 324-3p | 75 ± 17* | 100 ± 19 | 71 ± 14* | 75 ± 13* | Induces and activates NF-κB,/IBD | (6, 13, 21) |
| 455-5p | 61 ± 11* | 100 ± 17 | 64 ± 30* | 64 ± 15* | TGF-β Signaling/FSHD, LGMD2A, nemaline myopathy | (15, 67) |
| 455-3p | 63 ± 21* | 100 ± 24 | 62 ± 18* | 61 ± 14* | Innate immunity; cartilage development/IBD, Alzheimer's | (32, 50, 74, 82) |
| 497 | 72 ± 12* | 100 ± 22 | 49 ± 11*** | 65 ± 11** | NF-κB feedback mechanism via IKKβ | (42) |
| 652 | 66 ± 18* | 100 ± 30 | 62 ± 14* | 64 ± 18* | Inflammatory signals in immune cells | (61) |

Of these nine miRNAs, three have previously been found to be dysregulated in muscle disorders (miR-146a, miR-142-3p and miR-142-5p) (17, 28, 40). All nine of these miRNAs are involved in inflammatory signaling pathways and at least seven of them have been found to be upregulated in other inflammatory disorders, (see Table 1 for miRNA-specific references).

Figure 1C:
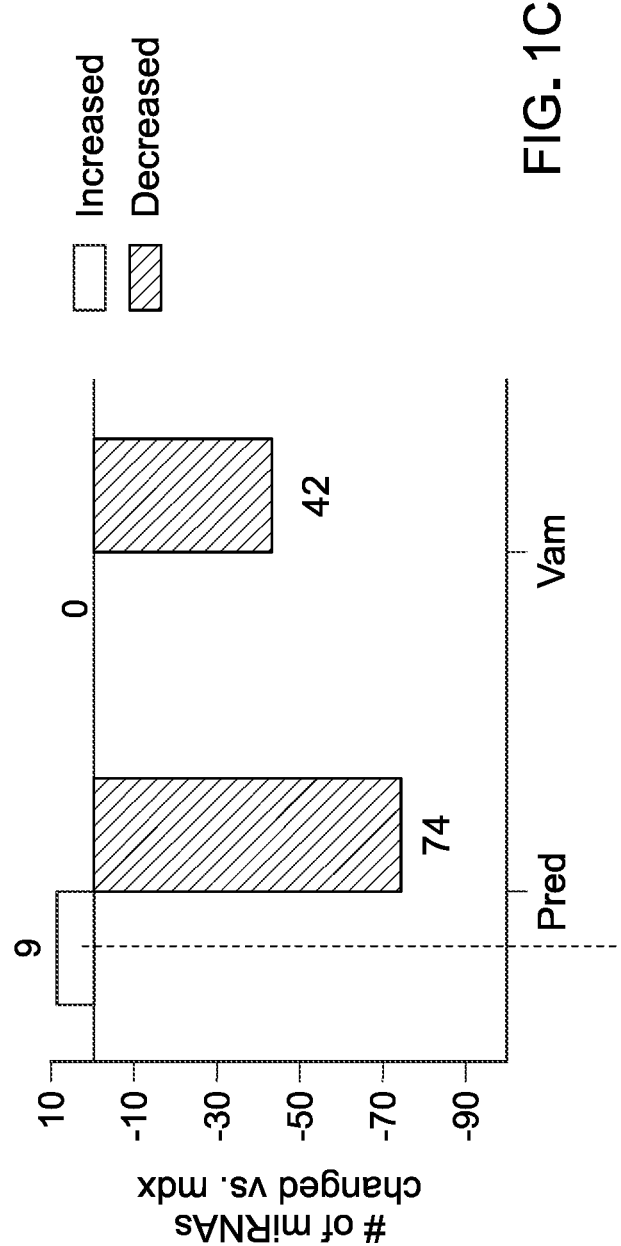
Figure 1D:
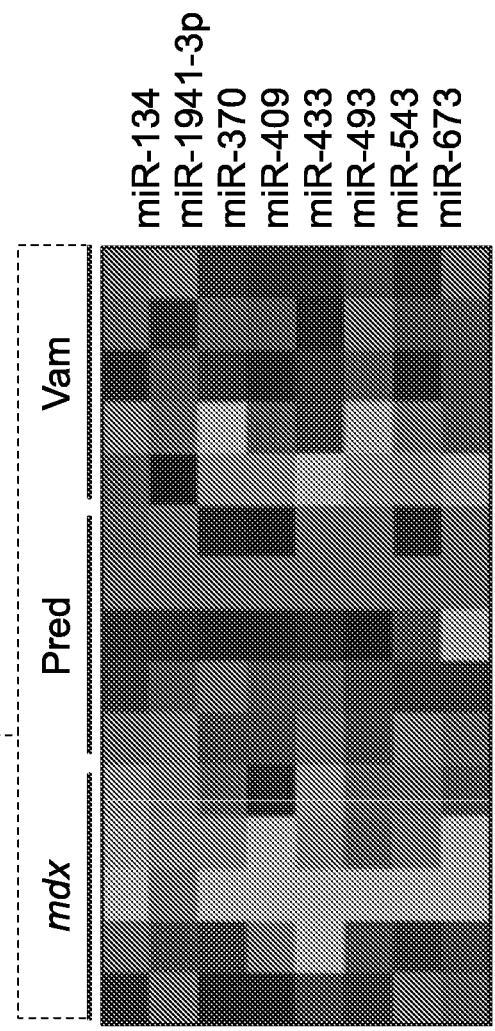

Next, the effects of the two drugs were compared to examine consequences of their differing chemistries on genomic miRNA regulation and steroid side effects. Prednisolone, a traditional glucocorticoid, both activated and inhibited expression of miRNAs (FIG. 1C-D). Treatment with prednisolone produced a significant increase in 9 miRNAs (P≤0.05), 8 of which were unique. Interestingly, none of the miRNAs queried in the TLDA cards were significantly increased in response to vamorolone treatment. This data is consistent with the more selective dissociative chemistry of vamorolone, which can inhibit inflammatory signaling without activation of individual GR-regulated genes. Additionally, this data identifies a set of prednisone-specific miRNAs whose activation is consistent with the activation of glucocorticoid side effects observed in these same mice.

Example 3. Efficacy miRNA Responses are Conserved in an Independent Validation Trial Having identified nine inflammatory miRNAs of interest in the discovery set of mice, the next step was to both validate the miRNA markers that were found and to expand upon the results to determine which ones are of utility in other disease stages or trial designs commonly studied in mdx literature (23, 25). To do this a validation set of samples was obtained from a separate, independent trial using a different trial design characterized by a prolonged treatment regimen in older mdx mice. Samples were obtained at a trial endpoint of 6 months. At this stage, mdx mice show less variability however they have gone through a recovery stage which results in milder phenotypes that typically require treadmill exercise to unmask. Here, gene-specific qRT-PCR was used to detect expression levels of each individual inflammatory miRNA within diaphragm muscle from the validation set. Differences in the trial design for the validation set of samples versus the previous discovery set include the age of mice (6 months old), the stage of mdx disease (characterized by a phenotypic recovery and increased fibrosis), the added exercise protocol (treadmill running), the length of treatment (4 months), and the dose (45 mg/kg) of vamorolone (23).

Figure 2:
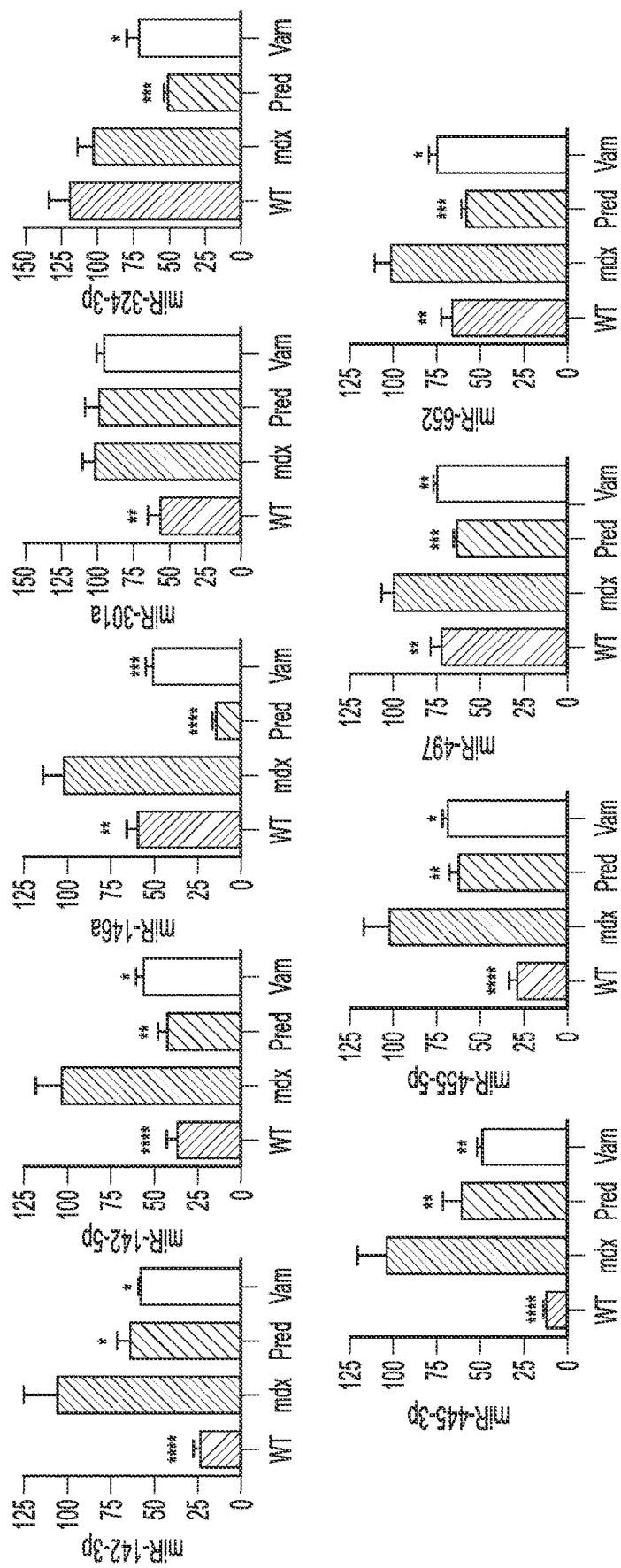
FIG. 2 is a panel of graphs that depicts the behavior of efficacy miRNA signature is maintained in an independent validation trial. A validation set of samples was obtained from a second, independent mdx trial performed at a different stage of the mdx disease. Mice received daily oral vehicle, prednisolone (5 mg/kg) or vamorolone (45 mg/kg) for four months, with treadmill running to unmask mdx phenotypes and muscle harvested at 6 months of age. The nine miRNAs identified as associated with efficacy in the TLDA arrays were quantified in diaphragm muscle using qRT-PCR in this second set of mice. (Values are Graphed as % of untreated mdx expression levels; 1 outlier removed from 455-5p after significant Grubb's test; n=5 per group; ANOVA with post-hoc comparison to mdx vehicle; *$P \leq 0.05$, $P \leq 0.01$, *$P \leq 0.0005$).

Upon miRNA analysis of the validation set, all nine miRNAs were found to show a conserved response to disease and/or drug treatments (FIG. 2). One miRNA, miR-301a, showed a roughly two-fold increase with disease (P=0.002) but did not respond to drug treatment at this age. One other, miR-324-3p, showed an approximately 30-50% decrease in response to both prednisolone (P=0.0005) and vamorolone (P=0.02), but did not show a difference between mdx and wild type mice at this age. The other seven miRNAs all showed both a significant increase with muscular dystrophy (P≤0.005), and a significant decrease towards healthy wild type levels in response to both drugs (P≤0.05). This confirmed that overall, inflammatory miRNAs can be reduced by vamorolone and prednisone at different stages of dystrophy.

Example 4. Efficacy Associated miRNAs Indicate NF-κB Inhibition Mechanism

Both NF-κB and GR transcription factor ChIP-seq data from ENCODE and the established literature were queried in order to gain insight into the transcriptional regulation of each miRNA (FIG. 3). It was found that the DNA promoters of eight out of the nine identified miRNAs contain one or more DNA sites that are bound by the inflammatory transcription factor NF-κB (74). This is supported by previous reports demonstrating NF-κB-specific regulation of miR-146a (68), miR-301a (35), and miR-455-3p (48). The other miRNA, miR-324-3p, is regulated by STAT6 and in turn activates NF-κB, thereby participating in inflammatory NF-κB signaling as well (13). In contrast only one miRNA, miR-497, had a DNA promoter site bound by the GR; however, it also possessed an NF-κB binding site with its promoter region (FIG. 3). In addition to being regulated by NF-κB, when inappropriately expressed these miRNAs are associated with chronic inflammation, muscle wasting, fibrosis and adipocyte formation (5, 6, 10, 24, 35, 49, 51, 54, 66, 67, 72, 76) (refer to FIG. 3).

Figures 3A, 3B:
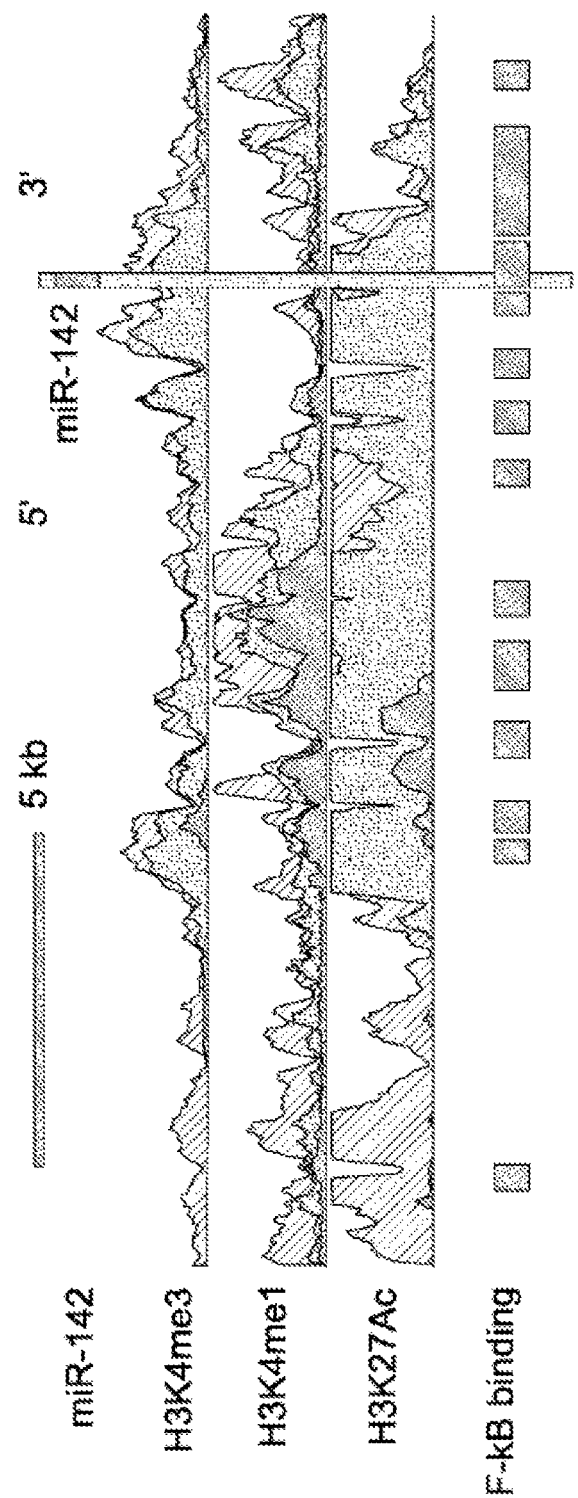

An interesting miRNA in the ChIP-seq analysis was miR-142, which was found to be in a DNA locus surrounded by at least 13 DNA elements bound directly by NF-κB (FIG. 3A-B). All 13 of these NF-κB binding sites overlapped with corresponding ChIP-seq data that detects histone modifications which correspond to active regions of transcription regulation (H3K4me3, H3K27Ac, and H3K4me1). Together, these data indicate that the upregulation of NF-κB-activated miRNAs is a signature of dystrophic muscle, and that inhibition of chronic NF-κB signaling is a signature shared by two distinctly different but effective steroidal drugs.

Figure 4A:
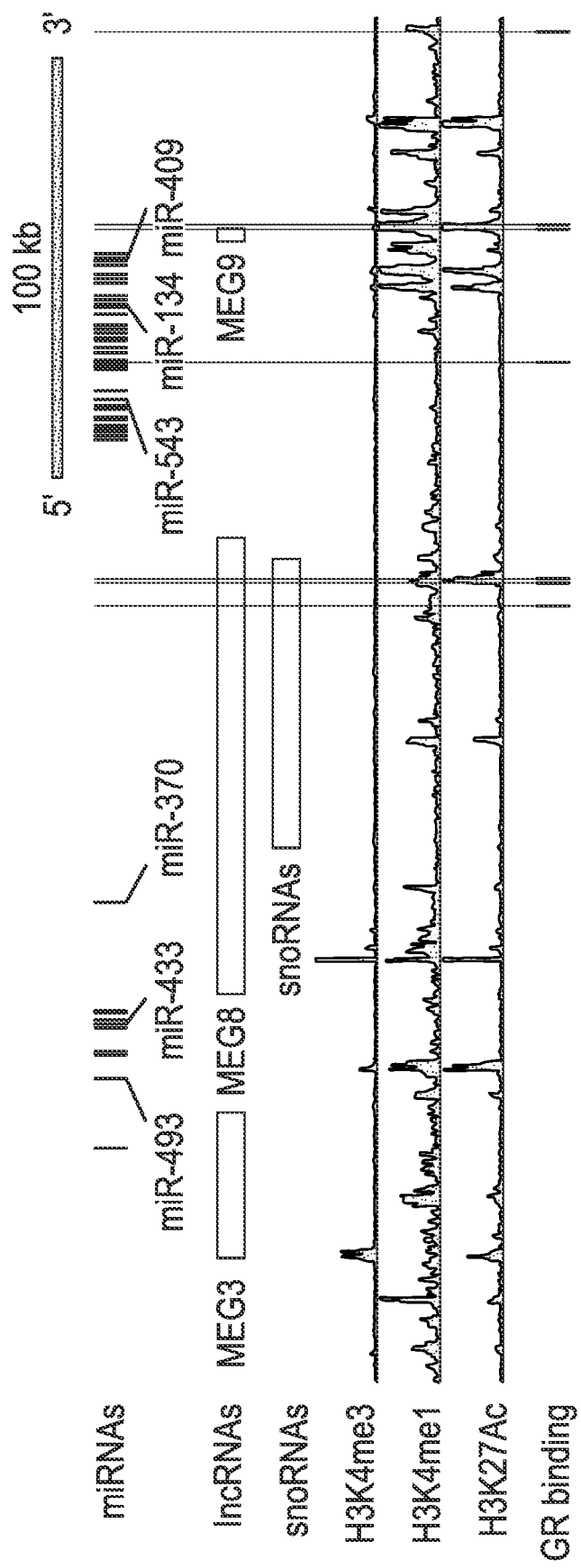

Example 5. Prednisone Activates miRNAs Associated with Side Effects and the 14q32 Locus Next, ChIP-seq data and established literature were queried to gain insight into the set of miRNAs that we found were specifically activated by prednisolone (FIG. 4). Here, the six miRNAs conserved between mouse and human, and pathways relevant to DMD or steroids were focused on. It was found that all six of these miRNAs (miR-134, miR-370, miR-409, miR-433, miR-493, miR-543) are transcribed from the same miRNA cluster on mouse chromosome 12F1. This locus is well conserved and has been extensively documented in humans where it resides on chromosome 14q32 (63). The analysis thus focused specifically on the homologous human cluster (FIG. 4A-B). It was found that this 14q32 cluster contains seven GR-DNA binding sites and is devoid of NF-κB binding sites (74). At least six of these GR binding sites corresponded to active regulatory enhancer elements. miR-543 has been previously shown to be upregulated by pharmacological glucocorticoids (11). This locus has also been observed to be upregulated by acute stress consistent with upregulation of cortisol, the body's natural glucocorticoid (43). Examining the functional roles of miRNAs upregulated by prednisolone, it was found that all are upregulated in states consistent with known side effects of prednisolone treatment. These include insulin resistance (27, 73, 81), behavior changes (43, 81), fibrosis (45, 69), increased risk for heart failure (22, 77), stress (43, 84), and hypertension (11). Together, these data indicate that prednisone specifically activated a separate set of miRNAs in a manner that is consistent with the negative side effects of currently prescribed steroids.

Figure 5:
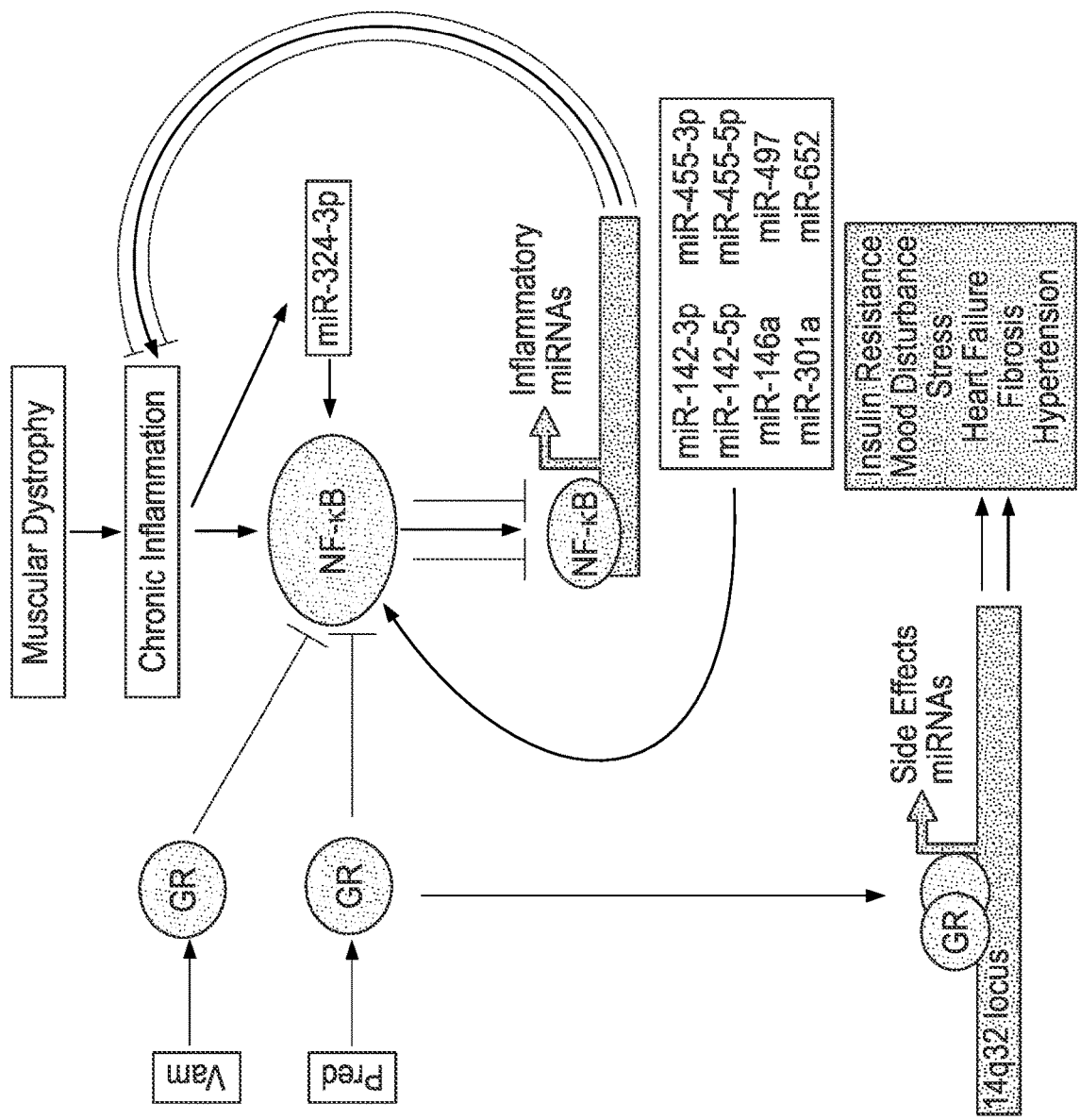
FIG. 5 is a schematic that depicts a proposed model of NF-κB and GR-regulated miRNAs in the treatment of muscular dystrophy. In DMD, inflammatory signaling promotes the chronic activation of NF-κB. This, in turn, activates NF-κB gene targets including miRNAs that regulate the expression of proteins in the NF-κB signaling pathway, creating a chronic inflammatory feedback loop. Here it was shown that the NF-κB-regulated miRNAs miR-142-3p, miR-142-5p, miR-146a, miR-301a, miR-455-3p, miR-455-5p, miR-497, and miR-652 are all elevated in dystrophic muscle. These NF-κB-regulated miRNAs are all effectively decreased by both vamorolone (Vam) and prednisone (Pred) treatment, via the GR. miR-324-3p, a miRNA that activates NF-κB in a positive feedback loop, is also decreased by both drugs. Acting through a separate pathway which can be selectively avoided by dissociative steroid chemistries, prednisone also directly causes GR-mediated transactivation of gene transcription. This results in elevated levels of a miRNA cluster located on chromosome 14q32. These microRNAs are associated with steroid side effects such as insulin resistance, hypertension, stress, and mood disturbances. (blue lines=pathways affected by vamorolone; red lines=pathways affected by prednisolone).

The Examples described herein identify a set of miRNAs that are elevated by dystrophic disease and that respond to treatment with both prednisolone and the dissociative steroid vamorolone. Of the nine miRNAs identified, three have been previously found to be elevated in DMD or mdx muscle (miR-146a, miR-142-3p and miR-142-5p), while the elevated expression of six others in dystrophic muscle are novel. Analyzing the regulation and functions of these 9 miRNAs reveals that all 9 are involved in pro-inflammatory signaling. By comparing prednisone and vamorolone, it was found that these two effective but distinctly different GR ligands share efficacy as anti-inflammatory drugs that downregulate this network of inflammatory miRNAs. In contrast vamorolone, unlike prednisolone, avoids off-target activation of miRNA transcription associated with negative steroid side effects such as insulin resistance, adrenal suppression, hypertension, and behavior issues. This is consistent with both preclinical mdx mouse and recently completed human Phase I trials which show vamorolone avoids or has substantially reduced steroidal side effects in comparison to prednisone (23, 26). Together, the Examples described herein identify a network of miRNAs associated with chronic inflammation and validates NF-κB signaling as an in vivo target of efficacious dissociative steroids (see FIG. 5 for model).

miRNAs fine tune gene expression in a multitude of signaling pathways and cellular processes. Similarly, miRNAs play a key regulatory role in the core inflammatory signaling pathway driven by NF-κB. This pathway is inappropriately upregulated in many inflammatory disorders and drives chronic muscle inflammation in DMD (7, 47). Of the miRNAs described here, eight are directly regulated by NF-κB (6, 13, 35, 48, 51, 74). Some, in turn, also regulate the initiation and resolution of the inflammatory response by targeting other key factors in the NF-κB signaling pathway. Thus, understanding the mechanisms governing miRNA dysregulation in relation to NF-κB signaling is particularly relevant to anti-inflammatory drug development in DMD. A discussion of some of the miRNAs of note follows.

miR-142 is dysregulated across multiple diseases and may provide a novel therapeutic target. As described herein, both mature miR-142 family members (miR142-3p, miR-142-5p) are elevated with dystrophic disease and their expression is quelled by both prednisolone and vamorolone treatment. miR-142-3p is highly expressed in monocytes (18) and lymphocytes (30), suggesting it is a marker of inflammatory infiltration.

miR-146a is one of the most prevalent miRNAs that appears in the literature in instances of chronic inflammatory disorders (5, 15, 34, 36, 39, 49, 51, 71). miR-146a is highly associated with inflammation, is induced by NF-κB in immune cells (68), and is also expressed directly in muscle (17). Acute miR-146a activation dampens NF-κB-mediated inflammation (68), however, prolonged induction of miR-146a exacerbates inflammation (19, 37). In diseases where chronic inflammation is present, miR-146a levels are highly elevated both in the serum as well as in tissues affected by disease (15, 34, 36, 39, 49, 51, 71). These current findings strengthen claims that miR-146a is both a promising therapeutic target and a pharmacodynamic biomarker.

Previous reports describe a role for miR-455 family members in immune signaling and muscle wasting. The transcription of miR-455-3p is controlled by NF-κB in macrophages (48). A report by Eisenberg et al. shows increased miR-455-5p in muscle biopsies from facioscapulohumeral muscular dystrophy (FSHD), limb girdle muscular dystrophy 2A, and nemaline myopathy patients (15). miR-455-3p is encoded within the intron of COL27A1 that encodes a cartilage collagen (67). Expression of miR-455 is induced by TNF-like weak inducer of apoptosis (TWEAK) which plays a key role in skeletal muscle wasting (51), and miR-455-5p is implicated in skeletal muscle atrophy (72). Interestingly, miR-455-3p is also implicated in Alzheimer's disease (32). Together, these data suggest miR-455 family members may function as a potential marker of inflammation, atrophy, and drug efficacy.

Three miRNAs found in this work specifically regulate the duration and extent of NF-κB signaling via feedback mechanisms. miR-301a was reported to be the most potent activator of NF-κB out of hundreds of miRNAs, and it exerts its actions via downregulation of the NF-κB repressing factor (NKRF) (35). The miR-301a promoter contains an NF-κB DNA consensus element, allowing a positive feedback mechanism of NF-κB signaling: miR-301a represses NKRF, in turn promoting NF-κB activation, which activates miR-301a transcription. Another identified miRNA, miR-324-3p, functions in a transcription factor-like manner to trigger NF-κB transcription via sequence-specific promoter binding (13). Elevated miR-324-3p is also observed in Inflammatory Bowel Disease (52) and is rapidly induced after focal cerebral ischemia (12) further implicating this miRNA in driving inflammatory processes. miR-497 transcription is driven by NF-κB (42). In cases of acute inflammation, miR-497 participates in a feedback mechanism by targeting IKKβ, a kinase required for NF-κB activation (42). miR-497 is associated with regenerative capacity of muscle stem cells (62) suggesting it is transcribed both in immune cells and skeletal muscle. The above reports describing miRNA involvement in NF-κB-mediated feedback focus specifically on acute inflammation; the consequences of chronic miR-301a/miR-324-3p/miR-497 overexpression on NF-κB signaling have not been documented. The data presented herein, however, suggests that persistent expression of these miRNAs drives a feed-forward loop of prolonged NF-κB activation and inflammation; this can be effectively attenuated by prednisolone and vamorolone treatment.

For the first time, it has been shown that expression of a non-coding RNA cluster in the genome is increased by prednisone treatment of dystrophic muscle. Specifically, six miRNAs have been identified within this cluster that appear to be co-regulated and located by GR-bound enhancer elements. This cluster is well conserved across mammalian species and is among the largest polycistronic clusters. It is best characterized in humans where this cluster is on chromosome 14q32 and encodes 54 miRNAs (63). All six of the miRNAs increased from this locus are also known to be elevated in conditions that are consistent with prednisone side effects, including insulin resistance (27, 76, 81), mood disturbances (43, 81), stress (43, 84), and hypertension (11). Since prednisolone increases mdx heart fibrosis (9) and heart failure is a leading cause of death in DMD, increases here in miR-433 and miR-134 are interesting as they are a regulator of heart fibrosis and a serum biomarker indicative of increased risk of heart failure, respectively (22, 69). In addition to miRNAs, the 14q32 locus encodes two long non-coding RNAs (lncRNAs) which also may have functions that are relevant to DMD and its treatment with steroids. These lncRNAs are maternally expressed gene 8 (MEG8) and MEG3. MEG8 is preferentially expressed in skeletal muscle and is increased in muscle hypertrophy as observed in callipyge (or "beautiful buttocks") sheep (4). MEG3 expression is enriched in cardiac fibroblasts, and intriguingly the inhibition of MEG3 prevents heart fibrosis and diastolic dysfunction via regulation of matrix metalloproteinase 2 (MMP2) in a mouse model of heart damage (53). Moving forward, it will be interesting to determine the full extent of upregulation at the 14q32 locus upon prednisone treatment, and the health impact that this may have on muscular dystrophy patients.

One of the miRNAs identified in the discovery set of samples, miR-301a, did increase with disease but did not show a response to either drug in the validation set of samples. This could be due to a switch being made in its transcriptional control as the mdx disease transitions from a younger and more inflammatory stage, to an older and more fibrotic stage. In addition to NF-κB, the transcriptional promoter of miR-301a is affected by pathways that increase with fibrosis and with age, via transcription factors within the TGF-β (7, 55, 56, 74, 83) and β-catenin (78, 79) pathways, respectively. Since fibrosis increases with mdx age, particularly in the diaphragm, a shift to combinatorial control of miR-301a expression by TGF-β and/or β-catenin pathway transcription factors could circumvent the effects of GR ligands on NF-κB. Since miR-301a increases NF-κB signaling and in some instances appears to avoid inhibition by GR ligands, it will be interesting to further study this miRNA as inhibitors of it could provide a mechanism to further enhance anti-inflammatory efficacy through a co-therapy strategy.

There is growing enthusiasm with regards to targeting miRNAs as therapeutic agents via antisense technology. There are currently nine miRNA therapeutics that are in preclinical or clinical development, reviewed in (8). The miRNAs described here may be a defining signature of chronic inflammation and inappropriate immune cell-muscle cross talk. These findings provide a rationale for the development of miRNA inhibition agents as a potential strategy to treat diseases of chronic inflammation.

In broader terms, this work highlights muscular dystrophy as a good scientific system to provide insights into chronic inflammation pathways relevant to a much larger group of disorders. Elevated NF-κB signaling is present in dystrophic muscle even in DMD infants, years before the onset of symptoms (7). It was found that prednisone, the DMD standard of care and one of the most widely prescribed drugs in the world, shares efficacy with a more selective steroid by inhibiting this chronically elevated NF-κB signaling in mdx mice. Here nine miRNAs are identified that appear to largely behave as a set, all increasing with dystrophy and responding to treatment with drugs that share NF-κB inhibition as a mechanism of action. At least one of these miRNAs, miR-146a, shows conserved behavior across species with muscular dystrophy (mouse, dog and human) (17). It was also found that miR-146a shows conserved drug responses between tissue and serum (47), providing a non-invasive serum biomarker that responds to both disease and treatment. Moving forward, it will be important to determine if the other miRNAs here can provide serum biomarkers as well, and if these miRNAs can be targeted as a next-generation approach to treat diseases of chronic inflammation.

Example 6. miRNA Dysregulation in the Serum of Duchenne Muscular Dystrophy Patients Summary: Serum miRNAs are emerging as promising therapeutic targets and biomarkers. Applicants identified panels of miRNAs that increase in response to either inflammation or steroid treatment in muscle from the mdx mouse model of Duchenne muscular dystrophy (DMD). Here Applicants performed miRNA profiling in human serum from DMD patients and healthy controls. Approximately 750 miRNAs were quantified. Applicants' data show that the same miRNA panels which are tied to inflammation, muscle disease and steroid response in mdx mice show a conserved effect of significantly different expression in the serum of DMD patients versus healthy controls. These data validate the miRNA panels as a feature of human DMD, illustrate conservation of the mechanisms of their regulation, and confirm their differential expression across both muscle and serum.

Introduction: Serum miRNAs are rapidly emerging as objective biomarkers that can reflect disease state and/or drug response in human patients. They have become particularly attractive for this field due to their high stability, their conservation across species, and their ability to reflect specific signaling pathways or tissues that are being affected by disease. In Duchenne muscular dystrophy (DMD), muscle-specific miRNAs (or "myo-miRs") have been detected as differentially expressed in human serum. Recently, Applicants identified several panels of miRNAs that are differentially affected in muscle from the mdx mouse model of DMD versus healthy control muscle. Bioinformatic analyses of these miRNA panels indicate that they are involved with inflammation, muscle hypertrophy, and/or steroid responses.

The primary function established for miRNAs is to affect gene expression pathways. They typically do this by binding to the 3' UTR of messenger RNA and inhibiting the translation of the bound transcripts into protein. This mechanism provides a pathway by which new types of therapeutics can be developed. By interfering with the function of specific miRNAs, new treatments can be developed that affect their target gene expression pathways Several strategies can be pursued to do this. One is to develop small molecule inhibitors that specifically bind to and inhibit or cause degradation of the miRNA target. Another strategy is to develop anti-sense oligonucleotide (ASO)-based methods that can specifically bind to and inactivate a miRNA. These methods can use anti-sense oligos consisting of various chemistries such as morpholino, phosphorodiamidate morpholino oligomer (PMO), peptide-conjugated PMO (PPMO), tricyclo-DNA, etc. Anti-sense "sponges" for miRNAs, as well as Tough Decoy (TuD) RNA constructs, are other variations of this strategy where oligo sequences are modified to optimize their effects as inhibitors. Several delivery methods are available or in development for the delivery of miRNA-targeting therapeutics as well. One route they can be administered is through IV injection. Additional routes include adeno-associated virus (AAV) vectors which deliver constructs that express anti-sense based therapeutics for expression within host or patient cells. Additional administration routes in development include exosomal delivery, nanotech-based drug delivery, and the use of macrophage cell types to deliver oligo-based therapeutics.

Previously, Applicants have identified panels of mechanism-defined miRNAs that are dysregulated in inflammatory and/or muscle disease states. Here, Applicants detect and quantify these same miRNAs in human DMD serum versus healthy controls. Applicants find that many of the same miRNAs dysregulated in mdx mouse muscle are also dysregulated in human DMD serum. These miRNAs have functions in inflammation, muscle hypetrophy or disease, and steroid side effects. Applicants' findings here show conservation of both the disease mechanism of miRNA dysregulation, as well as conservation of the miRNAs as drug targets across species. Further, it indicates that the miRNAs may be therapeutically targeted in serum as well as in affected tissues.

Materials and Methods:

Serum was isolated from 36 human patients. This included 10 healthy controls and 26 patients with DMD. 21 of the DMD patients were taking glucocorticoid steroids (prednisone, deflazacort) at the time of serum sampling. Serum miRNAs were then isolated using a modified TRIzol protocol with overnight isopropanol precipitation at −20° C. RNA was reverse transcribed using a High Capacity cDNA Reverse Transcription Kit with RNase Inhibitor (Thermo Fisher Scientific). Expression of approximately 750 miRNAs was assayed using quantitative polymerase chain reaction (qPCR) based TaqMan Low-Density Array (TLDA) Cards Set v3.0, with both the A and B cards included (Thermo Fisher Scientific). Data was analyzed using ThermoFisher Cloud software with the Relative Quantification Application tool, with comparison of DMD to healthy controls. The miRNA panels previously discovered in mdx muscle studies (consisting of inflammatory, muscle disease, and steroid response "sets" of miRNAs) were specifically examined for validation in this experiment.

Results:

Applicants assayed expression of 750 miRNAs in human serum from 26 DMD patients and 10 healthy controls. Applicants then examined the expression of miRNA panels previously established in mdx mouse muscle, to determine both 1) their ability to be detected in human serum, and 2) to examine differences in their expression levels between DMD patients versus healthy controls.

Figure 6:
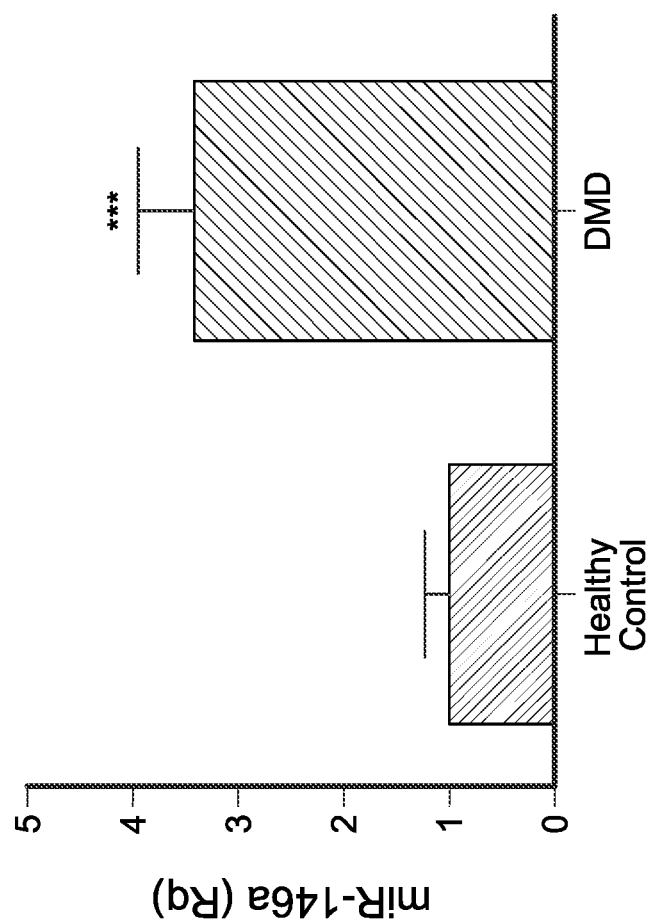
FIG. 6 is a graph that depicts miR-146a is increased in serum from human DMD patients. Serum was collected from 36 individuals, which included 26 DMD patients and 10 healthy controls. Levels of miRNAs were assayed by TLDA array cards. miR-146a was detected in all 36 samples. DMD patients showed a significantly higher level of miR-146a expression than healthy controls, consistent with our findings in mdx muscle and with the chronic inflammation disease state present in DMD. (p=0.003; two-tailed Students t-test).
Figure 7:
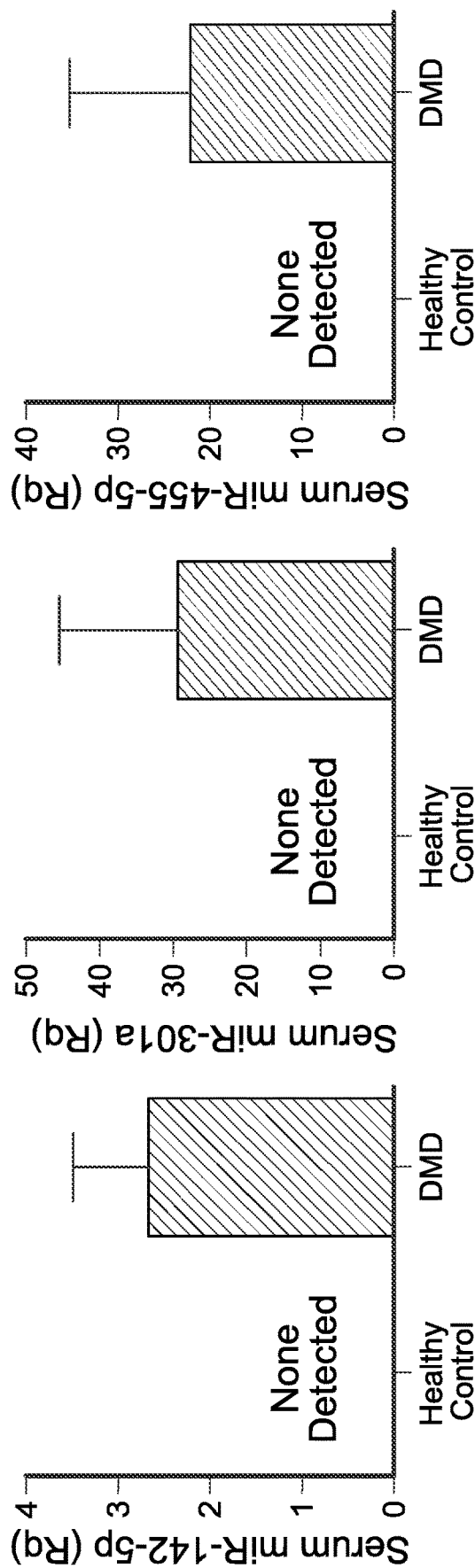
FIG. 7 is a panel of graphs that depict inflammatory miRNAs are expressed at levels above detection thresholds more frequently in serum from DMD patients than in healthy controls. Serum was collected from 36 individuals, which included 26 DMD patients and 10 healthy controls.

The inflammatory panel of miRNAs (miR-146a, miR-142-5p, miR-301a, miR-455-5p) showed a conserved pattern of expression in human serum. First, miR-146a was detected in all patients (FIG. 6). It showed a significant increase in DMD patients versus healthy controls ($p<0.0005$), which is consistent with its pattern of expression detected previously in mdx muscle. The other three inflammatory miRNAs examined here all showed a similar pattern. Each of these three inflammatory miRNAs (miR-142-5p, miR-301a, miR-455-5p) were detected in DMD patients, however no healthy control patient expressed detectable levels of any of these three (FIG. 7). This is consistent with a much greater expression in an inflammatory disease state (DMD) than in a healthy baseline state.

Next, Applicants examined the miRNA panel which consists of miRNAs encoded by the human 14q32 mega cluster of non-coding RNAs. Applicants previously found this panel to be increased in mdx muscle, both 1) in response to muscle disease, and 2) in response to steroid treatment. Of these, three (miR-134, miR-370, miR-433) showed a pattern of expression similar to the inflammatory miRNAs in FIG. 2. Each of these three miRNAs were detected in a majority (n≥20) of DMD patients (FIG. 8), however they were rarely detected in health control patients (n=1 to 2 patients). This is consistent with both 1) their increased expression during states of muscle disease/hypertrophy, and 2) their increased expression in response to glucocorticoid steroids (21 of the 26 DMD patients were taking glucocorticoids).

Discussion: Applicants' data identify a set of mechanism-defined miRNAs that are elevated in DMD as well as in other diseases featuring inflammation, muscle disease, or glucocorticoid steroid treatments. Of the miRNAs Applicants identified, all have been demonstrated to be elevated in the dystrophic muscle of animal models of DMD. At least seven of these have now also been shown to be both detectable and dysregulated in human serum from DMD patients versus healthy controls. Moving forward, these miRNAs can be divided into three panels, each of which provides a valuable new set of therapeutic targets. The inflammatory panel of miRNAs Applicants identified are regulated by the inflammatory transcription factor NF-κB. As many of them also regulate NF-κB expression, these miRNAs are found to participate in a feedback loop that maintains a state of chronic inflammation. Applicants find these are elevated in animal models of DMD and this elevated expression is conserved in human serum. Additionally, Applicants have found several of these miRNAs to be increased in patients with Becker muscular dystrophy and with inflammatory bowel disease, and in myositis mouse models. Together, this information indicates the miRNA panel Applicants identified is a general contributor to inflammatory diseases. It is therefore a therapeutic target for DMD as well as other inflammatory diseases, particularly those characterized by elevated NF-κB signaling. Inhibition of these miRNAs could be applied as a stand-alone therapy to treat inflammatory pathology, or in combination with current anti-inflammatory treatments as a precision medicine strategy to enhance their efficacy.

Two of the miRNA panels Applicants identified are encoded by the same genomic locus, which is the human 14q32 mega cluster of non-coding RNAs. Dysregulation of this 14q32 cluster has not been previously described in DMD, but is known to be associated with muscle diseases and with muscle hypertrophy such as in "callipyge" sheep, a breed where sheep accumulate excess muscle instead of fat around the pelvis. Here Applicants find for the first time that expression of a number of miRNAs distributed across this genomic locus is elevated by muscular dystrophy in both mdx muscle and DMD serum, in comparison to healthy controls. Therefore, treatments that seek to decrease expression of miRNAs and non-coding RNAs from this locus provide a novel line of therapeutics for DMD and other muscle diseases.

Additionally, Applicants find expression of miRNAs at the 14q32 locus is further increased in prednisone-treated versus vehicle-treated mdx muscle. Consistent with this, Applicants find these same miRNAs are increased in human serum from DMD patients, the majority of which were currently taking prescription prednisone during the time samples were obtained. Bioinformatic analyses of these same miRNAs indicate that each one is known to be increased in conditions related to known side effects of glucocorticoid drugs such as prednisone, deflazacort, dexamethasone, etc. These side effects include insulin resistance, diabetes, stress, heart failure, fibrosis, heart fibrosis, depression, mood disturbances, hypertension, and osteosarcoma. Accordingly, treatments that decrease expression of this 14q32 non-coding RNA mega cluster, and/or these specific miRNAs, provide a novel line of therapeutics which may reduce or eliminate the side effects of elevated or chronic glucocorticoids. Since glucocorticoids represent one of the most widely prescribed drug classes in the world, this new line of therapeutics provides 1) a valuable co-therapy that can be used to improve steroid treatments, 2) a co-therapy that can be used to increase steroid dosage by improving safety, and 3) a precision medicine-based strategy that could be used in a wide array of diseases which are treated with chronic or high dose glucocorticoids (DMD, inflammatory bowel disease, arthritis, asthma, multiple sclerosis, etc.).

This work identifies three panels of miRNAs which each behave as a set to maintain pathogenic gene expression pathways, and which therefore represent novel drug targets. The three miRNA groups identified participate in the pathogenesis of inflammation, muscle disease, and/or debilitating corticosteroid side effects. These miRNAs can be targeted using strategies including but not limited to anti-sense oligos, small molecules, decoys, and AAV-based methods. By inhibiting these miRNA targets either as a stand-alone therapy or in combination with other anti-inflammatory therapies such as glucocorticoid steroids, new and improved treatments for inflammatory diseases, for muscle diseases, and for other diseases treated by corticosteroids can be provided.

Example 7. Muscle Function in Mdx Mice Treated with a miR-146a Inhibitor

MicroRNAs have emerged as a promising therapy for muscle disorders and inflammatory disorders as multiple studies have shown that they are highly dysregulated in states of chronic inflammation. We previously discovered a set of inflammatory, NFκB-activated microRNAs(miR-146a, miR-146b and miR-223, miR-142-3p, miR-142-5p, miR-652, miR-455-3p, and miR-455-5p) that are elevated in Duchenne Muscular Dystrophy (DMD) and Becker Muscular Dystrophy (BMD)(17)We also found muscle expression of miR-146a/miR-146b/miR-223, increases with DMD disease severity and anti-inflammatory (steroidal ligand) treatment reduces all identified microRNAs in dystrophic muscle (17) Elevated levels of these miRNAs have also been described in other inflammatory diseases. Together this suggests that these NFκB-regulated mRNAs may initiate and perpetuate chronic inflammatory signaling in inflammatory muscle diseases such as DMD and BMD. These converging roles provide a unique opportunity to therapeutically target this set of miRNAs in inflammatory muscle disorders.

Figure 9A:
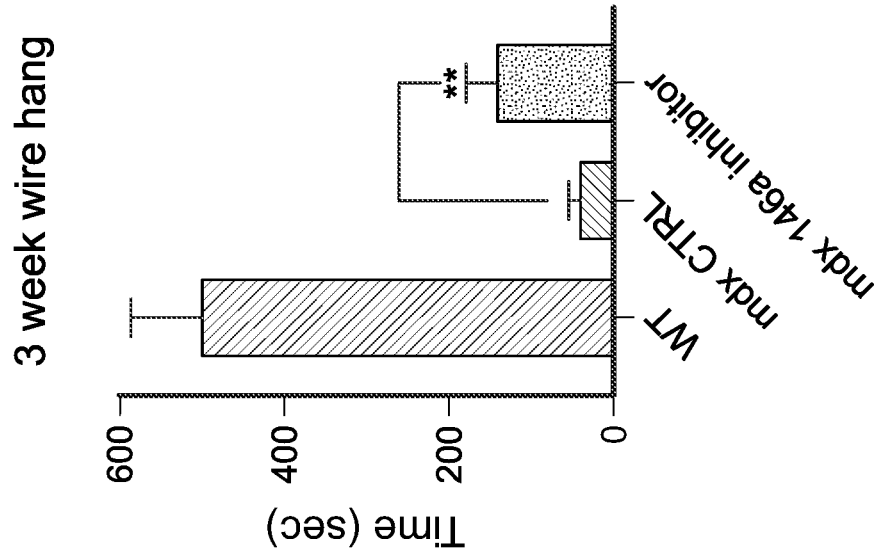

We first tested miR-146a inhibition in dystrophic mice to demonstrate proof-of principle. We chose miR-146a as it is the most highly and consistently upregulated microRNA in inflammatory diseases within the described set. In this initial experiment we wanted to determine feasibility of miR-146a inhibition as a potential therapeutic, testing the hypothesis that miR-146 inhibition (miR-146aI) would reduce inflammation and therefore enhance muscle function in mdx (dystrophic) mice. Because miR-146a is upregulated from birth in mdx mice, we chose to perform inhibitor injections from 1 week of age (12.5 mg/kg, vivo-morpholino chemistry, intraperitoneal injection route). miR-146aI injections (or control inhibitor injections, "CTRLI") were performed bi-weekly from week 1 to week 7 (12 injections total). Saline-injected WT mice were used as control and received one saline injection for each injection experimental groups received. We analyzed muscle strength using a simple wire hang test [2]. At both 3 and 6 weeks of age, miR-146aI-treated mice showed improved hang time (FIG. 9a, b). This data suggests miR-146a inhibition could improve muscle function in dystrophic mice.

Method Details:

Mice. All mouse studies were performed in adherence to the NIH Guide for the Care and Use of Laboratory Animals. All experiments were conducted according to protocols that were within the guidelines and approval of the Institutional Animal Care and Use Committee of Children's National Medical Center. All mdx (C57BL/10ScSn-Dmd<mdx>/J) and wild type control (C57BL/10ScSnJ) mice were obtained from The Jackson Laboratory (Bar Harbor, Me.) and were bred in-house.

Inhibitor injections. Vivo-morpholinos were resuspended in sterile water to make a stock concentration of 3.125 mg/mL. Injections were performed using 4 μl of morpholino per gram body weight of the mice at time of injection. Mdx mice were injected with a miR-146a inhibitor vivo-morpholino or a CTRL-vivo morpholino; age-matched Wild-type control mice were given an equivalent saline injection. 31-gauge insulin syringes were used to inject mice bi-weekly into the interperitonal cavity, twice a week starting at 7 days of age. To measure muscle strength a wire hang test was perform at 3 and 6 weeks of age as previously described (85).As a cutoff, WT mice were removed from wire after 10 m (600 sec).

Example 8: Inflammatory microRNAs are Elevated in a Mouse Model of Myositis

Introduction: The idiopathic inflammatory myopathies are a group of autoimmune diseases that are characterized by proximal muscle weakness, and skeletal muscle inflammation and systemic pain. These diseases affect both adults and children; however, in general, women are more likely to be affected by these diseases. Class I major histocompatibility complex (MHC) is overexpressed in skeletal muscle from all types of idiopathic inflammatory muscle diseases including juvenile dermatomyositis, polymyositis and inclusion body myositis. The conditional transgenic model of myositis (termed HT mice) drives muscle-specific overexpression of MHC Class I and exhibits phenotypic and immunological features that parallel that of these muscle diseases(86). Interestingly, similar pathological observations have been made in Duchenne muscular dystrophy, sometimes complicating the diagnosis of myositis without a DNA diagnosis. Given this, we hypothesized that HT myositis mouse muscle may similarly have elevated levels of the inflammatory set of microRNAs that we have previously observed in DMD and BMD.

Study design/methods: The generation and characterization of the mouse model, referred to at the HT myositis mouse, has been previously described [3]. In this study, we utilized all female mice because the disease phenotype is more severe than age-matched males. Mice were sacrificed at peak disease age (from 10-14 weeks) and we analyze the quadricep muscle, as this muscle is severely affected. Mice were classified as "severe" or "mild" based on their histopathology, weight (≤16 g at time of sacrifice) and the extent of transgene (MHC Class I) expression (FIG. 10a). Based on the classification of "mild" or "severe," we analyzed muscles for expression of inflammatory microRNAs. Severe mice showed significant upregulation of miR-146a, miR-146b and miR-223, miR-142-3p, miR-142-5p, miR-652, miR-455-3p, and miR-455-5p (FIG. 10B-H) as compared to both CTRL and mild mice. These results suggest inflammatory microRNA dysregulation may be a "fingerprint" of inflammatory muscle disorders.

Method Details:

Mice. All mouse studies were performed in adherence to the NIH Guide for the Care and Use of Laboratory Animals. All experiments were conducted according to protocols that were within the guidelines and approval of the Institutional Animal Care and Use Committee of Children's National Medical Center. "HT" myositis mice were bred and maintained in house. As a control age-match mice containing only the T transgene were utilized.

qRT-PCR of mRNAs and miRNAs. Specific miRNAs were quantified in the validation set of samples using individual TaqMan assays specific for each miRNA (ThermoFisher; Carlsbad, Calif.) according to the manufacturer's protocol. Total RNA was converted to cDNA using multiplexed RT primers and High Capacity cDNA Reverse Transcription Kit (ThermoFisher; Carlsbad, Calif.). For miRNA, cDNA was pre-amplified using TaqMan PreAmp Master Mix (ThermoFisher; Carlsbad, Calif.). For mRNA, no pre-amplification was performed. The miRNAs were then quantified using individual TaqMan assays on an ABI QuantStudio 7 real time PCR machine (Applied Biosystems; Foster City, Calif.).

Sectioning and H+E. 8 µm sections of were cut from frozen mouse quadricep muscles. Sections were air-dried and then Hematoxylin and eosin was performed by the Children's National Medical Center Pathology Core using a HistoCore SPECTRA ST Stainer. Stained slides were imaged on the VS120 Virtual Slide Microscope (Olympus) at 20× magnification.

Example 9. Treatment of Inflammation Through Administration of Antisense RNA to miR-146a, miR-142, and miR-301a Antisense oligonucleotides complementary to miR-146a, miR-142, and miR-301a are synthesized and tested for their ability to reduce miR-146a, miR-142, and miR-301a activity after inflammation.

Adeno-associated virus (AAV) vectors are constructed that express inhibitors for miR-146a, miR-142, and miR-301a. These AAV vectors are then injected into mouse models of inflammatory diseases and tested for improvements (e.g., models of muscular dystrophy and inflammatory bowel disease).

For any inhibitors that show a benefit, antisense oligonucleotide drugs are designed for intravenous injections in the same mouse models as above.

Example 10. Treatment of Steroid Side Effects Through Administration of Antisense RNA to miR-134, miR-370, and miR-409 and Co-Treatment with Prednisone Antisense oligonucleotides complementary to miR-134, miR-370, and miR-409 are synthesized and tested for their ability to reduce miR-134, miR-370, and miR-409 activity due to prednisone treatment.

Adeno-associated virus (AAV) vectors are constructed that express inhibitors for miR-134, miR-370, and miR-409. These AAV vectors are then injected into mice along with a co-injection of prednisone and tested for improvements to steroid side effects.

For any inhibitors that show a benefit, antisense oligonucleotide drugs are designed for intravenous injections in the same mice as above.

Example 11. Determination of Muscle Disease miRNA Targets

A mouse mdx line is bred with a mouse line that has a deletion of the 14q32 genomic locus, which is hyperexpressed in muscle diseases. Another mouse mdx line is bred with a mouse line having long non-coding RNAs deleted (e.g., MEG3, MEG8, and/or MEG9). If this mouse line shows a benefit to muscular dystrophy, microRNA targets within the 14q32 locus would be identified and tested with antisense inhibitors of the targets.

Example 12. Treatment of Inflammation Through Administration of Modulators if miRNAs Implicated in Inflammation and/or Muscle Disease Small molecules capable of modulating the regulation of gene expression by the presence of miRNAs can be used to treat and/or prevent an underlying condition caused by or exacerbated by the presence of the miRNAs or the long non-coding RNAs in the system. Therapeutically effective amounts of the following compounds will be tested to show that improvement of inflammatory disease and/or muscle disease can occur by silencing or other neutralizing the effects of the miRNAs present in subjects suffering from the disorders.

TABLE 6

Inhibitors of the biological effect of miRNA sequences.

| Compound | Structure | Activity |
| --- | --- | --- |
| 2'-Deoxy-5-fluorocytidine | 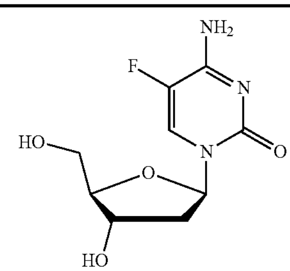 | DNA methyltransferase (DNMT) inhibitor |

TABLE 6-continued

Inhibitors of the biological effect of miRNA sequences.

| Compound | Structure | Activity |
| --- | --- | --- |
| 5-Aza-2'-deoxycytidine (Decitabine) | 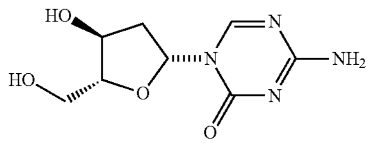 | DNMT inhibitor |
| 5-Azacytidine | 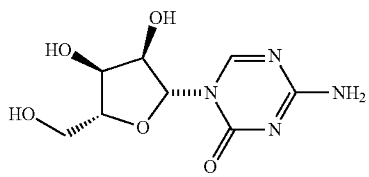 | DNMT inhibitor |
| 6-Thioguanine | 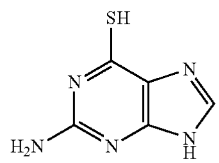 [SMILES: Nc1nc(S)c2nc[nH]c2n1] | DNMT inhibitor |
| AK-7 | 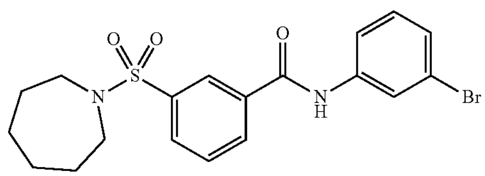 [SMILES: O=C(Nc1cccc(Br)c1)c1cccc(S(=O)(=O)N2CCCCCC2)c1] | NAD-dependent deacetylase sirtuin 2 (SIRT2) inhibitor |
| Apicidin | 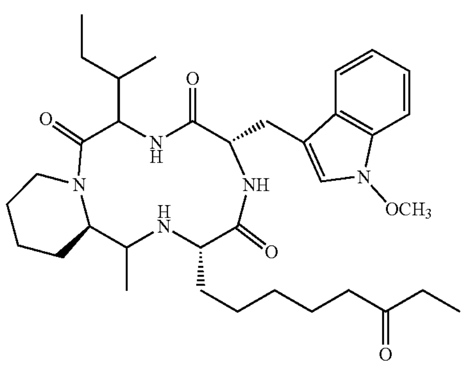 [SMILES: CCC(=O)CCCCC[C@@H]1NC(C)[C@H]2CCCCN2C(=O)C(C(C)CC)NC(=O)[C@H](Cc2cn(OC)c3ccccc23)NC1=O] | Histone deacetylase (HDAC) inhibitor |
| Arecoline hydrobromide | 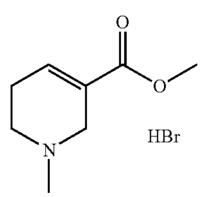 | Acetyl-CoA acetyltransferase 1 (ACAT1) inhibitor |
| AS-8351 | 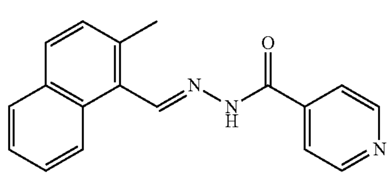 [SMILES: Cc1ccc2ccccc2c1/C=N/NC(=O)c1ccncc1] | Lysine-specific demethylase 5B (KDM5B) Inhibitor |

TABLE 6-continued
Inhibitors of the biological effect of miRNA sequences.
| Compound | Structure | Activity |
|---|---|---|
| BIX-01294 | 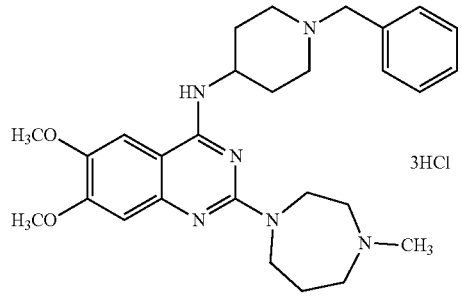 [SMILES: COc1cc2nc(N3CCCN(C)CC3)nc(NC3CCN(Cc4ccccc4)CC3)c2cc1OC] | G9a histone methyltransferase/ GLP histone methyltransferase (G9a/GLP) inhibitor |
| BML-210 | 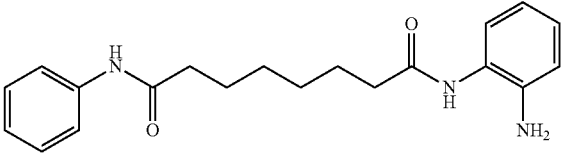 [SMILES: Nc1ccccc1NC(=O)CCCCCCC(=O)Nc1ccccc1] | HDAC inhibitor |
| BML-278 | 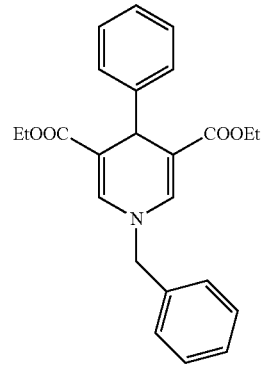 [SMILES: CCOC(=O)C1=CN(Cc2ccccc2)C=C(C(=O)OCC)C1c1ccccc1] | SIRT1 activator |
| C646 | 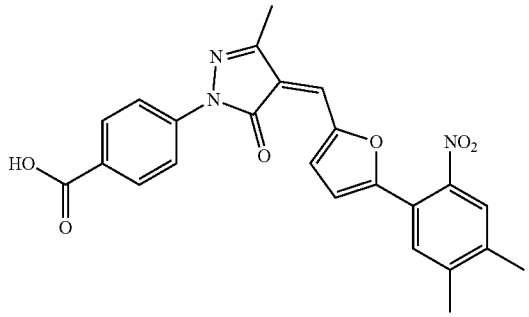 [SMILES: CC1=NN(c2ccc(C(=O)O)cc2)C(=O)/C1=C\c1ccc(-c2cc(C)c(C)cc2[N+](=O)[O-])o1] | Histone acetyltransferase P300/CBP inhibitor |

TABLE 6-continued

Inhibitors of the biological effect of miRNA sequences.

| Compound | Structure | Activity |
|---|---|---|
| Chaetocin | 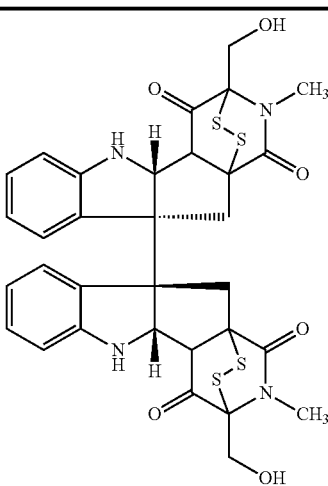 | SU(VAR)3-9 methyltransferase inhibitor |
| CI-994 | 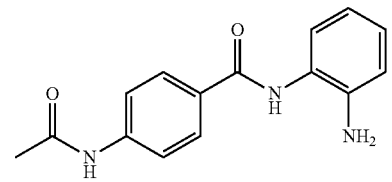 [SMILES: CC(=O)Nc1ccc(C(=O)Nc2ccccc2N)cc1] | HDAC inhibitor |
| CPTH2 | 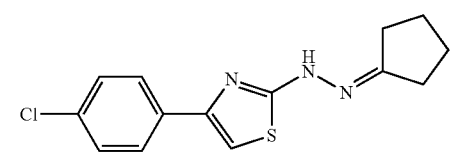 [SMILES: Clc1ccc(-c2csc(NN=C3CCCC3)n2)cc1] | Gcn5P histone acetyltransferase inhibitor |
| CTPB | 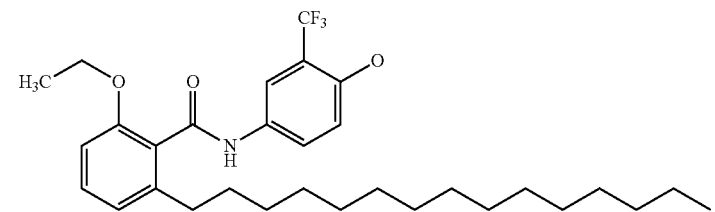 [SMILES: CCCCCCCCCCCCCCCc1cccc(OCC)c1C(=O)Nc1ccc(O)c(C(F)(F)F)c1] | p300 activator |
| CUDC-101 | 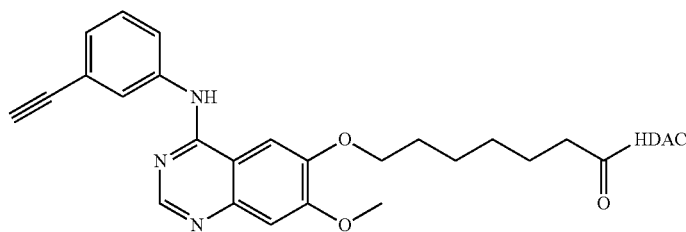 | HDAC and receptor tyrosine kinase inhibitor |
| Daminozide | 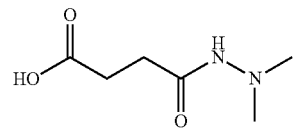 | KDM2/KDM7 JmjC subfamily of histone demethylase inhibitor |
| DMOG | 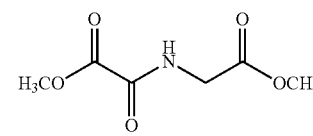 | Prolyl hydroxylase domain-containing protein (PHD/JMJD2A) inhibitor |

TABLE 6-continued

Inhibitors of the biological effect of miRNA sequences.

| Compound | Structure | Activity |
| --- | --- | --- |
| Embelin | 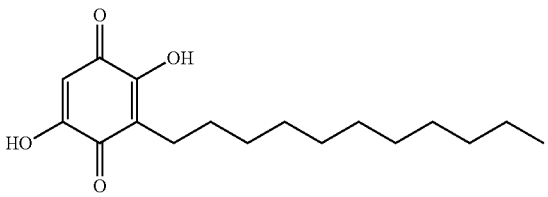 [SMILES: CCCCCCCCCCCC1=C(O)C(=O)C=C(O)C1=O] | Lysine acetyltransferase (PCAF) inhibitor |
| EX-527 | 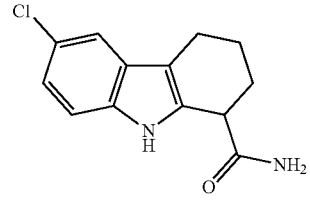 [SMILES: NC(=O)C1CCCc2c1[nH]c1ccc(Cl)cc21] | SIRT1 inhibitor |
| FK-866 HCl | 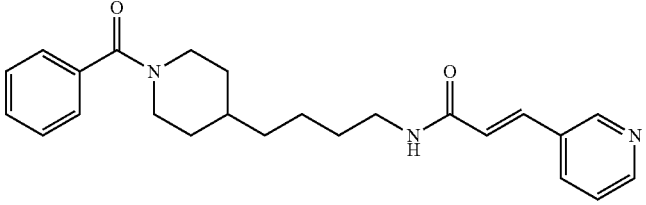 [SMILES: O=C(/C=C/c1cccnc1)NCCCCC1CCN(C(=O)c2ccccc2)CC1] | Nicotinamide phosphoribosyl-transferase (Nampt) inhibitor |
| Garcinol | 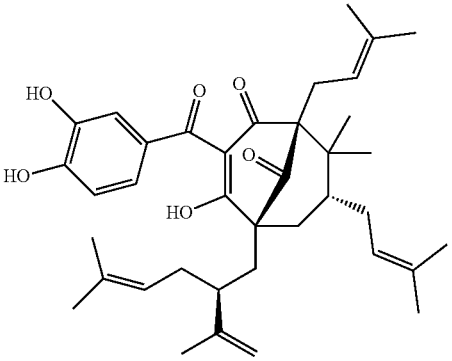 [SMILES: C=C(C)[C@@H](CC=C(C)C)C[C@@]12C[C@@H](CC=C(C)C)C(C)(C)[C@@](CC=C(C)C)(C(=O)C(C(=O)c3ccc(O)c(O)c3)=C1O)C2=O] | p300/pCAF inhibitor |
| GSK-J1 (cell impermeable) | 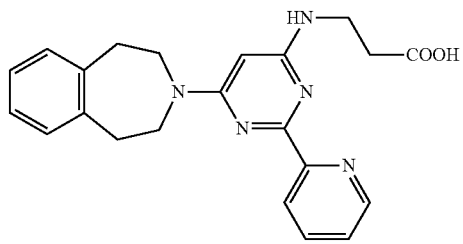 [SMILES: O=C(O)CCNc1cc(N2CCc3ccccc3CC2)nc(-c2ccccn2)n1] | Jumonji H3K27 histone demethylase (JMJD3/UTX) inhibitor |
| GSK-J4 (cell permeable) | 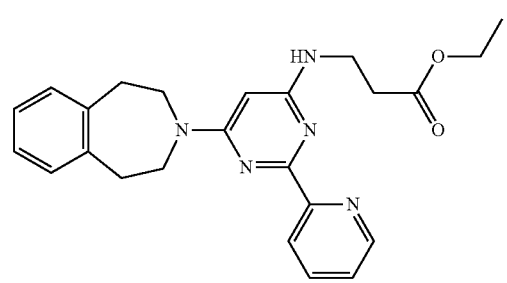 [SMILES: CCOC(=O)CCNc1cc(N2CCc3ccccc3CC2)nc(-c2ccccn2)n1] | JMJD3/UTX inhibitor |

TABLE 6-continued

Inhibitors of the biological effect of miRNA sequences.

| Compound | Structure | Activity |
| --- | --- | --- |
| HPA (Hexyl-4-pentynoic acid) | 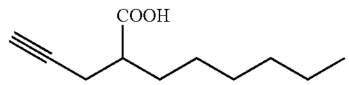 | HDAC inhibitor |
| IOX1 | 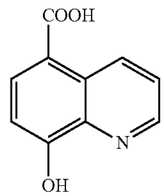 [SMILES: O=C(O)c1ccc(O)c2ncccc12] | JMJD family inhibitor |
| JIB-04 | 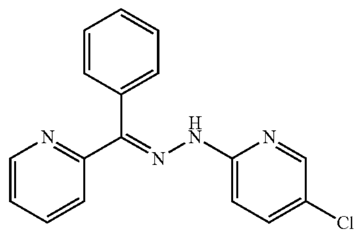 [SMILES: Clc1ccc(N/N=C(\c2ccccc2)c2ccccn2)nc1] | JMJD family inhibitor |
| JQ1 (+/−) | 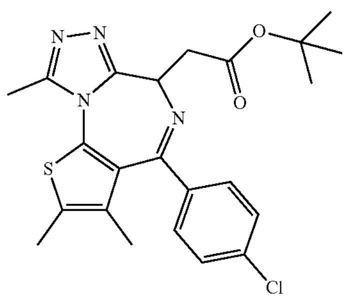 [SMILES: Cc1sc2c(c1C)C(c1ccc(Cl)cc1)=NC(CC(=O)OC(C)(C)C)c1nnc(C)n1-2] | BET bromodomain inhibitor |
| Mithramycin A | 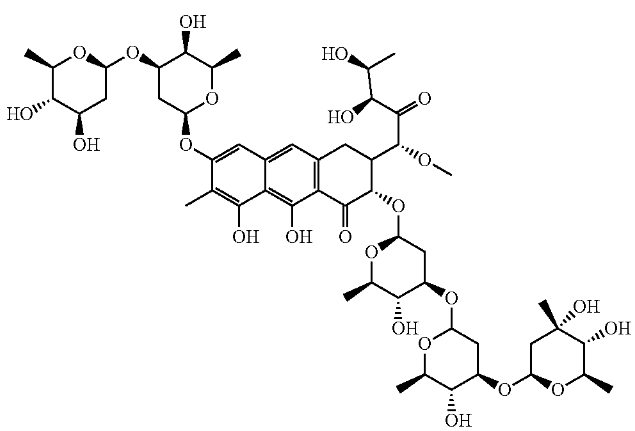 [SMILES: CO[C@@H](C(=O)[C@@H](O)[C@H](C)O)C1Cc2cc3cc(O[C@H]4C[C@@H](O[C@H]5C[C@@H](O)[C@H](O)[C@@H](C)O5)[C@@H](O)[C@@H](C)O4)c(C)c(O)c3c(O)c2C(=O)[C@H]1O[C@H]1C[C@@H](OC2C[C@@H](O[C@H]3C[C@](C)(O)[C@H](O)[C@@H](C)O3)[C@H](O)[C@@H](C)O2)[C@H](O)[C@@H](C)O1] | DNMT1 inhibitor |
| ML-324 | 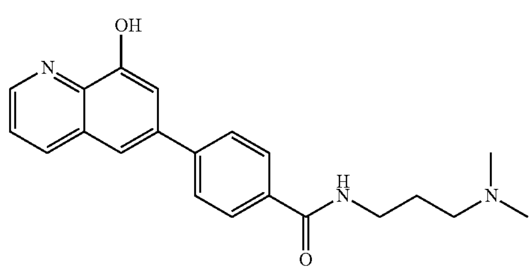 [SMILES: CN(C)CCCNC(=O)c1ccc(-c2cc(O)c3ncccc3c2)cc1] | JMJD2 inhibitor |

TABLE 6-continued

Inhibitors of the biological effect of miRNA sequences.

| Compound | Structure | Activity |
| --- | --- | --- |
| Mocetinostat | 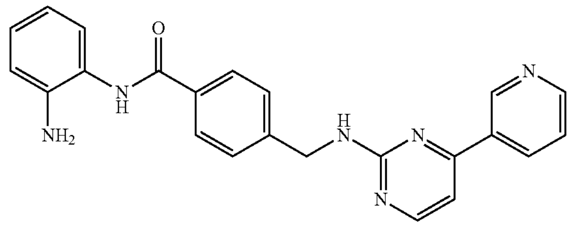 [SMILES: Nc1ccccc1NC(=O)c1ccc(CNc2nccc(-c3cccnc3)n2)cc1] | HDAC inhibitor |
| MS-275 | 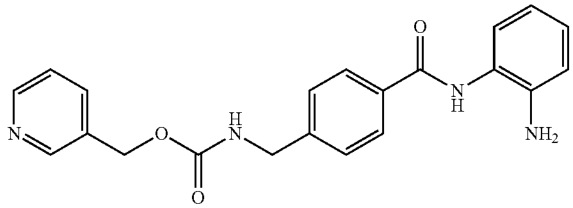 [SMILES: Nc1ccccc1NC(=O)c1ccc(CNC(=O)OCc2cccnc2)cc1] | HDAC inhibitor |
| NSC-663284 | 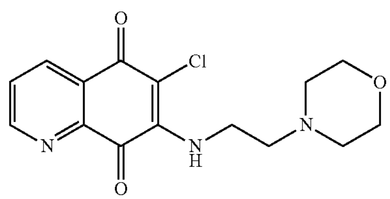 [SMILES: O=C1C(Cl)=C(NCCN2CCOCC2)C(=O)c2ncccc21] | Protein lysine methyltransferase (SETD8) Inhibitor |
| Panobinostat | 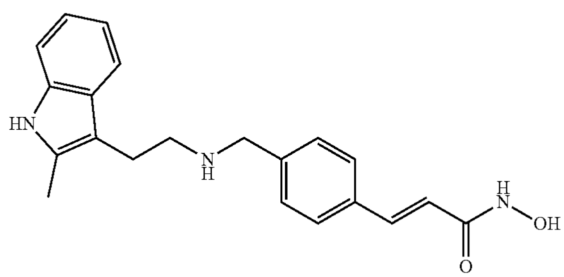 [SMILES: Cc1[nH]c2ccccc2c1CCNCc1ccc(/C=C/C(=O)NO)cc1] | Class I and II HDAC inhibitor |
| PBIT | 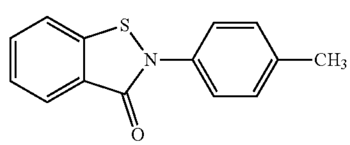 [SMILES: Cc1ccc(-n2sc3ccccc3c2=O)cc1] | Jumanji AT-rich interactive domain 1 family of lysine demethylases (JARID1) inhibitor |
| Piceatanno: | 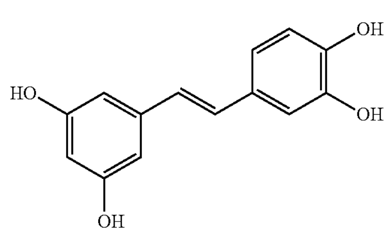 [SMILES: Oc1cc(O)cc(/C=C/c2ccc(O)c(O)c2)c1] | SIRT1 activator |
| Resveratrol | 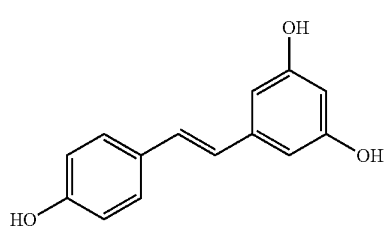 [SMILES: Oc1ccc(/C=C/c2cc(O)cc(O)c2)cc1] | SIRT1 activator |

TABLE 6-continued

Inhibitors of the biological effect of miRNA sequences.

| Compound | Structure | Activity |
| --- | --- | --- |
| RG108 | 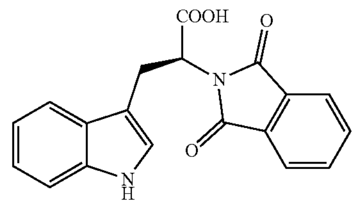 | Non-nucleoside DNMT inhibitor |
| Romidepsin | 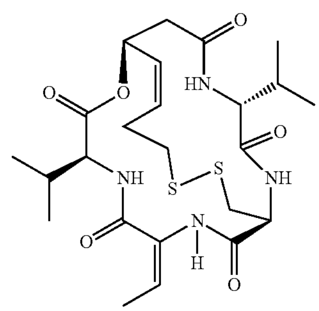 [SMILES: C/C=C1/NC(=O)[C@H]2CSSCC/C=C\[C@H](CC(=O)N[C@H](C(C)C)C(=O)N2)OC(=O)[C@H](C(C)C)NC1=O] | HDAC inhibitor |
| RVX-208 | 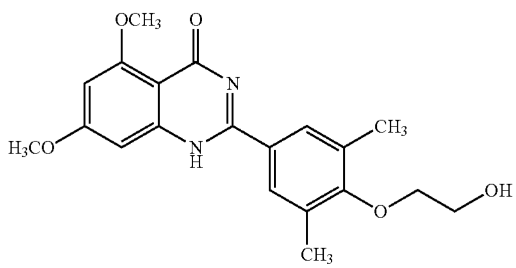 [SMILES: COc1cc(OC)c2c(=O)nc(-c3cc(C)c(OCCO)c(C)c3)[nH]c2c1] | BET bromodomain antagonist |
| Salermide | 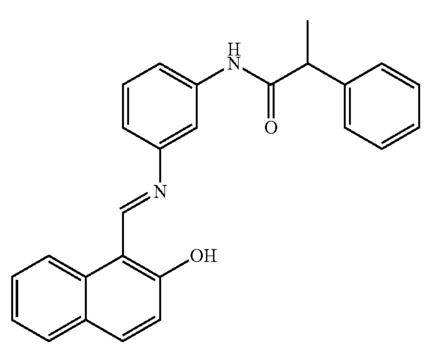 [SMILES: CC(C(=O)Nc1cccc(/N=C/c2c(O)ccc3ccccc23)c1)c1ccccc1] | SIRT inhibitor |
| SGC707 | 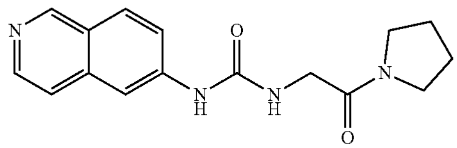 [SMILES: O=C(NCC(=O)N1CCCC1)Nc1ccc2cnccc2c1] | Protein arginine methyltransferase 3 (PRMT3) inhibitor |
| Sinefungin | 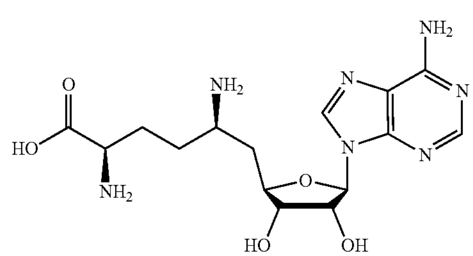 | Methyltransferase inhibitor |

TABLE 6-continued

Inhibitors of the biological effect of miRNA sequences.

| Compound | Structure | Activity |
| --- | --- | --- |
| SirtAct | 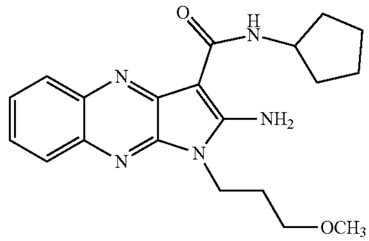 [SMILES: COCCCn1c(N)c(C(=O)NC2CCCC2)c2nc3ccccc3nc21] | SIRT1 activator |
| Sodium phenylbutyrate | 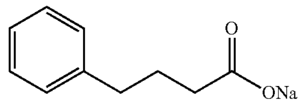 | HDAC inhibitor |
| Splitomicin | 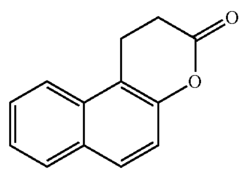 [SMILES: O=C1CCc2c(ccc3ccccc23)O1] | Sir2p (yeast Sirt1 homolog) inhibitor |
| TC-E-5003 | 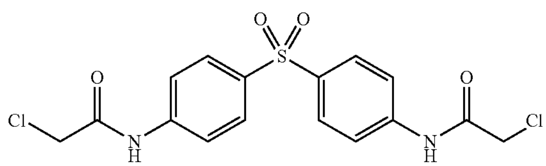 [SMILES: O=C(CCl)Nc1ccc(S(=O)(=O)c2ccc(NC(=O)CCl)cc2)cc1] | PRMT1 inhibitor |
| TM-2-51 | 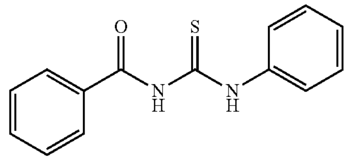 [SMILES: O=C(NC(=S)Nc1ccccc1)c1ccccc1] | HDAC8 activator |
| Tranylcypromine hemisulfate | | Lysine-specific demethylase 1 (LSD1/BHC110) inhibitor |
| Triacetyl resveratrol | 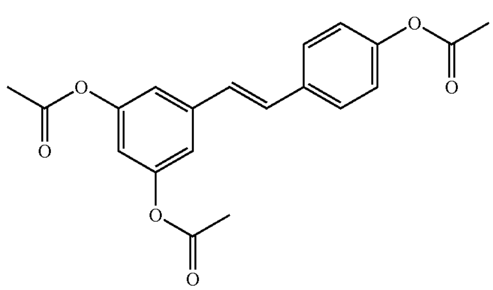 [SMILES: CC(=O)Oc1ccc(/C=C/c2cc(OC(C)=O)cc(OC(C)=O)c2)cc1] | SIRT activator |
| Trichostatin A | 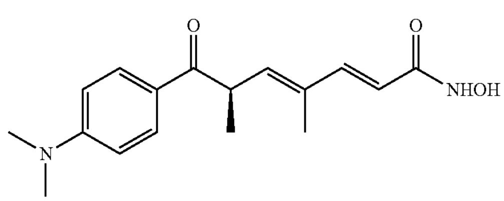 | HDAC inhibitor |

TABLE 6-continued
Inhibitors of the biological effect of miRNA sequences.
| Compound | Structure | Activity |
| --- | --- | --- |
| Tubastatin A hydrochloride | 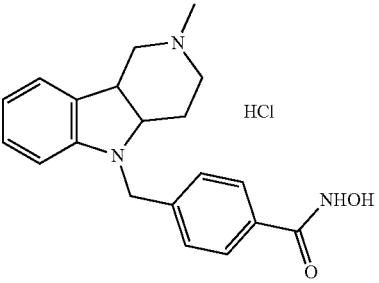 | HDACE inhibitor |
| UNC1999 | 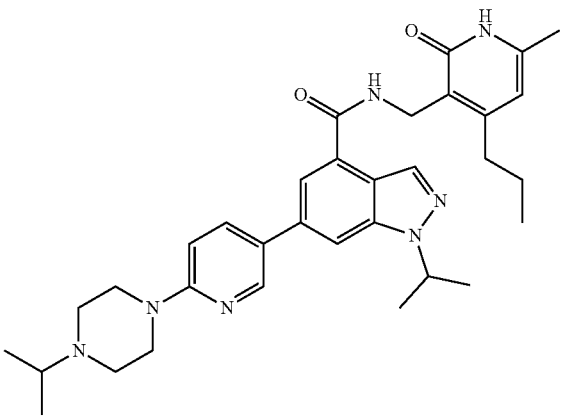 [SMILES: CCCc1cc(C)[nH]c(=O)c1CNC(=O)c1cc(-c2ccc(N3CCN(C(C)C)CC3)nc2)cc2c1cnn2C(C)C] | Lysine methyltransferase (EZH1 & EZH2) inhibitor |
| UNC-2170 | 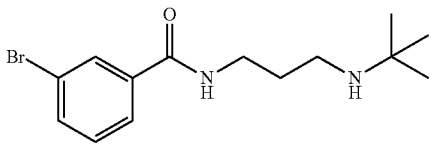 [SMILES: CC(C)(C)NCCCNC(=O)c1cccc(Br)c1] | Methyl-lysine binding protein inhibitor |
| Valproic Acid, sodium salt | 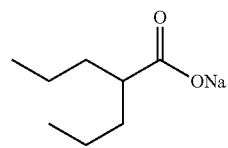 | HDAC inhibitor |
| Vorinostat (SAHA) | 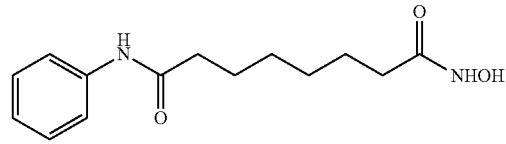 | HDAC inhibitor |
| Zebularine | 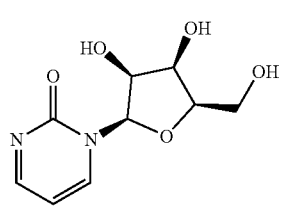 [SMILES: O=c1ncccn1[C@@H]1O[C@H](CO)[C@H](O)[C@@H]1O] | DNMT inhibitor |

REFERENCES

1. Bello L, Gordish-Dressman H, Morgenroth L P, Henricson E K, Duong T, Hoffman E P, Cnaan A, and McDonald C M. Prednisone/prednisolone and deflazacort regimens in the CINRG Duchenne Natural History Study. *Neurology* 85: 1048-1055, 2015.
2. Cai D, Frantz J D, Tawa N E, Jr., Melendez P A, Oh B C, Lidov H G, Hasselgren P O, Frontera W R, Lee J, Glass D J, and Shoelson S E. IKKbeta/N F-kappaB activation causes severe muscle wasting in mice. *Cell* 119: 285-298, 2004.
3. Chapman C G, and Pekow J. The emerging role of miRNAs in inflammatory bowel disease: a review. *Therapeutic advances in gastroenterology* 8: 4-22, 2015.
4. Charlier C, Segers K, Wagenaar D, Karim L, Berghmans S, Jaillon O, Shay T, Weissenbach J, Cockett N, Gyapay G, and Georges M. Human-ovine comparative sequencing of a 250-kb imprinted domain encompassing the callipyge (clpg) locus and identification of six imprinted transcripts: DLK1, DAT, GTL2, PEG11, antiPEG11, and MEG8. *Genome research* 11: 850-862, 2001.
5. Chen X, Shi C, Wang C, Liu W, Chu Y, Xiang Z, Hu K, Dong P, and Han X. The role of miR-497-5p in myofibroblast differentiation of L R-MSCs and pulmonary fibrogenesis. *Scientific reports* 7: 40958, 2017.
6. Chen Y, Wang S X, Mu R, Luo X, Liu Z S, Liang B, Zhuo H L, Hao X P, Wang Q, Fang D F, Bai Z F, Wang Q Y, Wang H M, Jin B F, Gong W L, Zhou T, Zhang X M, Xia Q, and Li T. Dysregulation of the miR-324-5p-CUEDC2 axis leads to macrophage dysfunction and is associated with colon cancer. *Cell reports* 7: 1982-1993, 2014.
7. Chen Y W, Nagaraju K, Bakay M, McIntyre O, Rawat R, Shi R, and Hoffman E P. Early onset of inflammation and later involvement of TGFbeta in Duchenne muscular dystrophy. *Neurology* 65: 826-834, 2005.
8. Christopher A F, Kaur R P, Kaur G, Kaur A, Gupta V, and Bansal P. MicroRNA therapeutics: Discovering novel targets and developing specific therapy. *Perspectives in clinical research* 7: 68-74, 2016.
9. Curtale G, Citarella F, Carissimi C, Goldoni M, Carucci N, Fulci V, Franceschini D, Meloni F, Barnaba V, and Macino G. An emerging player in the adaptive immune response: microRNA-146a is a modulator of IL-2 expression and activation-induced cell death in T lymphocytes. *Blood* 115: 265-273, 2010.
10. Czimmerer Z, Varga T, Kiss M, Vazquez C O, Doan-Xuan Q M, Ruckert D, Tattikota S G, Yan X, Nagy Z S, Daniel B, Poliska S, Horvath A, Nagy G, Varallyay E, Poy M N, Allen J E, Bacso Z, Abreu-Goodger C, and Nagy L. The IL-4/STAT6 signaling axis establishes a conserved microRNA signature in human and mouse macrophages regulating cell survival via miR-342-3p. *Genome medicine* 8: 63, 2016.
11. Davis T E, Kis-Toth K, Szanto A, and Tsokos G C. Glucocorticoids suppress T cell function by up-regulating microRNA-98. *Arthritis and rheumatism* 65: 1882-1890, 2013.
12. Dharap A, Bowen K, Place R, Li L C, and Vemuganti R. Transient focal ischemia induces extensive temporal changes in rat cerebral microRNAome. *Journal of cerebral blood flow and metabolism: official journal of the International Society of Cerebral Blood Flow and Metabolism* 29: 675-687, 2009.
13. Dharap A, Pokrzywa C, Murali S, Pandi G, and Vemuganti R. MicroRNA miR-324-3p induces promoter-mediated expression of RelA gene. *PloS one* 8: e79467, 2013.
14. Duijvis N W, Moerland P D, Kunne C, Slaman M M W, van Dooren F H, Vogels E W, de Jonge W J, Meijer S L, Fluiter K, and Te Velde A A. Inhibition of miR-142-5P ameliorates disease in mouse models of experimental colitis. *PloS one* 12: e0185097, 2017.
15. Eisenberg I, Eran A, Nishino I, Moggio M, Lamperti C, Amato A A, Lidov H G, Kang P B, North K N, Mitrani-Rosenbaum S, Flanigan K M, Neely L A, Whitney D, Beggs A H, Kohane I S, and Kunkel L M. Distinctive patterns of microRNA expression in primary muscular disorders. *Proc Natl Acad Sci USA* 104: 17016-17021, 2007.
16. Fasseu M, Treton X, Guichard C, Pedruzzi E, Cazals-Hatem D, Richard C, Aparicio T, Daniel F, Soule J C, Moreau R, Bouhnik Y, Laburthe M, Groyer A, and Ogier-Denis E. Identification of restricted subsets of mature microRNA abnormally expressed in inactive colonic mucosa of patients with inflammatory bowel disease. *PloS one* 5: 2010.
17. Fiorillo A A, Heier C R, Novak J S, Tully C B, Brown K J, Uaesoontrachoon K, Vila M C, Ngheim P P, Bello L, Kornegay J N, Angelini C, Partridge T A, Nagaraju K, and Hoffman E P. TNF-alpha-Induced microRNAs Control Dystrophin Expression in Becker Muscular Dystrophy. *Cell reports* 12: 1678-1690, 2015.
18. Fordham J B, Naqvi A R, and Nares S. Regulation of miR-24, miR-30b, and miR-142-3p during macrophage and dendritic cell differentiation potentiates innate immunity. *Journal of leukocyte biology* 98: 195-207, 2015.
19. Ghorpade D S, Sinha A Y, Holla S, Singh V, and Balaji K N. NOD2-nitric oxide-responsive microRNA-146a activates Sonic hedgehog signaling to orchestrate inflammatory responses in murine model of inflammatory bowel disease. *The Journal of biological chemistry* 288: 33037-33048, 2013.
20. Grounds M D, and Shavlakadze T. Growing muscle has different sarcolemmal properties from adult muscle: a proposal with scientific and clinical implications: reasons to reassess skeletal muscle molecular dynamics, cellular responses and suitability of experimental models of muscle disorders. *BioEssays: news and reviews in molecular, cellular and developmental biology* 33: 458-468, 2011.
21. He C, Shi Y, Wu R, Sun M, Fang L, Wu W, Liu C, Tang M, Li Z, Wang P, Cong Y, and Liu Z. miR-301a promotes intestinal mucosal inflammation through induction of IL-17A and TNF-alpha in IBD. *Gut* 65: 1938-1950, 2016.
22. He F, Lv P, Zhao X, Wang X, Ma X, Meng W, Meng X, and Dong S. Predictive value of circulating miR-328 and miR-134 for acute myocardial infarction. *Molecular and cellular biochemistry* 394: 137-144, 2014.
23. Heier C R, Damsker J M, Yu Q, Dillingham B C, Huynh T, Van der Meulen J H, Sali A, Miller B K, Phadke A, Scheffer L, Quinn J, Tatem K, Jordan S, Dadgar S, Rodriguez O C, Albanese C, Calhoun M, Gordish-Dressman H, Jaiswal J K, Connor E M, McCall J M, Hoffman E P, Reeves E K, and Nagaraju K. VBP15, a novel anti-inflammatory and membrane-stabilizer, improves muscular dystrophy without side effects. *EMBO molecular medicine* 5: 1569-1585, 2013.
24. Heier C R, Fiorillo A A, Chaisson E, Gordish-Dressman H, Hathout Y, Damsker J M, Hoffman E P, and Conklin L S. Identification of Pathway-Specific Serum Biomarkers of Response to Glucocorticoid and Infliximab Treatment in Children with Inflammatory Bowel Disease. *Clinical and translational gastroenterology* 7: e192, 2016.

25. Heier C R, Guerron A D, Korotcov A, Lin S, Gordish-Dressman H, Fricke S, Sze R W, Hoffman E P, Wang P, and Nagaraju K. Non-invasive MRI and spectroscopy of mdx mice reveal temporal changes in dystrophic muscle imaging and in energy deficits. *PloS one* 9: e112477, 2014.
26. Hoffman E P, Riddle V, Siegler M A, Dickerson D, Backonja M, Kramer W G, Nagaraju K, Gordish-Dressman H, Damsker J M, and McCall J M. Phase 1 trial of vamorolone, a first-in-class steroid, shows improvements in side effects via biomarkers bridged to clinical outcomes. *Steroids* 2018.
27. Hu X, Chi L, Zhang W, Bai T, Zhao W, Feng Z, and Tian H. Down-regulation of the miR-543 alleviates insulin resistance through targeting the SIRT1. *Biochemical and biophysical research communications* 468: 781-787, 2015.
28. Israeli D, Poupiot J, Amor F, Charton K, Lostal W, Jeanson-Leh L, and Richard I. Circulating miRNAs are generic and versatile therapeutic monitoring biomarkers in muscular dystrophies. *Scientific reports* 6: 28097, 2016.
29. Kent W J, Sugnet C W, Furey T S, Roskin K M, Pringle T H, Zahler A M, and Haussler D. The human genome browser at UCSC. *Genome research* 12: 996-1006, 2002.
30. Kramer N J, Wang W L, Reyes E Y, Kumar B, Chen C C, Ramakrishna C, Cantin E M, Vonderfecht S L, Taganov K D, Chau N, and Boldin M P. Altered lymphopoiesis and immunodeficiency in miR-142 null mice. *Blood* 125: 3720-3730, 2015.
31. Krutzfeldt J, Rajewsky N, Braich R, Rajeev K G, Tuschl T, Manoharan M, and Stoffel M. Silencing of microRNAs in vivo with 'antagomirs'. *Nature* 438: 685-689, 2005.
32. Kumar S, Vijayan M, and Reddy P H. MicroRNA-455-3p as a potential peripheral biomarker for Alzheimer's disease. *Human molecular genetics* 26: 3808-3822, 2017.
33. Lewis B P, Burge C B, and Bartel D P. Conserved seed pairing, often flanked by adenosines, indicates that thousands of human genes are microRNA targets. *Cell* 120: 15-20, 2005.
34. Lu J, Yan M, Wang Y, Zhang J, Yang H, Tian F F, Zhou W, Zhang N, and Li J. Altered expression of miR-146a in myasthenia gravis. *Neuroscience letters* 555: 85-90, 2013.
35. Lu Z, Li Y, Takwi A, Li B, Zhang J, Conklin D J, Young K H, and Martin R. miR-301a as an N F-kappaB activator in pancreatic cancer cells. *The EMBO journal* 30: 57-67, 2011.
36. Lukiw W J. Micro-RNA speciation in fetal, adult and Alzheimer's disease hippocampus. *Neuroreport* 18: 297-300, 2007.
37. Lukiw W J, Zhao Y, and Cui J G. An N F-kappaB-sensitive micro RNA-146a-mediated inflammatory circuit in Alzheimer disease and in stressed human brain cells. *The Journal of biological chemistry* 283: 31315-31322, 2008.
38. Ma X, Becker Buscaglia L E, Barker J R, and Li Y. MicroRNAs in N F-kappaB signaling. *Journal of molecular cell biology* 3: 159-166, 2011.
39. Ma X, Zhou J, Zhong Y, Jiang L, Mu P, Li Y, Singh N, Nagarkatti M, and Nagarkatti P. Expression, regulation and function of microRNAs in multiple sclerosis. *International journal of medical sciences* 11: 810-818, 2014.
40. Maciotta S, Meregalli M, Cassinelli L, Parolini D, Farini A, Fraro G D, Gandolfi F, Forcato M, Ferrari S, Gabellini D, Bicciato S, Cossu G, and Torrente Y. Hmgb3 is regulated by microRNA-206 during muscle regeneration. *PloS one* 7: e43464, 2012.
41. Mathelier A, Fomes O, Arenillas D J, Chen C Y, Denay G, Lee J, Shi W, Shyr C, Tan G, Worsley-Hunt R, Zhang A W, Parcy F, Lenhard B, Sandelin A, and Wasserman W W. JASPAR 2016: a major expansion and update of the open-access database of transcription factor binding profiles. *Nucleic acids research* 44: D110-115, 2016.
42. Mechtler P, Singhal R, Kichina J V, Bard J E, Buck M J, and Kandel E S. MicroRNA analysis suggests an additional level of feedback regulation in the N F-kappaB signaling cascade. *Oncotarget* 6: 17097-17106, 2015.
43. Meerson A, Cacheaux L, Goosens K A, Sapolsky R M, Soreq H, and Kaufer D. Changes in brain MicroRNAs contribute to cholinergic stress reactions. *Journal of molecular neuroscience: MN* 40: 47-55, 2010.
44. Mildner A, Chapnik E, Manor O, Yona S, Kim K W, Aychek T, Varol D, Beck G, Itzhaki Z B, Feldmesser E, Amit I, Hornstein E, and Jung S. Mononuclear phagocyte miRNome analysis identifies miR-142 as critical regulator of murine dendritic cell homeostasis. *Blood* 121: 1016-1027, 2013.
45. Milosevic J, Pandit K, Magister M, Rabinovich E, Ellwanger D C, Yu G, Vuga L J, Weksler B, Benos P V, Gibson K F, McMillan M, Kahn M, and Kaminski N. Profibrotic role of miR-154 in pulmonary fibrosis. *American journal of respiratory cell and molecular biology* 47: 879-887, 2012.
46. Mitchell P S, Parkin R K, Kroh E M, Fritz B R, Wyman S K, Pogosova-Agadjanyan E L, Peterson A, Noteboom J, O'Briant K C, Allen A, Lin D W, Urban N, Drescher C W, Knudsen B S, Stirewalt D L, Gentleman R, Vessella R L, Nelson P S, Martin D B, and Tewari M. Circulating microRNAs as stable blood-based markers for cancer detection. *Proc Natl Acad Sci USA* 105: 10513-10518, 2008.
47. Monici M C, Aguennouz M, Mazzeo A, Messina C, and Vita G. Activation of nuclear factor-kappaB in inflammatory myopathies and Duchenne muscular dystrophy. *Neurology* 60: 993-997, 2003.
48. Monk C E, Hutvagner G, and Arthur J S. Regulation of miRNA transcription in macrophages in response to Candida albicans. *PloS one* 5: e13669, 2010.
49. Olivieri F, Lazzarini R, Recchioni R, Marcheselli F, Rippo M R, Di Nuzzo S, Albertini M C, Graciotti L, Babini L, Mariotti S, Spada G, Abbatecola A M, Antonicelli R, Franceschi C, and Procopio A D. MiR-146a as marker of senescence-associated pro-inflammatory status in cells involved in vascular remodelling. *Age (Dordr)* 35: 1157-1172, 2013.
50. Palmieri O, Creanza T M, Bossa F, Latiano T, Corritore G, Palumbo O, Martino G, Biscaglia G, Scimeca D, Carella M, Ancona N, Andriulli A, and Latiano A. Functional Implications of MicroRNAs in Crohn's Disease Revealed by Integrating MicroRNA and Messenger RNA Expression Profiling. *International journal of molecular sciences* 18: 2017.
51. Panguluri S K, Bhatnagar S, Kumar A, McCarthy J J, Srivastava A K, Cooper N G, and Lundy R F. Genomic profiling of messenger RNAs and microRNAs reveals potential mechanisms of TWEAK-induced skeletal muscle wasting in mice. *PloS one* 5: e8760, 2010.
52. Pekow J R, and Kwon J H. MicroRNAs in inflammatory bowel disease. *Inflammatory bowel diseases* 18: 187-193, 2012.
53. Piccoli M T, Gupta S K, Viereck J, Foinquinos A, Samolovac S, Kramer F L, Garg A, Remke J, Zimmer K, Batkai S, and Thum T. Inhibition of the Cardiac Fibroblast-Enriched lncRNA Meg3 Prevents Cardiac Fibrosis and Diastolic Dysfunction. *Circulation research* 121: 575-583, 2017.
54. Pilbrow A P, Cordeddu L, Cameron V A, Frampton C M, Troughton R W, Doughty R N, Whalley G A, Ellis C J, Yandle T G, Richards A M, and Foo R S. Circulating miR-323-3p and miR-652: candidate markers for the presence and progression of acute coronary syndromes. *International journal of cardiology* 176: 375-385, 2014.
55. Plumb-Rudewiez N, Clotman F, Strick-Marchand H, Pierreux C E, Weiss M C, Rousseau G G, and Lemaigre F P. Transcription factor HNF-6/OC-1 inhibits the stimulation of the HNF-3alpha/Foxa1 gene by TGF-beta in mouse liver. *Hepatology* 40: 1266-1274, 2004.
56. Poncelet A C, and Schnaper H W. Sp1 and Smad proteins cooperate to mediate transforming growth factor-beta 1-induced alpha 2(I) collagen expression in human glomerular mesangial cells. *The Journal of biological chemistry* 276: 6983-6992, 2001.
57. Quattrocelli M, Barefield D Y, Warner J L, Vo A H, Hadhazy M, Earley J U, Demonbreun A R, and McNally E M. Intermittent glucocorticoid steroid dosing enhances muscle repair without eliciting muscle atrophy. *The Journal of clinical investigation* 127: 2418-2432, 2017.
58. Ray A, and Prefontaine K E. Physical association and functional antagonism between the p65 subunit of transcription factor NF-kappa B and the glucocorticoid receptor. *Proc Natl Acad Sci USA* 91: 752-756, 1994.
59. Recchiuti A, Krishnamoorthy S, Fredman G, Chiang N, and Serhan C N. MicroRNAs in resolution of acute inflammation: identification of novel resolvin D1-miRNA circuits. *FASEB journal: official publication of the Federation of American Societies for Experimental Biology* 25: 544-560, 2011.
60. Rieu I, and Powers S J. Real-time quantitative RT-PCR: design, calculations, and statistics. *The Plant cell* 21: 1031-1033, 2009.
61. Roderburg C, Mollnow T, Bongaerts B, Elfimova N, Vargas Cardenas D, Berger K, Zimmermann H, Koch A, Vucur M, Luedde M, Hellerbrand C, Odenthal M, Trautwein C, Tacke F, and Luedde T. Micro-RNA profiling in human serum reveals compartment-specific roles of miR-571 and miR-652 in liver cirrhosis. *PloS one* 7: e32999, 2012.
62. Sato T, Yamamoto T, and Sehara-Fujisawa A. miR-195/497 induce postnatal quiescence of skeletal muscle stem cells. *Nature communications* 5: 4597, 2014.
63. Seitz H, Royo H, Bortolin M L, Lin S P, Ferguson-Smith A C, and Cavaille J. A large imprinted microRNA gene cluster at the mouse Dlk1-Gtl2 domain. *Genome research* 14: 1741-1748, 2004.
64. Sonkoly E, and Pivarcsi A. microRNAs in inflammation. *International reviews of immunology* 28: 535-561, 2009.
65. Stedman H H, Sweeney H L, Shrager J B, Maguire H C, Panettieri R A, Petrof B, Narusawa M, Leferovich J M, Sladky J T, and Kelly A M. The mdx mouse diaphragm reproduces the degenerative changes of Duchenne muscular dystrophy. *Nature* 352: 536-539, 1991.
66. Su S, Zhao Q, He C, Huang D, Liu J, Chen F, Chen J, Liao J Y, Cui X, Zeng Y, Yao H, Su F, Liu Q, Jiang S, and Song E. miR-142-5p and miR-130a-3p are regulated by IL-4 and IL-13 and control profibrogenic macrophage program. *Nature communications* 6: 8523, 2015.
67. Swingler T E, Wheeler G, Carmont V, Elliott H R, Barter M J, Abu-Elmagd M, Donell S T, Boot-Handford R P, Hajihosseini M K, Munsterberg A, Dalmay T, Young D A, and Clark I M. The expression and function of microRNAs in chondrogenesis and osteoarthritis. *Arthritis and rheumatism* 64: 1909-1919, 2012.
68. Taganov K D, Boldin M P, Chang K J, and Baltimore D. NF-kappaB-dependent induction of microRNA miR-146, an inhibitor targeted to signaling proteins of innate immune responses. *Proc Natl Acad Sci USA* 103: 12481-12486, 2006.
69. Tao L, Bei Y, Chen P, Lei Z, Fu S, Zhang H, Xu J, Che L, Chen X, Sluijter J P, Das S, Cretoiu D, Xu B, Zhong J, Xiao J, and Li X. Crucial Role of miR-433 in Regulating Cardiac Fibrosis. *Theranostics* 6: 2068-2083, 2016.
70. Vandesompele J, De Preter K, Pattyn F, Poppe B, Van Roy N, De Paepe A, and Speleman F. Accurate normalization of real-time quantitative RT-PCR data by geometric averaging of multiple internal control genes. *Genome biology* 3: RESEARCH0034, 2002.
71. Vasa-Nicotera M, Chen H, Tucci P, Yang A L, Saintigny G, Menghini R, Mahe C, Agostini M, Knight R A, Melino G, and Federici M. miR-146a is modulated in human endothelial cell with aging. *Atherosclerosis* 217: 326-330, 2011.
72. Walden T B, Timmons J A, Keller P, Nedergaard J, and Cannon B. Distinct expression of muscle-specific microRNAs (myomirs) in brown adipocytes. *Journal of cellular physiology* 218: 444-449, 2009.
73. Wang H W, Su S H, Wang Y L, Chang S T, Liao K H, Lo H H, Chiu Y L, Hsieh T H, Huang T S, Lin C S, Cheng S M, and Cheng C C. MicroRNA-134 Contributes to Glucose-Induced Endothelial Cell Dysfunction and This Effect Can Be Reversed by Far-Infrared Irradiation. *PloS one* 11: e0147067, 2016.
74. Wang J, Zhuang J, Iyer S, Lin X, Whitfield T W, Greven M C, Pierce B G, Dong X, Kundaje A, Cheng Y, Rando O J, Birney E, Myers R M, Noble W S, Snyder M, and Weng Z. Sequence features and chromatin structure around the genomic regions bound by 119 human transcription factors. *Genome research* 22: 1798-1812, 2012.
75. Wang W X, Huang Q, Hu Y, Stromberg A J, and Nelson P T. Patterns of microRNA expression in normal and early Alzheimer's disease human temporal cortex: white matter versus gray matter. *Acta neuropathologica* 121: 193-205, 2011.
76. Wang Y, Liang J, Qin H, Ge Y, Du J, Lin J, Zhu X, Wang J, and Xu J. Elevated expression of miR-142-3p is related to the pro-inflammatory function of monocyte-derived dendritic cells in SLE. *Arthritis research & therapy* 18: 263, 2016.
77. Wei L, MacDonald T M, and Walker B R. Taking glucocorticoids by prescription is associated with subsequent cardiovascular disease. *Annals of internal medicine* 141: 764-770, 2004.
78. White B D, Nguyen N K, and Moon R T. Wnt signaling: it gets more humorous with age. *Current biology: C B* 17: R923-925, 2007.
79. Yue X, Cao D, Lan F, Pan Q, Xia T, and Yu H. MiR-301a is activated by the Wnt/beta-catenin pathway and promotes glioma cell invasion by suppressing SEPT7. *Neuro-oncology* 18: 1288-1296, 2016.
80. Zeng Y, Wagner E J, and Cullen B R. Both natural and designed micro RNAs can inhibit the expression of cognate mRNAs when expressed in human cells. *Molecular cell* 9: 1327-1333, 2002.
81. Zhang X R, Fu X J, Zhu D S, Zhang C Z, Hou S, Li M, and Yang X H. Salidroside-regulated lipid metabolism with down-regulation of miR-370 in type 2 diabetic mice. *European journal of pharmacology* 779: 46-52, 2016.

82. Zhang Z, Hou C, Meng F, Zhao X, Huang G, Chen W, Fu M, and Liao W. MiR-455-3p regulates early chondrogenic differentiation via inhibiting Runx2. *FEBS letters* 589: 3671-3678, 2015.
83. Zhou L, Porter J D, Cheng G, Gong B, Hatala D A, Merriam A P, Zhou X, Rafael J A, and Kaminski H J. Temporal and spatial mRNA expression patterns of TGF-beta1, 2, 3 and TbetaRI, I I, III in skeletal muscles of mdx mice. *Neuromuscular disorders: NMD* 16: 32-38, 2006.
84. Zhou M, Wang M, Wang X, Liu K, Wan Y, Li M, Liu L, and Zhang C. Abnormal Expression of MicroRNAs Induced by Chronic Unpredictable Mild Stress in Rat Hippocampal Tissues. *Molecular neurobiology* 2017.
85. Aartsma-Rus, A. and M. van Putten, Assessing functional performance in the mdx mouse model. *J Vis Exp*, 2014(85).
86. Nagaraju, K., et al., Conditional up-regulation of MHC class I in skeletal muscle leads to self-sustaining autoimmune myositis and myositis-specific autoantibodies. *Proc Natl Acad Sci USA*, 2000. 97(16): p. 9209-14.

Example 12: miRNA Binds TLR7

Experiments from FIG. 12 and FIG. 13 were performed to visualize the binding of how miRNAs used in the experiments functioned. The experiments included staining and imaging of macrophages grown in culture. The FIG. 12 data collectively show that both miR-146a and miR-142-3p act as ligands of TLR7, promoting downstream activation of inflammatory gene expression. Data from FIG. 13 collectively suggest that myositis and DMD muscle are primed to receive inflammatory signals because they inappropriately express the RNA-sensing immune receptor Toll-like receptor 7 (Tlr7). Therefore these miRNA sequences and mutant sequences can modulate the inflammatory pathways and the muscle-related disorders.

Example 13: Injection of Mdx Mice with Mutant miRNAs that Bind to, but do not Activate, TLR7 (PROPHETIC)

We will treat mdx mice starting at 2 weeks of age to determine if we can quell inflammation using injection of a "mutant" microRNA that we have demonstrated binds to TLR7 but inhibits its activity. The two microRNA sequences that will be utilized are: 5'-agagaacagaaaaccacgggaa-3' (miR-146amut or mut1) and 5'-agaagagaaaccaacaaaaugga-3' (miR-142-3pmut or mut2). Mice will be treated bi-weekly using either intraperitoneal or intravenous injections of one of the antisense oligonucleotide chemistries (morpholino, PMO or locked nucleic acid, LNA) at a dose of 10-200 mg/kg/day depending on a dose escalation pilot study that will be performed. Groups will be: 1) WT mice injected with saline, 2) mdx mice injected with saline; 3) mdx mice injected with mut1; and 4) mdx mice injected with mut2. Mice will be treated for a total of 6 weeks (aged 2-8 weeks). We will perform the following functional assays to determine muscle strength: 1) Forelimb and hindlimb grip strength at 5 weeks [1], 2) two- and four-limb wire hang at 6-8 weeks; 3) Extent of free wheel running at 6-8 weeks, and 4) In vivo muscle force measurements of the tibialis anterior at 8 weeks (Aurora Scientific apparatus). Endpoint measures will include: in situ muscle force measurement, flow cytometry to measure inflammatory cells in the muscle (CD45+ to measure leukocytes and F4/80+, Cd11b+ to measure macrophages), H&E staining to assess muscle pathology and TNF-α ELISA to measure the extent of TLR7 activation. We expect that injection of mut1 and mut2 into mdx will significantly improve the extent of inflammation, resulting in improved muscle function, reduced inflammatory cell infiltration, improved muscle pathology and reduction of TNF-α secretion.

Example 14: Myositis Mice Injected with a microRNA Inhibitor or a TLR7-Blocking miRNA Mice with conditional muscle-specific overexpression of major histocompatibility complex Class I (MHC, H-2Kb) develop an inflammatory myopathy that closely resembles some aspects of human myositis, with female mice developing more severe disease [2]. In the proposed study, we will utilize female mice that overexpress MHC Class I after doxycycline withdrawal at 5 weeks of age. Female HT mice (myositis) and H or T mice (control) will be generated through in-house breeding and genotyped at 21 days of age. Experiments will performed when the mice are 16 weeks of age and mice will receive bi-weekly injections of a microRNA inhibitor or a mutant microRNA (PMO or LNA) ranging in concentration from 10-200 mg/kg for a total of 6 weeks (dosing will be determined by a pilot study using dose escalation). 6 mice per group will be utilized. Treatment groups will be: 1) Control mice injected with saline (expressing only the H or T transgene); 2) HT myositis mice injected with saline; 3) HT myositis mice injected with a microRNA inhibitor; 4) HT myositis mice injected with mut1 miRNA, and 5) HT myositis mice injected with mut2 miRNA. We will perform functional assays to determine muscle strength at 19-20 weeks (grip strength), 20-22 weeks (wire hang and free wheel running) and 22-24 weeks (in vivo muscle force measurements of the tibialis anterior, Aurora Scientific apparatus). Endpoint measures will include: in situ muscle force measurement, flow cytometry to measure inflammatory cells in the muscle, H&E staining to assess muscle pathology and TNF-α ELISA to measure the extent of TLR7 activation. We expect that injection of mut1 and mut2 into HT myositis mice will significantly improve the extent of inflammation, resulting in improved muscle function, reduced inflammatory cell infiltration, improved muscle pathology and reduction of TNF-α secretion.

References for Examples 13 and 14

1. Heier, C. R., et al., *VBP15, a novel anti-inflammatory and membrane-stabilizer, improves muscular dystrophy without side effects.* EMBO Mol Med, 2013. 5(10): p. 1569-85.
2. Nagaraju, K., et al., *Conditional up-regulation of MHC class I in skeletal muscle leads to self-sustaining autoimmune myositis and myositis-specific autoantibodies.* Proc Natl Acad Sci USA, 2000. 97(16): p. 9209-14.
3. Khachigian, L. M., *Collagen antibody-induced arthritis.* Nat Protoc, 2006. 1(5): p. 2512-6.
4. Bender, A. T., et al., *Evaluation of a candidate anti-arthritic drug using the mouse collagen antibody induced arthritis model and clinically relevant biomarkers.* Am J Transl Res, 2013. 5(1): p. 92-102.
5. Gross, S., et al., *Bioluminescence imaging of myeloperoxidase activity in vivo.* Nat Med, 2009. 15(4): p. 455-61.

What is claimed is:

1. A method of treating a muscle disease in a subject in need thereof, the method comprising administering one or more inhibitory antisense oligonucleotide (ASO) molecules or one or more expression vectors encoding the one or more inhibitory ASO molecules, the one or more inhibitory antisense oligonucleotide molecules inhibit or reduce activity of at least one NF kappa B regulated micro RNA (miRNA) molecules in an amount sufficient to reduce one or more symptoms of the muscle disease,
    wherein the ASO molecule is complementary to one or a combination of miR-142-3p (SEQ ID NO:12), miR-142-5p (SEQ ID NO:13), miR-652 (SEQ ID NO:19), miR-455-3p (SEQ ID NO:6), and miR-497-5p (SEQ ID NO:7) or at least 70% complementary to miR-142-3p (SEQ ID NO:12), miR-142-5p (SEQ ID NO:13), miR-652 (SEQ ID NO:19), miR-455-3p (SEQ ID NO:6), and miR-497-5p (SEQ ID NO:7).

2. The method of claim 1, wherein the muscle disease is Duchenne muscular dystrophy.

3. The method of claim 1, wherein the muscle disease is a muscular dystrophy caused by expression of a mutation in the dystrophin (DMD) gene of the subject.

4. The method of claim 1, further comprising administering a steroid receptor ligand prior to, contemporaneously with or subsequent to administration of the one or more inhibitory antisense oligonucleotide (ASO) molecules or one or more expression vectors encoding the one or more inhibitory ASO molecules.

5. A method of treating inflammation in a subject in need thereof, the method comprising administering one or more inhibitory ASO molecules or one or more expression vectors encoding the one or more inhibitory ASO molecules, the one or more inhibitory ASO molecules inhibit or reduce activity of at least one NF kappa B regulated micro RNA (miRNA) molecules in an amount sufficient to treat inflammation, wherein the ASO molecule is complementary to one or a combination of miR-142-3p (SEQ ID NO:12), miR-142-5p (SEQ ID NO:13), miR-652 (SEQ ID NO:19), miR-455-3p (SEQ ID NO:6), and miR-497-5p (SEQ ID NO:7) or at least 70% complementary to miR-142-3p (SEQ ID NO:12), miR-142-5p (SEQ ID NO:13), miR-652 (SEQ ID NO:19), miR-455-3p (SEQ ID NO:6), and miR-497-5p (SEQ ID NO:7).

6. The method of claim 5, wherein the subject has muscular dystrophy.

7. The method of claim 5, further comprising administering a steroid receptor ligand prior to, contemporaneously with, or subsequent to administration of the pharmaceutical composition.

8. The method of claim 7, wherein the steroid is an anti-inflammatory corticosteroid.

9. A method of reducing one or more side effects of steroid therapy in a subject in need thereof, the method comprising administering to the subject having been previously administered a steroid therapy and/or concurrent with a steroid therapy one or more inhibitory antisense oligonucleotide (ASO) or one or more expression vectors encoding the one or more inhibitory ASO molecules, the one or more interfering molecules inhibit or reduce activity of at least one glucocorticoid receptor regulated or mineralocorticoid receptor regulated micro RNA (miRNA) molecules in an amount sufficient to reduce one or more symptoms of steroid treatment side effects in the muscle disease;
wherein the ASO molecule is complementary to one or a combination of miR-142-3p (SEQ ID NO:12), miR-142-5p (SEQ ID NO:13), miR-652 (SEQ ID NO:19), miR-455-3p (SEQ ID NO: 6), and miR-497-5p (SEQ ID NO:7) or at least 70% complementary to miR-142-3p (SEQ ID NO:12), miR-142-5p (SEQ ID NO:13), miR-652 (SEQ ID NO:19), miR-455-3p (SEQ ID NO: 6), and miR-497-5p (SEQ ID NO:7).

10. The method of claim 9, wherein the steroid is an anti-inflammatory corticosteroid.

11. The method of claim 1, wherein the muscle disease comprises chronic inflammation.

12. The method of claim 9, wherein the ASO molecule is complementary to one of miR-142-3p, miR-142-5p, miR-652, miR-455-3p, miR-455-5p, miR-146a-5p, miR-301a-3p, miR-324-3p, and miR-497-5p or at least 70% complementary to miR-142-3p, miR-455-5p, miR-652, miR-455-3p, and miR-455-5p, miR-146a-5p, miR-301a-3p, miR-324-3p, and miR-497-5p.

13. The method of claim 1, wherein the ASO molecule is complementary to one or a combination of miR-142-3p (SEQ ID NO: 12), miR-142-5p (SEQ ID NO: 13), miR-652 (SEQ ID NO:19), and miR-455-3p (SEQ ID NO:6).

14. The method of claim 5, wherein the ASO molecule is complementary to one or a combination of miR-142-3p (SEQ ID NO:12), miR-142-5p (SEQ ID NO: 13), miR-652 (SEQ ID NO:19), and miR-455-3p (SEQ ID NO:6).

15. The method of claim 9, wherein the ASO molecule is complementary to one or a combination of miR-142-3p, miR-142-5p, miR-652, miR-455-3p, and miR-455-5p.

16. The method of claim 1, wherein the ASO molecule is at least 80% complementary to one or a combination of miR-142-3p (SEQ ID NO:12), miR-142-5p (SEQ ID NO:13), miR-652 (SEQ ID NO:19), and miR-455-3p (SEQ ID NO:6).

17. The method of claim 5, wherein the ASO molecule is at least 80% complementary to one or a combination of miR-142-3p (SEQ ID NO: 12), miR-142-5p (SEQ ID NO:13), miR-652 (SEQ ID NO:19), and miR-455-3p (SEQ ID NO:6).

18. The method of claim 9, wherein the ASO molecule is at least 80% complementary to one or a combination of miR-142-3p, miR-142-5p, miR-652, miR-455-3p, and miR-455-5p.

19. The method of claim 1, wherein the ASO molecule is at least 97% complementary to one or a combination of miR-142-3p (SEQ ID NO: 12), miR-142-5p (SEQ ID NO:13), miR-652 (SEQ ID NO:19), and miR-455-3p (SEQ ID NO:6).

20. The method of claim 5, wherein the ASO molecule is at least 97% complementary to one or a combination of miR-142-3p (SEQ ID NO:12), miR-142-5p (SEQ ID NO:13), miR-652 (SEQ ID NO:19), and miR-455-3p (SEQ ID NO:6).

21. The method of claim 9, wherein the ASO molecule is at least 97% complementary to one or a combination of miR-142-3p, miR-142-5p, miR-652, miR-455-3p, and miR-455-5p.

22. The method of claim 1, wherein the muscle disease is a muscular dystrophy caused by expression of a mutation in a dystrophin-associated protein product of the subject.

23. The method of claim 1, wherein the disease is a dystrophin disorder.

24. The method of claim 5, wherein the disease is an inflammatory disorder.

* * * * *